US011667904B2

(12) United States Patent
Cheng et al.

(10) Patent No.: US 11,667,904 B2
(45) Date of Patent: Jun. 6, 2023

(54) CRISPR-ASSOCIATED SYSTEMS AND COMPONENTS

(71) Applicant: ARBOR BIOTECHNOLOGIES, INC., Cambridge, MA (US)

(72) Inventors: David R. Cheng, Boston, MA (US); David A. Scott, Cambridge, MA (US); Winston X. Yan, Boston, MA (US)

(73) Assignee: ARBOR BIOTECHNOLOGIES, INC., Cambridge, MA (US)

( * ) Notice: Subject to any disclaimer, the term of this patent is extended or adjusted under 35 U.S.C. 154(b) by 437 days.

(21) Appl. No.: 16/862,261

(22) Filed: Apr. 29, 2020

(65) Prior Publication Data

US 2020/0299659 A1 Sep. 24, 2020

Related U.S. Application Data

(63) Continuation of application No. PCT/US2019/032750, filed on May 16, 2019.

(60) Provisional application No. 62/672,489, filed on May 16, 2018.

(51) Int. Cl.
| | |
|---|---|
| C12N 9/22 | (2006.01) |
| C12N 15/113 | (2010.01) |
| A61K 31/7088 | (2006.01) |
| A61K 38/46 | (2006.01) |
| C12N 15/11 | (2006.01) |
| C12N 15/90 | (2006.01) |
| C12Q 1/6832 | (2018.01) |
| C12N 9/96 | (2006.01) |

(52) U.S. Cl.
CPC ............ *C12N 9/22* (2013.01); *A61K 31/7088* (2013.01); *A61K 38/465* (2013.01); *C12N 9/96* (2013.01); *C12N 15/11* (2013.01); *C12N 15/113* (2013.01); *C12N 15/907* (2013.01); *C12Q 1/6832* (2013.01); *C07K 2319/80* (2013.01); *C12N 2310/20* (2017.05); *C12N 2310/531* (2013.01); *C12N 2800/80* (2013.01)

(58) Field of Classification Search
None
See application file for complete search history.

(56) References Cited

U.S. PATENT DOCUMENTS

| | | |
|---|---|---|
| 5,580,859 A | 12/1996 | Feigner et al. |
| 5,589,466 A | 12/1996 | Feigner et al. |
| 5,593,972 A | 1/1997 | Weiner et al. |
| 8,454,972 B2 | 6/2013 | Nabel et al. |
| 8,795,965 B2 | 8/2014 | Zhang |
| 8,871,445 B2 | 10/2014 | Cong et al. |
| 10,808,245 B2 | 10/2020 | Chong et al. |
| 2017/0211142 A1 | 7/2017 | Smargon et al. |
| 2018/0371487 A1 | 12/2018 | Yang |

FOREIGN PATENT DOCUMENTS

| | | |
|---|---|---|
| EP | 3009511 A2 | 4/2016 |
| WO | 2012164565 A1 | 12/2012 |
| WO | 2014/093622 A2 | 6/2014 |
| WO | 2015/070083 A1 | 5/2015 |
| WO | 2016094872 A1 | 6/2016 |
| WO | 2016094874 A1 | 6/2016 |
| WO | 2016106236 A1 | 6/2016 |
| WO | 2016205764 A1 | 12/2016 |
| WO | 2017070605 A1 | 4/2017 |
| WO | 2017091630 A1 | 6/2017 |
| WO | 2017127807 A1 | 7/2017 |
| WO | 2017219027 A1 | 12/2017 |
| WO | 2018035250 A1 | 2/2018 |
| WO | 2018035388 A1 | 2/2018 |
| WO | 2019178427 A1 | 9/2019 |
| WO | 2019178428 A1 | 9/2019 |
| WO | 2020028823 A1 | 2/2020 |
| WO | 2020181101 A1 | 9/2020 |

OTHER PUBLICATIONS

Carabias, et al. (Nature Communications 12.1 (2021): 1-12). (Year: 2021).*
Guo et al. (2004, Proc. Natl. Acad. Sci. USA 101: 9205-9210). (Year: 2004).*
Chylinski, et al. "Classification and evolution of type II CRISPR-Cas systems." Nucleic acids research 42.10 (2014): 6091-6105. (Year: 2014).*
Abudayyeh et al. "C2c2 is a single-component programmable RNA-guided RNA-targeting CRISPR effector" Science (2016) vol. 353, No. 6299, pp. aaf5573-1-aaf5573-9.
Allerson et al. "Fully 2'-modified oligonucleotide duplexes with improved in vitro potency and stability compared to unmodified small interfering RNA," J. Med. Chem., 48.4 (2005): 901-904.
Al-Shayeb et al., "Clades of huge phages from across Earth's ecosystems," Nature (2020) vol. 578, pp. 425-431 and Methods pages.
Aravind et al. "Classification of the caspase-hemoglobinase fold: detection of new families and implications for the origin of the eukaryotic separins" (2002) Proteins 46(4): 355-67.
Baba et al. "Construction of *Escherichia coli* K-12 in-frame, single-gene knockout mutants: the Keio collection" (2006) Mol. Syst. Biol. 2: 2006.0008.
Bell et al., "A high-throughput screening strategy for detecting CRISPR-Cas9 induced mutations using next-generation sequencing," BMC Genomics (2014) vol. 15, No. 1002, pp. 1-7.
Bramsen et al., "Development of therapeutic-grade small interfering RNAs by chemical engineering," Front. Genet., Aug. 20, 2012; 3:154.
Canver et al., "BCL11A enhancer dissection by Cas9-mediated in situ saturating mutagenesis," Nature, Nov. 12, 2015; 527(7577):192-7.

(Continued)

*Primary Examiner* — Charles Logsdon
(74) *Attorney, Agent, or Firm* — K&L Gates LLP

(57) ABSTRACT

The disclosure describes novel systems, methods, and compositions for the manipulation of nucleic acids in a targeted fashion. The disclosure describes non-naturally occurring, engineered Type III-E CRISPR-Cas systems, components, and methods for targeted modification of DNA, RNA, and protein substrates. Each system includes one or more protein components and one or more nucleic acid components that together target DNA, RNA, or protein substrates.

20 Claims, 14 Drawing Sheets

Specification includes a Sequence Listing.

(56) References Cited

OTHER PUBLICATIONS

Chen et al., "CRISPR-Cas12a target binding unleashes indiscriminate single-stranded DNase activity," Science 360 (6387) 436-9 (Feb. 2018).
Chen et al., "Spatially resolved, highly multiplexed RNA profiling in single cells," Science, Apr. 24, 2015; 348(6233): aaa6090.
Chou-Zheng et al. "A type III-A CRISPR-Cas system employs degradosome nucleases to ensure robust Immunity" (2019) eLife 8:e45393.
Cooper et al., "RNA and disease," Cell, 136.4 (2009): 777-793.
Databse EMBL Online—Speth D.R. et al. "Candidatus Scalindua brodae CHAT domain protein," retrieved from UNIPARC accession No. UPI0005442945, database Accession No. KHE91663, dated Dec. 14, 2014.
Datlinger et al., "Pooled CRISPR screening with single-cell transcriptome read-out," Nat. Methods., Mar. 2017; 14(3):297-3.
Dong et al., "The crystal structure of Cpf1 in complex with CRISPR RNA," Nature 532(7600): 522-6 (Apr. 2016).
Eckstein et al. "Phosphorothioates, essential components of therapeutic oligonucleotides," Nucl. Acid Ther., 24 (2014), pp. 374-387.
Epstein et al. "Engineering a Self-Inactivating CRISPR System for AAV Vectors," Mol. Ther., 24 (2016): S50.
Estrella et al., "RNA-activated DNA cleavage by the Type III-B CRISPR-Cas effector complex" (2019) Genes & Dev 30:460-470.
Garrett et al., "CRISPR-based immune systems of the Sulfolobales: complexity and diversity," Biochem Soc Trans (2011) vol. 39, pp. 51-57.
Gaudelli et al., "Programmable base editing of A.T to G.C in genomic DNA without DNA cleavage," Nature 551 (7681): 464-71 (Oct. 2017).
Gerdes et al. "Experimental determination and system level analysis of essential genes in *Escherichia coli* MIG1655" (2003) J. Bacteriol. 185(19): 5673-84.
Goldfless et al. "Direct and specific chemical control of eukaryotic translation with a synthetic RNA-protein Interaction," Nucl. Acids Res., 40.9 (2012): e64-e64.
Gootenberg et al. "Nucleic acid detection with CRISPR-Cas13a/C2c2," Science, Apr. 28, 2017; 356(6336):438-442.
Hallbrink et al., "Prediction of cell-penetrating peptides," Methods Mol. Biol., 2015; 1324:39-58.
Hammond et al., "A CRISPR-Cas9 gene drive system targeting female reproduction in the malaria mosquito vector Anopheles gambiae," Nat. Biotechnol., Jan. 2016; 34(1):78-83.
Hirosawa et al. "Cell-type-specific genome editing with a microRNA-responsive CRISPR-Cas9 switch," Nucl. Acids Res., Jul. 27, 2017; 45(13): e118.
Hlavova et al., "Improving microalgae for biotechnology—from genetics to synthetic biology," Biotechnol. Adv., Nov. 1, 2015; 33:1194-203.
International Search Report and Written Opinion for International Application No. PCT/US2019/022376 dated Jun. 17, 2019.
International Search Report for International Application No. PCT/US2019/022375, dated Jun. 13, 2019 (6 pages).
International Search Report for PCT/US2019/032750, dated Sep. 25, 2019.
Kelley et al., "Versatility of chemically synthesized guide RNAs for CRISPR-Cas9 genome editing," J. Biotechnol. Sep. 10, 2016; 233:74-83.
Kim et al., "Efficient Transcriptional Gene Repression by Type V-A CRISPR-Cpf1 from Eubacterium eligens," ACS Synthetic Biology 6(7): 1273-82 (Apr. 2017).
Konermann et al. "Optical control of mammalian endogenous transcription and epigenetic states," Nature, 500.7463 (2013): 472.
Koonin et al., "Diversity, classification and evolution of CRISPR-Cas systems," Current Opinion in Microbiology 37: 67-78 (Jun. 2017).
Liu et al., "C2c1-sgRNA Complex Structure Reveals RNA-Guided DNA Cleavage Mechanism," Mol Cell. 65(2):310-22 (Dec. 2016).

Makarova et al., "An updated evolutionary classification of CRISPR-Cas systems," Nat. Rev. Microbiol. 13(11):722-36 (Sep. 2015).
Makarova et al., "Annotation and Classification of CRISPR-Cas Systems," Methods Mol Biol (2015) vol. 1311, pp. 47-75.
Makarova et al., "Classification and Nomenclature of CRISPR-Cas Systems: Where from Here?" Crispr J. 1(5):325-36 (Oct. 2018).
Makarova et al., "Unification of Cas protein families and a simple scenario for the origin and evolution of CRISPR-Cas systems," Biology Direct (2011) vol. 6, Article 38, 27 pages.
Murugan et al., "The Revolution Continues: Newly Discovered Systems Expand the CRISPR-Cas Toolkit," Molecular Cell 68(1): 15-25 (Oct. 2017).
Nicolaou et al., "Molecular diagnosis of peanut and legume allergy," Curr. Opin. Allergy Clin. Immunol., Jun. 2011; 11(3):222-8.
Nowak et al., "Guide RNA engineering for versatile Cas9 functionality," Nucl. Acid. Res., Nov. 16, 2016; 44(20):9555-9564.
O'Connell et al. "Programmable RNA recognition and cleavage by CRISPR/Cas9" Nature (2014) vol. 516, No. 7530, pp. 263-266.
Osborne et al., "Transcriptional and post-transcriptional impact of toxic RNA in myotonic dystrophy," Hum. Mol. Genet., Apr. 15, 2009; 18(8):1471-81.
Pausch et al., "CRISPR-Cas-Phi from huge phages is a hypercompact genome editor," Science (2020) vol. 369, pp. 333-337.
Ramakrishna et al., "Gene disruption by cell-penetrating peptide-mediated delivery of Cas9 protein and guide RNA," Genome Res., Jun. 2014;24(6):1020-7.
Ran et al., "Double nicking by RNA-guided CRISPR Cas9 for enhanced genome editing specificity," Cell 154(6):1380-9 (Aug. 2013).
Sequence Alignment of SEQ ID No. 5 with BGX25975, Search conducted on Jun. 5, 2020, 4 pages. (Year: 2020).
Sequence Alignment of SEQ ID No. 5 with BGX25978, Search conducted on Jun. 11, 2020, 7 pages. (Year: 2020).
Sequence Alignment of SEQ ID No. 5 with BGX25997, Search conducted on Jun. 11, 2020, 7 pages. (Year: 2020).
Shmakov et al., "Discovery and Functional Characterization of Diverse Class 2 CRISPR-Cas Systems," Molecular Cell 60(3): 385-97 (Oct. 2015).
Smargon et al. "Cas13b is a Type VI-B CRISPR-Associated RNA-Guided RNase Differentially Regulated by Accessory Proteins Csx27 and Csx28" Molecular Cell (2017) vol. 65, No. 4, pp. 618-630.
Stella et al., "Class 2 CRISPR-Cas RNA-guided endonucleases: Swiss Army knives of genome editing," Nature Structural & Molecular Biology 24(11): 882-92 (Oct. 2017).
Strutt et al. "RNA-dependent RNA targeting by CRISPR-Cas9" eLIFE (2018) vol. 7, e 32724, pp. 1-17.
Tamulaitis et al., "Type III CRISPR-Cas Immunity: Major Differences Brushed Aside," Trends Microbiol (2017) vol. 25, No. 1, pp. 49-61.
Verwaal et al., "CRISPR/Cpf1 enables fast and simple genome editing of *Saccharomyces cerevisiae*," Yeast, Sep. 8, 2017. doi: 10.1002/yea.3278.
Wright et al. "Rational design of a split-Cas9 enzyme complex," Proc. Nat'l. Acad. Sci., 112.10 (2015): 2984-2989.
Written Opinion of the International Searching Authority for International Application No. PCT/US2019/022375 (7 pages).
Wu et al., "Structural basis of stringent PAM recognition by CRISPR-C2c1 in complex with sgRNA," Cell Res. 27(5):705-8 (Apr. 2017).
Yamano et al., "Crystal Structure of Cpf1 in Complex with Guide RNA and Target DNA," Cell 165(4):949-62 (Apr. 2016).
Yan et al., "Cas13d is a Compact RNA-Targeting Type VI CRISPR Effector Positively Modulated by a WYL-Domain-Containing Accessory Protein," Mol. Cell 70(2)327-39.e5 (Mar. 2018).
Yan et al., "Functionally diverse type V CRISPR-Cas systems," Science 363(6422):88-91 (Dec. 2018).
Yang et al., "PAM-Dependent Target DNA Recognition and Cleavage by C2c1 CRISPR-Cas Endonuclease," Cell 167(7):1814-28 (Dec. 2016).
Zetsche et al, "A split-Cas9 architecture for inducible genome editing and transcription modulation," Nature Biotech., 33.2 (2015): 139-142.

(56) References Cited

OTHER PUBLICATIONS

Zetsche et al., "Cpf1 is a single RNA-guided endonuclease of a class 2 CRISPR-Cas system," Cell 163(3), 759-71 (Sep. 2015).

* cited by examiner

Type III-E | Direct Repeat

FIG. 2

Type III-E  Effector A - Functional Domains

```
Query:  CLUST.019911  [M=796]
Scores for complete sequences (score includes all domains):
    --- full sequence ---   --- best 1 domain ---   -#dom-
    E-value  score  bias    E-value  score  bias    exp  N  Sequence                        Description
    -------  -----  ----    -------  -----  ----    ---  -  --------                        -----------
    5.3e-89  309.6   0.0    5.8e-89  309.5   0.0    1.0  1  A0A0B0EKL4_9BACT/474-681         A0A0B0EKL4.1 PF12770.6;CHAT;
    6.4e-76  266.4   0.1    7.5e-76  266.1   0.1    1.0  1  I3IJ32_9BACT/506-720             I3IJ32.1 PF12770.6;CHAT;
    2.7e-59  211.4   0.0    3e-59    211.2   0.0    1.0  1  A0A0M2UUX8_9BACT/510-766         A0A0M2UUX8.1 PF12770.6;CHAT;
    6.4e-57  203.5   0.2    7.4e-57  203.3   0.2    1.0  1  A0A0M9E5G0_9DELT/841-1101        A0A0M9E5G0.1 PF12770.6;CHAT;
    7.1e-24   94.3   0.7    8.9e-24   93.9   0.7    1.0  1  K9ZFL8_ANACC/786-1097            K9ZFL8.1 PF12770.6;CHAT;
    1.4e-20   83.4   0.1    1.7e-20   83.0   0.1    1.0  1  A7BQU5_9GAMM/952-1233            A7BQU5.1 PF12770.6;CHAT;
```

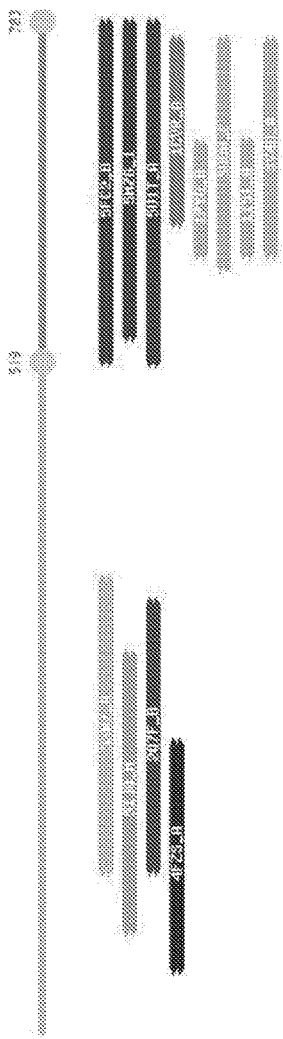

TPR   CHAT

FIG. 5

CRISPR-ASSOCIATED SYSTEMS AND COMPONENTS

CROSS REFERENCE TO RELATED APPLICATIONS

This application is a continuation of International Application No. PCT/US2019/032750, filed on May 16, 2019, which claims the benefit of priority of U.S. Application No. 62/672,489, filed on May 16, 2018. The contents of the foregoing applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Apr. 27, 2020, is named A2186-703220_SL.txt and is 341,967 bytes in size.

FIELD OF THE INVENTION

The present disclosure relates to novel CRISPR systems and components, and methods and compositions for the use of CRISPR systems in, for example, nucleic acid detection.

BACKGROUND

Recent application of advances in genome sequencing technologies and analysis have yielded significant insights into the genetic underpinning of biological activities in many diverse areas of nature, ranging from prokaryotic biosynthetic pathways to human pathologies. To fully understand and evaluate the vast quantities of information produced by genetic sequencing technologies, equivalent increases in the scale, efficacy, and ease of technologies for genome and epigenome manipulation are needed. These novel genome and epigenome engineering technologies will accelerate the development of novel applications in numerous areas, including biotechnology, agriculture, and human therapeutics.

Clustered Regularly Interspaced Short Palindromic Repeats (CRISPR) and the CRISPR-associated (Cas) genes, collectively known as the CRISPR-Cas or CRISPR/Cas systems, are currently understood to provide immunity to bacteria and archaea against phage infection. The CRISPR-Cas systems of prokaryotic adaptive immunity are an extremely diverse group of proteins effectors, non-coding elements, as well as loci architectures, some examples of which have been engineered and adapted to produce important biotechnologies.

The components of the system involved in host defense include one or more effector proteins capable of modifying DNA or RNA and an RNA guide element that is responsible to targeting these protein activities to a specific sequence on the phage DNA or RNA. The RNA guide is composed of a CRISPR RNA (crRNA) and may require an additional trans-activating RNA (tracrRNA) to enable targeted nucleic acid manipulation by the effector protein(s). The crRNA consists of a direct repeat responsible for protein binding to the crRNA and a spacer sequence that is complementary to the desired nucleic acid target sequence. CRISPR systems can be reprogrammed to target alternative DNA or RNA targets by modifying the spacer sequence of the crRNA.

Citation or identification of any document in this application is not an admission that such document is available as prior art to the present invention.

SUMMARY

The present disclosure provides methods for computational identification of new CRISPR-Cas systems from genomic databases, together with the development of the natural loci into engineered systems, and experimental validation and application translation.

In one aspect, the present disclosure relates to non-naturally occurring Clustered Regularly Interspaced Short Palindromic Repeat (CRISPR)—Cas systems of CLUST.019911 (Type III-E) including a Type III-E RNA guide or a nucleic acid encoding the Type III-E RNA guide, where the Type III-E RNA guide includes a direct repeat sequence and a spacer sequence capable of hybridizing to a target nucleic acid; and at least one Type III-E CRISPR-Cas effector protein or a nucleic acid encoding the effector protein, where the effector protein includes an amino acid sequence that is at least 80% (e.g., 85, 90, 91, 92, 93, 94, 95, 96, 97, 98, 99, or 100%) identical to an amino acid sequence provided in Table 2 or Table 3; where the Type III-E CRISPR-Cas effector protein is capable of binding to the Type III-E RNA guide and of targeting the target nucleic acid sequence complementary to the spacer sequence.

In some embodiments, the Type III-E CRISPR-Cas system also includes two or more Type III-E RNA guides. In some embodiments, the Type III-E RNA guide includes a direct repeat sequence, a spacer sequence, and a second direct repeat sequence, arranged in order within Type III-E the RNA guide. In some embodiments, the Type III-E CRISPR-Cas system includes at least one Repeat Associated Mysterious Protein (RAMP) domain. In certain embodiments, the Type III-E CRISPR-Cas effector protein also includes two or more Repeat Associated Mysterious Protein (RAMP) domains. In some of these embodiments, the RAMP-domain includes at least about 1400 amino acids or least about 1550 amino acids.

In some embodiments, the RAMP-domain includes an amino acid sequence that is homologous to CRISPR Cmr4, CRISPR Cmr6, or CRISPR Cas7. In certain embodiments, the RAMP-domain does not include an amino acid sequence that is homologous to CRISPR Cas10 or CRISPR Cas 5.

In some embodiments, the Type III-E CRISPR-Cas effector also includes a protease domain. In some of these embodiments, the protease domain is activated when the system binds to the target nucleic acid, thereby exhibiting protease activity. In certain embodiments, the protease activity is a peptidase activity, e.g., an endopeptidase or exopeptidase activitye, e.g., the protease domain can be a caspase domain. In some embodiments, the caspase domain is a Caspase HetF Associated with Tprs (CHAT) domain.

In some embodiments, the target nucleic acid is a transcriptionally active site.

In certain embodiments, the direct repeat sequence includes a nucleotide sequence that is at least 80% (e.g., 85%, 90%, 91%, 92%, 93%, 94%, 95%, 96%, 97%, 98%, 99%, or 100%) identical to a nucleotide sequence provided in Table 4.

In some embodiments, the target nucleic acid is a DNA or a RNA.

In another aspect, the targeting of the target nucleic acid by the Type III-E CRISPR-Cas effector protein and Type III-E RNA guide results in a modification in the target nucleic acid. For example, the modification of the target nucleic acid can be a cleavage event, such as a double-stranded cleavage event or a single-stranded cleavage event. In some embodiments, the modification of the target nucleic acid is a deletion or an insertion event.

In some embodiments, the system inserts a nucleic acid sequence into a DNA via reverse transcription from an RNA template.

In another aspect, the Type III-E CRISPR-Cas effector protein has non-specific protease activity or non-specific nuclease activity. For example, the non-specific activity can be reduced after targeting the target nucleic acid sequence. In some embodiments, the modification results in cell toxicity.

In another aspect, the Type III-E CRISPR-Cas system is present within a cell. For example the cell can be a eukaryotic cell, such as a prokaryotic cell or a eukaryotic cell.

In other aspects, the Type III-E CRISPR-Cas system includes a tracrRNA.

In yet another aspect, the present disclosure relates to methods of targeting and editing a target nucleic acid. The methods include contacting the target nucleic acid with a Type III-E CRISPR-Cas system described herein.

In another aspect, the present disclosure relates to methods of detecting a target nucleic acid in a sample, wherein the methods include contacting the sample with a Type III-E CRISPR-Cas system described herein and a labeled reporter nucleic acid, where hybridization of the Type III-E guide RNA to the target nucleic acid causes cleavage of the labeled reporter nucleic acid; and measuring a detectable signal produced by cleavage of the labeled reporter nucleic acid, thereby detecting the presence of the target nucleic acid in the sample.

In some embodiments, the methods further include comparing a level of the detectable signal with a reference signal level, and determining an amount of target nucleic acid in the sample based on the level of the detectable signal.

In some embodiments, the measuring is performed using gold nanoparticle detection, fluorescence polarization, colloid phase transition/dispersion, electrochemical detection, or semiconductor based-sensing.

In certain embodiments, the labeled reporter nucleic acid includes a fluorescence-emitting dye pair, a fluorescence resonance energy transfer (FRET) pair, or a quencher/fluorophore pair, where cleavage of the labeled reporter nucleic acid by the effector protein results in an increase or a decrease of the amount of signal produced by the labeled reporter nucleic acid.

In another aspect, the present disclosure relates to methods of detecting a target nucleic acid in a sample, wherein the methods include contacting the sample with a Type III-E CRISPR-Cas system described herein and a labeled reporter peptide, where hybridization of the Type III-E guide RNA to the target nucleic acid causes cleavage of the labeled reporter peptide; and measuring a detectable signal produced by cleavage of the labeled reporter peptide, thereby detecting the presence of the target nucleic acid in the sample.

In yet another aspect, the present disclosure relates to methods of specifically editing a double-stranded nucleic acid, wherein the methods include contacting, under sufficient conditions and for a sufficient amount of time, a Type III-E CRISPR-Cas effector protein and one other enzyme with sequence-specific nicking activity, and a crRNA that guides the Type III-E CRISPR-Cas effector protein to nick the opposing strand relative to the activity of the other sequence-specific nickase; and the double-stranded nucleic acid, where the method results in the formation of a double-stranded break.

In another aspect, the present disclosure relates to methods of editing a double-stranded nucleic acid. The methods include contacting, under sufficient conditions and for a sufficient amount of time, a fusion protein including a the Type III-E CRISPR-Cas effector and a protein domain with DNA modifying activity and a Type III-E RNA guide targeting the double-stranded nucleic acid; and the double-stranded nucleic acid, where the Type III-E CRISPR-Cas effector of the fusion protein is modified to nick a non-target strand of the double-stranded nucleic acid.

In yet another aspect, the present disclosure relates to methods of inducing genotype-specific or transcriptional-state-specific cell death or dormancy in a cell, wherein the methods include contacting a cell with a Type III-E CRISPR-Cas system described herein, where the RNA guide hybridizing to the target DNA causes a collateral DNase activity-mediated cell death or dormancy.

In some embodiments of these methods, the cell is a prokaryotic cell such as an infectious cell or a cell infected with an infectious agent, or a eukaryotic cell such as a mammalian cell. For example, the cell can be a cancer cell. In some embodiments, the cell is a cell infected with a virus, a cell infected with a prion, a fungal cell, a protozoan, or a parasite cell.

In another aspect, the present disclosure relates to methods of treating a condition or disease in a subject in need thereof, e.g., in a human or animal subject. The methods include administering to the subject a Type III-E CRISPR-Cas system described herein, where the spacer sequence is complementary to at least 12 nucleotides of a target nucleic acid associated with the condition or disease; where the Type III-E CRISPR-Cas effector protein associates with the Type III-E RNA guide to form a complex; where the complex binds to a target nucleic acid sequence that is complementary to the at least 12 nucleotides of the spacer sequence; and where upon binding of the complex to the target nucleic acid sequence the Type III-E CRISPR-Cas effector protein cleaves the target nucleic acid, thereby treating the condition or disease in the subject.

In some embodiments, the condition or disease is a cancer or an infectious disease. For example, the cancer can be selected from the group consisting of Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

In some embodiments, the Type III-E CRISPR-Cas system described herein is for use as a medicament.

In some embodiments, the Type III-E CRISPR-Cas system described herein is for use in the treatment or prevention of a cancer or an infectious disease.

The term "cleavage event," as used herein, refers to a DNA break in a target nucleic acid created by a nuclease of a CRISPR system described herein. In some embodiments, the cleavage event is a double-stranded DNA break. In some embodiments, the cleavage event is a single-stranded DNA break.

The term "CRISPR-Cas system" as used herein refers to nucleic acids and/or proteins involved in the expression of, or directing the activity of, CRISPR-Cas effectors, including sequences encoding CRISPR-Cas effectors, RNA guides, and other sequences and transcripts from a CRISPR locus.

The term "CRISPR array" as used herein refers to the nucleic acid (e.g., DNA) segment that includes CRISPR repeats and spacers, starting with the first nucleotide of the first CRISPR repeat and ending with the last nucleotide of the last (terminal) CRISPR repeat. Typically, each spacer in a CRISPR array is located between two repeats. The term "CRISPR repeat." or "CRISPR direct repeat," or "direct repeat," as used herein, refers to multiple short direct repeating sequences, which show very little or no sequence variation within a CRISPR array.

The term "CRISPR RNA" or "crRNA" as used herein refers to an RNA molecule comprising a guide sequence used by a CRISPR effector to specifically target a nucleic acid sequence. In some embodiments, the crRNA contains a sequence that mediates target recognition and a sequence that forms a duplex with a tracrRNA. The crRNA:tracrRNA duplex binds to a CRISPR effector.

The term "donor template nucleic acid." as used herein refers to a nucleic acid molecule that can be used by one or more cellular proteins to alter the structure of a target nucleic acid after a CRISPR enzyme described herein has altered a target nucleic acid. In some embodiments, the donor template nucleic acid is a double-stranded nucleic acid. In some embodiments, the donor template nucleic acid is a single-stranded nucleic acid. In some embodiments, the donor template nucleic acid is linear. In some embodiments, the donor template nucleic acid is circular (e.g., a plasmid). In some embodiments, the donor template nucleic acid is an exogenous nucleic acid molecule. In some embodiments, the donor template nucleic acid is an endogenous nucleic acid molecule (e.g., a chromosome).

The term "CRISPR-Cas effector," "CRISPR effector," "effector," "CRISPR-associated protein." "CRISPR enzyme," "Type III-E CRISPR-Cas effector protein," "Type III-E CRISPR-Cas effector," or "Type III-E effector" as used herein refers to a protein that carries out an enzymatic activity or that binds to a target site on a nucleic acid specified by an RNA guide.

In some embodiments, a Type III-E CRISPR-Cas effector protein has nuclease activity, peptidase activity, or protease activity.

The term "RNA guide" as used herein refers to any RNA molecule that facilitates the targeting of a protein described herein to a target nucleic acid. Exemplary "RNA guides" include, but are not limited to, crRNAs, as well as crRNAs fused to tracrRNAs. In some embodiments, an RNA guide includes both a crRNA and a tracrRNA, either as separate RNAs (dual guide) or fused into a single RNA.

As used herein, the term "targeting" refers to the ability of a complex including a CRISPR-associated protein and an RNA guide, such as a crRNA, to preferentially or specifically bind to, e.g., hybridize to, a specific target nucleic acid compared to other nucleic acids that do not have the same or similar sequence as the target nucleic acid.

The terms "trans-activating crRNA" or "tracrRNA" as used herein refer to an RNA including an anti-repeat region complementary to all or part of the direct repeat sequence of a CRISPR RNA (crRNA). A CRISPR effector bound to the crRNA and tracrRNA (RNA guide) form a functional complex capable of binding to a target nucleic acid.

A "transcriptionally-active site" as used herein refers to a site in a nucleic acid sequence comprising promoter regions at which transcription is initiated and actively occurring.

The term "collateral nuclease activity," "collateral DNase activity," or "collateral RNase activity" as used herein in reference to a CRISPR enzyme, refers to non-specific nuclease activity of a CRISPR enzyme after the enzyme has specifically targeted a nucleic acid.

The term "collateral peptidase activity" or "collateral protease activity" as used herein in reference to a CRISPR enzyme, refers to non-specific peptidase or protease activity of a CRISPR enzyme after the enzyme has specifically targeted a nucleic acid.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF FIGURE DESCRIPTION

The figures are a series of schematics and nucleic acid and amino acid sequences that represent the results of locus analysis of various protein clusters.

Figure 2:
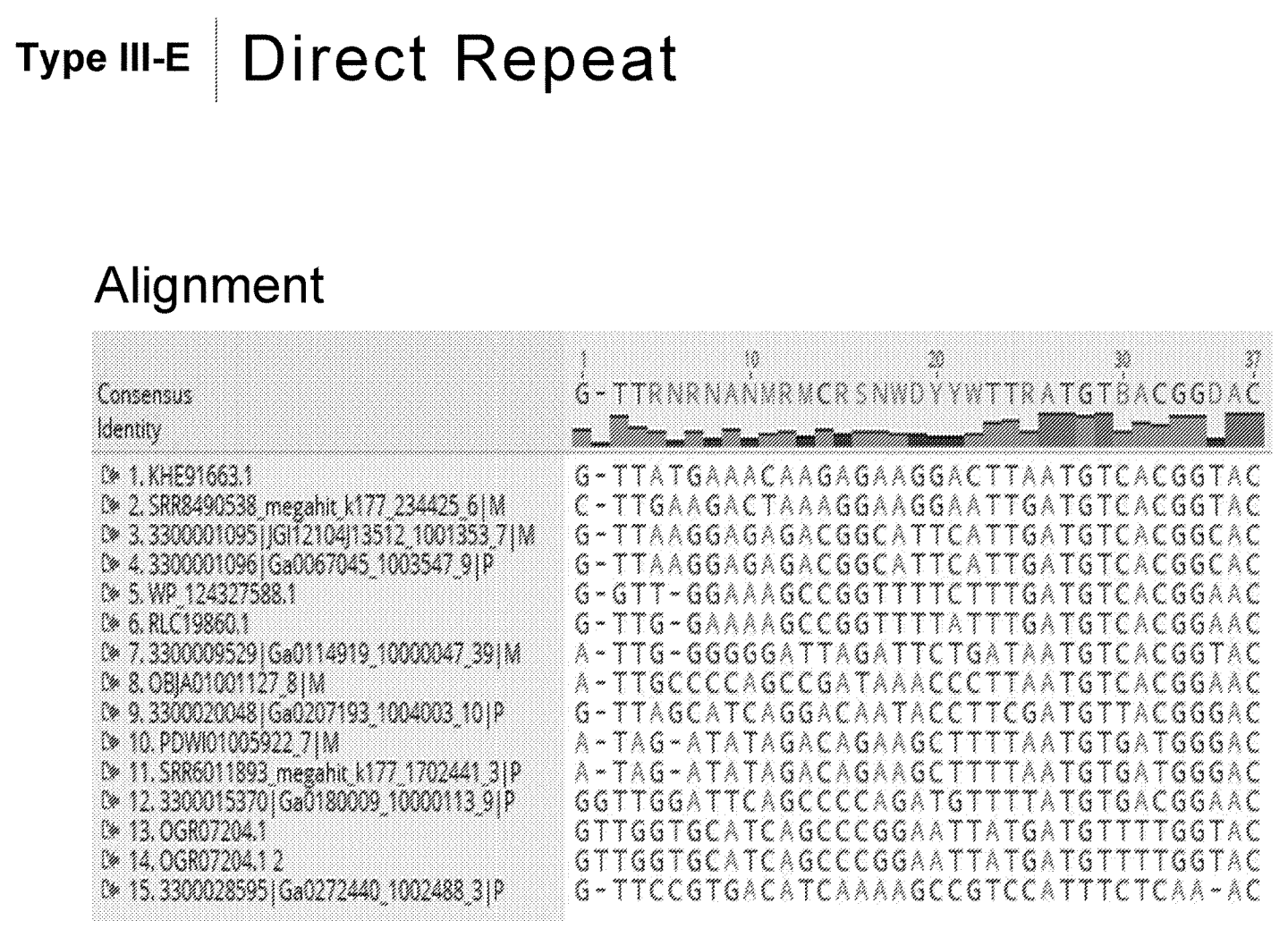

FIG. 2 is a schematic of a consensus sequence (SEQ ID NO: 100) and a multiple sequence alignment under the consensus sequence that are examples of Type III-E direct repeat elements described herein (SEQ ID NOs:27-38).

FIG. 5 is a schematic representation of PFAM domain mapping results for Type III-E (CLUST.019911) Effector A proteins; a schematic of HHpred domain predictions of an exemplary CLUST.019911 Effector A is depicted below, with a C-terminal match to the CHAT domain, and an N-terminal match to the TPR domain.

Figure 7A:
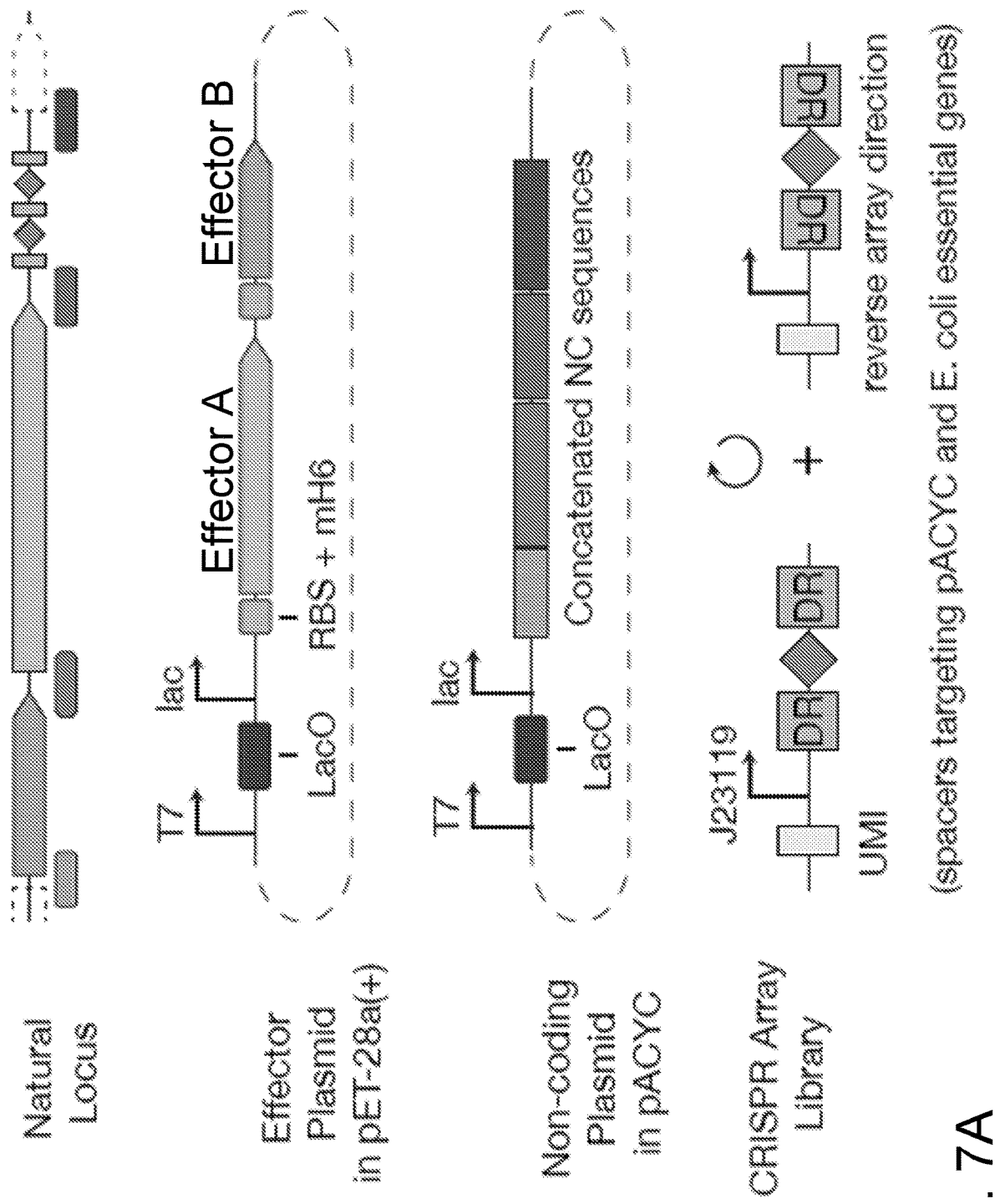
FIG. 7A is a schematic representation of the design of in vivo screen Effector and Non-coding Plasmids. CRISPR array libraries were designed including non-repetitive spacers uniformly sampled from both strands of pACYC184 or E. coli essential genes flanked by two DRs and expressed by J23119.
Figure 7B:
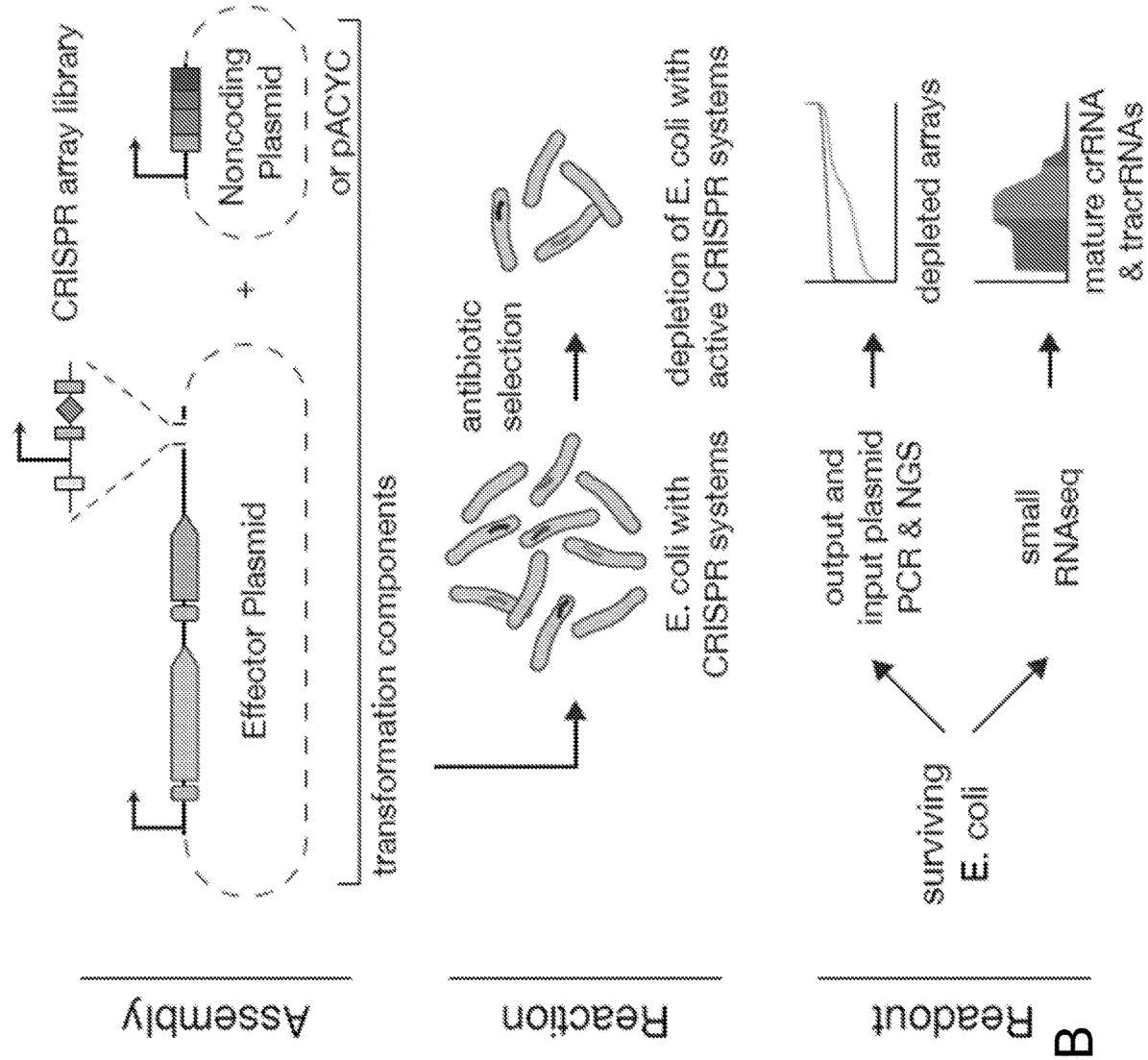

FIG. 7B is a schematic representation of the negative selection screening workflow; 1) CRISPR array libraries were cloned into the Effector Plasmid, 2) the Effector Plasmid and, when present, the Non-coding Plasmid were transformed into E. coli followed by outgrowth for negative selection of CRISPR arrays conferring interference against DNA or RNA transcripts from pACYC184 or E. coli essential genes, and 3) Targeted sequencing of the Effector Plasmid was used to identify depleted CRISPR arrays and small RNA sequencing was used to identify mature crRNAs and tracrRNAs.

Figure 8:
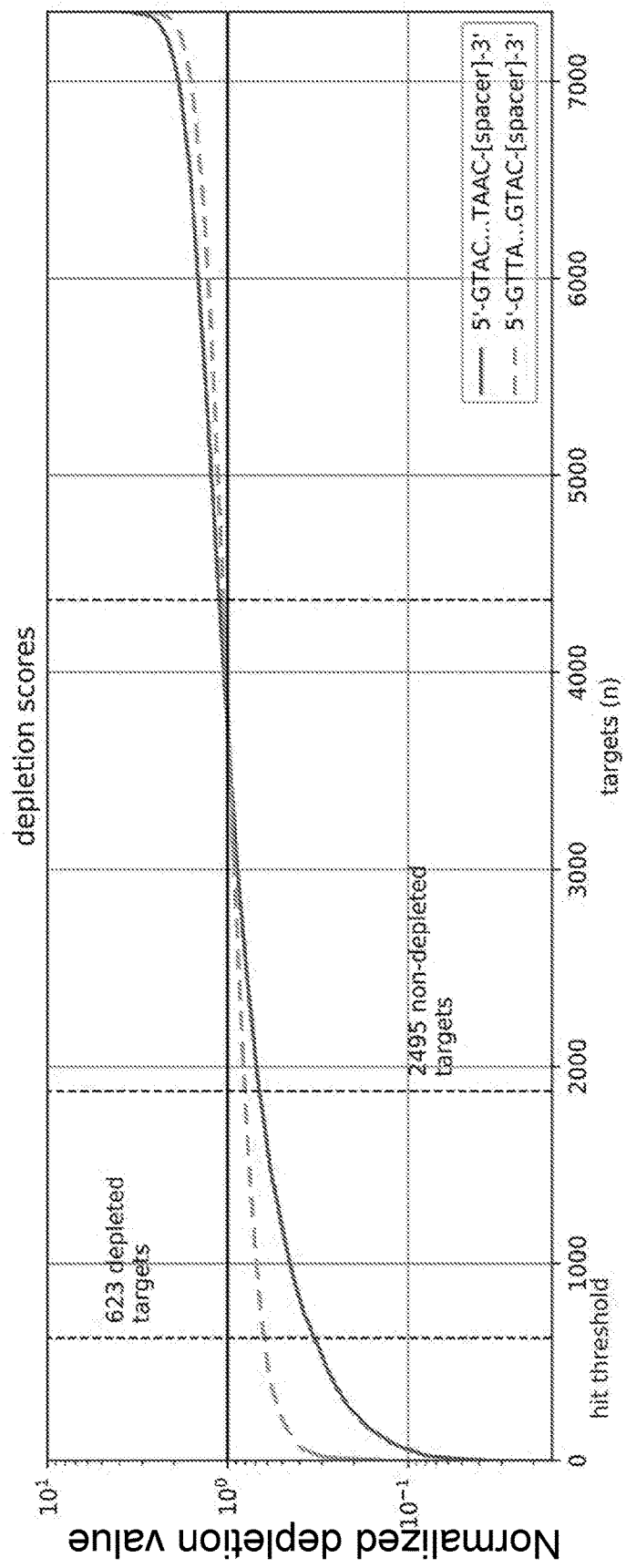

FIG. 8 is a graph that shows depletion values for crRNAs targeting pACYC and E. coli essential genes. To quantify depletion, a fold-depletion ratio was calculated as $R_{treated}/R_{input}$ for each direct repeat and spacer. The normalized input read count is computed as:

$R_{input}$=# reads containing crRNA/total reads without expressing the Type III-E system and RNA guide. The treated read count is computed as:

$R_{treated}$=(1+# reads containing crRNA)/total reads with expression of the Type III-E system and RNA guide. A strongly depleted target has a fold depletion greater than 3, which is marked by the vertical line "hit threshold."

Figure 9:
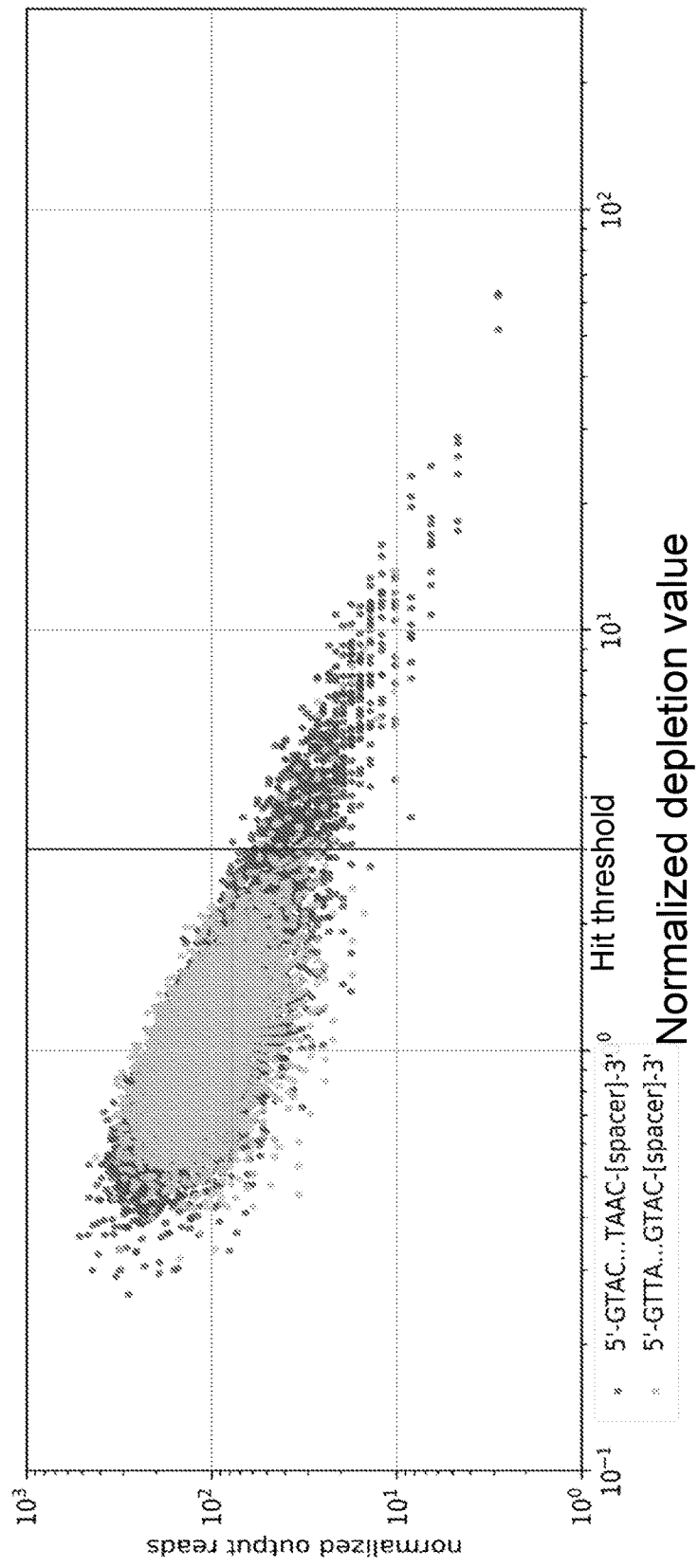

FIG. 9 is a scatter plot where the depletion value and output read count is depicted for each Type III-E system and crRNA tested. Notably, many of the points with high depletion value fall in the range where normalized output read counts are high.

Figure 10:
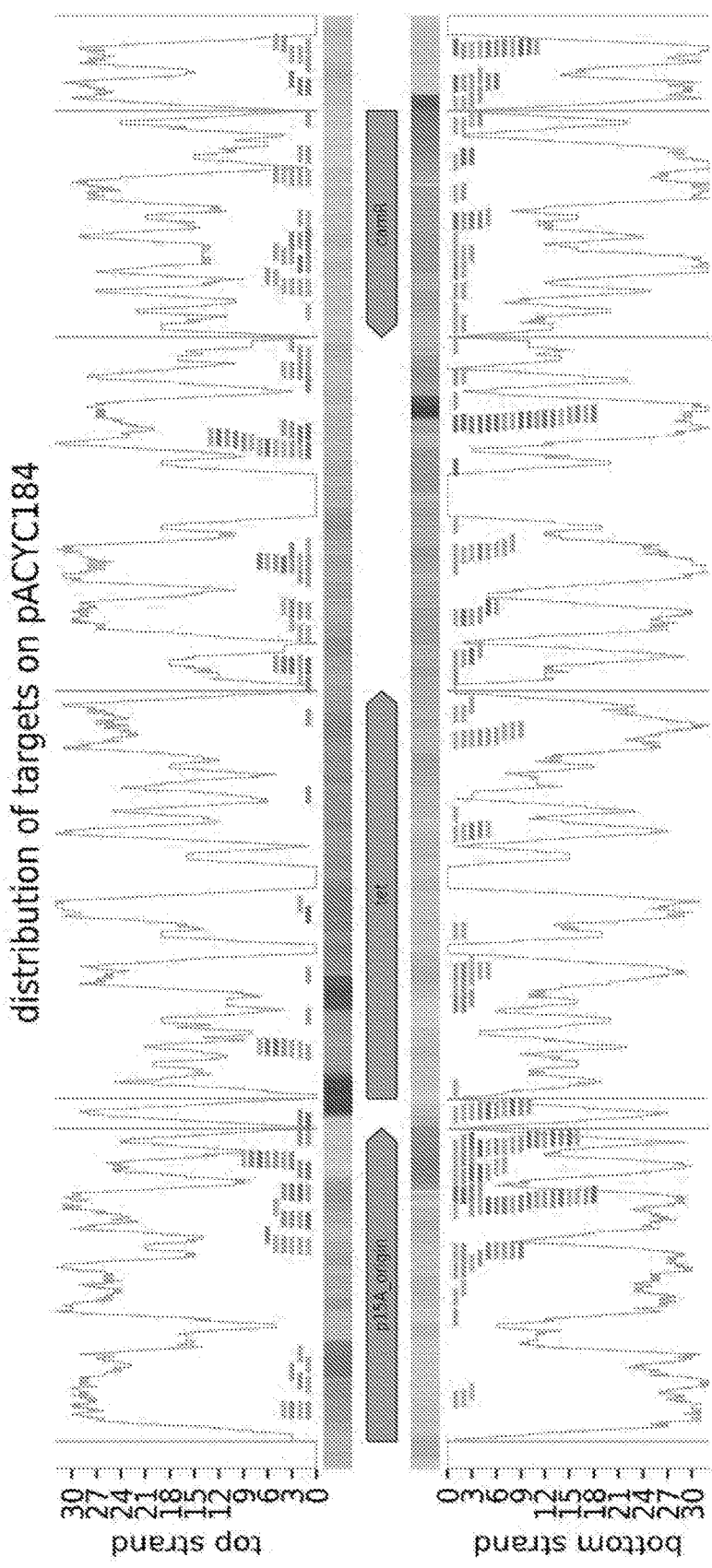

FIG. 10 is a graphic representation of the location of depleted and non-depleted crRNAs for the Type III-E system JRYO01000185 targeting the pACYC184 plasmid. Targets on the top strand and bottom strand are shown separately, and in relation to the orientation of the annotated genes.

Figure 11:
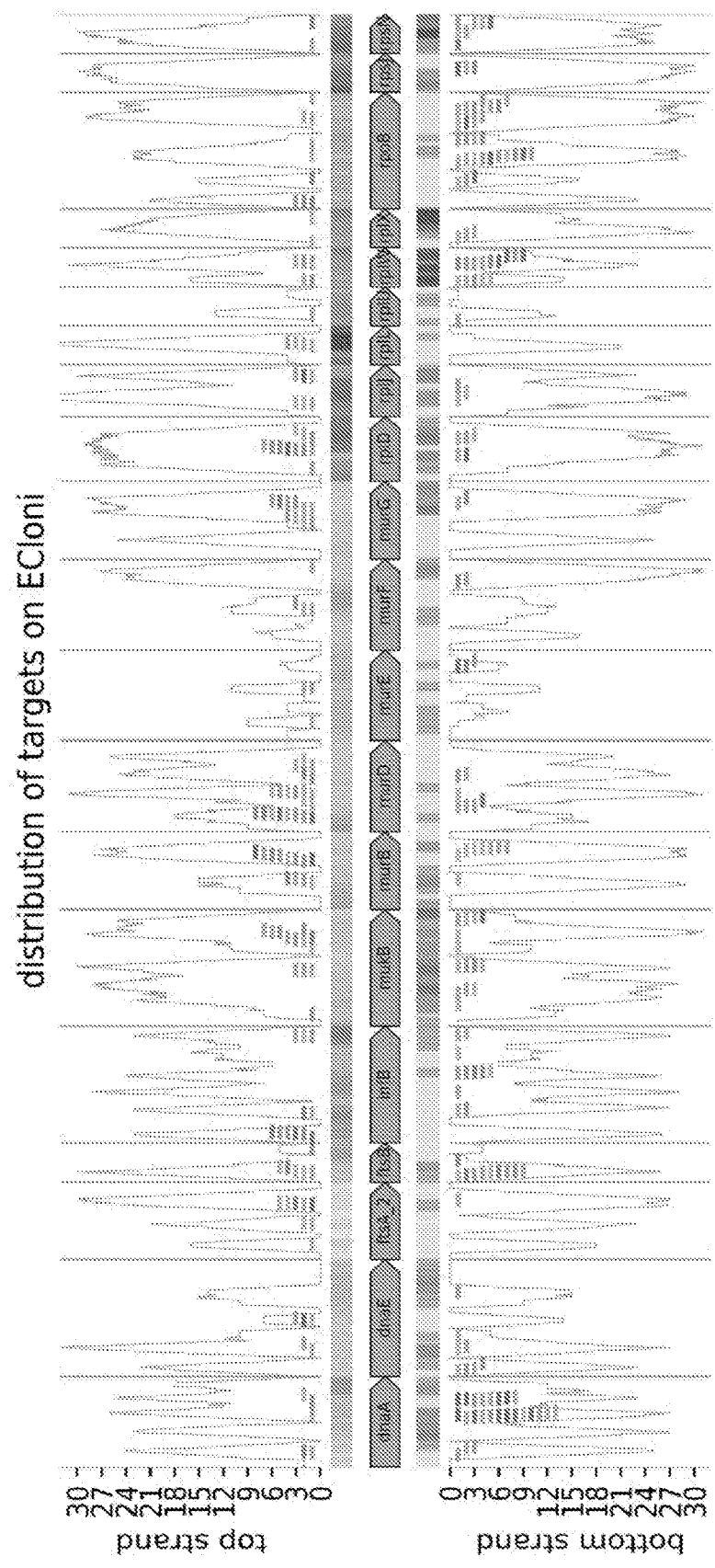

FIG. 11 is a graphic representation of the location of depleted and non-depleted crRNAs for the Type III-E system JRYO01000185 targeting E. coli essential genes (strain E. Cloni). Targets on the top strand and bottom strand are shown separately, and in relation to the orientation of the annotated genes.

Figure 12:
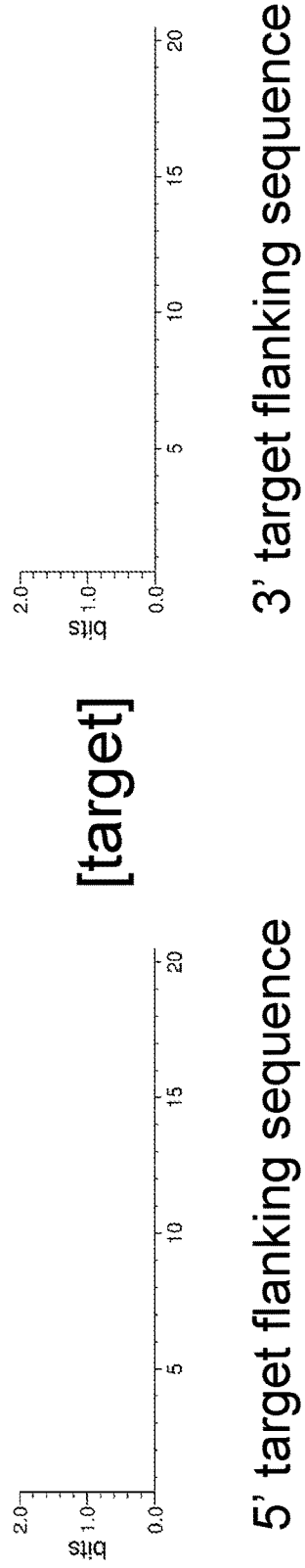

FIG. 12 is a weblogo of the sequences flanking depleted targets for the Type III-E system JRYO01000185, indicating there is no prominent motif adjacent to depleted targets (PAM).

DETAILED DESCRIPTION

The broad natural diversity of CRISPR-Cas defense systems contains a wide range of activity mechanisms and functional elements that can be harnessed for programmable biotechnologies. In a natural system, these mechanisms and parameters enable efficient defense against foreign DNA and viruses while providing self vs. non-self discrimination to avoid self-targeting. In an engineered system, the same mechanisms and parameters also provide a diverse toolbox of molecular technologies and define the boundaries of the targeting space. For instance, systems Cas9 and Cas13a have canonical DNA and RNA endonuclease activity and their targeting spaces are defined by the protospacer adjacent motif (PAM) on targeted DNA and protospacer flanking sites (PFS) on targeted RNA, respectively.

The methods described herein have been used to discover additional mechanisms and parameters within single subunit Class 2 effector systems that can expand the capabilities of RNA-programmable nucleic acid manipulation.

In one aspect, the disclosure relates to the use of computational methods and algorithms to search for and identify novel protein families that exhibit a strong co-occurrence pattern with certain other features within naturally occurring genome sequences. In certain embodiments, these computational methods are directed to identifying protein families that co-occur in close proximity to CRISPR arrays. However, the methods disclosed herein are useful in identifying proteins that naturally occur within close proximity to other features, both non-coding and protein-coding (e.g., fragments of phage sequences in non-coding areas of bacterial loci; or CRISPR Cas1 proteins). It is understood that the methods and calculations described herein may be performed on one or more computing devices.

In some embodiments, a set of genomic sequences is obtained from genomic or metagenomic databases. The databases comprise short reads, or contig level data, or assembled scaffolds, or complete genomic sequences of organisms. Likewise, the database may comprise genomic sequence data from prokaryotic organisms, or eukaryotic organisms, or may include data from metagenomic environmental samples. Examples of database repositories include the National Center for Biotechnology Information (NCBI) RefSeq, NCBI GenBank, NCBI Whole Genome Shotgun (WGS), and the Joint Genome Institute (JGI) Integrated Microbial Genomes (IMG).

In some embodiments, a minimum size requirement is imposed to select genome sequence data of a specified minimum length. In certain exemplary embodiments, the minimum contig length may be 100 nucleotides, 500 nt, 1 kb, 1.5 kb, 2 kb, 3 kb, 4 kb, 5 kb, 10 kb, 20 kb, 40 kb, or 50 kb.

In some embodiments, known or predicted proteins are extracted from the complete or a selected set of genome sequence data. In some embodiments, known or predicted proteins are taken from extracting coding sequence (CDS) annotations provided by the source database. In some embodiments, predicted proteins are determined by applying a computational method to identify proteins from nucleotide sequences. In some embodiments, the GeneMark Suite is used to predict proteins from genome sequences. In some embodiments, Prodigal is used to predict proteins from genome sequences. In some embodiments, multiple protein prediction algorithms may be used over the same set of sequence data with the resulting set of proteins de-duplicated.

In some embodiments. CRISPR arrays are identified from the genome sequence data. In some embodiments. PILER-CR is used to identify CRISPR arrays. In some embodiments, CRISPR Recognition Tool (CRT) is used to identify CRISPR arrays. In some embodiments, CRISPR arrays are identified by a heuristic that identifies nucleotide motifs repeated a minimum number of times (e.g. 2, 3, or 4 times), where the spacing between consecutive occurrences of a repeated motif does not exceed a specified length (e.g. 50, 100, or 150 nucleotides). In some embodiments, multiple CRISPR array identification tools may be used over the same set of sequence data with the resulting set of CRISPR arrays de-duplicated.

In some embodiments, proteins in close proximity to CRISPR arrays are identified. In some embodiments, proximity is defined as a nucleotide distance, and may be within 20 kb, 15 kb, or 5 kb. In some embodiments, proximity is defined as the number of open reading frames (ORFs) between a protein and a CRISPR array, and certain exemplary distances may be 10, 5, 4, 3, 2, 1, or 0 ORFs. The proteins identified as being within close proximity to a CRISPR array are then grouped into clusters of homologous proteins. In some embodiments, blastclust is used to form protein clusters. In certain other embodiments, mmseqs2 is used to form protein clusters.

To establish a pattern of strong co-occurrence between the members of a protein cluster with CRISPR arrays, a BLAST search of each member of the protein family may be performed over the complete set of known and predicted proteins previously compiled. In some embodiments, UBLAST or mmseqs2 may be used to search for similar proteins. In some embodiments, a search may be performed only for a representative subset of proteins in the family.

In some embodiments, the clusters of proteins within close proximity to CRISPR arrays are ranked or filtered by a metric to determine co-occurrence. One exemplary metric is the ratio of the number of elements in a protein cluster against the number of BLAST matches up to a certain E value threshold. In some embodiments, a constant E value threshold may be used. In other embodiments, the E value threshold may be determined by the most distant members of the protein cluster. In some embodiments, the global set of proteins is clustered and the co-occurrence metric is the ratio of the number of elements of the CRISPR associated cluster against the number of elements of the containing global cluster(s).

In some embodiments, a manual review process is used to evaluate the potential functionality and the minimal set of components of an engineered system based on the naturally occurring locus structure of the proteins in the cluster. In some embodiments, a graphical representation of the protein cluster may assist in the manual review, and may contain information including pairwise sequence similarity, phylogenetic tree, source organisms/environments, predicted functional domains, and a graphical depiction of locus structures. In some embodiments, the graphical depiction of locus structures may filter for nearby protein families that have a high representation.

In some embodiments, representation may be calculated by the ratio of the number of related nearby proteins against the size(s) of the containing global cluster(s). In certain exemplary embodiments, the graphical representation of the protein cluster may contain a depiction of the CRISPR array structures of the naturally occurring loci. In some embodiments, the graphical representation of the protein cluster may contain a depiction of the number of conserved direct repeats versus the length of the putative CRISPR array, or the number of unique spacer sequences versus the length of the putative CRISPR array. In some embodiments, the graphical representation of the protein cluster may contain a depiction of various metrics of co-occurrence of the putative effector with CRISPR arrays predict new CRISPR-Cas systems and identify their components.

Pooled-Screening

To efficiently validate the activity of the engineered novel CRISPR-Cas systems and simultaneously evaluate in an unbiased manner different activity mechanisms and functional parameters, we developed a new pooled-screening approach in E. coli.

First, from the computational identification of the conserved protein and noncoding elements of the novel CRISPR-Cas system. DNA synthesis and molecular cloning was used to assemble the separate components into a single artificial expression vector, which in one embodiment is based on a pET-28a+ backbone. In a second embodiment, the effectors and noncoding elements are transcribed on a single mRNA transcript, and different ribosomal binding sites are used to translate individual effectors.

Second, the natural crRNA and targeting spacers were replaced with a library of unprocessed crRNAs containing non-natural spacers targeting a second plasmid, pACYC184. This crRNA library was cloned into the vector backbone containing the protein effectors and noncoding elements (e.g. pET-28a+), and then subsequently transformed the library into E. coli along with the pACYC184 plasmid target. Consequently, each resulting E. coli cell contains no more than one targeting spacer. In an alternate embodiment, the library of unprocessed crRNAs containing non-natural spacers additionally target E. coli essential genes, drawn from resources such as those described in Baba et al. (2006) Mol. Syst. Biol. 2: 2006.0008; and Gerdes et al. (2003) J. Bacteriol. 185(19): 5673-84, the entire contents of each of which are incorporated herein by reference. In this embodiment, positive, targeted activity of the novel CRISPR-Cas systems that disrupts essential gene function results in cell death or growth arrest. In some embodiments, the essential gene targeting spacers can be combined with the pACYC184 targets to add another dimension to the assay.

Third, the E. coli were grown under antibiotic selection. In one embodiment, triple antibiotic selection is used: kanamycin for ensuring successful transformation of the pET-28a+ vector containing the engineered CRISPR-Cas effector system, and chloramphenicol and tetracycline for ensuring successful co-transformation of the pACYC184 target vector. Since pACYC184 normally confers resistance to chloramphenicol and tetracycline, under antibiotic selection, positive activity of the novel CRISPR-Cas system targeting the plasmid will eliminate cells that actively express the effectors, noncoding elements, and specific active elements of the crRNA library.

Examining the population of surviving cells at a later time point compared to an earlier time point results in a depleted signal compared to the inactive crRNAs. In some embodiments, double antibiotic selection is used. For example, withdrawal of either chloramphenicol or tetracycline to remove selective pressure can provide novel information about the targeting substrate, sequence specificity, and potency. In some embodiments, only kanamycin is used to ensure successful transformation of the pET-28a+ vector containing the engineered CRISPR-Cas effector system. This embodiment is suitable for libraries containing spacers targeting E. coli essential genes, as no additional selection beyond kanamycin is needed to observe growth alterations. In this embodiment, chloramphenicol and tetracycline dependence is removed, and their targets (if any) in the library provides an additional source of negative or positive information about the targeting substrate, sequence specificity, and potency.

Since the pACYC184 plasmid contains a diverse set of features and sequences that may affect the activity of a CRISPR-Cas system, mapping the active crRNAs from the pooled screen onto pACYC184 provides patterns of activity that can be suggestive of different activity mechanisms and functional parameters in a broad, hypothesis-agnostic manner. In this way, the features required for reconstituting the novel CRISPR-Cas system in a heterologous prokaryotic species can be more comprehensively tested and studied.

The key advantages of the in vivo pooled-screen described herein include:

(1) Versatility—Plasmid design allows multiple effectors and/or noncoding elements to be expressed; library cloning strategy enables both transcriptional directions of the computationally predicted crRNA to be expressed;

(2) Comprehensive tests of activity mechanisms & functional parameters—Evaluates diverse interference mechanisms, including DNA or RNA cleavage; examines co-occurrence of features such as transcription, plasmid DNA replication; and flanking sequences for crRNA library can be used to reliably determine PAMs with complexity equivalence of 4N's;

(3) Sensitivity—pACYC184 is a low copy plasmid, enabling high sensitivity for CRISPR-Cas activity since even modest interference rates can eliminate the antibiotic resistance encoded by the plasmid; and (4) Efficiency—Optimized molecular biology steps to enable greater speed and throughput RNA-sequencing and protein expression samples can be directly harvested from the surviving cells in the screen.

The novel CRISPR-Cas families described herein were evaluated using this in vivo pooled-screen to evaluate their operational elements, mechanisms and parameters, as well as their ability to be active and reprogrammed in an engineered system outside of their natural cellular environment.

Type III-E CRISPR-Cas System

In one aspect, this disclosure provides the Type III-E CRISPR-Cas system, wherein a Type III-E effector protein may include a Repeat Associated Mysterious Protein (RAMP) domain (see e.g., Makarova and Koonin (2018) *Methods Mol Biol.*, 1311:47-75). In some embodiments, the RAMP-domain containing protein is a single large protein. In some embodiments, the RAMP-domain containing single protein is at least approximately 1400 amino acids. In some embodiments, the RAMP-domain containing single protein is at least approximately 1550 amino acids. In some embodiments, the RAMP-domain containing single protein contains multiple RAMP domains. In some embodiments, the RAMP-domain containing single protein contains domains with homology to CRISPR Cmr4 (e.g., AYLVGLYTLTPTHPGSGTELGVVDQPIQRERHTGFPVIWGQSLKGVLRSYLKLVEKVDEEKINKIFGPPTEKAHEQAGLISVGDAKILFFPVRSLKGVYAYVTSPLVLNRFKRDLELAG V (SEQ ID NO: 50)). In some embodiments, the RAMP-domain containing single protein contains domains with homology to CRISPR Cmr6 (e.g., HHHHDMLNSLHAITGKFKTQSRLVVGLGDESVYETSIRLLRNYGVPYIPGSAIKGVTRHLTYYVLAEF (SEQ ID NO: 51)). In some embodiments, the RAMP-domain containing single protein contains domains with homology to CRISPR Cas7. In some embodiments, the RAMP-domain containing single protein does not contain a domain with homology to CRISPR Cas10. In some embodiments, the RAMP-domain containing single protein does not contain a domain with homology to CRISPR Cas5.

In one aspect, this disclosure provides the Type III-E CRISPR-Cas system, wherein a Type III-E effector protein includes a protease domain. In some embodiments, a complex formed by a CRISPR-associated protein having a protease domain and an RNA guide is activated upon binding to a target nucleic acid, and exhibits protease activity. In some embodiments, the protease activity of the activated complex may induce programmed cell death (e.g., apoptosis). In some embodiments, the protease domain is a caspase domain. In some embodiments, the caspase domain is a Caspase HetF Associated with Tprs (CHAT) domain (see, e.g., Aravind and Koonin (2002) *Proteins* 46(4): 355-67). In some embodiments, a first CRISPR-associated protein comprising a CHAT domain interacts with a second effector protein comprising a RAMP domain to form a complex, whereby the second effector protein targets the complex to a target nucleic acid (e.g., as mediated by an RNA guide). In some embodiments, a protease activity of the CRISPR-associated protein comprising a CHAT domain is activated upon binding of the complex to a target nucleic acid (e.g., as mediated by an RNA guide and/or the CRISPR-associated protein comprising a RAMP domain). In some embodiments, a CRISPR-associated protein described herein exhibits a peptidase activity (e.g., endopeptidase or exopeptidase activity).

In some embodiments, the Type III-E CRISPR-Cas system provided herein is specific to a transcriptionally active site (see e.g., Estrella et al., (2019) *Genes & Dev* 30:460-470). In some embodiments, the Type III-E CRISPR-Cas system provided herein is specific to a site of DNA replication. In some embodiments, the Type III-E CRISPR-Cas system depends on endogenous bacterial host factors (Chou-Zheng and Hatoum-Aslan (2019) eLife 8:e45393).

CRISPR Enzyme Modifications

Deactivated/Inactivated CRISPR Enzymes

Where the CRISPR enzymes described herein have nuclease activity, the CRISPR enzymes can be modified to have diminished nuclease activity, e.g., nuclease inactivation of at least 50%, at least 60%, at least 70%, at least 80%, at least 90%, at least 95%, at least 97%, or 100% as compared with the wild type CRISPR enzymes. The nuclease activity can be diminished by several methods known in the art, e.g., introducing mutations into the nuclease domains of the proteins. In some embodiments, catalytic residues for the nuclease activities are identified, and these amino acid residues can be substituted by different amino acid residues (e.g., glycine or alanine) to diminish the nuclease activity.

The inactivated CRISPR enzymes can comprise or be associated with one or more functional domains (e.g., via fusion protein, linker peptides, "GS" linkers, etc.). These functional domains can have various activities, e.g., methylase activity, demethylase activity, transcription activation activity, transcription repression activity, transcription release factor activity, histone modification activity, RNA cleavage activity, DNA cleavage activity, nucleic acid binding activity, and switch activity (e.g., light inducible). In some embodiments, the functional domains are Krüppel associated box (KRAB), VP64, VP16, Fok1, P65, HSF1, MyoD1, and biotin-APEX.

The positioning of the one or more functional domains on the inactivated CRISPR enzymes allows for correct spatial orientation for the functional domain to affect the target with the attributed functional effect. For example, if the functional domain is a transcription activator (e.g., VP16, VP64, or p65), the transcription activator is placed in a spatial orientation that allows it to affect the transcription of the target. Likewise, a transcription repressor is positioned to affect the transcription of the target, and a nuclease (e.g., Fok1) is positioned to cleave or partially cleave the target. In some embodiments, the functional domain is positioned at the N-terminus of the CRISPR enzyme. In some embodiments, the functional domain is positioned at the C-terminus of the CRISPR enzyme. In some embodiments, the inactivated CRISPR enzyme is modified to comprise a first functional domain at the N-terminus and a second functional domain at the C-terminus.

Split Enzymes

The present disclosure also provides a split version of the CRISPR enzymes described herein. The split version of the CRISPR enzymes may be advantageous for delivery. In some embodiments, the CRISPR enzymes are split to two parts of the enzymes, which together substantially comprises a functioning CRISPR enzyme.

The split can be done in a way that the catalytic domain(s) are unaffected. The CRISPR enzymes may function as a nuclease or may be inactivated enzymes, which are essentially RNA-binding proteins with very little or no catalytic activity (e.g., due to mutation(s) in its catalytic domains).

In some embodiments, the nuclease lobe and α-helical lobe are expressed as separate polypeptides. Although the lobes do not interact on their own, the guide RNA recruits them into a ternary complex that recapitulates the activity of full-length CRISPR enzymes and catalyzes site-specific DNA cleavage. The use of a modified guide RNA abrogates split-enzyme activity by preventing dimerization, allowing for the development of an inducible dimerization system. The split enzyme is described, e.g., in Wright, Addison V., et al. "Rational design of a split-Cas9 enzyme complex," Proc. Nat'l. Acad. Sci., 112.10 (2015): 2984-2989, which is incorporated herein by reference in its entirety.

In some embodiments, the split enzyme can be fused to a dimerization partner, e.g., by employing rapamycin sensitive dimerization domains. This allows the generation of a chemically inducible CRISPR enzyme for temporal control of CRISPR enzyme activity. The CRISPR enzymes can thus be rendered chemically inducible by being split into two fragments and rapamycin-sensitive dimerization domains can be used for controlled reassembly of the CRISPR enzymes.

The split point is typically designed in silico and cloned into the constructs. During this process, mutations can be introduced to the split enzyme and non-functional domains can be removed. In some embodiments, the two parts or fragments of the split CRISPR enzyme (i.e., the N-terminal and C-terminal fragments), can form a full CRISPR enzyme, comprising, e.g., at least 70%, at least 80%, at least 90%, at least 95%, or at least 99% of the sequence of the wild-type CRISPR enzyme.

Self-Activating or Inactivating Enzymes

The CRISPR enzymes described herein can be designed to be self-activating or self-inactivating. In some embodiments, the CRISPR enzymes are self-inactivating. For example, the target sequence can be introduced into the CRISPR enzyme coding constructs. Thus, the CRISPR enzymes can cleave the target sequence, as well as the construct encoding the enzyme thereby self-inactivating their expression. Methods of constructing a self-inactivating CRISPR system is described, e.g., in Epstein, Benjamin E., and David V. Schaffer. "Engineering a Self-Inactivating CRISPR System for AAV Vectors," Mol. Ther., 24 (2016): S50, which is incorporated herein by reference in its entirety.

In some other embodiments, an additional guide RNA, expressed under the control of a weak promoter (e.g., 7SK promoter), can target the nucleic acid sequence encoding the CRISPR enzyme to prevent and/or block its expression (e.g., by preventing the transcription and/or translation of the nucleic acid). The transfection of cells with vectors expressing the CRISPR enzyme, guide RNAs, and guide RNAs that target the nucleic acid encoding the CRISPR enzyme can lead to efficient disruption of the nucleic acid encoding the CRISPR enzyme and decrease the levels of CRISPR enzyme, thereby limiting the genome editing activity.

In some embodiments, the genome editing activity of the CRISPR enzymes can be modulated through endogenous RNA signatures (e.g., miRNA) in mammalian cells. The CRISPR enzyme switch can be made by using a miRNA-complementary sequence in the 5'-UTR of mRNA encoding the CRISPR enzyme. The switches selectively and efficiently respond to miRNA in the target cells. Thus, the switches can differentially control the genome editing by sensing endogenous miRNA activities within a heterogeneous cell population. Therefore, the switch systems can provide a framework for cell-type selective genome editing and cell engineering based on intracellular miRNA information (Hirosawa, Moe et al. "Cell-type-specific genome editing with a microRNA-responsive CRISPR-Cas9 switch," Nucl. Acids Res., 2017 Jul. 27; 45(13): e118).

Inducible CRISPR Enzymes

The CRISPR enzymes can be inducible, e.g., light inducible or chemically inducible. This mechanism allows for activation of the functional domain in the CRISPR enzymes. Light inducibility can be achieved by various methods known in the art, e.g., by designing a fusion complex wherein CRY2 PHR/CIBN pairing is used in split CRISPR Enzymes (see, e.g., Konermann et al. "Optical control of mammalian endogenous transcription and epigenetic states," Nature, 500.7463 (2013): 472). Chemical inducibility can be achieved, e.g., by designing a fusion complex wherein FKBP/FRB (FK506 binding protein/FKBP rapamycin binding domain) pairing is used in split CRISPR Enzymes. Rapamycin is required for forming the fusion complex, thereby activating the CRISPR enzymes (see, e.g., Zetsche, Volz, and Zhang, "A split-Cas9 architecture for inducible genome editing and transcription modulation," Nature Biotech., 33.2 (2015): 139-142).

Furthermore, expression of the CRISPR enzymes can be modulated by inducible promoters, e.g., tetracycline or doxycycline controlled transcriptional activation (Tet-On and Tet-Off expression system), hormone inducible gene expression system (e.g., an ecdysone inducible gene expression system), and an arabinose-inducible gene expression system. When delivered as RNA, expression of the RNA targeting effector protein can be modulated via a riboswitch, which can sense a small molecule like tetracycline (see, e.g., Goldfless, Stephen J. et al. "Direct and specific chemical control of eukaryotic translation with a synthetic RNA-protein interaction," Nucl. Acids Res., 40.9 (2012): e64-e64).

Various embodiments of inducible CRISPR enzymes and inducible CRISPR systems are described, e.g., in U.S. Pat. No. 8,871,445, US20160208243, and WO2016205764, each of which is incorporated herein by reference in its entirety.

Functional Mutations

Various mutations or modifications can be introduced into CRISPR enzymes as described herein to improve specificity and/or robustness. In some embodiments, the amino acid residues that recognize the Protospacer Adjacent Motif (PAM) are identified. The CRISPR enzymes described herein can be modified further to recognize different PAMs, e.g., by substituting the amino acid residues that recognize PAM with other amino acid residues.

In some embodiments, the CRISPR-associated proteins include at least one (e.g., 1, 2, 3, 4, 5, 6, 7, 8, 9, or 10) Nuclear Localization Signal (NLS) attached to the N-terminal or C-terminal of the protein. Non-limiting examples of NLSs include an NLS sequence derived from: the NLS of the SV40 virus large T-antigen, having the amino acid sequence PKKKRKV (SEQ ID NO: 300); the NLS from nucleoplasmin (e.g., the nucleoplasmin bipartite NLS with the sequence KRPAATKKAGQAKKKK (SEQ ID NO: 301)); the c-myc NLS having the amino acid sequence PAAKRVKLD (SEQ ID NO: 302) or RQRRNELKRSP (SEQ ID NO: 303); the hRNPA1 M9 NLS having the sequence NQSSNFGPMKGGNFG-GRSSGPYGGGGQYFAKPRNQGGY (SEQ ID NO: 304); the sequence RMRIZFKNKGKDTAELRRRRVEVS-VELRKAKKDEQILKRRNV (SEQ ID NO: 305) of the IBB domain from importin-alpha; the sequences VSRKRPRP (SEQ ID NO: 306) and PPKKARED (SEQ ID NO: 307) of the myoma T protein; the sequence PQPKKKPL (SEQ ID NO: 308) of human p53; the sequence SALIKKKKKMAP (SEQ ID NO: 309) of mouse c-abl IV; the sequences DRLRR (SEQ ID NO: 310) and PKQKKRK (SEQ ID NO: 311) of the influenza virus NS 1; the sequence RKLKKKIKKL (SEQ ID NO: 312) of the Hepatitis virus delta antigen; the sequence REKKKFLKRR (SEQ ID NO: 313) of the mouse Mx1 protein; the sequence KRKGDEVDGVDEVAKKKSKK (SEQ ID NO: 314) of the human poly(ADP-ribose) polymerase; and the sequence RKCLQAGMNLEARKTKK (SEQ ID NO: 315) of the human glucocorticoid receptor. In some embodiments, the CRISPR-associated protein includes at least one (e.g., 1, 2, 3, 4, 5, 6, 7, 8, 9, or 10) Nuclear Export Signal (NES) attached the N-terminal or C-terminal of the protein. In a preferred embodiment, a C-terminal and/or N-terminal NLS or NES is attached for optimal expression and nuclear targeting in eukaryotic cells, e.g., human cells.

In some embodiments, the CRISPR enzymes described herein are mutated at one or more amino acid residues to alter one or more functional activities. For example, in some embodiments, the CRISPR enzyme is mutated at one or more amino acid residues to alter its peptidase or protease activity. In some embodiments, the CRISPR enzyme is mutated at one or more amino acid residues to alter its nuclease activity (e.g., endonuclease activity or exonuclease activity). In some embodiments, the CRISPR enzyme is mutated at one or more amino acid residues to alter its ability to functionally associate with a RNA guide. In some embodiments, the CRISPR enzyme is mutated at one or more amino acid residues to alter its ability to functionally associate with a target nucleic acid.

In some embodiments, the CRISPR enzymes described herein are capable of cleaving a target nucleic acid molecule. In some embodiments, the CRISPR enzyme cleaves both strands of the target nucleic acid molecule. However, in some embodiments, the CRISPR enzyme is mutated at one or more amino acid residues to alter its cleaving activity. For example, in some embodiments, the CRISPR enzyme may comprise one or more mutations that render the enzyme incapable of cleaving a target nucleic acid. In other embodiments, the CRISPR enzyme may comprise one or more mutations such that the enzyme is capable of cleaving a single strand of the target nucleic acid (i.e., nickase activity). In some embodiments, the CRISPR enzyme is capable of cleaving the strand of the target nucleic acid that is complementary to the strand to which the RNA guide hybridizes. In some embodiments, the CRISPR enzyme is capable of cleaving the strand of the target nucleic acid to which the RNA guide hybridizes.

In some embodiments, a CRISPR enzyme described herein may be engineered to comprise a deletion in one or more amino acid residues to reduce the size of the enzyme while retaining one or more desired functional activities (e.g., nuclease activity and the ability to interact functionally with a RNA guide). The truncated CRISPR enzyme may be advantageously used in combination with delivery systems having load limitations.

In one aspect, the present disclosure provides nucleic acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the nucleic sequences described herein. In another aspect, the present disclosure also provides amino acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the amino acid sequences described herein.

In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are the same as the sequences described herein. In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from the sequences described herein.

In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as the sequences described herein. In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from the sequences described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In general, the length of a reference sequence aligned for comparison purposes should be at least 80% of the length of the reference sequence, and in some embodiments is at least 90%, 95%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blosum 62 scoring matrix with a gap penalty of 12, a gap extend penalty of 4, and a frameshift gap penalty of 5.

Beyond the biochemical and diagnostic applications described herein, programmable Type III-E CRISPR-Cas systems described herein have important applications in eukaryotic cells such as genotype-gated cell death or therapeutic modification of the genome, with examples of applications including, but not limited to: targeted, sequence-based destruction of specific cell population, such as for treatment of neoplasms by specific targeting of mutated tumor cells, treatment of infections by destroying cells infected with bacteria or virus, preserving a cell lineage surveiling the genome and destroying mutated cells; additionally, in prokaryotic cellular environments, defense against transformants or infections, as well as defense against spontaneous mutations.

In some embodiments, the CRISPR-associated proteins and accessory proteins described herein can be fused to one or more peptide tags, including a His-tag, GST-tag, FLAG-tag, or myc-tag. In some embodiments, the CRISPR-associated proteins or accessory proteins described herein can be fused to a detectable moiety such as a fluorescent protein (e.g., green fluorescent protein or yellow fluorescent protein). In other embodiments, CRISPR-associated proteins or accessory proteins described herein are fused to a peptide or non-peptide moiety that allows these proteins to enter or localize to a tissue, a cell, or a region of a cell. For instance, a CRISPR-associated protein or accessory protein of this disclosure may comprise a nuclear localization sequence (NLS) such as an SV40 (simian virus 40) NLS, c-Myc NLS, or other suitable monopartite NLS. The NLS may be fused to an N-terminal and/or a C-terminal of the CRISPR-associated protein or accessory protein, and may be fused singly (i.e., a single NLS) or concatenated (e.g., a chain of 2, 3, 4, etc. NLS).

In those embodiments where a tag is fused to a CRISPR-associated protein, such tag may facilitate affinity-based or charge-based purification of the CRISPR-associated protein, e.g., by liquid chromatography or bead separation utilizing an immobilized affinity or ion-exchange reagent. As a non-limiting example, a recombinant CRISPR-associated protein of this disclosure comprises a polyhistidine (His) tag, and for purification is loaded onto a chromatography column comprising an immobilized metal ion (e.g. a $Zn^{2+}$, $Ni^{2+}$, $Cu^{2+}$ ion chelated by a chelating ligand immobilized on the resin, which resin may be an individually prepared resin or a commercially available resin or ready to use column such as the HisTrap FF column commercialized by GE Healthcare Life Sciences, Marlborough, Mass.). Following the loading step, the column is optionally rinsed, e.g., using one or more suitable buffer solutions, and the His-tagged protein is then eluted using a suitable elution buffer. Alternatively or additionally, if the recombinant CRISPR-associated protein of this disclosure utilizes a FLAG-tag, such protein may be purified using immunoprecipitation methods known in the industry. Other suitable purification methods for tagged CRISPR-associated proteins or accessory proteins of this disclosure will be evident to those of skill in the art.

The proteins described herein (e.g., CRISPR-associated proteins or accessory proteins) can be delivered or used as either nucleic acid molecules or polypeptides. When nucleic acid molecules are used, the nucleic acid molecule encoding the CRISPR-associated proteins can be codon-optimized, as discussed in further detail below. The nucleic acid can be codon optimized for use in any organism of interest, in particular human cells or bacteria. For example, the nucleic acid can be codon-optimized for any non-human eukaryote including mice, rats, rabbits, dogs, livestock, or non-human primates. Codon usage tables are readily available, for example, at the "Codon Usage Database" available at world wide web address: kazusa.orjp/codon/ and these tables can be adapted in a number of ways. See Nakamura et al. *Nucl. Acids Res.* 28:292 (2000), which is incorporated herein by reference in its entirety. Computer algorithms for codon optimizing a particular sequence for expression in a particular host cell are also available, such as Gene Forge (Aptagen; Jacobus, Pa.).

In some instances, nucleic acids of this disclosure which encode CRISPR-associated proteins or accessory proteins for expression in eukaryotic (e.g., human, or other mammalian cells) cells include one or more introns, i.e., one or more non-coding sequences comprising, at a first end (e.g., a 5' end), a splice-donor sequence and, at second end (e.g., the 3' end) a splice acceptor sequence. Any suitable splice donor/splice acceptor can be used in the various embodiments of this disclosure, including without limitation simian virus 40 (SV40) intron, beta-globin intron, and synthetic introns. Alternatively or additionally, nucleic acids of this disclosure encoding CRISPR-associated proteins or accessory proteins may include, at a 3' end of a DNA coding sequence, a transcription stop signal such as a polyadenylation (polyA) signal. In some instances, the polyA signal is located in close proximity to, or adjacent to, an intron such as the SV40 intron.

RNA Guides

In some embodiments, the CRISPR systems described herein include at least one Type III-E RNA guide. The architecture of many RNA guides is known in the art (see, e.g., International Publication Nos. WO 2014/093622 and WO 2015/070083, the entire contents of each of which are incorporated herein by reference). In some embodiments, the CRISPR systems described herein include multiple RNA guides (e.g., two, three, four, five, six, seven, eight, or more RNA guides).

In some embodiments, the CRISPR systems described herein include at least one Type III-E RNA guide or a nucleic acid encoding at least one Type III-E RNA guide. In some embodiments, the RNA guide includes a crRNA. Generally, the crRNAs described herein include a direct repeat sequence and a spacer sequence. In certain embodiments, the crRNA includes, consists essentially of, or consists of a direct repeat sequence linked to a guide sequence or spacer sequence. In some embodiments, the crRNA includes a direct repeat sequence, a spacer sequence, and a direct repeat sequence (DR-spacer-DR), which is typical of precursor crRNA (pre-crRNA) configurations in other CRISPR systems. In some embodiments, the crRNA includes a truncated direct repeat sequence and a spacer sequence, which is typical of processed or mature crRNA. In some embodiments, the CRISPR-Cas effector protein forms a complex with the RNA guide, and the spacer sequence directs the complex to a sequence-specific binding with the target nucleic acid that is complementary to the spacer sequence.

Guide RNA Modifications

Spacer Lengths

The spacer length of guide RNAs can range from about 15 to 50 nucleotides. In some embodiments, the spacer length of a guide RNA is at least 16 nucleotides, at least 17 nucleotides, at least 18 nucleotides, at least 19 nucleotides, at least 20 nucleotides, at least 21 nucleotides, or at least 22 nucleotides. In some embodiments, the spacer length is from 15 to 17 nucleotides, from 17 to 20 nucleotides, from 20 to 24 nucleotides (e.g., 20, 21, 22, 23, or 24 nucleotides), from 23 to 25 nucleotides (e.g., 23, 24, or 25 nucleotides), from 24 to 27 nucleotides, from 27 to 30 nucleotides, from 30 to 45 nucleotides (e.g., 30, 31, 32, 33, 34, 35, 40, or 45 nucleotides), from 30 or 35 to 40 nucleotides, from 41 to 45 nucleotides, from 45 to 50 nucleotides, or longer. In some embodiments, the direct repeat length of the guide RNA is at least 16 nucleotides, or is from 16 to 20 nucleotides (e.g., 16, 17, 18, 19, or 20 nucleotides). In some embodiments, the direct repeat length of the guide RNA is 19 nucleotides.

The guide RNA sequences can be modified in a manner that allows for formation of the CRISPR complex and successful binding to the target, while at the same time not allowing for successful nuclease activity (i.e., without nuclease activity/without causing indels). These modified guide sequences are referred to as "dead guides" or "dead guide sequences." These dead guides or dead guide sequences may be catalytically inactive or conformationally inactive with regard to nuclease activity. Dead guide sequences are typically shorter than respective guide sequences that result in active RNA cleavage. In some embodiments, dead guides are 5%, 10%, 20%, 30%, 40%, or 50%, shorter than respective guide RNAs that have nuclease activity. Dead guide sequences of guide RNAs can be from 13 to 15 nucleotides in length (e.g., 13, 14, or 15 nucleotides in length), from 15 to 19 nucleotides in length, or from 17 to 18 nucleotides in length (e.g., 17 nucleotides in length).

Thus, in one aspect, the disclosure provides non-naturally occurring or engineered CRISPR systems including a functional CRISPR enzyme as described herein, and a guide RNA (gRNA) wherein the gRNA comprises a dead guide sequence whereby the gRNA is capable of hybridizing to a target sequence such that the CRISPR system is directed to a genomic locus of interest in a cell without detectable cleavage activity.

A detailed description of dead guides is described, e.g., in WO 2016094872, which is incorporated herein by reference in its entirety.

Inducible Guides

Guide RNAs can be generated as components of inducible systems. The inducible nature of the systems allows for spatiotemporal control of gene editing or gene expression. In some embodiments, the stimuli for the inducible systems include, e.g., electromagnetic radiation, sound energy, chemical energy, and/or thermal energy.

In some embodiments, the transcription of guide RNA can be modulated by inducible promoters, e.g., tetracycline or doxycycline controlled transcriptional activation (Tet-On and Tet-Off expression systems), hormone inducible gene expression systems (e.g., ecdysone inducible gene expression systems), and arabinose-inducible gene expression systems. Other examples of inducible systems include, e.g., small molecule two-hybrid transcription activations systems (FKBP, ABA, etc.), light inducible systems (Phytochrome, LOV domains, or cryptochrome), or Light Inducible Transcriptional Effector (LITE). These inducible systems are described, e.g., in WO 2016205764 and U.S. Pat. No. 8,795,965, both of which are incorporated herein by reference in the entirety.

Chemical Modifications

Chemical modifications can be applied to the guide RNA's phosphate backbone, sugar, and/or base. Backbone modifications such as phosphorothioates modify the charge on the phosphate backbone and aid in the delivery and nuclease resistance of the oligonucleotide (see, e.g., Eckstein, "Phosphorothioates, essential components of therapeutic oligonucleotides," *Nucl. Acid Ther.*, 24 (2014), pp. 374-387); modifications of sugars, such as 2'-O-methyl (2'-OMe), 2'-F, and locked nucleic acid (LNA), enhance both base pairing and nuclease resistance (see, e.g., Allerson et al. "Fully 2'-modified oligonucleotide duplexes with improved in vitro potency and stability compared to unmodified small interfering RNA," *J. Med. Chem.*, 48.4 (2005): 901-904). Chemically modified bases such as 2-thiouridine or N6-methyladenosine, among others, can allow for either stronger or weaker base pairing (see, e.g., Bramsen et al., "Development of therapeutic-grade small interfering RNAs by chemical engineering," *Front. Genet.*, 2012 Aug. 20; 3:154). Additionally, RNA is amenable to both 5' and 3' end conjugations with a variety of functional moieties including fluorescent dyes, polyethylene glycol, or proteins.

A wide variety of modifications can be applied to chemically synthesized guide RNA molecules. For example, modifying an oligonucleotide with a 2'-OMe to improve nuclease resistance can change the binding energy of Watson-Crick base pairing. Furthermore, a 2'-OMe modification can affect how the oligonucleotide interacts with transfection reagents, proteins or any other molecules in the cell. The effects of these modifications can be determined by empirical testing.

In some embodiments, the guide RNA includes one or more phosphorothioate modifications. In some embodiments, the guide RNA includes one or more locked nucleic acids for the purpose of enhancing base pairing and/or increasing nuclease resistance.

A summary of these chemical modifications can be found, e.g., in Kelley et al., "Versatility of chemically synthesized guide RNAs for CRISPR-Cas9 genome editing," *J. Biotechnol.* 2016 Sep. 10; 233:74-83; WO 2016205764; and U.S. Pat. No. 8,795,965 B2; each which is incorporated by reference in its entirety.

Sequence Modifications

The sequences and the lengths of the guide RNAs, tracrRNAs, and crRNAs described herein can be optimized. In some embodiments, the optimized length of guide RNA can be determined by identifying the processed form of tracrRNA and/or crRNA, or by empirical length studies for guide RNAs, tracrRNAs, crRNAs, and the tracrRNA tetraloops.

The guide RNAs can also include one or more aptamer sequences. Aptamers are oligonucleotide or peptide molecules that can bind to a specific target molecule. The aptamers can be specific to gene effectors, gene activators, or gene repressors. In some embodiments, the aptamers can be specific to a protein, which in turn is specific to and recruits/binds to specific gene effectors, gene activators, or gene repressors. The effectors, activators, or repressors can be present in the form of fusion proteins. In some embodiments, the guide RNA has two or more aptamer sequences that are specific to the same adaptor proteins. In some embodiments, the two or more aptamer sequences are specific to different adaptor proteins. The adaptor proteins can include, e.g., MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, and PRR1. Accordingly, in some embodiments, the aptamer is selected from binding proteins specifically binding any one of the adaptor proteins as described herein. In some embodiments, the aptamer sequence is a MS2 loop. A detailed description of aptamers can be found, e.g., in Nowak et al., "Guide RNA engineering for versatile Cas9 functionality," *Nucl. Acid. Res.*, 2016 Nov. 16; 44(20):9555-9564; and WO 2016205764, which are incorporated herein by reference in their entirety.

Guide: Target Sequence Matching Requirements

In classic CRISPR systems, the degree of complementarity between a guide sequence and its corresponding target sequence can be about 50%, 60%, 75%, 80%, 85%, 90%, 95%, 97.5%, 99%, or 100%. In some embodiments, the degree of complementarity is 100%. The guide RNAs can be about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length.

To reduce off-target interactions, e.g., to reduce the guide interacting with a target sequence having low complementarity, mutations can be introduced to the CRISPR systems so that the CRISPR systems can distinguish between target and off-target sequences that have greater than 80%, 85%, 90%, or 95% complementarity. In some embodiments, the degree of complementarity is from 80% to 95%, e.g., about 83%, 84%, 85%, 86%, 87%, 88%, 89%, 90%, 91%, 92%, 93%, 94%, or 95% (for example, distinguishing between a target having 18 nucleotides from an off-target of 18 nucleotides having 1, 2, or 3 mismatches). Accordingly, in some embodiments, the degree of complementarity between a guide sequence and its corresponding target sequence is greater than 94.5%, 95%, 95.5%, 96%, 96.5%, 97%, 97.5%, 98%, 98.5%, 99%, 99.5%, or 99.9%. In some embodiments, the degree of complementarity is 100%.

It is known in the field that complete complementarity is not required, provided there is sufficient complementarity to be functional. Modulations of cleavage efficiency can be exploited by introduction of mismatches, e.g., one or more mismatches, such as 1 or 2 mismatches between spacer sequence and target sequence, including the position of the mismatch along the spacer/target. The more central (i.e., not at the 3' or 5' ends) a mismatch, e.g., a double mismatch, is located; the more cleavage efficiency is affected. Accordingly, by choosing mismatch positions along the spacer sequence, cleavage efficiency can be modulated. For example, if less than 100% cleavage of targets is desired (e.g., in a cell population), 1 or 2 mismatches between spacer and target sequence can be introduced in the spacer sequences.

Methods of Using CRISPR Systems

The CRISPR systems described herein have a wide variety of utilities including modifying (e.g., deleting, inserting, translocating, inactivating, or activating) a target polynucleotide in a multiplicity of cell types. The CRISPR systems have a broad spectrum of applications in, e.g., DNA/RNA detection (e.g., specific high sensitivity enzymatic reporter unlocking (SHERLOCK)), tracking and labeling of nucleic acids, enrichment assays (extracting desired sequence from background), detecting circulating tumor DNA, preparing next generation library, drug screening, disease diagnosis and prognosis, and treating various genetic disorders.

DNA/RNA Detection

In one aspect, the CRISPR systems described herein can be used in DNA/RNA detection. While many CRISPR enzymes target DNA, single effector RNA-guided RNases can be reprogrammed with CRISPR RNAs (crRNAs) to provide a platform for specific RNA sensing. Upon recognition of its RNA target, activated single effector RNA-guided RNases engage in "collateral" cleavage of nearby non-targeted RNAs. This crRNA-programmed collateral cleavage activity allows the CRISPR systems to detect the presence of a specific RNA by triggering programmed cell death or by nonspecific degradation of labeled RNA.

The SHERLOCK method (Specific High Sensitivity Enzymatic Reporter UnLOCKing) provides an in vitro nucleic acid detection platform with attomolar sensitivity based on nucleic acid amplification and collateral cleavage of a reporter RNA, allowing for real-time detection of the target. To achieve signal detection, the detection can be combined with different isothermal amplification steps. For example, recombinase polymerase amplification (RPA) can be coupled with T7 transcription to convert amplified DNA to RNA for subsequent detection. The combination of amplification by RPA, T7 RNA polymerase transcription of amplified DNA to RNA, and detection of target RNA by collateral RNA cleavage-mediated release of reporter signal is referred as SHERLOCK. Methods of using CRISPR in SHERLOCK are described in detail, e.g., in Gootenberg, et al. "Nucleic acid detection with CRISPR-Cas13a/C2c2," *Science*, 2017 Apr. 28; 356(6336):438-442, which is incorporated herein by reference in its entirety.

The RNA targeting effector proteins can further be used in Northern blot assays, which use electrophoresis to separate RNA samples by size. The RNA targeting effector proteins can be used to specifically bind and detect the target RNA sequence. The RNA targeting effector proteins can also be fused to a fluorescent protein (e.g., GFP) and used to track RNA localization in living cells. More particularly, the RNA targeting effector proteins can be inactivated in that they no longer cleave RNAs. Thus, RNA targeting effector proteins can be used to determine the localization of the RNA or specific splice variants, the level of mRNA transcripts, up- or down-regulation of transcripts and disease-specific diagnosis. The RNA targeting effector proteins can be used for visualization of RNA in (living) cells using, for example, fluorescent microscopy or flow cytometry, such as fluorescence-activated cell sorting (FACS), which allows for high-throughput screening of cells and recovery of living cells following cell sorting. A detailed description regarding how to detect DNA and RNA can be found, e.g., in WO 2017070605, which is incorporated herein by reference in its entirety.

In some embodiments, the CRISPR systems described herein can be used in multiplexed error-robust fluorescence in situ hybridization (MERFISH). These methods are described in, e.g., Chen et al., "Spatially resolved, highly multiplexed RNA profiling in single cells," *Science*, 2015 Apr. 24; 348(6233):aaa6090, which is incorporated herein by reference herein in its entirety.

Tracking and Labeling of Nucleic Acids

Cellular processes depend on a network of molecular interactions among proteins, RNAs, and DNAs. Accurate detection of protein-DNA and protein-RNA interactions is key to understanding such processes. In vitro proximity labeling techniques employ an affinity tag combined with, a reporter group, e.g., a photoactivatable group, to label polypeptides and RNAs in the vicinity of a protein or RNA of interest in vitro. After UV irradiation, the photoactivatable groups react with proteins and other molecules that are in close proximity to the tagged molecules, thereby labelling them. Labelled interacting molecules can subsequently be recovered and identified. The RNA targeting effector proteins can for instance be used to target probes to selected RNA sequences. These applications can also be applied in animal models for in vivo imaging of diseases or difficult-to-culture cell types. The methods of tracking and labeling of nucleic acids are described, e.g., in U.S. Pat. No. 8,795,965, WO 2016205764, and WO 2017070605; each of which is incorporated herein by reference herein in its entirety.

RNA Isolation, Purification, Enrichment, and/or Depletion

The CRISPR systems (e.g., RNA targeting effector proteins) described herein can be used to isolate and/or purify the RNA. The RNA targeting effector proteins can be fused to an affinity tag that can be used to isolate and/or purify the RNA-RNA targeting effector protein complex. These applications are useful, e.g., for the analysis of gene expression profiles in cells.

In some embodiments, the RNA targeting effector proteins can be used to target a specific noncoding RNA (ncRNA) thereby blocking its activity. In some embodiments, the effector protein as described herein can be used to specifically enrich a particular RNA (including but not limited to increasing stability, etc.), or alternatively, to specifically deplete a particular RNA (e.g., particular splice variants, isoforms, etc.).

These methods are described, e.g., in U.S. Pat. No. 8,795,965, WO 2016205764, and WO 2017070605; each of which is incorporated herein by reference herein in its entirety.

High-Throughput Screening

The CRISPR systems described herein can be used for preparing next generation sequencing (NGS) libraries. For example, to create a cost-effective NGS library, the CRISPR systems can be used to disrupt the coding sequence of a target gene, and the CRISPR enzyme transfected clones can be screened simultaneously by next-generation sequencing (e.g., on the Ion Torrent PGM system). A detailed description regarding how to prepare NGS libraries can be found, e.g., in Bell et al., "A high-throughput screening strategy for detecting CRISPR-Cas9 induced mutations using next-generation sequencing," *BMC Genomics*, 15.1 (2014): 1002, which is incorporated herein by reference in its entirety.

Engineered Microorganisms

Microorganisms (e.g., *E. coli*, yeast, and microalgae) are widely used for synthetic biology. The development of synthetic biology has a wide utility, including various clinical applications. For example, the programmable CRISPR systems can be used to split proteins of toxic domains for targeted cell death, e.g., using cancer-linked RNA as target transcript. Further, pathways involving protein-protein interactions can be influenced in synthetic biological systems with e.g. fusion complexes with the appropriate effectors such as kinases or enzymes.

In some embodiments, guide RNA sequences that target phage sequences can be introduced into the microorganism. Thus, the disclosure also provides methods of vaccinating a microorganism (e.g., a production strain) against phage infection.

In some embodiments, the CRISPR systems provided herein can be used to engineer microorganisms, e.g., to improve yield or improve fermentation efficiency. For example, the CRISPR systems described herein can be used to engineer microorganisms, such as yeast, to generate biofuel or biopolymers from fermentable sugars, or to degrade plant-derived lignocellulose derived from agricultural waste as a source of fermentable sugars. More particularly, the methods described herein can be used to modify the expression of endogenous genes required for biofuel production and/or to modify endogenous genes, which may interfere with the biofuel synthesis. These methods of engineering microorganisms are described e.g., in Verwaal et al., "CRISPR/Cpf1 enables fast and simple genome editing of *Saccharomyces cerevisiae*," *Yeast*, 2017 Sep. 8. doi: 10.1002/yea.3278; and Hlavova et al., "Improving microalgae for biotechnology—from genetics to synthetic biology," *Biotechnol. Adv.*, 2015 Nov. 1; 33:1194-203, both of which are incorporated herein by reference in the entirety.

Application in Plants

The CRISPR systems described herein have a wide variety of utility in plants. In some embodiments, the CRISPR systems can be used to engineer genomes of plants (e.g., improving production, making products with desired post-translational modifications, or introducing genes for producing industrial products). In some embodiments, the CRISPR systems can be used to introduce a desired trait to a plant (e.g., with or without heritable modifications to the genome), or regulate expression of endogenous genes in plant cells or whole plants.

In some embodiments, the CRISPR systems can be used to identify, edit, and/or silence genes encoding specific proteins, e.g., allergenic proteins (e.g., allergenic proteins in peanuts, soybeans, lentils, peas, green beans, and mung beans). A detailed description regarding how to identify, edit, and/or silence genes encoding proteins is described, e.g., in Nicolaou et al., "Molecular diagnosis of peanut and legume allergy," *Curr. Opin. Allergy Clin. Immunol.*, 2011 June; 11(3):222-8, and WO 2016205764 A1; both of which are incorporated herein by reference in the entirety.

Gene Drives

Gene drive is the phenomenon in which the inheritance of a particular gene or set of genes is favorably biased. The CRISPR systems described herein can be used to build gene drives. For example, the CRISPR systems can be designed to target and disrupt a particular allele of a gene, causing the cell to copy the second allele to fix the sequence. Because of the copying, the first allele will be converted to the second allele, increasing the chance of the second allele being transmitted to the offspring. A detailed method regarding how to use the CRISPR systems described herein to build gene drives is described, e.g., in Hammond et al., "A CRISPR-Cas9 gene drive system targeting female reproduction in the malaria mosquito vector *Anopheles gambiae*," *Nat. Biotechnol.*, 2016 January; 34(1):78-83, which is incorporated herein by reference in its entirety.

Pooled-Screening

As described herein, pooled CRISPR screening is a powerful tool for identifying genes involved in biological mechanisms such as cell proliferation, drug resistance, and viral infection. Cells are transduced in bulk with a library of guide RNA (gRNA)-encoding vectors described herein, and the distribution of gRNAs is measured before and after applying a selective challenge. Pooled CRISPR screens work well for mechanisms that affect cell survival and proliferation, and they can be extended to measure the activity of individual genes (e.g., by using engineered reporter cell lines). Arrayed CRISPR screens, in which only one gene is targeted at a time, make it possible to use RNA-seq as the readout. In some embodiments, the CRISPR systems as described herein can be used in single-cell CRISPR screens. A detailed description regarding pooled CRISPR screenings can be found, e.g., in Datlinger et al., "Pooled CRISPR screening with single-cell transcriptome read-out," *Nat. Methods.*, 2017 March; 14(3):297-301, which is incorporated herein by reference in its entirety.

Saturation Mutagenesis ("Bashing")

The CRISPR systems described herein can be used for in situ saturating mutagenesis. In some embodiments, a pooled guide RNA library can be used to perform in situ saturating mutagenesis for particular genes or regulatory elements. Such methods can reveal critical minimal features and discrete vulnerabilities of these genes or regulatory elements (e.g., enhancers). These methods are described, e.g., in Canver et al., "BCL11A enhancer dissection by Cas9-mediated in situ saturating mutagenesis," *Nature*, 2015 Nov. 12; 527(7577):192-7, which is incorporated herein by reference in its entirety.

RNA-Related Applications

The CRISPR systems described herein can have various RNA-related applications, e.g., modulating gene expression, inhibiting RNA expression, screening RNA or RNA products, determining functions of lincRNA or non-coding RNA, inducing cell dormancy, inducing cell cycle arrest, reducing cell growth and/or cell proliferation, inducing cell anergy, inducing cell apoptosis, inducing cell necrosis, inducing cell death, and/or inducing programmed cell death. A detailed description of these applications can be found, e.g., in WO 2016205764 A1, which is incorporated herein by reference in its entirety.

Modulating Gene Expression

The CRISPR systems described herein can be used to modulate gene expression. The CRISPR systems can be used, together with suitable guide RNAs, to target gene expression, via control of RNA processing. The control of RNA processing can include, e.g., RNA processing reactions such as RNA splicing (e.g., alternative splicing), viral replication, and tRNA biosynthesis. The RNA targeting proteins in combination with suitable guide RNAs can also be used to control RNA activation (RNAa). RNA activation is a small RNA-guided and Argonaute (Ago)-dependent gene regulation phenomenon in which promoter-targeted short double-stranded RNAs (dsRNAs) induce target gene expression at the transcriptional/epigenetic level. RNAa leads to the promotion of gene expression, so control of gene expression may be achieved that way through disruption or reduction of RNAa. In some embodiments, the methods include the use of the RNA targeting CRISPR as substitutes for e.g., interfering ribonucleic acids (such as siRNAs, shRNAs, or dsRNAs). The methods of modulating gene expression are described, e.g., in WO 2016205764, which is incorporated herein by reference in its entirety.

Controlling RNA Interference

Control over interfering RNAs or microRNAs (miRNA) can help reduce off-target effects by reducing the longevity of the interfering RNAs or miRNAs in vivo or in vitro. In some embodiments, the target RNAs can include interfering RNAs, i.e., RNAs involved in the RNA interference pathway, such as small hairpin RNAs (shRNAs), small interfering (siRNAs), etc. In some embodiments, the target RNAs include, e.g., miRNAs or double stranded RNAs (dsRNA).

In some embodiments, if the RNA targeting protein and suitable guide RNAs are selectively expressed (for example spatially or temporally under the control of a regulated promoter, for example a tissue- or cell cycle-specific promoter and/or enhancer), this can be used to protect the cells or systems (in vivo or in vitro) from RNA interference (RNAi) in those cells. This may be useful in neighboring tissues or cells where RNAi is not required or for the purposes of comparison of the cells or tissues where the effector proteins and suitable guide RNAs are and are not expressed (i.e., where the RNAi is not controlled and where it is, respectively). The RNA targeting proteins can be used to control or bind to molecules comprising or consisting of RNAs, such as ribozymes, ribosomes, or riboswitches. In some embodiments, the guide RNAs can recruit the RNA targeting proteins to these molecules so that the RNA targeting proteins are able to bind to them. These methods are described, e.g., in WO 2016205764 and WO 2017070605, both of which are incorporated herein by reference in the entirety.

Modifying Riboswitches and Controlling Metabolic Regulations

Riboswitches are regulatory segments of messenger RNAs that bind small molecules and in turn regulate gene expression. This mechanism allows the cell to sense the intracellular concentration of these small molecules. A specific riboswitch typically regulates its adjacent gene by altering the transcription, the translation or the splicing of this gene. Thus, in some embodiments, the riboswitch activity can be controlled by the use of the RNA targeting proteins in combination with suitable guide RNAs to target the riboswitches. This may be achieved through cleavage of, or binding to, the riboswitch. Methods of using CRISPR systems to control riboswitches are described, e.g., in WO 2016205764 and WO 2017070605, both of which are incorporated herein by reference in their entireties.

Therapeutic Applications

The CRISPR systems described herein can have various therapeutic applications. In some embodiments, the new CRISPR systems can be used to treat various diseases and disorders, e.g., genetic disorders (e.g., monogenetic diseases), diseases that can be treated by nuclease activity (e.g., Pcsk9 targeting, Duchenne Muscular Dystrophy (DMD), BCL11a targeting), and various cancers, etc.

In some embodiments, the CRISPR systems described herein can be used to edit a target nucleic acid to modify the target nucleic acid (e.g., by inserting, deleting, or mutating one or more amino acid residues). For example, in some embodiments the CRISPR systems described herein comprise an exogenous donor template nucleic acid (e.g., a DNA molecule or an RNA molecule), which comprises a desirable nucleic acid sequence. Upon resolution of a cleavage event induced with the CRISPR system described herein, the molecular machinery of the cell will utilize the exogenous donor template nucleic acid in repairing and/or resolving the cleavage event. Alternatively, the molecular machinery of the cell can utilize an endogenous template in repairing and/or resolving the cleavage event. In some embodiments, the CRISPR systems described herein may be used to alter a target nucleic acid resulting in an insertion, a deletion, and/or a point mutation). In some embodiments, the insertion is a scarless insertion (i.e., the insertion of an intended nucleic acid sequence into a target nucleic acid resulting in no additional unintended nucleic acid sequence upon resolution of the cleavage event). Donor template nucleic acids may be double stranded or single stranded nucleic acid molecules (e.g., DNA or RNA). Methods of designing exogenous donor template nucleic acids are described, for example, in PCT Publication No. WO 2016094874 A1, the entire contents of which are expressly incorporated herein by reference.

In one aspect, the CRISPR systems described herein can be used for treating a disease caused by overexpression of RNAs, toxic RNAs and/or mutated RNAs (e.g., splicing defects or truncations). For example, expression of the toxic RNAs may be associated with the formation of nuclear inclusions and late-onset degenerative changes in brain, heart, or skeletal muscle. In some embodiments, the disorder is myotonic dystrophy. In myotonic dystrophy, the main pathogenic effect of the toxic RNAs is to sequester binding proteins and compromise the regulation of alternative splicing (see, e.g., Osborne et al., "RNA-dominant diseases," *Hum. Mol. Genet.*, 2009 Apr. 15; 18(8):1471-81). Myotonic dystrophy (dystrophia myotonica (DM)) is of particular interest to geneticists because it produces an extremely wide range of clinical features.

The classical form of DM, which is now called DM type 1 (DM1), is caused by an expansion of CTG repeats in the 3'-untranslated region (UTR) of DMPK, a gene encoding a cytosolic protein kinase. The CRISPR systems as described herein can target overexpressed RNA or toxic RNA, e.g., the DMPK gene or any of the mis-regulated alternative splicing in DM1 skeletal muscle, heart, or brain.

The CRISPR systems described herein can also target trans-acting mutations affecting RNA-dependent functions that cause various diseases such as, e.g., Prader Willi syndrome, Spinal muscular atrophy (SMA), and Dyskeratosis congenita. A list of diseases that can be treated using the CRISPR systems described herein is summarized in Cooper et al., "RNA and disease," *Cell,* 136.4 (2009): 777-793, and WO 2016205764 A1, both of which are incorporated herein by reference in the entirety. Those of skill in this field will understand how to use the new CRISPR systems to treat these diseases.

The CRISPR systems described herein can also be used in the treatment of various tauopathies, including, e.g., primary and secondary tauopathies, such as primary age-related tauopathy (PART)/Neurofibrillary tangle (NFT)-predominant senile dementia (with NFTs similar to those seen in Alzheimer Disease (AD), but without plaques), dementia pugilistica (chronic traumatic encephalopathy), and progressive supranuclear palsy. A useful list of tauopathies and methods of treating these diseases are described, e.g., in WO 2016205764, which is incorporated herein by reference in its entirety.

The CRISPR systems described herein can also be used to target mutations disrupting the cis-acting splicing codes that can cause splicing defects and diseases. These diseases include, e.g., motor neuron degenerative disease that results from deletion of the SMN1 gene (e.g., spinal muscular atrophy), Duchenne Muscular Dystrophy (DMD), frontotemporal dementia, and Parkinsonism linked to chromosome 17 (FTDP-17), and cystic fibrosis.

The CRISPR systems described herein can also be used in methods of treating a condition or disease in a subject in need thereof. The methods include administering to the subject a CRISPR system as described herein, wherein the spacer sequence is complementary to at least 12 (e.g., 12, 13, 14, 15, 16, 17, 18, 19, 20, 21, or more) nucleotides of a target nucleic acid associated with the condition or disease; wherein the Type III-E CRISPR-Cas effector protein associates with the Type III-E RNA guide to form a complex; wherein the complex binds to a target nucleic acid sequence that is complementary to the at least 12 (e.g., 12-21 or more) nucleotides of the spacer sequence; and wherein upon binding of the complex to the target nucleic acid sequence the Type III-E CRISPR-Cas effector protein cleaves the target nucleic acid, thereby treating the condition or disease in the subject.

For example, the condition or disease can be a cancer or an infectious disease. For example, the condition or disease can be a cancer selected from the group including or consisting of Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

The CRISPR systems described herein can further be used for antiviral activity, in particular against RNA viruses. The effector proteins can target the viral RNAs using suitable guide RNAs selected to target viral RNA sequences.

Furthermore, in vitro RNA sensing assays can be used to detect specific RNA substrates. The RNA targeting effector proteins can be used for RNA-based sensing in living cells. Examples of applications are diagnostics by sensing of, for examples, disease-specific RNAs.

A detailed description of therapeutic applications of the CRISPR systems described herein can be found, e.g., in U.S. Pat. No. 8,795,965, EP 3009511, WO 2016205764, and WO 2017070605; each of which is incorporated herein by reference in its entirety.

Delivery of CRISPR Systems

Through this disclosure and the knowledge in the art, the CRISPR systems described herein, or components thereof, nucleic acid molecules thereof, or nucleic acid molecules encoding or providing components thereof, can be delivered by various delivery systems such as vectors, e.g., plasmids, viral delivery vectors. The new CRISPR enzymes and/or any of the RNAs (e.g., guide RNAs) can be delivered using suitable vectors, e.g., plasmids or viral vectors, such as adeno-associated viruses (AAV), lentiviruses, adenoviruses, and other viral vectors, or combinations thereof. The proteins and one or more guide RNAs can be packaged into one or more vectors, e.g., plasmids or viral vectors.

In some embodiments, the vectors, e.g., plasmids or viral vectors, are delivered to the tissue of interest by, e.g., intramuscular injection, intravenous administration, transdermal administration, intranasal administration, oral administration, or mucosal administration. Such delivery may be either via a single dose, or multiple doses. One skilled in the art understands that the actual dosage to be delivered herein may vary greatly depending upon a variety of factors, such as the vector choices, the target cells, organisms, tissues, the general conditions of the subject to be treated, the degrees of transformation/modification sought, the administration routes, the administration modes, the types of transformation/modification sought, etc.

In certain embodiments, the delivery is via adenoviruses, which can be at a single dose containing at least $1\times10^5$ particles (also referred to as particle units, pu) of adenoviruses. In some embodiments, the dose preferably is at least about $1\times10^6$ particles, at least about $1\times10^7$ particles, at least about $1\times10^8$ particles, and at least about $1\times10^9$ particles of the adenoviruses. The delivery methods and the doses are described, e.g., in WO 2016205764 A1 and U.S. Pat. No. 8,454,972 B2, both of which are incorporated herein by reference in the entirety.

In some embodiments, the delivery is via plasmids. The dosage can be a sufficient number of plasmids to elicit a response. In some cases, suitable quantities of plasmid DNA in plasmid compositions can be from about 0.1 to about 2 mg. Plasmids will generally include (i) a promoter; (ii) a sequence encoding a nucleic acid-targeting CRISPR enzymes, operably linked to the promoter; (iii) a selectable marker; (iv) an origin of replication; and (v) a transcription terminator downstream of and operably linked to (ii). The plasmids can also encode the RNA components of a CRISPR complex, but one or more of these may instead be encoded on different vectors. The frequency of administration is within the ambit of the medical or veterinary practitioner (e.g., physician, veterinarian), or a person skilled in the art.

In another embodiment, the delivery is via liposomes or lipofectin formulations and the like, and can be prepared by methods known to those skilled in the art. Such methods are described, for example, in WO 2016205764 and U.S. Pat. Nos. 5,593,972; 5,589,466; and 5,580,859; each of which is incorporated herein by reference in its entirety.

In some embodiments, the delivery is via nanoparticles or exosomes. For example, exosomes have been shown to be particularly useful in delivery RNA.

Further means of introducing one or more components of the new CRISPR systems to the cell is by using cell penetrating peptides (CPP). In some embodiments, a cell penetrating peptide is linked to the CRISPR enzymes. In some embodiments, the CRISPR enzymes and/or guide RNAs are coupled to one or more CPPs to effectively transport them inside cells (e.g., plant protoplasts). In some embodiments, the CRISPR enzymes and/or guide RNA(s) are encoded by one or more circular or non-circular DNA molecules that are coupled to one or more CPPs for cell delivery.

CPPs are short peptides of fewer than 35 amino acids either derived from proteins or from chimeric sequences capable of transporting biomolecules across cell membrane in a receptor independent manner. CPPs can be cationic peptides, peptides having hydrophobic sequences, amphipathic peptides, peptides having proline-rich and anti-microbial sequences, and chimeric or bipartite peptides. Examples of CPPs include, e.g., Tat (which is a nuclear transcriptional activator protein required for viral replication by HIV type 1), penetratin, Kaposi fibroblast growth factor (FGF) signal peptide sequence, integrin β3 signal peptide sequence, polyarginine peptide Args sequence, Guanine rich-molecular transporters, and sweet arrow peptide. CPPs and methods of using them are described, e.g., in Hållbrink et al., "Prediction of cell-penetrating peptides," Methods Mol. Biol., 2015; 1324:39-58; Ramakrishna et al., "Gene disruption by cell-penetrating peptide-mediated delivery of Cas9 protein and guide RNA," Genome Res., 2014 June; 24(6):1020-7; and WO 2016205764 A1; each of which is incorporated herein by reference in its entirety.

Various delivery methods for the CRISPR systems described herein are also described, e.g., in U.S. Pat. No. 8,795,965, EP 3009511, WO 2016205764, and WO 2017070605; each of which is incorporated herein by reference in its entirety.

EXAMPLES

The invention is further described in the following examples, which do not limit the scope of the invention described in the claims.

Example 1—Identification of Minimal Components for Type III-E (CLUST.019911) CRISPR-Cas System (FIGS. 1-6)

Figure 1:
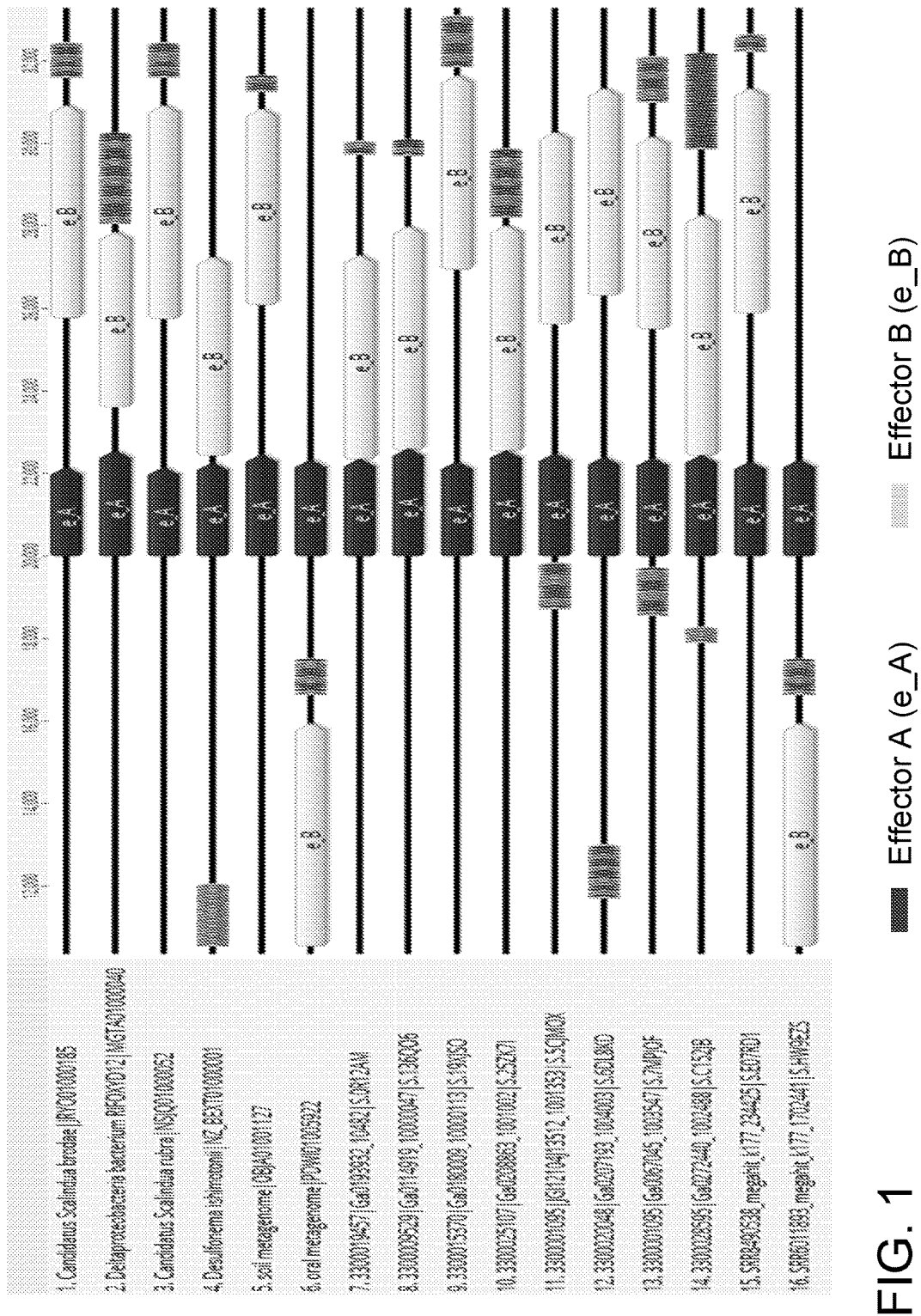
FIG. 1 is a schematic that shows conserved Effector A (e_A), Effector B (e_B), and CRISPR array elements by bacterial genome accession and species for representative Type III-E (CLUST.019911) loci.
Figure 3A:
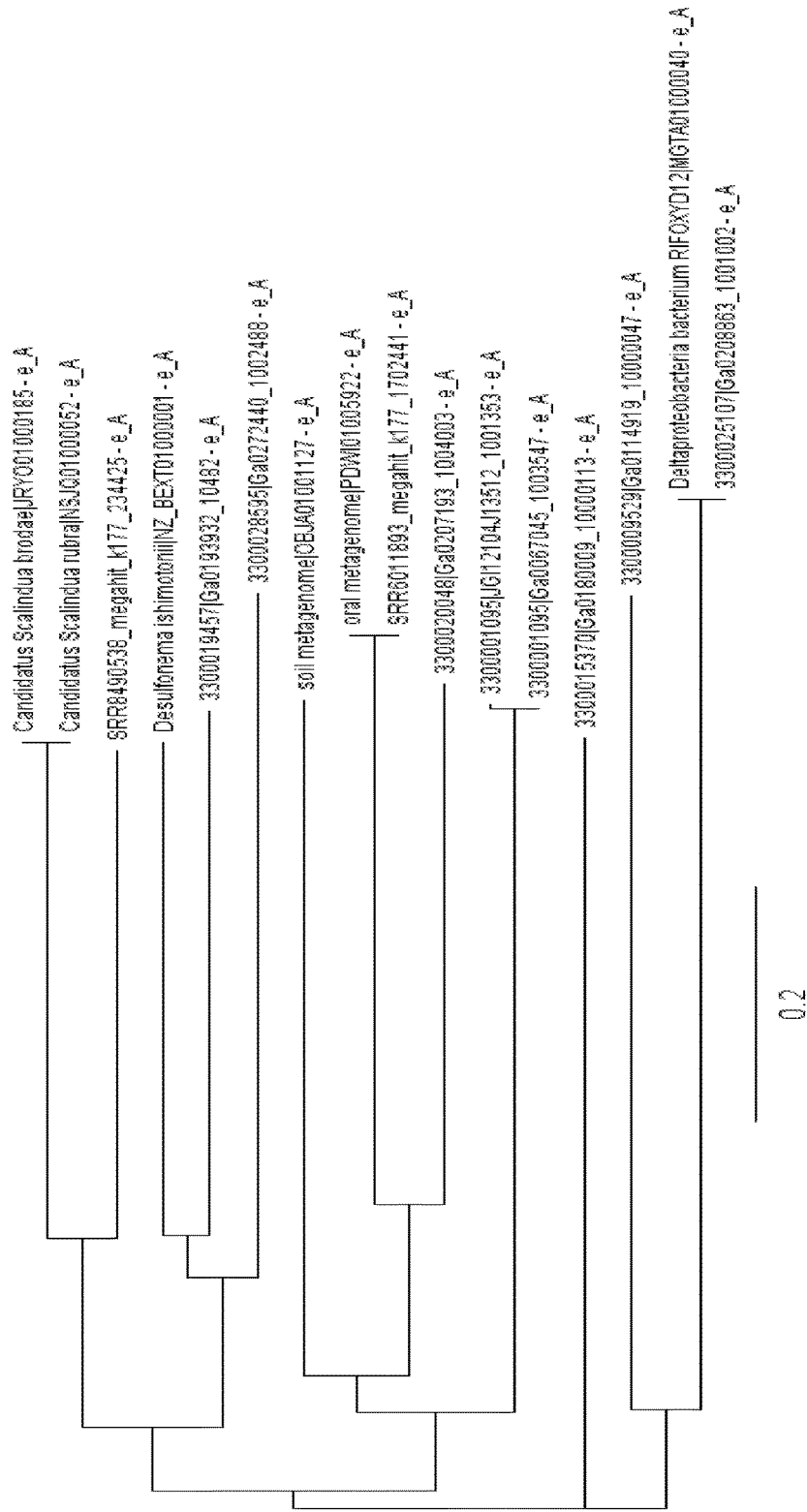
FIG. 3A is a phylogenetic tree of Type III-E (CLUST.019911) Effector A proteins.
Figure 3B:
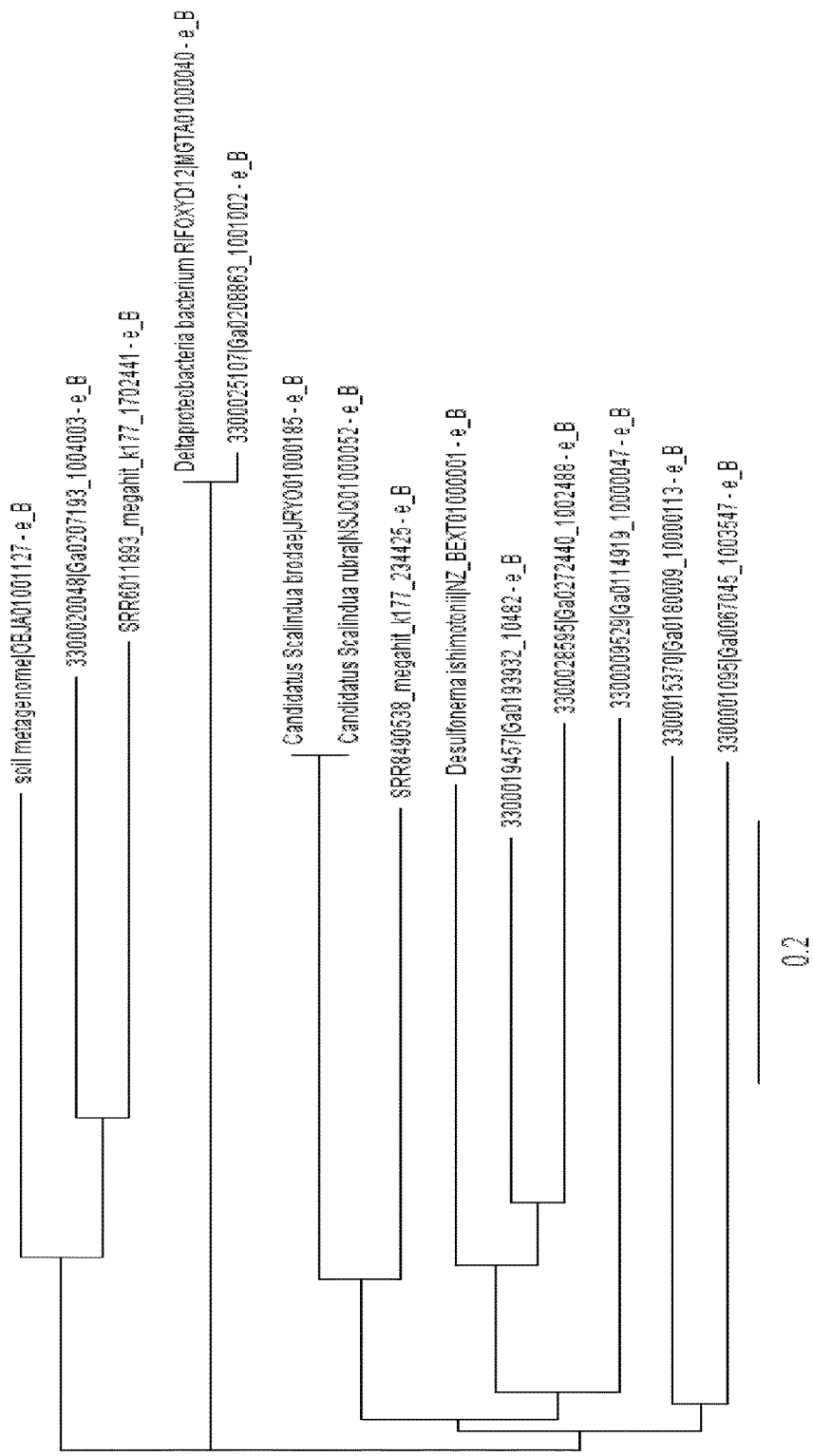
FIG. 3B is a phylogenetic tree of Type III-E (CLUST.019911) Effector B proteins.

This protein family describes a CRISPR system found in organisms including, but not limited to, *Deltaproteobacteria, Candidatus Scalindua*, and uncultured metagenomic sequences collected from aquatic freshwater and marine environments (FIGS. 3A-3B). Exemplary naturally occurring loci containing this effector complex are depicted in FIG. 1, indicating that the effector protein Effector A (~800 amino acids) has a high co-occurrence with the effector protein Effector B (~1700 aa). Type III-E CRISPR-Cas systems include the exemplary effectors detailed in TABLES 1-3 and crRNAs containing exemplary sequences detailed in TABLE 4.

Type III-E CRISPR-Cas direct repeat sequences (consensus sequence being GTTRNRNANMRM-CRSNWDYYWTTRATGTBACGGDAC (SEQ ID NO: 100)) show a conserved TGTNWYGGNAC (SEQ ID NO: 99) at the 3' end (see FIG. 2), wherein the various letters used in these consensus sequences (other than A, G, C, and T) have the following standard meanings:

| | | |
|---|---|---|
| R | A or G | puRine |
| Y | C, T or U | pYrimidines |
| K | G, T or U | bases which are Ketones |
| M | A or C | bases with aMino groups |
| S | C or G | Strong interaction |
| W | A, T or U | Weak interaction |
| B | not A (i.e. C, G, T or U) | B comes after A |
| D | not C (i.e. A, G, T or U) | D comes after C |
| H | not G (i.e., A, C, T or U) | H comes after G |
| V | neither T nor U (i.e. A, C or G) | V comes after U |
| N | A C G T U | Nucleic acid |
| — | gap of indeterminate length | |

FIGS. 3A and 3B show phylogenetic trees of Type III-E effector A and effector B proteins, respectively, showing that the both effectors exhibit diversity.

Figure 4:
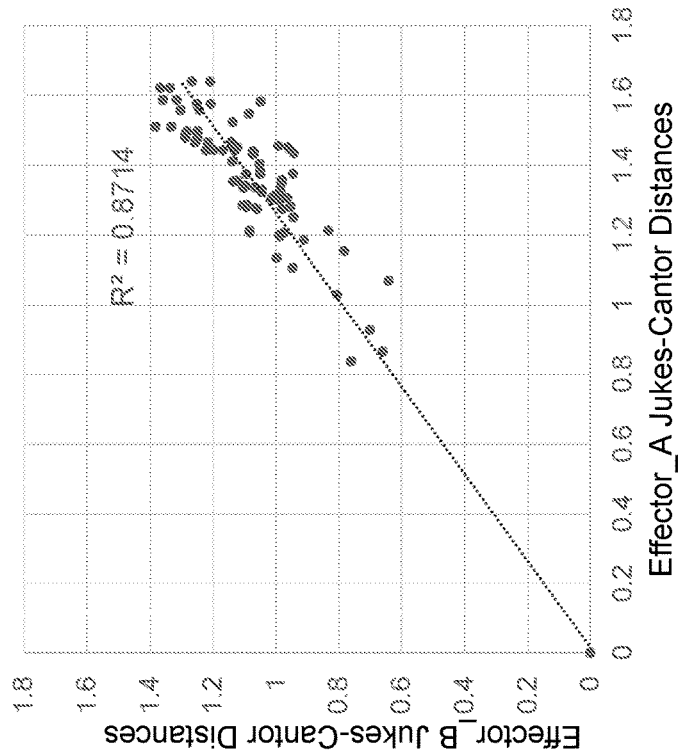
FIG. 4 is a scatter plot that depicts one point for each pair of genomic loci, where the x-value is the pairwise Jukes-Cantor distance of the Type III-E Effector_A proteins from the two loci, and the y-value is the pairwise Jukes_Cantor distance of the Type III-E Effector_B proteins from the two loci.

FIG. 4 shows the pairwise Jukes-Cantor distances for effector A and effector B proteins, indicating that two loci containing similar effector A proteins also contain correspondingly similar effector B proteins, indicative of co-evolution and potential functional association.

Figure 6:
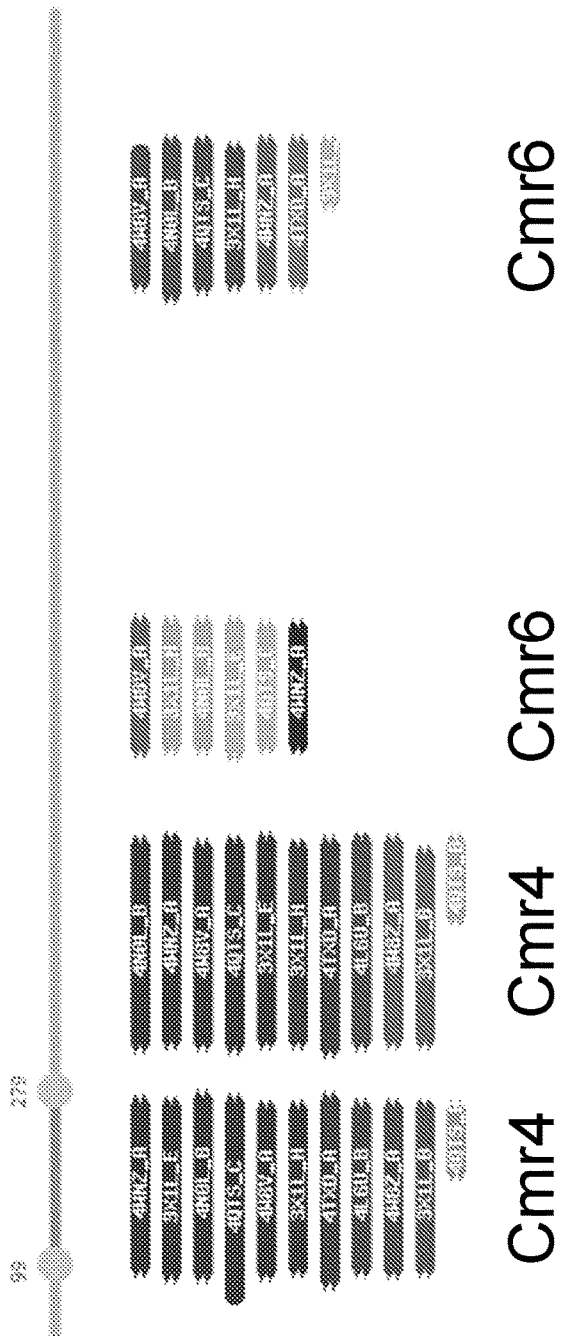
FIG. 6 is a schematic representation of HHpred domain predictions of an example of a Type III-E (CLUST.019911) Effector B, depicting multiple partial matches in different regions of the protein to CRISPR Cmr4 and CRISPR Cmr6.

An HMM profile search of the multiple sequence alignment of Type III-E effector A proteins against the PFAM database indicated the presence of the CHAT domain. HHpred domain predictions of an exemplary Type III-E Effector A are also depicted in FIG. 4, indicating a C-terminal match to the CHAT domain, and an N-terminal match to the TPR domain. HHpred domain predictions of an exemplary Type III-E Effector B are depicted in FIG. 6, which indicates multiple partial matches in different regions of the protein to Cmr4 and Cmr6.

Optionally, the CLUST.019911 CRISPR system includes a transactivating RNA (tracrRNA) with a DR homology as detailed in TABLE 5 and a complete tracrRNA contained in the DR homology loci detailed in TABLE 6. Optionally, the system includes a tracrRNA that is a subset of a non-coding sequence listed in TABLE 7.

Optionally, the system includes a RNA modulator that is a subset of a non-coding sequence listed in TABLE 7.

TABLE 1

Representative Type III-E (CLUST.019911) Effector Proteins

| Source | Effector_A accession | Effector_B accession | # spacers |
|---|---|---|---|
| *Candidatus Scalindua brodae* (JRYO01000185) | KHE91663.1 | JRYO01000185_8\|M | 11 |
| Deltaproteobacteria bacterium RIFOXYD12_FULL_50_9 (MGTA01000040) | OGR07204.1 | OGR07205.1 | 31 |
| *Desulfonema ishimotonii* (NZ_BEXT01000001) | WP_124327588.1 | WP_124327589.1 | 22 |
| soil metagenome (OBJA01001127) | OBJA01001127_8\|M | OBJA01001127_4\|M | 5 |
| oral metagenome (PDWI01005922) | PDWI01005922_7\|M | PDWI01005922_5\|M | 12 |
| aquatic-marine-hydrothermal vent microbial mat (3300019457\|Ga0193932_10482) | RLC19860.1 | 3300019457\|Ga0193932_10482_5\|M | 4 |
| aquatic-marine-deep subsurface (3300009529\|Ga0114919_10000047) | 3300009529\|Ga0114919_10000047_39\|M | 3300009529\|Ga0114919_10000047_40\|M | 5 |
| aquatic-freshwater-groundwater (3300015370\|Ga0180009_10000113) | 3300015370\|Ga0180009_10000113_9\|P | 3300015370\|Ga0180009_10000113_2\|P | 17 |

TABLE 1-continued

Representative Type III-E (CLUST.019911) Effector Proteins

| | | | |
|---|---|---|---|
| bioremediation-terephthalate-wastewater bioreactor (3300001095\|JGI12104J13512__1001353) | 3300001095\|JGI12104J13512__1001353__7\|M | 3300001095\|JGI12104J13512__1001353__10\|M | 15 |
| aquatic-freshwater-freshwater lake sediment (3300020048\|Ga0207193__1004003) | 3300020048\|Ga0207193__1004003__10\|P | 3300020048\|Ga0207193__1004003__13\|M | 17 |
| bioremediation-terephthalate-wastewater bioreactor (3300001096\|Ga0067045__1003547) | 3300001096\|Ga0067045__1003547__9\|P | 3300001096\|Ga0067045__1003547__12\|M | 31 |
| terrestrial-soil (3300025107\|Ga0208863__1001002) | OGR07204.1 | 3300025107\|Ga0208863__1001002__11\|M | 23 |
| aquatic-marine-marine sediment (3300028595\|Ga0272440__1002488) | 3300028595\|Ga0272440__1002488__3\|P | 3300028595\|Ga0272440__1002488__4\|M | 39 |
| anammox bioreactor (SRR8490538) | SRR8490538__megahit_k177__234425__6\|M | SRR8490538__megahit_k177__234425__10\|M | 5 |
| dolphin oral metagenome (SRR6011893) | SRR6011893__megahit_k177__1702441__3\|P | SRR6011893__megahit_k177__1702441__5\|M | 12 |

| Source | cas1 | cas2 | Effector_A size | Effector_B size |
|---|---|---|---|---|
| *Candidatus Scalindua brodae* (JRYO01000185) | N | N | 716 | 1722 |
| Deltaproteobacteria bacterium RIFOXYD12_FULL_50_9 (MGTA01000040) | N | N | 849 | 1403 |
| *Desulfonema ishimotonii* (NZ_BEXT01000001) | Y | Y | 751 | 1601 |
| soil metagenome (OBJA01001127) | Y | Y | 816 | 1575 |
| oral metagenome (PDWI01005922) | Y | Y | 769 | 1801 |
| aquatic-marine-hydrothermal vent microbial mat (3300019457\|Ga0193932__10482) | Y | N | 778 | 1652 |
| aquatic-marine-deep subsurface (3300009529\|Ga0114919__10000047) | Y | Y | 860 | 1806 |
| aquatic-freshwater-groundwater (3300015370\|Ga0180009__10000113) | N | N | 757 | 1559 |
| bioremediation-terephthalate-wastewater bioreactor (3300001095\|JGI12104J13512__1001353) | Y | Y | 822 | 1549 |
| aquatic-freshwater-freshwater lake sediment (3300020048\|Ga0207193__1004003) | Y | Y | 797 | 1668 |
| bioremediation-terephthalate-wastewater bioreactor (3300001096\|Ga0067045__1003547) | Y | Y | 789 | 1549 |
| terrestrial-soil (3300025107\|Ga0208863__1001002) | N | N | 849 | 1821 |
| aquatic-marine-marine sediment (3300028595\|Ga0272440__1002488) | N | N | 809 | 1940 |
| anammox bioreactor (SRR8490538) | N | N | 760 | 1812 |
| dolphin oral metagenome (SRR6011893) | Y | Y | 769 | 1801 |

TABLE 2

Amino Acid Sequences of Representative Type III-E (CLUST.019911) Effector_A Proteins >KHE91663.1
[Candidatus Scalindua brodae]
MNNTEENIDRIQEPTREDIDRKEAERLLDEAFNPRTKPVDRKKIINSALKILIGLYKEKKDDLTSASFISIARAYYLVSITILP
KGTTIPEKKKEALRKGIEFIDRAINKFNGSILDSQRAFRIKSVLSIEFNRIDREKCDNIKLKNLLNEAVDKGCTDFDTYEWDIQ
IAIRLCELGVDMEGHFDNLIKSNKANDLQKAKAYYFIKKDDHKAKEHMDKCTASLKYTPCSHRLWDETVGFIERLKGDSSTLWR
DFAIKTYRSCRVQEKETGTLRLRWYWSRHRVLYDMAFLAVKEQADDEEPDVNVKQAKIKKLAEISDSLKSRFSLRLSDMEKMPK
SDDESNHEFKKFLDKCVTAYQDGYVINRSEDKEGQGENKSTTSKQPERPQAKLLELTQVPEGWVVVHFYLNKLEGMGNAIVFD
KCANSWQYKEFQYKELFEVFLTWQANYNLYKENAAEHLVTLCKKIGETMPFLFCDNFIPNGKDVLFVPHDFLHRLPLHGSIENK
TNGKLFLENHSCCYLPAWSFASEKEASTSDEYVLLKNFDQGHFETLQNNQIWGTQSVKDGASSDDLENIRNNPRLLTILCHGEA
NMSNPFRSMLKLANGGITYLEILNSVKGLKGSQVILGACETDLVPPLSDVMDEHYSVATALLLIGAAGVVGTMWKVRSNKTKSL
IEWKLENIEYKLNEWQKETGGAAYKDHPPTFYRSIAFRSIGFPL (SEQ ID NO: 1)

TABLE 2-continued

Amino Acid Sequences of Representative Type III-E (CLUST.019911) Effector_A Proteins \>OGR07204.1
[Deltaproteobacteria bacterium RIFOXYD12_FULL_50_9]
MNQNIDRAVGAILAIETATPLTESSTLAQRERHQKLLHDETKKIEQAFIALAQPPQCRAVEIAALSRFLQMTPLAVGPLRKRVI
CRAEPLKDDAHEQEIASHFNGLLLRLAKGLLASALNPAGIPWRRRVLWLEKAAHIAHRFDKEPLADDKERTEAAGVLARCCLHL
ALAHLPKGKDKSAMAERQEDLLQSLMWAQKAIVLAGQDKLSGEEYKLLKALVLIELDNLSPGRFQQQLNYVLYDLAVIWLERDT
ATKPFHPQELFVLWRYLATDFEPDLNMLLFKGSNTSERTAAVQQASPEAERFRPLLPLIHAWSAWKLDPPNNKIAEVILQAVNN
LDEHQVYEQVWKWTVDFLQELRNTGAVDWQLPAIAAWELCNKKEKELPFGFQIRQYWSRLDSLYRLAFDGALELKDCMTAARIV
DSLKSRTPLTWRDMDTLFAKLPKEKADQLREAFYSMEVQARMGFYAEAAKEDANKLKKLLAAQVRKIRDIESVPAGWTVVHFHLR
EDQDLGYALACRLTADGMSYWTNHIFPVAGIRRAYDCWLEAYHGMEPGAREKSGYQLVELSEIMGKDLDFLFELAGEDGARGLL
FVPHGFSHLLPLHAAKKDGSYLFEKIPSLTLPAWEFAPDVDQIPVSDGQDFCFISQRANEQDLVGNIERSHTWNGVCNKNAAWT
NVLNTNKEWSKAPPRWLVFWCHGQADPHVAFRSKLLLGTLGVSLFEIQEAALSLTGTKVVLAVCESDLAPPEEYEKTDDHLSLA
APFLLKGARQVLAAIWEGAQLDLLKAMKEMLSNQDKHSWEILRELQSCWMRQPGAIFNDEYIRLYYAASFRILGFPEVATTNMA
TATAQEEIA (SEQ ID NO: 2)

\>WP_124327588.1
[Desulfonema ishimotonii]
MSNPIRDIQDRLKTAKFDNKDDMMNLASSLYKYEKQLMDSSEATLCQQGLSNRPNSFSQLSQFRDSDIQSKAGGQTGKFWQNEY
EACKNFQTHKERRETLEQIIRFLQNGAEEKDADDLLLKTLARAYFHRGLLYRPKGFSVPARKVEAMKKAIAYCEIILDKNEEES
EALRIWLYAAMELRRCGEEYPENFAEKLFYLANDGFISELYDIRLFLEYTEREEDNNFLDMILQENQDRERLFELCLYKARACF
HLNQLNDVRIYGESAIDNAPGAFADPFWDELVEFIRMLRNKKSELWKEIAIKAWDKCREKEMKVGNNIYLSWYWARQRELYDLA
FMAQDGIEKKTRIADSLKSRTTLRIQELNELRKDAHRKQNRRLEDKLDRIIEQENEARDGAYLRRNPPCFTGGKREEIPFARLP
QNWIAVHFYLNELESHEGGKGGHALIYDPQKAEKDQWQDKSFDYKELHRKFLEWQENYILNEEGSADFLVTLCREIEKAMPFLF
KSEVIPEDRPVLWIPHGFLHRLPLHAAMKSGNNSNIEIFWERHASRYLPAWHLFDPAPYSREESSTLLKNFEEYDFQNLENGEI
EVYAPSSPKKVKEAIRENPAILLLLCHGEADMTNPFRSCLKLKNKDMTIFDLLTVEDVRLSGSRILLGACESDMVPPLEFSVDE
HLSVSGAFLSHKAGEIVAGLWTVDSEKVDECYSYLVEEKDFLRNLQEWQMAETENFRSENDSSLFYKIAPFRIIGFPAE (SEQ
ID NO: 3)

\>OBJA01001127_8|M
[soil metagenome]
MEHKTMTEPAGQNPSATDNDFEKFIIDTGCVFFATPQEDPKYQNNKVEWHQGLCRFAQNDSPPTVIGSAIFFLQKLQEPGLFSG
LPVSPELCSKISKDKNEIVAYHQQCILRLCEELLVKGREAKEHRERQAFDQAIKFLLVLKKGTSSDTPSPNGHIHFQDQVSIL
LAEAYYLRGKIIRPKGFSVPAKKIETLEVAEKILVDLVARDTTGKARRLRAMVHIDLAALRDPADDSGNLQDYRQALEQAVSSI
GDTKTCGRDEIVIILARAEDNAGWTGSDGLSARLEELVNNGAAGPLDQARAYLLLGQNNLAVTQTEKAITRMAATDNPTPFSHE
DWRLLVRLLRDLKHQNTAGIDKLILDTWRKVHQIERQTKNGMHVRWYWSRQRDLYDLAFHAAGNDARLKAQIADSLKARPALHL
GQAADLGLAVEQMEAGLLDRYMPGKMLEQTTDMAAPAAPGSAGWPELPRPWIAVHFYLSNGFGHPEGKQQGHALIQDSSKGDGK
DTWSERTFDYFPIWAAFMTWQENYQRLKKEAAPDLERLCQVMERQMPFLFAPEDLPLERPVVFVPHDFLHRLPLHAALIDNGEE
SGIPAQSHPITYLPGWWMVTSQAANPNETASKNTPSPVAPVALVHWDNSEDIHDIIKQANGTVVVNASRSDWLKLKHNAVGLKV
LYCHGQAGYTNPFASSLKLDGGGLYLKDVVKGPPLVGRFILAACESDLVLPASTTLDEYFSFSTGLLQKGAAEILGTLWEVNET
DALSLIETVLRAPASGNLSFVLRDWLRDNLRSLTTELFYDIAAFRALGGPYPVDTKEEHR (SEQ ID NO: 4)

\>PDWI01005922_7|M
[oral metagenome]
MNTVELLQEEERLTLDLVFLPPGSKNKEQKKNALVDLLLKIVEHGELTRKYSALLTLSRGALRGEVHFGEKLLPSPEACANLAK
PEEIKKMIRQHFQYRLDLLEAIVKKAADNTYSHARRRKALRIAIKELEQICEEALDELCFKARLLLAEALFERGRIVRPKGFSE
PGKKKELFQKAINCIEGNCSEEALRLRARIYLQWYRFFHDEPPCDLDDIFTKALAVTDDKMLKTELLLLCGERKEPDPYTDDLR
ALLNDQNVSPLSRARAAVLLEDWERCNVEIYEAIEDLGKTDFFQQDWELVVTLLKKNYNQFHGWSRACTRLWEITVEKESKDAG
HGCVLRWYWSRQRDVYNLAFAAFEECEDKARVVDSLKNRPAHHFSQLEQLAQSSDIIKQWIEBSEEIINQDSFAHSLRRHEKGAK
SHSGGSLRIFPCLPKGWIAVHFFLASWPEPKGYALIHNADTNTWEQRDFKYEQLWATYIAWQEVSLHNKIRESALLLKSLCETL
GKEMRWLFDEFLFPKERRRVLFVPHDFLHRLPLHMAIDIESQTVFAAKQPVCYLPAYHLQNNITENKKTSIYALVNLRENKQQK
KDEEIFAEKVEKMGAIVRRPALESDLLNLNPVPEKLVLYCHGIGHSANPFASKLCLGDTGVSYRDILALNRSLAGCRVLLFACE
TDLVPAQTSSIDEHLSISNALLQKGAFEVLGSLWALPGKTIYGITKTFIDNDDTSAVLHSSLKRLFEHYEKKNEKTRAQLLYNW
ASLRVLAPAREFS (SEQ ID NO: 5)

\>RLC19860.1
[aquatic-marine-hydrothermal vent microbial mat]
MRYSSRTNCEAIDNLAEALQDQENMPEIARRVLEFEAENAKPENALCQHGLPHTKKAASQIAGVRDKHSEFYDNALLDLVEEWL
KTYEEAKKLTHRERRQEMEDKIRVLQPVLQAKGKDADPRFLSLLARIYLYRGMLFRPKGFTTPARKIEALKKAVQLSEKAVEKE
KDNPNFLRTWAQAALELEAIPETSFKVSSGLLKDAAVCINRDGIHSLNDLQVILEYAESEGKTSFLQHVLVEKRYWKRPFDLFL
LKARAAFALNRMDDVRYFLKSAMDKTPKALSSPFWDHLVDFLKKLRTKEGSDLWKEMAVAAHRLCREKEVKIANNIYLYRHWAR
QKSLYNMAFLAQNDLKEKAKIADSLKSRPVLRYQALREMKEHQNIALKLEQDDQERDGGYRNLQQVEMDERTGKRLSEKMEKAGV
SYENLPVPWISVHFYLNESENSEDEGSKGYALIFDALTQSWKERRFDYAKLHRKFMTWQEAYISAKKSSFAKDSLVELCREIGN
TMPFLFDTACIRDGAPVLWIPHGFLHRLPHAAIRDEATNEIFLENHASRYLPAWSILNSASARRGKDSYMIKRFRAEDYEKEP
FSELEDMEWDNEEHEKLATPDDLKHFMAKNPGVFAVLCHGHGDILNPLKSWLELEGGGVSVLDILRYEKANLSGTRVLLGACEA
DMAPPVEYAIDEHVSLSAAFLSHKAQEVIAGLWEINIGEADECYAEILDCSDLSTELKDWQCDWVEKWRDDVEASGDNSTFYHI
TPFRIMGFPLKLKENNESEAKQ (SEQ ID NO: 6)

\>3300009529|Ga0114919_10000047_39|M
[aquatic-marine-deep subsurface]
MVTPQASKNPAVDEILKQLTPYDMETENAKAIETRKSCIECLKGICERAQKQNDWVAFGTALHFLHELSGTTAPVFYGAVKGQS
ACGQLHNMQASIKEAVARITKSRAEHLRDKALKPYGIPYLSRHRFLEKAIRMVWELLQSDNGWPDSVWLHREASQFIARCFLDR
GRLVLPKGSSIPQKKIEALKKAWHWALKGALKAKEDDADSMKLWLEFREYILQTAKENDADISMKLLIEIGLELELYEKSFSP
QVNELTRKIASGKLLEDPKSSADWPIIDRGRSIGCFDEKQDEALFKLDLNKKEYKELPTLPLLRAKAGHRLKRDLASAFDEASF
FRVVCDAVRKLADVPFSSPIWVETIEFLAQLDPGSEIRNAASVAAWQICKLKEEDLDLGLQVRMMWSRHKMLYDLAFHAALSKD
DWALAARIADSPKSRPTIKALAMESVLDGDTLKGYYELEARGVARGYDSTYHRKKKSLEKAEAKKKRASKDTQGLRPLDFEEDI
PAGWAAIHLYLDQDKKGHALMRSAGSTKDGWLYKDFEISDIWQKFQAWQAADRYNPKFGGAATELHALCESLGYDDDHLGFLFN
KDLPDNLIIIPHDILHLVPIHSVMKNGEILLKQKKCIYLPAWGLPRETDSASTPEGEGLFDNFEDHDPLRQYLQPVLQAWKHSS TABLE 2-continued Amino Acid Sequences of Representative Type III-E (CLUST.019911) Effector_A Proteins VSARNIKVPDATANDVRNYLKNTTNPEWMVFLCHGKADPVNPYNSGLLLRGSHLTHAALVELPKKMAGTKVFLGACETDMSPPK
QKSVDEHLSVSTAFFQKGASEIAGGLWRVHSAIAKKMVEHISENRKKPLVDVVWEKQKDWWDNGIQYVVDGITVKVSNCFKKLY
YLSSYRVVGFPRAIGENTDE (SEQ ID NO: 7)

>3300015370|Ga0180009_10000113_9|P
[aquatic-freshwater-groundwater]
MYSDFPALRLPELSVDQKKLFKISGTNPQLIYILMNEFDGEGDEPFFTGLVPDETDLSENKQAPLLKELARHLLKEYEDIGRNR
WKHADQRRVLEKAIRLLDKSHQAEENVSLELGKAYLYRARIIRPKGFTVPAKKIEALNNALHFCEDATNHGKAWADHFAGLVAL
ELYRCGKTHDNLSELLNKATADAELSEPDRRVEFYQMRVRLEELRQDEGNGSPYFIQNVLTKIFEFQEPGMELEKLKVSLQSPS
SSKDKISSSLEDLILVLKEYPFSHPLWEDTVRFARRLYFNRLEFWKELALRLWEAAEDESRKISSVHLRWYWSRQRDLYDLSFL
AALKQGNPNLAAQVTDSAKSRPALSWQAIERLKHGNEELKDEIENYAQALSGGYIKGLLKPYRKPEVPNEEKPFFEQHLIDNNL
IAIQFYLVHLEEFEKVERSRERGYALIYDQESEKKWSFKTFDFAPIWEKYVAWQSVYFDLPPQQRDASGTQLRYLCEALGKALE
FLFKSPEKQFSSNEKSKDILFIPHDFLHRVPLHGAMLDNENVLLKTFNCFYLPAISYSAKNQGPQQNKNSVLLYYSGKSEESDD
PLFNHLKTKFDTPINFASATDLLDAAQNPPSLLVLYCHGEADATNPYLSRLKLKDDLMLLDFASAAGTFTGSKIFLGACETDLM
PPLDAPLDEQISMATIFLIKRSESVIGSMWEAKRMKVLNLLFMKEGLFDHFFEQQREWWKEEYEHTDSNTALYDCLCFRMYRCY
F (SEQ ID NO: 8)

>3300001095|JGI12104J13512_1001353_7|M
[bioremediation-terephthalate-wastewater bioreactor]
MFGGVEKNCLALSLGRHEKRQIYKSILAAGGLLLAQPADETFLPMITKYYREILAAEVKLAFCLPDEAHNVVYKRDEACRELVQ
ACRNQAGGLTEQGYQYLGSALLFLSGGLGEAPGLVALPVLSQELCEALASREADIHAFHARQGLEVAAAIIERAREPQWQHAQR
RQALEAVIKDLQQRSAICPPDLQDRLRLLLAQAYLERSRIIRPKGFTISPKKKEALDKALEQLDQVTDTGKTTLDYHRFRGDIF
LELGRLEARTGKEIEACLAEAILFLDPRTPANLTPVDCRLIVAYARLARDPSYLPLVLGSSKATALDRAWAAYLSNNASGAAKE
INTVLQDLQRRWFSHPDWEGLVDLLVDWARSSQKGWEDLATAAWQVCQKNEQELRYSGCQLRWYWSRHQDLYDLAFQAAPTLEE
KARVADSLKSRPLVRLALAEQLAQAQAKKKRGADVDFAQLIEQDARAYANQYIAGGLAAGSASAPVAPLSFTELPDEQWLAVHF
YLSSGAAAGLKKNMAYALVYDAKDQKWSCEGPYETTDLWQAYRRWQDNYAAVSQASAPELESLCRQIGTTFPPFLWALPSERPVV
FIPHGFLHRLPLHMALREDGATLEVWAATHPSTYLPAWSLRPRADAGGSQNVAAVYLPDELHDAEDFQNILAGQSFAAAASWPV
FRKQAGQARRLALVCHGLAHAVNPFAARLLLPEEPQLVDFLTDLPALPGSQVFLAACEADMAPAQEAPLDEHLSLATAFLQKGA
REVLGGVFEVNKYLANELLSSFGATSAAACYSLLWKWQQARLDNFLDNPDPLNLYWLAPWRVLGLS (SEQ ID NO: 9)

>3300020048|Ga0207193_1004003_10|P
[aquatic-freshwater-freshwater lake sediment]
MTETNHLSSDYQKAITLETKLAFLRPTQEQDTIESTRRELAETLSRLVNQKISPETLSAITTLHGMDLQGLGVLSGSLPNKDRC
AFAGNKKKFSAAWEFHWLQRIDLMRKIIDKASGQDDKLSHASRRQALGVAINSLEKAIAEIGDTGILVSKARLDLARALFHRGR
IVRPKGFSVPGKKKELFLKALDQIRIATNNKDDDQTLFLKAEIYLEWLRFFPMELPEDLDVVFKAAQQKADEPLKTNLILMIGE
RGSAKPIELEALQNIEVDEKQEPLTRARAAAISGNWDICAKYLSEAIKKLEIKSFFHQDWEEAVELLKKGRTKISNYQWATICK
SLWKLTVQKENRTSNGCHLRWYWSRQREVYDLAFEAAGNDYSKKAKITDSLKGRPALHFAQMETIAEGEDEIKTWIEHQEAGFL
NQYISAFESADQGKKPGNLSWPKLPKGWIAVHFYLGLGTCSGEKKGYALIQNGQDWYQRTFDYEVLWVAYLAWQTMYGKCGHLD
DILKQQEVLSPVVESLCEQIGKEMPWLFDPGLFPEGQAVVFIPHDFLHRLPLHMALDPKPDPGKAQLFLSLHLVLSLPAWWQAS
ETNSPPAPDTVKANEKIFLANFENPSDAFQSLIDAIPKSVKVERVAKKSNLLEANSPSLLVVYCNGEAQPGNPFASRLLFSDSG
LPVSGILGSTINLRRSNIILGACETDLMLALNKTLDEHITLSSAFIQKGAELVSGTLWKIHENDEIDFIKLALVENSSLHEQWL
KWYDTNIKAYENDPKNNPRVFYKAAAIRIVGKPWTIEDIGK (SEQ ID NO: 10)

>3300001096|Ga0067045_1003547_9|P
[bioremediation-terephthalate-wastewater bioreactor]
MAQPADETFLPMITKYYREILAAEVKLAFCLPDEAHNVVYKRDEACRELVQACRNQAGGLTEQGYQYLGSALLFLSGGLGEAPG
LVALPVLSQELCEALASREADIHAFHARQGLEVAAAIIERAREPQWQRAQRRQALEAVIKDLQQRSAICPPDLQDRLRLLLAQA
YLERSRIIRPKGFTISPKKKEALDKALEQLDQVTDTGKTTLDYHRFRGDIFLELGRLEARTGKEIEACLAEAILFLDPRTPANL
TPVDCRLIVAYARLARDPSYLPLVLGSSKATALDRAWAAYLSNNASGAAKEINTVLQDLQRRWFSHPDWEGLVDLLVDWARSSQ
KGWEDLATAAWQVCQKNEQELRYSGCQLRWYWSRHQDLYDLAFQAAPTLEEKARVADSLKSRPLVRLALAEQLAQAQAKKKRGA
DVDFAQLIEQDARAYANQYIAGGLAAGSASAPVAPLSFTELPDEQWLAVHFYLSSGAAAGLKKNMAYALVYDAKDQKWSCEGPY
ETTDLWQAYRRWQDNYAAVSQASAPELESLCRQIGTTFPPFLWALPSERPVVFIPHGFLHRLPLHMALREDGATLEVWAATHPST
YLPAWSLRPRADAGGSQNVAAVYLPDELHDAEDFQNILAGQSFAAAASWPVFRKQAGQARRLALVCHGLAHAVNPFAARLLLPE
EPQLVDFLTDLPALPGSQVFLAACEADMAPAQEAPLDEHLSLATAFLQKGAREVLGGVFEVNKYLANELLSSFGATSAAACYSL
LWKWQQARLDNFLDNPDPLNLYWLAPWRVLGLS (SEQ ID NO: 11)

>OGR07204.1
[terrestrial-soil]
MNQNIDRAVGAILAIETATPLTESSTLAQRERHQKLLHDETKKIEQAFIALAQPPQCRAVEIAALSRFLQMTPLAVGPLRKRVI
CRAEPLKDDAHEQEIASHFNGLLLRLAKGLLASALNPAGIPWRRRVLWLEKAAHIAHRFDKEPLADDKERTEAAGVLARCCLHL
ALAHLPKGKDKSAMAERQEDLLQSLMWAQKAIVLAGQDKLSGEEYKLLKALVLIELDNLSPGRFQQQLNYVLYDLAVIWLERDT
ATKPFHPQELFVLWRYLATDFEPDLNMLLFKGSNTSERTAAVQQASPEAERFRPLLPLIHAWSAWKLDPPNNKIAEVILQAVNN
LDEHQVYEQVWKWTVDFPLQELRNTGAVDWQLPAIAAWELCNKKEKELPFGFQIRQYWSRLDSLYRLAFDGALELKDCMTAARIV
DSLKSRTPLTWRDMDTLFAKLPKEKADQLREAFYSMEVQARMGFYAEAKEDANKLKKLLAAQVRKIRDIESVPAGWTVVHFHLR
EDQDLGYALACRLTADGMSYWTNHIFPVAGIRRAYDCWLEAYHGMRGEARREKSGYQLVELSEIMGKDLDFLFELAGEDGARGLL
FVPHGFSHLLPLHAAKKDGSYLFEKIPSLTLPAWEFAPDVDQIPVSDGQDFCFISQRANEQDLVGNIERSHTWNGVCNKNAAWT
NVLNTNKEWSKAPPRWLVFEWCHGQADPHVAFRSKLLLGTLGVSLFEIQEAALSLTGTKVVLAVCESDLAPPEEYEKTDDHLSLA
APFLLKGARQVLAAIWEGAQLDLLKAMKEMLSNQDKHSWEILRELQSCWMRPGAIFNDEYIRLYYAASFRILGFPEVATTNMA
TATAQEEIA (SEQ ID NO: 2)

>3300028595|Ga0272440_1002488_3|P
[aquatic-marine-marine sediment]
MVSMQQSACNEIKNLENSIDKDVSELAEALSHFVQANLQPQTALCQRGIPDKNNAVLKIHKAHNTDIVFSTLFNILEKRLVVYE
SEVYDESKSSKKNMNHRQRRQMLEDIIQALIPLKKKVSDSELKLEKLERKESDSVTKLKSDIAQFNYIYAKVYFYRSLLFRPKG
RSIPARKIEAIQEAYSPIKKSLNLSETLSSWRLLGKITLELLSLNEPYLSDDIISSGLHIDENFCLENNSFILRNDIQTLLTFS
EITKDVSFVEKIPTFENINIKKKDKDYLLLLIFARIAFLRNKINESDTLLTKAISNAPEAFANPFWDDLVDFITCLKRNNCHVW
KKAAIDAHKACYKNETEIGNIYLRWYWSRQSDLYDLAFISENKLEEKARIADSLKSRPILGFQALNNMKKNIDILEQILEQENE
ARDNKYLKKIHSKSRKIFKKEKFIDFKLLDNHWMVIHFYLNELEQCGYALIFDCETKNTNIQTFRYNELFNTFLSWQETELHEQ TABLE 2-continued Amino Acid Sequences of Representative Type III-E (CLUST.019911) Effector_A Proteins KQKENNEEIFNKDLIQRGKSIHELCCEIGKTMPFIFELPENKSILWVPHGFIHRLPLHAAISIQTNAFLFEKHESRYLAAWHQL
NLKNFGNGEGKHFLRSGGSKFKTITKKCKTDKWEMVKRKANQKHFFESLNKNLKTLVIICHGECDITNSFQSCLEISASSVGES
DSNGLINPLEKKSITILDLLKSENNIKGCRIFLGACESDMASPIEFIVDEHLSLSAVLLSLGAKEVIGGLWKLYDIFVEDCYHQ
LLDSNNLSQSLNEWQLNMAKEWKEDKTDMRYLKLYSFASFRVTGFLPQKKQEP (SEQ ID NO: 12)

>SRR8490538_megahit_k177_234425_6|M
[anammox bioreactor]
MKNRVQIEAIIRNLQGAARDSKTNKLSENIIAYDEYRKIHKSASLYQFGIIPAKESSSVLAENETNHVAYENAIFEMAEKNIEN
FSSEDIHKKRKEMIESALRLLMGLYKDRHEKLQPRTFVLIAKAYLLRSLITRPKGITIPEKKKEALKKGIGFVESAIKKIQSSE
NILSHSSDIDLLEKAWRIKSQLYLEYYRVNKDECDKNTLKEVLENSLISGCDKFDKNIEDVQIAIRYCELESSREYLEQIISSH
LEGIEFEKARAYKLLELENENEDEIRKSMKVVIEEYLSGFSDPLWEDAVEFINKLKSDNKNCWKELSLDMYKVCREQEAETASL
HLRWYWSRQRRLYDLAFIAADKEEEKAKIADSLKSRLSLRWSALEETGKKSKNKREKEEISRILEAEAVAMLGGYIKGARKILK
KRRRPLPDEQRSIPKDWIVIHFYVNQLENKCYALIYNKDENTWKCEFVKEYQRLFHVFLTWQTNYNRCKERAADSLVQLCKEIG
NAMPFLFDECIIPQDKNVLFIPHDFLHRLPLHGAIHEKNNGVFLENHPCCYLPAWSFTAKENNAVVQGSILLKNFPEYSYEELV
SNSTLWTSPVKDPASPDDLKTIIASPEMLVILCHGEADAVNPFNARLKLTGNGISHLEILQSTKMILKGSKIILGACETDLVPP
LSDIMDEHLSIATAFLTNGTHEILGTMWQSRPEDIEDIIRLLCDKKTSDTKARGDLWNWQKERIRDYWAGEDAMFYRSVAFRII
GLTI (SEQ ID NO: 13)

>SRR6011893_megahit_k177_1702441_3|P
[dolphin oral metagenome]
MNTVELLQEEERLTLDLVFLPPGSKNKEQKKNALVDLLLKIVEHGELTRKYSALLTLSRGALRGEVHFGEKLLPSPEACANLAK
PEEIKKMIRQHFQYRLDLLEAIVKKAADNTYSHARRRKALRIAIKELEQICEEALDELCFKARLLLAEALFERGRIVRPKGFSE
PGKKKELFQKAINCIEGNCSEEALRLRARIYLQWYRFFHDEPPCDLDDIFTKALAVTDDKMLKTELLLLCGERKEPDPYTDDLR
ALLNDQNVSPLSRARAAVLLEDWERCNVEIYEAIEDLGKTDFFQQDWELVVTLLKKNYNQFHGWSRACTRLWEITVEKESKDAG
HGCVLRWYWSRQRDVYNLAFAAFEECEDKARVVDSLKNRPAHHFSVQLEQLAQSSDIIKQWIESEEIINQDSFAHSLRRHEKGAK
SHSGGSLRIFPCLPKGWIAVHFFLASWPEPKGYALIHNADTNTWEQRDFKYEQLWATYIAWQEVSLHNKIRESALLLKSLCETL
GKEMRWLFDEFLFPKERRRVLFVPHDFLHRLPLHMAIDIESQTVFAAKQPVCYLPAYHLQNNITENKKTSIYALVNLRENKQQK
KDEEIFAEKVEKMGAIVRRPALESDLLNLNPVPEKLVLYCHGIGHSANPFASKLCLGDTGVSYRDILALNRSLAGCRVLLFACE
TDLVPAQTSSIDEHLSISNALLQKGAFEVLGSLWALPGKTIYGITKTFIDNDDTSAVLHSSLKRLFEHYEKKNEKTRAQLLYNW
ASLRVLAPAREFS (SEQ ID NO: 5)

TABLE 3

Amino Acid Sequences of Representative Type III-E (CLUST.019911) Effector_B Proteins >JRY001000185_8|M
[Candidatus Scalindua brodae]
MKSNDMNITVELTFFEPYRLVEWFDWDARKKSHSAMRGQAFAQWTWKGKGRTAGKSFITGTLVRSAVIKAVEELLSLNNGKWEG
VPCCNGSFQTDESKGKKPSFLRKRHTLQWQANNKNICDKEEACPFCILLGRFDNAGKVHERNKDYDIHFSNFDLDHKQEKNDLR
LVDIASGRILNRVDFDTGKAKDYFRTWEADYETYGTYTGRITLRNEHAKKLLLASLGFVDKLCGALCRIEVIKKSESPLPSDTK
EQSYTLKDDTVEVLSEDHNDELRKQAEVIVEAFKQNDKLEKIRILADAIRTLRLHGEGVIEKDELPDGKEERDKGHHLWDIKVQG
TALRTKLKELWQSNKDIGWRKFTEMLGSNLYLIYKKETGGVSTRFRILGDTEYYSKAHDSEGSDLFIPVTPPEGIETKEWIIVG
RLKAATPFYFGVQQPSDSIPGKEKKSEDSLVINEHTSFNILLDKENRYRIPRSALRGALRRDLRTAFGSGCNVSLGGQILCNCK
VCIEMRRITLKDSVSDFSEPPEIRYRIAKNPGTATVEDGSLFDIEVGPEGLTFPFVLRYRGHKFPEQLSSVIRYWEENDGKNGM
AWLGGLDSTGKGRFALKDIKIFEWDLNQKINEYIKERGMRGKEKELLEMGESSLPDGLIPYKFFEERECLFPYKENLKPQWSEV
QYTIEVGSPLLTADTISALTEPGNRDAIAYKKRVYNDGNNAIEPEPRFAVKSETHRGIFRTAVGRRTGDLGKEDHEDCTCDMCI
IFGNEHESSKIRFEDLELINGNEFEKLEKHIDHVAIDRFTGGALDKAKFDTYPLAGSPKKPLKLKGRFWIKKGFSGDHKLLITT
ALSDIRDGLYPLGSKGGVGYGWVAGISIDDNVPDDFKEMINKTEMPLPEEVEESNNGPINNDYVHPGHQSPKQDHKNKNIYYPH
YFLDSGSKVYREKDIITHEEFTEELLSGKINCKLETLTPLIIPDTSDENGLKLQGNKPGHKNYKFFNINGELMIPGSELRGMLR
THFEALTKSCFAIFGEDSTLSWRMNADEKDYKIDSNSIRKMESQRNPKYRIPDELQKELRNSGNGLFNRLYTSERRFWSDVSNK
FENSIDYKREILRCAGRPKNYKGGIIRQRKDSLMAEELKVHRLPLYDNFDIPDSAYKANDHCRKSATCSTSRGCRERFTCGIKV
RDKNRVPLNAANNNRQYLNNIKKSNHDLYLQYLKGEKKIRFNSKVITGSERSPIDVIAELNERGRQTGFIKLSGLNNSNKSQGN
TGTTFNSGWDRFELNILLDDLETRPSKSDYPRPRLLFTKDQYEYNITKRCERVFEIDKGNKTGYPVDDQIKKNYEDILDSYDGI
KDQEVAERFDTFTRGSKLKVGDLVYFHIDGDNKIDSLIPVRISRKCASKTLGGKLDKALHPCTGLSDGLCPGCHLFGTTDYKGR
VKFGFAKYENGPEWLITRGNNPERSLTLGVLESPRPAFSIPDDESEIPGRKFYLHHNGWRIIRQKQLEIRETVQPERNVTTEVM
DKGNVFSFDVRFENLREWELGLLLQSLDPGKNIARKLGKGKPYGFGSVKIKIDSLHTFKINSNNDKIKRVPQSDIREYINKGYQ
KLIEWSGNNSIQKGNVLPQWHVIPHIDKLYKLLWVPFLNDSKLEPDVRYPVLNEESKGYIEGSDYTYKKLGDKDNLPYKTRVKG
LTTPWSPWNPFQVIAEHEEQEVNVTGSRPSVTDKIERDGKMV (SEQ ID NO: 14)

>OGR07205.1
[Deltaproteobacteria bacterium RIFOXYD12_FULL_50_9]
MTKKPGTEDKATLWGKESASKSVKTILEESIQGFFTVEQKRSFFANLADQLVSRAGEQGAKSVRSQGLIIGRKENYAKPSAQEPT
RHHLYRQPSNASAFLATGWLIAETPFFIGSGTEGQKQTDDQAESLHLRTLRDGHGRFRIPFTTIRGVMDKELRDILQAGCAKGR
SLRAPCPCQVCTLMRRIQVRDAIAADILPPDLRMRTRIDPSHGTVAHLFSLEMAPQGLKLPFFLKLKGVETIDPDKELLEILND
WSAGQCFLGGLWGTGKGRFRLDDLQWHRLELDNADYYTPLLQDRFFAGETISDLRQGLQSINIQPERIPAQTPSRNMPYCRVDC
ILEFKSPVLSGDPVAALFESDAPDNVAYKKPVVQYDETGRLRTTDPGPVEMLTCLKGEGVRGVVAYLAGKAYDQHDLSHDSCNC
TFCQAFGNGQKAGSLRFDDFMPVQFESDQAGNFSWSPHTPHAMRSDRVALDVFGGAMPEAKFDDRPLAASPGKPLNFKSTIWYR
EDMGKEAGKALKRALIDLQNNMAAIGSGGGIGRGWVSRVCFEGDIPDFLEDFPEPITVTEPEQDSQLLKNQAVADETAVSACDT
ADAPHPLAVTLEPGARYFPRVIIPRAPTVKRDECVTGQRYHTGRLSGKIFCELNTLGPLFVPDTDYSAGVPVPISDEQLAECQL
QAVFENTSKFNEFFATYPEETVTKLKDLLCAADDKWILAVKDITADLRQEIGEDTFQRIIRKAGHKTQRFHQINDEIGLPGASL
RGMVLSNYQILTNSCYRNLKATEEITRRMPADEAKYRKAGRVTVSGDGAQKKYSIQKEMEVLRLPIYDNMNTPDNMPDVAKQATT
AKRCNNLMNEAAKTSRVELKARWREGQSKIKYQIIDALNKVDPIIQVISSSKQINPNNGKTGWGYVKYTGANVFAKSLVAPIDC
LRKKDAGHVCCQVNLNPAWEASNFDILINEKCPVERQSGPRPTLRCKGQDSAWYTLTKRSERIFTDKKPVPDPINIPPREVKRY
NELRDSYKKNTAHVPKPLQTFFNQESLANGDLVYFEVNQFGEASQLTPVSISRTTDLFPIGGRLPQGHKDLFPCTAMCLSECKN
CVPASFCEFHSRSHEKLCPACSLAGTTGNRGRIKFSEAWLSGLPKWHSVSQDNVGRGLGVTMPRLERSRRTWHLPTKDAYLLGQ TABLE 3-continued Amino Acid Sequences of Representative Type III-E (CLUST.019911) Effector_B Proteins SIYLNHPVPAILPSDQVPSENNQTVEPLGPKNIFSFQLAFDNLSIEELGLLLYSLELESGMAHRLGRGRALGMGSVQISVKDIQ
IRDNKSFLFSSNISKKSEWIQCGKDEFAQEAWFGESWDNIDHIQRLRQALTIPVKGDVGCIRYPKLEAEGGMPDYIKLRKRLTP
LCDREEPVRYRINPVQLARMILPFVPWHGACPALLNEQVMIEAKRLTELXXXDRANWPC (SEQ ID NO: 15)

>WP_124327589.1
[Desulfonema ishimotonii]
MTTTMKISIEFLEPFRMTKWQESTRRNKNNKEFVRGQAFARWHRNKKDNTKGRPYITGTLLRSAVIRSAENLLTLSDGKISEKT
CCPGKFDTEDKDRLLQLRQRSTLRWTDKNPCPDNAETYCPFCELLGRSGNDGKKAEKKDWRFRIHFGNLSLPGKPDFDGPKAIG
SQRVLNRVDFKSGKAHDFFKAYEVDHTRFPRFEGEITIDNKVSAEARKLLCDSLKFTDRLCGALCVIRFDEYTPAADSGKQTEN
VQAEPNANLAEKTAEQIISILDDNKKTEYTRLLADAIRSLRRSSKLVAGLPKDHDGKDDHYLWDIGKKKKDENSVTIRQILTTS
ADTKELKNAGKWREFCEKLGEALYLKSKDMSGGLKITRRILGDAEFHGKPDRLEKSRSVSIGSVLKETVVCGELVAKTPFFGA
IDEDAKQTDLQVLLTPDNKYRLPRSAVRGILRRDLQTYFDSPCNAELGGRPCMCKTCRIMRGITVMDARSEYNAPPEIRHRTRI
NPFTGTVAEGALFNMEVAPEGIVFPFQLRYRGSEDGLPDALKTVLKWWAEGQAFMSGAASTGKGRFRMENAKYETLDLSDENQR
NDYLKNWGWRDEKGLEELKKRLNSGLPEPGNYRDPKWHEINVSIEMASPFINGDPIRAAVDKRGTDVVTFVKYKAEGEEAKPVC
AYKAESFRGVIRSAVARIHMEDGVPLTELTHSDCECLLCQIFGSEYEAGKIRFEDLVFESDPEPVTFDHVAIDRFTGGAADKKK
FDDSPLPGSPARPLMLKGSFWIRRDVLEDEEYCKALGKALADVNNGLYPLGGKSAIGYGQVKSLGIKGDDKRISRLMNPAFDET
DVAVPEKPKTDAEVRIEAEKVYYPHYFVEPHKKVEREEKPCGHQKFHEGRLTGKIRCKLITKTPLIVPDTSNDDFFRPADKEAR
KEKDEYHKSYAFFRLHKQIMIPGSELRGMVSSVYETVTNSCFRIFDETKRLSWRMDADHQNVLQDFLPGRVTADGKHIQKFSET
ARVPFYDKTQKHFDILDEQEIAGEKPVRMWVKRFIKRLSLVDPAKHPQKKQDNKWKRRKEGIATFIEQKNGSYYFNVVTNNGCT
SFHLWHKPDNFDQEKLEGIQNGEKLDCWVRDSRYQKAFQEIPENDPDGWECKEGYLHVVGPSKVEFSDKKGDVINNFQGTLPSV
PNDWKTIRTNDFKNRKRKNEPVFCCEDDKGNYYTMAKYCETFFFDLKENEEYEIPEKARIKYKELLRVYNNNPQAVPESVFQSR
VARENVEKLKSGDLVYFKHNEKYVEDIVPVRISRTVDDRMIGKRMSADLRPCHGDWVEDGDLSALNAYPEKRLLLRHPKGLCPA
CRLFGTGSYKGRVRFGFASLENDPEWLIPGKNPGDPFHGGPVMLSLLERPRPTWSIPGSDNKFKVPGRKFYVHHHAWKTIKDGN
HPTTGKAIEQSPNNRTVEALAGGNSFSFEIAFENLKEWELGLLIHSLQLEKGLAHKLGMAKSMGFGSVEIDVESVRLRKDWKQW
RNGNSEIPNWLGKGFAKLKEWFRDELDFIENLKKLLWFPEGDQAPRVCYPMLRKKDDPNGNSGYEELKDGEFKKEDRQKKLTTP
WTPWA (SEQ ID NO: 16)

>OBJA01001127_4|M
[soil metagenome]
MRLKINIHFLEPFRLIEWHEQDRRNKGNSRWQRGQSFARWHRRKDNDQGRPYITGTLLRSVVIRAVEEELARPDTAWQSCGGLF
ITPDGQTKPQHLRHRATVRARQTAKDKCADRQSACPFCLLLGRFDQVGKDGKRLRFDVRFSNLDLPKDFSPRDFDGPQEI
GSRRTINRVDDETGKAHDFFSIWEVDAVREFQGEIVLAADLPSRDQVESLLHHALGFVDRLCGARCVISIADQKPAEREERTVA
AGDEKATIADYDQVKGLPYTRLRPLADAVRNLRQLDLAELNKPDGKFLPPGRVNKDGRRVPHYVWDIPLGKGDTLRKRLEFLAA
SCEGDQAKWRNICESEGQALYEKSKKLKDSPAAPGRHLGAAEQVRPPQPPVSYSEESINSDLPLAEWIITGTLRAETPFAIGMD
APIDDDQTSSRTLVDRDGRYRLPRSTLRGILRRDLSLASGDQGCQVRLGPERPCTCPVCLILRQVVIADTVSETTVPADIRQRI
RRNPITGTAADGGLFDTERGPKGAGFPFSLRYRGHAPMPKALRTVLQWWSAGKCFAGSDGGVCGRFALDNLEVYRWDLGTFAF
RQAYSENNGLRSPEEEFDLAVIHELAEGLAKEDGQKILKGTEPFTCWQERSWQFSFTGPLLQGDPLAALNSDTADIISFRRTVV
DNGEVLREPVLRGEGLRGLLRTAVGRVAGDDLLTRSHQDCKCEICQLFGSEHRAGILRFEDLPPVSPTTVADKRLDHVAIDRFD
QSVVEKYDDRPLVGSPKQPLVFKGCFWVQTSGMTHQLTELLAQAWRDIAAGHYPVGGKGGIGYGWINSLVVDGEKITCRPDGDS
ISLTTVTGDIPPRPALTPPAGAIYYPHYFLPPNPEHKPKRSDKIIGHHTFATDPDSFTGRITCKLEVVTPLIVPDTEGEQPKDQ
HKNFPFFKINDEIMLPGAPLWAAVSQVYEALTNSCFRVMKQKRFLSWRMEAEDYKDFYPGRVLDGGKQIKKMGDKAIRMPLYDD
STATGSIKDDQLISDCCPKSDEKLQKALATNQKIALAAKHNQEYLAQLSPDEREEALQGLKKVSFWTESLANNEAPPFLIAKLG
EERGKPKRAGYLKITGPNNANIANTNNPDDGGYIPSWKDQFDYSFRLLGPPRCLPNTKGNREYPRPGFTCVIDGKEYSLTKRCE
RIFEDISGGENQVVRAVTERVREQYREILASYRANAAGIAEGRTRMYDTEELRENDLVYFKTAKQADGKERVVAISPVCISRE
ADDRRPLGGKRLPAGFQPCSHVCLEDCNTCSAKNCPVPLYREGWPVNGLCPACRLFGAQMYKGRVNFGFARLPDDKQPETKTLTLP
LLERPRPTWVLPKSVKGSNTEDATIPGRKFYLRHDGWRIVMAGTNPITGESIEKTANNATVEAIMPGATFTFDIVCENLDQQEL
GLLLYSLELEEGMSHTLGRGKPLGFGNVRIKVEKIEKRLSDGSRREMIPPKGAGLFMTDKVQDALRGLTEGGDWHQRPHISGLR
RLLTRYPEIKARYPKLSQGEDKEPGYIELKSQKDENGVPIYNPNRELRVSENGPLPWFLLAKK (SEQ ID NO: 17)

>PDWI01005922_5|M
[oral metagenome]
MIPDLRSLVVHISFLTPYRQAPWFPPEKRRNNNRDWLRMQSYARWHKVAPEEGHPFITGTLLRSRVIRAVEEELCLANGIWRGV
ACCPGEFNSQAKKKPKHLRRRTTLQWYPEGAKSCSKQDGRENACPFCLLLDRFGGEKSEEGRKKNNDYDVHFSNLNPFYPGSSP
KVWSGPEEIGRLRTLNRIDRLTTKAQDFFRIYEVDQVRDFFGTITLAGDLPRKVDVEFLLRRGLGFVSTLCGAQCEIKVVDLKK
KQNNKEDSILPVSEVPFFLEPEVLAKMCQDVFPSGKLRMLADVILRLREEGPDNLTLPMGSQGLGGRLPHHLWDVPLVSKDRET
QTLRSCLEKIAAQCKSEQTQFRLFCQKLGSSLFRINKGVYLAPNLKISPEPCLDPSKTIRTKGPVPGKQKHRFSLLPPFEWIIT
GTLKAQTPFFIPDEQGSHDHTSRKILLTRDFYYRLPRSLLRGIIRRDLHEATDKGGCRVELAPDVPCTCQVCRLLGRMLLADTT
STTKVAPDMRHRVGVDRSCGIVRDGALFDTEYGIEGVCFPLEIRYRGNKDLEGPIRQLLSWWQQGLLFLGGDFGIGKGRFRLEN
MKIHRWDLRDESARADYVQKCGLRRGVGDDTAINLEKDLSLNLPESGYPWKKHAWKLSFQVPLLTADPIMAQTRHEEDSVYFQK
RIFTSDGRVVLVPALRGEGLRGLLRTAVSRAYGISLINDEHEDCDCPLCKIFGNEHHAGMLRFDDMVPVGTWNDKKIDHVSCSR
FDASVVNKFDDRSLVGSPDSPLHFEGTFWLHRDFQNDVEIKTALQDFADGLYSIGGKGGIGYGWLFDMEIPRSLRKLNSGFREA
SSIQDALLDSAKEIPLSAPLTFTPVKGAVYNPYYYLPFPAEKPERCLVPPSHARLQSDRYTGCLTCELETVSPLLLPDTCREKD
GNYKEYPSFRLNNTPMIPGAGLRAAVSQVYEVLTNSCIRIMDQGQTLSWRMSTSEHKDYQPGKITDNGRKIQPMGKQAIRLPLY
DEVIHHVSTPGDTDDLEKLKAIVLELTRPWKELPEEQKKKRFEKCKNILDGRMLQQKELRALENSGFAYWRDKTSLTFDSFLKD
AIEQEYPRYSGDYQRIKALVVNITLPWKLLKKEERHKRFDKCRRILKGQPLTKDKERKALEESGFANWHGRELLFDRFLKDENS
CLIKAETTDRVIASVAKNNRDYLFEIKQQDFARYKRIIQGLERVPFSLRSLAKSKETSFQIACLGLRRGRFLRKGYLKISGPNN
ANVEISGGSHSNSGYSDIWDDPLDFSFRLSGKSELRPNTQKTREYPRPSFTCTVDGKQYTVNKRCERVFEDSAAPAIELPRMVR
EGYKGILTDYEQNAKHIPQGFQTRFSSYRELNDGDLVYYKTDSQGRVTDLAPVCLSRLADDRPLGKRLPEEYRPCAHVCLEECD
PCTGKDCPVPIYREGYPARGFCPACQLFGTQMYKGRVRFSFGVPVNSTRSPQLKYVTLPSQERPRPTWVLPESCKGKEKDVPGR
KFYLRHDGWREMWGDDDKPDSRPSSEECQDIIEGIGPGEKFHFRVAFENLDKNELGRLLYSLELDAGMNHHLGRGKAFGFGQVK
IRVTKLERRLEPGQWRSEKICTDLPVTSSELVISSLKKVEERRKLLRLVMTPYKGLTACYPGLERENGRPGYTDLKMLATYDPY
RELVVQIGSNQPLRPWYEPGKSFKPSPGNDCTGRGGSVSKSLISEPKVVPAIAPFCEGVVKWFNSVKGFGFIETKEQRDIFVHF
SAIRGEGYKILEPGEKVRFEIGEGRKGPQAINVIRIR (SEQ ID NO: 18)

>3300019457|Ga0193932_10482_5|M
[aquatic-marine-hydrothermal vent microbial mat]
MIINITVKFLGPFRMLEWTDPDNRNRKNREFMRGQAFARWHNSNPQKGSQPYITGTLVRSAVIRSAENLLMLSEGKVGKEKCCP
GEFRTENRKKRDAMLHLRQRSTLQWKTDKPLCNGKSLCPICELLGRRIGKTDEVKKKGDFRIHFGNLTPLNRYDDPSDIGTQRT TABLE 3-continued Amino Acid Sequences of Representative Type III-E (CLUST.019911) Effector_B Proteins

```
LNRVDYATGKAHDFFKVWEIDHSLLSVFQGKISIADNIGDGATKLLEDSLRFTDRLCGAICVISYDCIENSDGKENGKTGEAAH
IMGESDAGKTDAENIANAIADMMGTAGEPEKLRILADAVRALRIGKNTVSQLPLDHEGKENHHLWDIGEGKSIRELLLEKAESL
PSDQWRKFCEDVGEILYLKSKDPTGGLTVSQRILGDEAFWSKADRQLNPSAVSIPVTTETLICGKLISETPFFFGTEIEDAKHT
NLKVLLDRQNRYRLPRSAIRGVLRRDLRTAFGGKGCNVELGGRPCLCDVCRIMRGITIMDARSEYAEPPEIRHRIRLNPYTGTV
AEGALFDMELGPQGLSFDFILRYRGKGKSIPKALRNVLKWWTKGQAFLSGAASTGKGIFRLDDLKYISFDLSDKDKRKDYLDNY
GWRNRIEALSLEKMPLDRMNDYAEPLWQKVSVEIEIGSPFLNGDPIRALIEKDGSDIVSFRKYADDSGKEVYAYKAESFRGVVR
AALARQHFDKEGKPLDKEGKPLLTLIHQDCECLICRLFGSEHETGRLRFEDLLFDPQPEPMIFDHVAIDRFTGGAVDKKKFDDC
SLPGTPGHPLTLKGCFWIRKELEKPDEDKSEREALSKALADIHNGLYPLGGKGAIGYGQVMNLKIKGAGDVIKAALQSESSRMS
ASEPEHKKPDSGLKLSFDDKKAVYYPHYFLKPAAEEVNRKPIPTGHETLNSGLLTGKIRCRLTTRTPLIVPDTSNDDFFQTGVE
GHESYAFFSVNGDIMLPGSEIRGMLSSVYEALTNSCFRVFDEGYRLSWRMEADRNVLMQFKPGRVTDNGLRIEEMKEYRYPFYD
RDCSDKKSQEAYFDEWERSITLTDDSLEKMAERKGDISPKDLKVLKSLKGKNYKSTEGLLAAFKDKGGDTGGNILGLIFKYAER
IGDVPRYEHPTDTDRMMLSLSEYNRNQKSDGKRAYKIIKPASKLGKGAYFMFAGTSVENKRICNPACTDKANKSVKGYLKISGP
NKLEKYNISEPELDGVPEDRNCQIIHNRIYLRKIFVANAKKRKERDRLVGEFACYDPEKKVTYSMTKRCERIFIKDRGRTLPIT
HEASELFEILVQEYRENAKRQDTPEVFQTLLPDNGRLNPGDLVYFREEKGKTVEIIPVRISRKIDDSPIGKRLREDLRPCHGEW
IEGDDLSQLSEYPEKKLFTRNTEGLCPACRLFGTGAYKGRLRFGFAKLENDPKWLMKNSDGPSHGGPLTLPLLERPRPTWSMPD
DTLNRLKKDGKQEPKKQKGKKGPQVPGRKFYVHHDGWKEINCGCHPTTKENIVQNQNNRTVEPLDKGNTFSFEICFENLEPYEL
GLLLYTLELEKGLAHKLGMAKPMGFGSIDIEVENVSLRTDSGQWKDANEQISEWTDKGKKDAGKWFKTDWEAAEHIKNLKKLLF
LPGEEQNPRVIYPALKQKDIPNSRLPGYEELKKNLNMEKRKEMLTTPWAPWHPIKK (SEQ ID NO: 19)

>3300009529|Ga0114919_10000047_40|M
[aquatic-marine-deep subsurface]
MSDNRIDYDIKLTFFEPFRMSPWVKSHARAKSKTFFRTLSFVRWLETSPETKEGKEGDSIGVPFIPGTLLRSALLKEVEFLITL
KNKYDCCCGEFETPRQKRDEKKEQGRRFFGRVRKRPTYEFGNSQPCTDFENACPFCSILSRSFNNDDWFDDRGNPIVGKVPVHFSN
LDVTDSKLKRIRLSAIANQRIVNRVDFRSGKAQDYFKIWEVDNRLCPSFCGKITIRQDINQVDDLTCLLAAGLAKIKTLAGALC
RVDIIRDKTIDFHQRLIQKYVGPPGPPHNPTAHPTLPSQPTLSVDVHGLARTIAGTLTGSDKEAYLRRIADAVREMRNRKCSIL
HEPPFTKTGDKEPVWTIPAVQKALKETTACVARESWRLFCEELGEALYKKAKELKKKDEAIPRLLGDTEYYGQQAEAPVGTDYR
LTASALPKYEWIINGWLEARTPFFFGVGSASEQTSLAILLTRDHRYRLPRSVLRGALRRDLRTVIGSGCNVELGVDTPCDCDVC
RIMSRVIVMDSLSDYQEPPDIRHRIRINQHSGTVDEGALFDMELGPEGLRFPFRMYFSATCPTADVPLAKVLKMWQDRPAFLGG
DAGTGNGRFRLIKAKTRSEPFDWDGPKSSLNLLMARSYIDLEDHDTLLDSKLECAKAWKVKDELTSVWTDYQYEIDLHSPILSN
DPIAALLDPDWRDAVPVKKRVLQDGGLVPTEKYYIKGSGIRGILRTAVGRNCVNEDGIHLHNLPHDDCPVLCQLFGSEHHQGM
LRFEDAHFENDPMPETLDHVAIDRFTGRARDKFKFEDAPLIATPDQPIKLKGTFWLKRELHEASQEVFGKIDDFECKPKEDSDS
LLGAARALWCAFLDLKHGLFPIGSNGGIGYGWVSGLSVSEPDKNKKIPLGQLCRNEGAQETASTSGEKGEYNPSDAPNSLRQEG
HVFNPHYFLRSYRYEDKNGKIATHVERIDLPVTHEAYQDKLTGKITCKLNTRGPVFVADPSDLVVYFTAKEYEDFVKRWPKSAE
LLQSLVHEKDGMKLIPVKQIPKDSPEDGALKEISEHQGHKGYKFFRLNGSVMIPGSEIRGMVSSVYEALTNSCFRVFDQRRILS
KRMEADFRTVLTHFKAARVVPDNNSGSGLSVKEFTNMVRVPVYNCPQTFFDGLTQGQISGKEETKLWVKNYEWRISLCNPWTHH
SRKSKKEWEKNIPGRILNNQGDKIVLNISYKQEERKITLILDDKDRVVLDGITPKQLGGKEEIRLWLRISQYQKAFRKKPDNNG
GWKMQTGYLHIMGPNKVEIDSSGTSREGLQDLPETWKDAQCNSPDGKIFSGKDGNAVYTMNKYCEMFFYNEQKKSYRVPQAVLN
QYRQMIEESMSNPQAPPAIFRSKPIREKDTALKAGDLVYFRKNENREGEVDAVIPVRIYRESHRKPLGKRFPDGLHDLRPCTFE
CLDDCDKCPDRCNELKEFFNPHPKGLCPACRLFGTTSYKSRVSFGFARLCSEDKKAKWYGVEEDAEQGKPLTLPLLERPRPTWS
MPDKDAKIPGRKFYVHHPHSVDSSIRDMQFDPELSDKENQGKIRPMKNNRTVPLLDKNLAFGTNGCRAKLGLRRPCPCPVCNLL
ETGLAHKLGMGKAQGFGSVEIDVEKVEIRNGPGDWKSKTSHKITEWITKGKDKLEKWFKTDDWNNVDHIADLKKFLYFLDPQEI
KPKVRYPSLSRDDDKDHFPGYVDLKRKPSKEKPNPYYVPEDKRRALLTRPWEPWYVMPKSSMGTVKWFNEEKNYGFILRDNGE
DIFVHRSDINGSLGTLTEGQKVIFEVKQGPKGLQATNVKVIS (SEQ ID NO: 20)

>3300015370|Ga0180009_10000113_2|P
[aquatic-freshwater-groundwater]
MEYTLTLNFIEPFRLIEWHDAPDRENLRLRGFSFARWHKDREFGLGRPYITGTLIRSAVIRAVEEFLWLNNGKTGDVHCCQGEF
TKARFYRELTEKRLRRRQTLVWDNNGVCNQDQPCPFCLLLGRYWQPGPGYSENNDVNFGNFSIPQKKVVLLNLEDIAEPRIINR
VDQQSGKAEDFFEIREIDHRSCALFEGKISLSERAAENKALISLLNAALPLVNRISGALCYLTMEEVKVMDKSVNGGSDNLSGE
AMELKKSDRPGEGSHFARHPIGAEHASYEKIKTSAGEVVNAFEESNKLVHLRVFSDVIRELRRHDPRKLNLPGGHEDRSGKITD
HFLWDMKVESKPLRNWLPDKFNEFNEKHKLPWRIFCESLGQALFLEAKDKAPEQFTSARPLGAMVSTLESKEPEFLPGRSRQGP
RYEWLMRGQLVAEVPFFFGWSVDKNDTDHISMRLLSARDGRLRLPRSALRGILRRDLNLAFGTNGCRAKLGLRRPCPCPVCNLL
KNITIRDSLSDYKRPPQIRHRIRLDHRSGTVAKGALFDMEVGPTGAIFPPFELRLRSTSDKFSKELEQVLLWWKQGLAFLSGAGG
TGKGRFRLKELKCIFWDLQNDAGFAHYKETYGGRKKRISDDELIPWQVTSGDPVSEPPWTAWEINFLVCSPFLTKDPVESLLDP
GGTDAVCYRAVYLGENGGIKKRYLLKGESFRGILRTAVGRRENSLLKEHEECDCVLCRLFGNEHEAGKIRVEDLLIQDEPKEKN
LDRVAIDRFTGGARDKHKFDQKPLTGTPAFPLVLMGKIWIKNDLTDDDKAILKQALEDIRCGLYPFGGLGNVGFGWVNYLTCNS
DFEQNFDSMNLCFSDKVKVENEPDKIYWPHYFIPFGPKVVRENKPPGHAYPKTEFHSGRLICSLKTLTPLIIPDGQPASQEANG
HKSYNFELSGELCIPGSEIKGMISSVYEALTNSCMRIFEEKKRLSWRMKAENLDQWSPGRITEEADELFVEEMEEIRLPLYDN
PDLLPNIKKEGEKGFYRTKKIRDSNGRERLKKGQPTGTDSLINIHSAEIREFLKENKHLSSGQIPTKWFRCFPHPGKRGFDGLA
LLKIPKEWHNKNTSGWIAEGYVNLTGTNKVETRRSGKGISIRETSKDEQINIIHNEVTLEEKPVNSSKLGQVLRKRAIPKYVTY
KNGYEYTMTKRCERIFIPLQKPTKHIVSRNVENKFLQLCEEYKQNAELKIYFRQELGEVVEIIPV
RISRAVDDEVLGEKFVNDDFRPCVREILNRETEKKITSAGFKEVFHHHPKGLCPACAIFGTTFYKGRVSFGFAYLKNNETKLVE
NGAYITLPLLERPRPTWAMPTKDSKVPGRKFYVHHQGWKNIVEDSKNESTEKNENNRSVQAIDRNQVFLFEVRFENLRPWELGL
LIYSLQLEPKLAHKLGMGKPLGFGSVKIKVENVTSSRQKDVNDNTLPEAVEKELKEIWGKETEPDFTRSLEGLYKALHYESKNG
IQVRYPKLEKEKKDDPGEKPGYLELADGPFSTENRKEKLKEIWGNWA (SEQ ID NO: 21)

>3300001095|JGI12104J13512_1001353_10|M
[bioremediation-terephthalate-wastewater bioreactor]
MNRYKVSLEFLEPWRINHLGDDRGAAWARWVQTREGYQRPEITGTLVRSAVIRAAEELLALTGGVWAGQKCCPGEFCTPGGSKP
TFRRQRATRWWGEDSLCTPDSPCPFCQLLGRHDLAGKQARRGGGFHVHFGNLYPVAREGYGSLAEITRQRTSNRLDWLTGKAQD
ILTICEVEELRRFSGLITVAPELANGEAVSSLLTAAAALVDRLSGAACRLKLQPVEELWSGTAVSLTRAAVPETAYRQQLEEDI
DNYFQELIGDGSQLGPERLRLLADAIRELRYLPPEQTLPDWLQSLPQGKDGKAHRLWDALTAQRRPLRNMLQEVAAAYAAPATW
RDVVQGLGQALYAHYKKLWPQAMPVRPVGEAEYWQTKFRDRQPSRQRGTWSHEWIITGALQTLTPLYLGTQVEAARQTSLTVLL
TAEGRYRLPRTALRGALRQDLQLASRGQGCLMELNPERPCSCPICQIMRRLTVRDVTSSIALPPPLVRQRVRRNPWTGIVDEGA
LFDQEVAPEGLRFPFILRYRGFGGLDAWLQTVLSWWQEGRLFLGGAGGTGKGRLRLTDLRIWRWALDETGLPTYVAHLGYRGRE
EELANSASLPAGVEAVTCSDPATVPSPWQEVDWEFRFHGPVLANHPLTALLRGEADAVFTWKVQLEADQQHYREVCTLKGETVR
GLVRGLFGKSQGLLTKAHADCTCLLCRVFGNEHQRGKVRFEDLTLAGETVPKKRLDHVAIDRISGGAAEQLKFDTQPLYGTPEN
PLVFAGKFWVHTELDEEEQKALRAALTALRDGLATVGAKGSVGYGWLNGLRLHSGPAWLTDNWQETAAAPSDTNTPPEFSWPQL
```

TABLE 3-continued

Amino Acid Sequences of Representative Type III-E (CLUST.019911) Effector_B Proteins PDLTLDSRKIYYPHYFLPPDLQVPRLSQPHTHSLFDPQKYTGWLTCRLTTLTPLIIPDTSSDQTLTTGGPFPAGHQAFQFFRLG
DQPLIPGAELRGMISSVFEAITNSCFRVIRPRERLSWRMPAALAPQFRSGRVEIVNNQYYIRQMDMGRLPLYDDPATRRLFTPL
SLTSGHTLDFVDDNRTLLQSNPGIREGAIRTDLCFLNRFWLLRPPSAARCPRGNFSLTSGYVKFTGPNKVEVSRAGAGAGGLPA
PPADWTGVRLNQVAGNVPFYQAEQSGVIFTVNKRRERFFISRGNARSYPVPLATLKRYEQVLKEYRHFAQRGEVPAVFRTVLPD
VRHGASGYNRLNNGDLVYFRVKDDRWNDQNAPVEHIIPVSISRLVDQKFLGERVPEPLRPCAHVCLEECEACLKQESCPSSFYR
EGTPSRGLCPACHLFGTTGYQGRVRFGFARLEREPAWRQNDAGSTAITLPLLEQPRLTWSMLWERRNAEGTVEERQPVNWVPGR
KFYVHHQGWRTIVAQGINPIDGQRLERNENNRTVEVLDTGRTFTFQVFFENLDAWELGLLLYSLELEPGLAHKLGMAKAWGFGS
VQIDVASLRRYQAPGSMTDITCEKDTLLQAGFAWLKEQANSSSWDEIPRLRQLRQLLRYQEDGTLTVRYPILKQENAASGQVPG
YVELRDQGYRPEEQLRIPWSPWYSPPLEPPPAATAAA (SEQ ID NO: 22)

>3300020048|Ga0207193_1004003_13|M
[aquatic-freshwater-freshwater lake sediment]
MTTLTIHLHFLEPFRMAPWFSVEKRKKNNPDWQRVQTYARWHKNTAGDGRGRPFITGYLLRSALIQAVEEELVFSRGVWSGISC
CPGLFFTEPDKDKEKPLNERRRATLGWTENKAICQEEEGREKACPLCLLINRFKENGEDNVHFGNLSLPGSENERPVWDQPEQI
AKLRTLNRVDRATTKAHDHFKVYEVEDLTDFYGTITFADDLPQREVIESLIRRGLGFISDLCGALCEIRVEKQKPLPTEPKGIT
QSKASYVSGLAEMCWEKMAETELRSLAGAVLQLRCSDPKKFTLPKGRIDRNGNRLPHHIWDIELEGNGDKKTLRKHLKETAEKM
AEGGTAFRLFCEDVGNRLFRLSKGIPQETPNRQDAFSDPSQVFNLGRPVYGQENHRDPMIPSCEWIITGTLTAASPFFIADELI
DDDHISRKLLTTQDFHYRLPRSLLRGILRRDLHEASGGKGCRAELGPESSCICPVCRILNQVKIRDARSDSFVPPDIRQRVKQS
HHHRIVQDGALFDTEYGLEGVVFPPFELRFKGEKTIDKELRTVMGWWEEGLLFLGGDFGTGKAPFKLGIKQIHRWDLSTPGAREE
YEQTCGFRAGVPLDANCQGLSPVSNIDFPKVDYPWQKVPWELAFESPLLTADPIAAITQDEADTIYFQKRRLKSDGSVEYIPAL
RGEGLRGLIRTATARASGSDHLTVEHEDCTCVLCKTFGNEHRSGLLRFDDLEPKNWKDKRIDHVSIDRFDASVVEKFDDRPLIG
SPDKPLVFAGAFWIHRDFTENKALSNGFQDLKSGLYPLGGKVGIGYGRLSKLELPSDWLPNSAENESISVSGLLEGSPETSGIP
EKPTWKPEPDAIYNPYYYLSRPGDGPKRTLTPVSHATLSKERYTGRIACFLKVKSPLLLPDSEHDPVAPDKNGTMKAFRLNGTL
MIPGSALRSAVSQVYEALTDSCFRVMDQKRVLSWRMETGDHGNYKPGRISESGDQIFPMGEKALRLPLYDMAPGTHSAKYIKEL
EELHKKALEGNIHRLTIAPWEEMPEKTREKKPEKCNKILGRNLTEEEKKNLTDQGMAKLKISEMELKTLIGRFKKDEESCIEKA
QKTDSNIAEIAKHNRDILNVLEKETRQRVLAGKEKVPFLTERLAPNNDINFQIVKLLKNSEKNKKNKEIRWGYLKITGPNNAND
AVVETKEEDDKYKLEWEDPLDPFSFCLTGPPKNQPNTQKSRDFPRPGFECIKDDKRYTISKRCERLFEADEKSKPIPIPKRVREG
YKGILEDYQKNAKKIPKAFQTRLNSDLVYYKSDYVENQINVTALAPVCISRLADDRPLGKRLPVGYQPCSHICLEDCERCTGKA
CPIPLYREGYPVNGLCPACQLFGAQMYKGRVNFSFATLTPGKNLELRNVTLPAQERPRPTWILPKNVQGKDTEIPGAKFYLRHG
MWKKIWTDRKDPRTDKPIEEKNPNNVTIEGINTGAEFRFDVSFENLDENELGWLLYCLELEEDMSHMLGRGKPFGFGQVEIKIN
ELARRLAPNAWYTESPKEGSLIHSKLIVKALAGLKSLDSLRLLLTQYNNLTAYYPELEGKGGKPGYDTLKNSSGYNPHCFLTLQ
TKGNTPFVYPWFPIPISKPQATKSDIKPKVENHGITGNGFKKLVEGDKVTFEIEERPKGPCAVNVRKVKDIP (SEQ ID NO: 23)

>3300001096|Ga0067045_1003547_12|M
[bioremediation-terephthalate-wastewater bioreactor]
MNRYKVSLEFLEPWRINHLGDDRGAAWARWVQTREGYQRPEITGTLVRSAVIRAAEELLALTGGVWAGQKCCPGEFCTPGGSKP
TFRRQRATRWWGEDSLCTPDSPCPFCQLLGRHDLAGKQARRGGGFHVHFGNLYPVAREGYGSLAEIITRQRTSNRLDWLTGKAQD
ILTICEVEELRRFSGLITVAPELANGEAVSSLLTAAAALVDRLSGAACRLKLQPVEELWSGTAVSLTRAAVPETAYRQQLEEDI
DNYFQELIGDGSQLGPERLRLLADAIRELRYLPPEQTLPDWLQSLPGDKGKAHRLWDALTAQRRPLRNMLQEVAAAYAAPATW
RDVVQGLGQALYAHYKKLWPQAMPVRPVGEAEYWQTKFDRQPSRQRGTWSHEWIITGALQTLTPLYLGTQVEAARQTSLTVLL
TAEGRYRLPRTALRGALRQDLQLASRGQGCLMELNPERPCSCPICQIMRRLTVRDVTSSIALPPPLVRQRVRRNPWTGIVDEGA
LFDQEVAPEGLRFPFILRYRGFGGLDAWLQTVLSWWQEGRLFLGGAGGTGKGRLRLTDLRIWRWALDETGLPTYVAHLGYRGRE
EELANSASLPAGVEAVTCSDPATVPSPWQEVDWEFRFHGPVLANHPLTALLRGEADAVFTWKVQLEADQQHYREVCTLKGETVR
GLVRGLFGKSQGLLTKAHADCTCLLCRVFGNEHQRGKVRFEDLTLAGETVPKKRLDHVAIDRISGGAAEQLKFDTQPLYGTPEN
PLVFAGKFWVHTELDEEEQKALRAALTALRDGLATVGAKGSVGYGWLNGLRLHSGPAWLTDNWQETAAAPSDTNTPPEFSWPQL
PDLTLDSRKIYYPHYFLPPDLQVPRLSQPHTHSLFDPQKYTGWLTCRLTTLTPLIIPDTSSDQTLTTGGPFPAGHQAFQFFRLG
DQPLIPGAELRGMISSVFEAITNSCFRVIRPRERLSWRMPAALAPQFRSGRVEIVNNQYYIRQMDMGRLPLYDDPATRRLFTPL
SLTSGHTLDFVDDNRTLLQSNPGIREGAIRTDLCFLNRFWLLRPPSAARCPRGNFSLTSGYVKFTGPNKVEVSRAGAGAGGLPA
PPADWTGVRLNQVAGNVPFYQAEQSGVIFTVNKRRERFFISRGNARSYPVPLATLKRYEQVLKEYRHFAQRGEVPAVFRTVLPD
VRHGASGYNRLNNGDLVYFRVKDDRWNDQNAPVEHIIPVSISRLVDQKFLGERVPEPLRPCAHVCLEECEACLKQESCPSSFYR
EGTPSRGLCPACHLFGTTGYQGRVRFGFARLEREPAWRQNDAGSTAITLPLLEQPRLTWSMLWERRNAEGTVEERQPVNWVPGR
KFYVHHQGWRTIVAQGINPIDGQRLERNENNRTVEVLDTGRTFTFQVFFENLDAWELGLLLYSLELEPGLAHKLGMAKAWGFGS
VQIDVASLRRYQAPGSMTDITCEKDTLLQAGFAWLKEQANSSSWDEIPRLRQLRQLLRYQEDGTLTVRYPILKQENAASGQVPG
YVELRDQGYRPEEQLRIPWSPWYSPPLEPPPAATAAA (SEQ ID NO: 22)

>3300025107|Ga0208863_1001002_11|M
[terrestrial-soil]
MTTGNTSASHPQFVTLTVCLRFCSPFQIRPWIKETVRNKVKMPSTVNAHAETAHLPDDQDTDDTQDLLEEERFERYATAADWHK
GSINGNAKYSPYVRGDLVRSVVDRELQEHFHCYNEKLANENKGCPGKRDRHINAGGKASGFMAHLPAIKDPAGKEICKGSDNIC
PVCHFLGAFAEGIKPVKFRNFFSGYYVAKTEDLAKQRGRNCYSGQSRKSLDNFTVWEADHTACPVFFGRIEVNKTLLPKEQILA
LLAGGLARLDNLAGSACRFDIIDKYEGVFEDHEWTANILPNLLIAAREALGLPDDEHQALLNDFSRFFINPEKSPAVYTSSPVI
VPVQGAVDKVVLLEKAQDIAGRIAACVSDNPRHLHRLAAAIRTLGWPGRSLASVMTKKPGTEDKATLWGKESASKSVKTILEES
IQGFTVEQKRSFFANLADQLVSRAGEQGAKSVRSQGLIIGRKENYAKPSAQEPTRHHLYRQPSNASAFLATGWLIAETPFFIGS
GTEGQKQTDDQAESLHLRTLRDGHGRFRIPFTTIRGVMDKELRDILQAGCAKGRSLRAPCPCQVCTLMRRIQVRDAIAADILPP
DLRMRTRIDPSHGTVAHLFSLEMAPQGLKLPFFLKLKGVETIDPDKELLEILNDWSAGQCFLGGLWGTGKGRFRLDDLQWHRLE
LDNADYYTPLLQDRFFAGETISDLRQGLQSINIQPERIPAQTPSRNMPYCRVDCILEFKSPVLSGDPVAALFESDAPDNVAYKK
PVVQYDETGRLRTTDPGPVEMLTCLKGEGVRGVVAYLAGKAYDQHDLSHDSCNCTFCQAFGNGQKAGSLRFDDFMPVQFESDQA
GNFSWSPHTPHAMRSDRVALDVFGGAMPEAKFDDRPLAASPGKPLNFKSTIWYREDMGKEAGKALKRALIDLQNNMAAIGSGGG
IGRGWVSRVCFEGDIDPDFLEDFPEPITVTEPEQDSQLLKNQAVADETAVSACDTADAPHPLAVTLEPGARYFPRVIIPRAPTVK
RDECVTGQRYHTGRLSGKIFCELNTLGPLVPDTDYSAGVPVTDSDEQLAECQLQAVFENTSKFNEFFATYPEETVTKLKDLLC
AADDKWILAVKDITADLRQEIGEDTFQRIIRKAGHKTQRFHQINDEILPGAAESLRGMVLSNYQILTNSCYRNLKATEEITRRMP
ADEAKYRKAGRVTVSGDGAQKKYSIQEMEVLRLPIYDNMNTPDNMPDVAKQATTAKRCNNLMNEAAKTSRVELKARWREGQSKI
KYQIIIDALNKVDPIIQVISSSKQINPNNGKTGWGYVKYTGANVFAKSLVAPIDCLRKKDAGHVCCQVNLNPAWEASNFDILINE
KCPVERQSGPRPTLRCKGQDSAWYTLTKRSERIFTDKKPVPDPINIPPREVKRYNELRDSYKKNTAHVPKPLQTFFNQESLANG
DLVYFEVNQFGEASQLTPVSISRTTDLFPIGGRLPQGHKDLFPCTAMCLSECKNCVPASFCEFHSRSHEKLCPACSLAGTTGNR
GRIKFSEAWLSGLPKWHSVSQDNVGRGLGVTMPRLERSRRTWHLPTKDAYLLGQSIYLNHPVPAILPSDQVPSENNQTVEPLGP TABLE 3-continued Amino Acid Sequences of Representative Type III-E (CLUST.019911) Effector_B Proteins KNIFSFQLAFDNLSIEELGLLLYSLELESGMAHRLGRGRALGMGSVQISVKDIQIRDNKSFLFSSNISKKSEWIQCGKDEFAQE
AWFGESWDNIDHIQRLRQALTIPVKGDVGCIRYPKLEAEGGMPDYIKLRKRLTPLCDREEPVRYRINPVQLARMILPFVPWHGA
CPALLNEQVMIEAKRLTELLAQENLDMICRTKNCANCKQETKKDCLAFRYDRANWPC (SEQ ID NO: 24)

>3300028595|Ga0272440_1002488_4|M
[aquatic-marine-marine sediment]
MKVRIKFFEPIRVMPWVNPSDRKISNEQFMRGQSFARWHRYNKNSNSGKPFITGTLVRSAVIRAAEVLLSLSNGIIENKACCPG
MFETEGAARKKKMHFRQRSTPKWTENSTCNKDNQCPFCELLGRFGNDEIGAVIEKENNTKRLKYNFHFSNFQPSGNNSYPDHII
IKRTVNRVDYTTGKAHDFFTISEIDNSFFPAFEGHISISDRVSHEAKKLLSDSLKFIDKLCGSICVFEFDDSTWDDHLHIEKSM
EKNDGKEKSEEITKQIIKILESNSKLDYLRILSDAIRELARDKEMVHKLPLDYKGKKKHYIWDLAYNKISIREILCNQANKNAK
NDYVELCKTIGKELYHESQKKTELLTKPHRILGSKSFYGKPQRDIQPTDAKIVPTEETIFTGKLVSETPFFFGLENEDKQQTDF
TVLLDSQNRFRIPRSALRGVLRRDIRMMSGGNGCDVKLGGRQCLCPVCRMMRNITIMDVRSNKDIIPDIRQRIRINPYTGSVAE
GALFSMELGPQGMEFDFVLRFRGNDSIPKSLKKVLLCWAKGQAFLSGASSTGKGRFKLKNLFKFSFDLSTKEIRNDYLNQRGWR
NRENELPLEPLFLTDKYKEINTTLWNKVSVEIKLSSPFLNGDPVRSLVQGQGADIVSFKKTSLIDDEDIYAYKAESLKGIFRTA
LARRFHYKDKISQKVLPLTAISHKDCDCPLCRLFGSEFETGKIRFEDLEFSTNPIPKKFDHVAIDRFTGGAVDKKKFDDCALSA
TKQKPLLLKGNFWLRPDMTKDDFKYFEKAFLDIKSGFYPLGAKSGIGYGQIEDISISISDSDDYPRAIKENIKTINNKSYTQEA
KNNINDKDTDESKQSDFQIDLKDDAIYYPHYFLKPNKKVDRKTIPINHLTLHDECHTGKIVCTLTTKTPLIIPDTENDDAFGLK
KAKLAEDGEKYHKSYSFFSVNDEIMISGSEIRGMISSIYEAITNSCFRIFEEKHRLSWRMEAVPEVLEKFIPGRIIKINGELKM
VEMEEVRYPFYDKNCPDTKTQKDHFSSKGKGKLYYEQPTFSDKMILSLSEYNRKHQNPGKKEKYKIIKPDSKSNANFMFTATPA
NNTEGYDMDCVHKHSVKGYLKVSGPNKIEKERTDQPASNKIPMENEIVIHQKTNRREITVQNAKKNKKRYRLIPEYICSEKDTN
YIMNKRCERVFIEPEKCNHDGIPISKNAIELFKHLVDEYKKNADQQETPKVFRTKLPEKGELKEGSLVYFRKDSNEVVEIIPVK
ISRKIDDRFIGKRLTKNLRPCHGEWIEKDDLSILDQYPEKKLFTRHPKGLCPACQLFGTGAYKGRLRFGFATLTNKPEWLNKED
KDHKLTLPLLERPRPTWAIPDATQASKVPGRKFFIHHHAWTDIEKGIDPVTGKALQIDVNNRTVQPLDSNNTFTFEINFENLEP
HELGLLLYSLQLENSLSHKLGMGKAFGFGSIDIKVENLLLFDSTIDKYKNKTDQVKRFVDEGKNNLLEIFENEFDDIEHIKDLK
SLLYFPNDKNIRVQYPLLRKEDYPDKDLPGYKELKDNFSNGIQIRHNLLTIPWSPWAYQSKKKLENEKTIYPPLKKIEINNYYD
IKKVNIKIPDNAQWVFLTGNNSIGKSLFLKAIATGLYGKITEDDENDIDTNCGIRVFITNEWVNDVKKDYFNQKLSYKNYATYG
PSRLNKLAEGKKTKFPYFSLFNTEGVFYHDIEKEFIKWCDRDSSKFNLLKNIFIKLLPTIDDIKGIQTKTDFYIGYKEMETGKY
EKQSKLATGNISILRMFGDMFIRFSKEQPDTLPEDFSGIVIIDELDLHLHPIWLKKIPGLVSKLFPKIRFIASTHSAIPFLGAP
KNSVYLNVIRDEDNNIHVQEIDIDLTNLLPNTILTSPLFNMEDITQINLPDITDVRTEDTYKEIIEIDKIKARLKKFAKKDTLF
PDKLFKEL (SEQ ID NO: 25)

>SRR8490538_megahit_k177_234425_10|M
[anammox bioreactor]
MSKKHFIHLTFLEPYRLAEWHAKADRKKNKRYLRGMSFAQWHKDKDGIGKPYITGTLLRSAVLNAAEELISLNQGMWAKEPCCN
GKFETEKDKPAVLRKRPTIQWKTGRPAICDPEKQEKKDACPLCMLLGRFDKAGKRHRDNKYDKHDYDIHFDNLNLITDKKFSHP
DDIASERILNKVDYTTGKAHDYFKVWEVDDDQWWQFTGTITMHDDCSKAKGLLLASLCFVDKLCGALCRIEVTGNNSQDENKEY
AHPDTGIITSLNLKYQNNSTIHQDAVPLSGSAHDNDEPPVHDNDSSLDNDTITLLSMKAKEIVGAFHESGKIEKARTLADVIRA
MRLQKPDIWEKLPKGINDKHHLWDREVNGKKLRNILEELWRLMSKRNAWRTFCEVLGNELYRCYKEKTGGIVLRFRTLGETEYY
PEPEKTEPCLISDNSIPITPLGGVKEWIIIGRLKAETPFYFGAQSSFDSTQDDLDLVPDIVNTDEKLEANEQTSFRILMDKKGR
YRIPRSLIRGVLRRDLRTAFGGSGCIVELGRMIPCDCKVCAIMRKITVMDSRSENIELPDIRYRIRLNPYTATVDEGALFDMEI
GPEGITFPPFVFRYRGEDALPRELWSVIRYWMDGMAWLGGSGSTGKGRFALIDIKVFEWDLCNEEGLKAYICSRGLRGIEKEVLL
ENKTITEITNLFKTEEVKFFESYSKHIKQLCHEGIINQMSFSGGLRSYHEYLSPLWTEVKYEIKIASPLLSSDTISALLNKDNI
DCIAYEKRKWENGGIKFVPTIKGETIRGIVRMAVGKRSGDLGMDDHEDCSCTLCTIFGNEHEAGKLRFEDLEVVEEKLPSEQNS
DSNKIPFGPVQDGDGNREKECVAEVKIYKKKLIDHVAIDRFHSGANEDKMKFNTLPLVSGPERPIILKGRFWIKKDMVKDYRKKI
EDAMVDIRDGLYPIGGKTGIGYGWVTDLTILNPQSGFQIPVKKDISPEPGTYLTYPSYSAPSLNRGHIYYPHYFLAPANTVHRE
QEMIGHEQFHKEQKGELLVSGKIVCTLKTVTPLIIPDTENEDAFGLQNTYSGHKNYQFFHINDEIMVPGSEIRGMISSVYEAIT
NSCFRVYDETKYITRRLSSEKKDESNDKNKSQDDASQKIRKGLVKKTDEGFSIIEVERYSMKTKGRTKLVDKVYRLPLYDSEAV
IASIKFEQYGEKNEKRNAKILAAIKRNNVIAEVARKNLIFLSRLTPEQLEKVLQGEILVKESLKSGENPNDYLAELHENGTERG
LIKFTGLNMVNIKNVNEEDKDFNDTWDWEKLNIFHNAHEKRNSLKQGYPRPVLKFIKDRVEYTIPKRCERIFCIPVKNTIEYKV
SSKVCKQYKDVLSDYEKNFGHINKIFTTKIQKRELTGDLVYFIPNEGADKTVQAIMPVPLSRITDSRTLGERLPHKNLLPCVH
EVNEGLLSGILDSLDKKLLSIHPEGLCPTCRLFGTTYYKGRVRFGFANLINKPKWLTERENGCGGYVTLPLLERPRLTWSVPSD
KCDVPGRKFYVHHNGWQEVLRNNDITPKTENNRTVEPLAADNRFTDVYFENLREWELGLLCYCLELEPGMGHKLGMGKPLGFG
SVKIAIERLQTFTVHQDDINWKPSENEIGVYVQRGREKLVEWFTPSDSHKNMEWNEVKHIKDLRSLLSIPDDKPTVKYPALNKG
AEGAISDYTYERLSDTKLLPHDKRVEYLRTPWGPWNAFVKEAEYSTSENSDEKGRETIRTKPKSLPSVKSIGKVKWFDEGKGFG
ILIMDDGKEVSISKNSIRGNNLLKKDQKVTFHIVQGLIPKAEDIEIAK (SEQ ID NO: 26)

>SRR6011893_megahit_k177_1702441_5|M
[dophin oral metagenome]
MIPDLRSLVVHISFLTPYRQAPWFPPEKRRNNNRDWLRMQSYARWHKVAPEEGHPFITGTLLRSVIRAVEEELCLANGIWRGV
ACCPGEFNSQAKKKPKHLRRRTTLQWYPEGAKSCSKQDGRENACPFCLLLDRFGGEKSEEGRKKNNDYDVHFSNLNPFYPGSSP
KVWSGPEEIGRLRTLNRIDRLTTKAQDFFRIYEVDQVRDFFGTITLAGDLPRKVDVEFLLRRGLGFVSTLCGAQCEIKVVDLKK
KQNNKEDSILPVSEVPFFLEPEVLAKMCQDVFPSGKLRMLADVILRLREEGPDNLTLPMGSQGLGGRLPHHLWDVPLVSKDRET
QTLRSCLEKIAAQCKSEQTQFRLFCQKLGSSLFRINKGVYLAPNSKISPEPCLDPSKTIRTKGPVPGKQKHRFSLLPPFEWII
GTLKAQTPFFIPDEQGSHDHTSRKILLTRDFYYRLPRSLLRGIIRRDLHEATDKGGCRVELAPDVPCTCQVCRLLGRMLLADTT
STTKVAPDMRHRVGVDRSCGIVRDGALFDTEYGIEGVCFPLEIRYRGNKDLEGPIRQLLSWWQQGLLFLGGDFGIGKGRFRLEN
MKIHRWDLRDESARADYVQKCGLRRGVGDDTAINLEKDLSLNLPESGYPWKKHAWKLSFQVPLLTADPIMAQTRHEEDSVYFQK
RIFTSDGRVVLVPALRGEGLRGLLRTAVSRAYGISLINDEHEDCDCPLCKIFGNEHHAGMLRFDDMVPVGTWNDKKIDHVSCSR
FDASVVNKFDDRSLVGSPDSPLHFEGTFWLHRDFQNDVEIKTALQDFADGLYSIGGKGGIGYGWLFDMEIPRSLRKLNSGFREA
SSIQDALLDSAKEIPLSAPLTFTPVKGAVYNPYYYLPFPAEKPERCLVPPSHARLQSDRYTGCLTCELETVSPLLLPDTCREKD
GNYKEYPSFRLNNTPMIPGAGLRAAVSQVYEVLTNSCIRIMDQGQTLSWRMSTSEHKDYQPGKITDNGRKIQPMGKQAIRLPLY
DEVIHHVSTPGDTDDLEKLKAIVLELTRPWKELPEEQKKKRFEKCKNILDGRMLQQKELRALENSGFAYWRDKTSLTFDSFLKD
AIEQEYPRYSGDYQRIKALVVNITLPWKLLKKEERHKRFDKCRRILKGQQPLTKDERKALEESGFANWHGRELLFDRFLKDENS
CLIKAETTDRVIASVAKNNRDYLFEIKQQDFARYKRIIQGLERVPFSLRSLAKSKETFSQIACLGLRRGRFLRKGYLKISGPNN
ANVEISGGHSNSGYSDIWDDPLDFSPRLSGKSELRPNTQKTREYPRPSFTCTVDGKQYTVNKRCERVFEDSAAPAIELPRMVR
EGYKGILTDYEQNAKHIPQGFQTRFSSYRELNDGDLVYYKTDSQGRVTDLAPVCLSRLADDRPLGKRLPEEYRPCAHVCLEECD
PCTGKKDCPVPIYREGYPARGFCPACQLFGTQMYKGRVRFSFGVPVNSTRSPQLKYVTLPSQERPRPTWVLPESCKGKEKDVPGR
KFYLRHDGWREMWGDDDKPDSRPSSEECQDIIEGIGPGEKFHFRVAFENLDKNELGRLLYSLELDAGMNHHLGRGKAFGFGQVK TABLE 3-continued Amino Acid Sequences of Representative Type III-E (CLUST.019911) Effector_B Proteins IRVTKLERRLEPGQWRSEKICTDLPVTSSELVISSLKKVEERRKLLRLVMTPYKGLTACYPGLERENGRPGYTDLKMLATYDPY
RELVVQIGSNQPLRPWYEPGKSFKPSPGNDCTGRGGSVSKSLISEPKVVPAIAPFCEGVVKWFNSVKGFGFIETKEQRDIFVHF
SAIRGEGYKILEPGEKVRFEIGEGRKGPQAINVIRIR (SEQ ID NO: 18)

TABLE 4

Consensus Type III-E (CLUST.019911) Direct Repeat Sequence and Nucleotide
Sequences of Representative Type III-E (CLUST.019911) Direct Repeats

| CLUST.019911 Effector_A Protein Accession | Direct Repeat Nucleotide Sequence |
|---|---|
| CONSENSUS DIRECT REPEAT SEQUENCE | GTTRNRNANMRMCRSNWDYYWTTRATGTBACGGDAC (SEQ ID NO: 100) |
| KHE91663.1 (SEQ ID NO: 1) | GTTATGAAACAAGAGAAGGACTTAATGTCACGGTAC (SEQ ID NO: 27) |
| OGR07204.1 (SEQ ID NO: 2) | GTTGGTGCATCAGCCCGGAATTATGATGTTTTGGTAC (SEQ ID NO: 28) |
| WP_124327588.1 (SEQ ID NO: 3) | GGTTGGAAAGCCGGTTTTCTTTGATGTCACGGAAC (SEQ ID NO: 29) |
| OBJA01001127_8\|M (SEQ ID NO: 4) | ATTGCCCCAGCCGATAAACCCTTAATGTCACGGAAC (SEQ ID NO: 30) |
| PDWI01005922_7\|M (SEQ ID NO: 5) | ATAGATATAGACAGAAGCTTTTAATGTGATGGGAC (SEQ ID NO: 31) |
| RLC19860.1 (SEQ ID NO: 6) | GTTGGAAAAGCCGGTTTTATTTGATGTCACGGAAC (SEQ ID NO: 32) |
| 3300009529\|Ga0114919_10000047_39\|M (SEQ ID NO: 7) | ATTGGGGGATTAGATTCTGATAATGTCACGGTAC (SEQ ID NO: 33) |
| 3300015370\|Ga0180009_10000113_9\|P (SEQ ID NO: 8) | GGTTGGATTCAGCCCCAGATGTTTTATGTGACGGAAC (SEQ ID NO: 34) |
| 3300001095\|JGI12104J13512_1001353_7\|M (SEQ ID NO: 9) | GTTAAGGAGAGACGGCATTCATTGATGTCACGGCAC (SEQ ID NO: 35) |
| 3300020048\|Ga0207193_1004003_10\|P (SEQ ID NO: 10) | GTTAGCATCAGGACAATACCTTCGATGTTACGGGAC (SEQ ID NO: 36) |
| 3300001096\|Ga0067045_1003547_9\|P (SEQ ID NO: 11) | GTTAAGGAGAGACGGCATTCATTGATGTCACGGCAC (SEQ ID NO: 35) |
| OGR07204.1 (SEQ ID NO: 2) | GTTGGTGCATCAGCCCGGAATTATGATGTTTTGGTAC (SEQ ID NO: 28) |
| 3300028595\|Ga0272440_1002488_3\|P (SEQ ID NO: 12) | GTTCCGTGACATCAAAAGCCGTCCATTTCTCAAAC (SEQ ID NO: 37) |
| SRR8490538_megahit_k177_234425_6\|M (SEQ ID NO: 13) | CTTGAAGACTAAAGGAAGGAATTGATGTCACGGTAC (SEQ ID NO: 38) |
| SRR6011893_megahit_k177_1702441_3\|P (SEQ ID NO: 5) | ATAGATATAGACAGAAGCTTTTAATGTGATGGGAC (SEQ ID NO: 31) |

TABLE 5

Direct Repeat Homology-Containing Regions of Representative Type III-E (CLUST.019911) Systems

| family | effector accession | homologous region | start | end | strand |
|---|---|---|---|---|---|
| CLUST.019911 | S.XXMH0-MGM_5 | ACCGGCTTTTCCA (SEQ ID NO: 101) | 29649 | 29662 | BS |

TABLE 6

Direct Repeat Homology-Containing Loci Sequences of Representative Type III-E (CLUST.019911) Systems >CLUST.019911 | S.XXMH0-MGM_5 | 29649 | 29662
TTTTCCGAATCGGATGTGGGATTGCTCCGGCCCTGCCTTATTTTCATATA
AGACCGGCTTATCCGACTATCTCCCTAATATGACAGGGAAAATATCTTCC
CGGACTTTTCACCGGGATGGTATAAGAACAGGGAACCAGAATCATCTGTT
CCCTGACCACTGGAAAGTTTTTCATATCAGTATGTTGAATCCTGTCACCC
CTGGGGCACGGAGGGATTTCCAAATATCCGATCTGATGTTCGTAATCACC
GGCTTTTCCAGCCAATGGCTTGAGATGATTTAAGAAACTTGTGACTGGCT
TTTTCTGGTAAAATGGATTTTTGTATAATATCCTGTTG (SEQ ID
NO: 102)

TABLE 7

Non-Coding Flank Sequences of Representative Type III-E (CLUST.019911) Systems

>CLUST.019911 | JRYO01000185_8 | 19509 | 20000
AGAGTCAGGACAACACTCTGTACCATAGTTGTGGGATACAGAAAGCCTTTGATTACCATCGGAAATCCCACAAACATCCCAAT
GTGTATATAATGATTTGATCTCAGCTATGCGTTCCTGGTATAAGTTTCTTTTCGGTTTTGCCTGCATTGTATTAACCTCTTTT
CTTCATAAATAATAAAATTATAAAATACTAAACGTTGAAATATTATGCATCTCCTTCTCGAAAAATCAGATCATATAAAATCA
ATTTCACCCCTCACCATAATAAGACGTACACTGTGGGTGAAAAGTGACACTCTTTTTAAATATTTTTAAATTCAAATAACTGT
TTATATTGAGCAAATGGAAATGCATCCTTTCCTCGTGTTATCATCAGTGCTGTCATTTGAATTAATCGTATTTAATGGAGAAA
AGGTGACAATTTTTTATAAAAAGACTTGTACAAAAAAATTAAATTGTACTGAACTTTTTTTTGTCACTTTGGTTTGGTGATTA
ACGACTGAATATATTAGAGTATTTTTTTCTCTTTTTATTCTTGAAAAAATTGTTCTTGAATAACAGTGTTTACTTAACTAAAG
TACCTCTAATAAATATTTGTTCACACCAAAAACAGTAAGGTTATAAAGAGAAAATCTGTCATGAACAATACAGAAGAAAACAT
TGACCGTATCCAGGAACCGACCAGAGAAGACATTGATAGAAAAGAAGCAGAACGGCTTCTTGATGAGGCTTTTAATCCAAGGA
CCAAACCCGTCGATAGGAAGAAGATAATTAATTCTGCCCTGAAG (SEQ ID NO: 103)

>CLUST.019911 | JRYO01000185_8 | 25772 | 25776
AAGTTGAAGAGTGTATCCATTACTGAAAAGGGTCAACGCACATATCCTGTAGATGCATCCGGTAGCAGGATAGCGGAAGAGGT
CAGGGATTATACGCAGAAACCACTAAACGTTGTTGTGCTGATTATTAAATATACATATGAAGAGTAACGATATGAACATCACT
GTAGAACTCACCTTCTTTGAACCCTACCGTCTGGTTGAGTGGTTTGACTGGGACGCAAGAAAAAAGAGTCATAGCGCAATGAG
AGGTCAGGCTTTCGCGCAGTGGACGTGGAAAGGAAAAGGTCGCACAGCAGGCAAG (SEQ ID NO: 104)

>CLUST.019911 | JRYO01000185_8 | 31078 | 31608
AGCACCGTTAAGAAGTTTGGATTCATCAGTAAAGGTGATGGAGAAGATATTTTTGAAAGAATCAAGGAAAAATATATTAAAGC
ATTGGAAAACAATATACAATTATTTGAGATCTATTTGTCGGATGAAAAGGATACTCGGAATAAATAACAGACAAACGGTTTGC
GAAGAAATACGCGACAGGGTGATTGGACCGTAACCTCATGATTATATGATTGATACACGATTTAACCCTGACTTGCCGGTTTT
TGAAAAAGTTCGCAAACCCTGTTTTGCTTCATGAAGTGAGTTGGGTTTGCGAAAAAAGGTTATTACAGCCTGATATCTAAGTA
GAAGAGTACCGGTATTGAAGACCAAAGTTGCTGCGTATGGCGGTCCGGTTGTCCTTGCTTTCGCAAGGATTCCAATACTGGAA
TCCTCCCGAAAGGGAGGTCGCAAAAGGCCGTTTTTCGAAAACCATAGTTTCATACAAACCGGCGATGAGGTTTGCGAACTTTT
TGATTGTAGTAGTATTATTAAAATAATGGCTTAATATTTTTGGTATATACAATTCTCAACTTTTTCACCTTGCCGGAAATGA
GGTTTGCGAAATTTTAGAGAGCCGCATATCTATATTATTTACAATCAGTTACAAAATGGCCCCTTCTCGCCATATACGTAACC
TCAGAGTTGTTGGAGG (SEQ ID NO: 105)

>CLUST.019911 | JRYO01000185_8 | 32437 | 32673
GGTTTGATTGAATATTGATGGTTGAAAATCGTCTGCCCTATGGGGAGGCAATGTCATTGAATTAAGGGCAAAATATGGAGTG
CATCATCCCTGCCCGAGAATGACACTACAGTGTCAACATCCCTTTAGGTAGGCGTCCACGTCAGCCTGGCGGGAATCCAGCAA
CCTCTGCTTTGAGAGTCAATTCCATTTTAGTTGTCACCTTTCTGATAGAATCCTCGACTAAATCAGTAAGATGACAACTGATA
CTCTACTTGAACAATTTTTAAGCAAGTCCAATTTCATTTCTGCCTATGAGCGTATTGCCTCAAAGAAGGCTGCAGGCGGATTG
GATAATGTCACGGTTGAATCATTCGGCAACCGACTGGACCAGCATATCAGCAAA (SEQ ID NO: 106)

>CLUST.019911 | MGTA01000040_4 | 19908 | 20000
GTTATCCTTGGCCATTTAGAGGCTTCGGTCAAAAAGGCGCTCGATGCGGTCGAAAACATTGCGTCTGGCCAGCCAAGTAATGA
GGACTCGCCAGTATTACCCACGAGCCCGGCGGAGGTGGCGGTTATTCACTGGAGCATAAACCAGTGACCACAAATTTCCGGAA
ATGATGTCCACTTCGATAGTGTAGATGGTGCGGACGTATCACCCCTTCCCCAAGGCAGCTCAAGGAGAGCAATGATATGAATC
AAAATATCGATCGTGCGGTTGGTGCAATTCTAGCGATTGAAACAGCGACACCCCTTACCGAATCTTCAACACTCGCGCAACGT
GAAAGGCATCAGAAGCTGCTGCATGATGAAACCAAAAAGATTGAGCAAGCCTTCATAGCC (SEQ ID NO: 107)

>CLUST.019911 | MGTA01000040_4 | 22550 | 23634
CTGCAAAGCTGTTGGATGCGCCAACCCGGTGCCATTTTTAATGATGAGTACATCCGCCTTTATTATGCCGCCTCTTTCCGGAT
ACTGGGTTTCCCGGAAGTTGCGACTACAAATATGGCGACTGCAACCGCCCAGGAGGAAATAGCATGACTACCGGCAACACTTC
CGCTTCTCACCCGCAATTTGTCACGTTGACAGTCTGTTTGCAGCCCCTTCCAGATCCGACCCTGGATCAAGGAAA
CGGTGCGCAACAAGGTTAAAATGCCATCCACTGTCAACGCTCATGCTGAAACTGCTCACCTGCCGGATGACCAGGATACCGAC
GACACACAAGATCTATTGGAAGAAGAACGTTTTGAGCGGTATGCCACTGCCGCTGATTGGCACAAGGGAAGTATCAACGGAAA
CGCGAAGTATTCACCCTATGTGAGGGGCGATCTGGTCCGCAGCGTGGTGGACAGGGAATTGCAGGAGCATTTCCACTGTTATA
ATGAAAAGCTTGCCAATGAGAATAAGGGGTGCCCTGGAAAACGGGACCGCCATATTAACGCCGGCGGCAAGGCGTCCGGTTTT
ATGGCACACCTGCCCGCGATCAAGGACCCGGCCGGCAAGGAGATCTGCAAGGGCAGCGATAACATCTGCCCGGTCTGCCATTT
CCTCGGGGCGTTTGCGGAAGGAATAAAGCCGGTTAAGTTCAGGAATCGGAAGATCTGGCCAAGCAGCGCGGCCGGAACTGTTA
CAGCGGGCAAAGCCGGAAATCCCTTGATAATTTTACTGTCTGGGAAGCGGATCATACCGCCTGCCCTGTTTTCTTCGGCAGAA
TCGAGGTGAACAAAACTCTTTTGCCGAAAGAACAAATCCTCGCCCTGCTGGCTGGCGGCCTTGCTCGGCTTGACAATTTGGCG
GGTGCGGCGAGGGAGGCACTTGGGCTACCAGACGACGAGCACCAGGCACTCCTCAACGATTTTTCAAGATTTTTCATTAATCC
CGAGAAATCGCCTGCTGTTTATACTTCCTCCCCGGTTATTGTCCCTGTCCAGGGAGCTGTTGATAAGGTTGTGCTCTTGAAA
AAGCCCAAGATATCGCCGGCAGAATTGCCGCGTGTGTCTCCGACAATCCCCGCCACCTCCATCGGCTGGCTGCGGCTATCCGG

TABLE 7-continued

Non-Coding Flank Sequences of Representative Type III-E (CLUST.019911) Systems

ACCCTGGGCTGGCCGGGCCGGTCTCTTGCTTCGGTTATGACTAAAAAACCGGGTACCGAAGACAAGGCCACCCTCTGGGGAAA
AGAATCAGCGAGTAAATCGGTCAAGACGATTCTGGAAGAATCAATCCAAGGCTTCACTGTAGAACAAAAGCGAAGCTTTTTTG
CCAACCTTGCCGACCAGCTC (SEQ ID NO: 108)

>CLUST.019911 | MGTA01000040_4 | 27846 | 28045
CGTATCAATCCGGTACAACTCGCCCGAATGATTTTACCATTTGTACCTTGGCATGGTGCATGTCCTGCTTTGCTGAACGAACA
GGTAATGATAGAGGCCAAACGATTGACTGAGTTAGACCGCGCCAATTGGCCATGTTGAATGCCAGCACAACCAGCTAATATAT
CGAAATCGCTGGCAAAGTTAGCTTTTATTGTAAAATTAGATGATTAGGAACGATCCGGCAGGTTATTTAAATGAAGTAAAGTC
TGGGGTCGTAGCATAATCGCAAAAAAAATTATTTAACAGAAACAAACAAATAGACAGCATAAAGTTGAATTGAGTATTATAGA
AAGCAGGG (SEQ ID NO: 109)

>CLUST.019911 | MGTA01000040_4 | 30276 | 42550
TTTTTCTGTAACTATTCAGCACACCATATTTTAGCATAACAACTGAGTAGTCATTGGGGCATCATAAATTGAGGCCATTTCCC
TTCAAATAATAAGCGCA (SEQ ID NO: 110)

>CLUST.019911 | S.12JQSS-MGM_10 | 15939 | 16630
GAGACAAAAGAGCAACGGGATATTTTTGTTCATTTTAGCGCTATTCGGGGTGAGGGTTATAAAATCCTGGAACCGGGCGAAAA
AGTACGTTTTGAAATAGGTGAGGGGAGAAAAGGTCCCCAGGCCATCAATGTTATTCGTATAAGATGACAAAATTACTCCAGTC
TCTATTCTTTTTGTAATTACTTGTTCGCTGTTTTGTGAAGATTATATTAAGCTATGGAGCTTTCAGGTAAAAAAGCGTAAAGT
ACGCGAATATTCTGCGTAAAACTATTCCGGCTATGAAAGATGATGTTCATAGCCGGAATAGTTTTTTATCGAGTTTGGTGGGG
TATTCATTTTGGGAGATGGTTGATGAAAGTTTCAAGGCAGGGTTTCATTTATTGGCGATGGTTTAAATATCTCTTTATTCTTT
CTTCAACAATCTGATATTATTGTTTTTTTATCTAAAGATACTCTGTTTTTATTTATCGTAAAATATTCGACATACATATGAAA
CCTTTGAAAAGGCAGGAGTTTGGCGAAGATGTAGTGATTGTGGCTAAAATTACGGAAAATTTTTTTTGTAAAATTAAGGTGA
TATGAATATAGTTTTTCTGGTGCGGTCGCCAATTTCCTTTTTTGAAATTAGGAAACTGGTTTGGCGAATTTTTTGACAGTATC
TTTTTATAATAAATACGAATAGTTGTGATTAGACAGGTGTTAATTTAGTAGTATTTCCCCTTTAACTGAAGAATGATTGGCGT
AATATTTAATAACATGAGAGAACTCCTTGGTATAATAGAGATTATTAAGTATAGTGTCAGAATGCAGCTTTTGTTTGTTCTTT
GATTCTAAAGG (SEQ ID NO: 111)

>CLUST.019911 | S.12JQSS-MGM_10 | 17528 | 17702
TCTCAAAATAATGTTAAAGAAATTTTCATTTTATTTTGATGGTTTAGGCCACACTGACTTTGTGGTTCTCTTTATACCGATAG
AAAAATTTTATTTTTTCGAAAAAAAACACTCTTCCATTCGTAAGGTTAAATAAAGGCAATTACTTAACCATCTAGCAATGGAG
GATTGATCATGAAAAGCACACATTCTCTTTTTTACCGTTTTGCTCATGTTGATACCTTTCGCTCCGCATATGAAAGAATTTCT
CTAAAAAATTCCAGCCCGGGACTTGATAGAGTTTCCGTAGAAGAGTTCGGCAAGAAACTTGAAAAAAAATATCCAA (SEQ ID
NO: 112)

>CLUST.019911 | S.12JQSS-MGM_10 | 19997 | 20000
ATTCAGGCAATCCTCAATAGATTGGGGCAGGAGGTAAAAGGTCGAGGTAAGGCTTTAACATTGCAGGAAATGATCCATCGGCA
GGCGCAGTTGTTGAAAAGCTATTTGATGGATAAATCTGTTTACAAACCATATCTGGCAAGGTGGTAACCTATGAATACAGTCG
AATTACTTCAGGAGGAAGAACGCTTGACCCTGGATTTGGTCTTTTTGCCACCAGGTAGTAAGAATAAAGAGCAAAAAAAGAAT
GCTTTGGTAGACCTTTTGTTGAAAATAGTGGAGCATGGGGAATTAACCCGTAAA (SEQ ID NO: 113)

>CLUST.019911 | S.12JQSS-MGM_10 | 22310 | 22413
ATCGACAATGATGATACCTCCGCTGTGCTCCATAGTTCATTAAAAAGATTATTTGAGCATTACGAGAAGAAAAATGAAAAAAC
TCGTGCACAGCTTCTCTATAATTGGGCGTCTTTACGTGTTCTCGCTCCTGCCAGGGAATTTAGTTGAAAAAAAATCATAAAAT
TTCCGAAAAAATAGATGATGTCGAACGTAATAGGTTTTAGAGCAACGAATAACCGTTGCTCTAAAACCTATACTCTGGGAGAA
CATCATGAAAAAGAGCACGGTAAAGAAAACTATTCTATCGAAACAGTTGTTTTCGTCGTTTTGCAGGACATCATGAGTATTG
TTCTAATACCGTTTGCGGTAATCGCCTCAATTTATCTTTCTTATTTTTTTGAGTTATCTGTATACAAATCT (SEQ ID NO:
114)

>CLUST.019911 | S.XXMH0-MGM_5 | 27292 | 27576
CCCCGCGTTATTTATCCGGCCCTGAAGCAGAAGGATATTCCTAACAGCAGGCTTCCCGGGTATGAGGAGTTGAAGAAGAACCT
CAATATGGAGAAACGGAAAGAGATGCTGACGACCCCTTGGGCCCCTGGCATCCCATCAAAAATAAGATGCCTGCGAATTCC
CGGAAATATGACAGCGGATTTAAAGGATTGAACGGATATCATTTTCCCAAAAAATGACAGCGGATTTAAAGGATTGAGCGGAT
ATCCGTTTCATCCTTTGATCCGTTGTCATATTTCCTACAAATATGTCGCCCCTACGGGGCTTTAATCCTTTCCTCTTCTTTGT
GTCCTTTGTGGCTTTGTGTGAGAAAACAAAAAATTTTTGTCACATTTTCAGCACAGAACACGACTAAGTATGCAGAGAAGGG
AAACGCCCTCCTTTTCTTTGTGTCCTTTGTGGCTTTGTGTGAGAAAACAAAAAATTTTTGTCACATTTTCAGCACGACATAC
GACTAAGTTTGCAGAAAGGGAAAAAACATATCTTTTTACTCATAAAGGAGGTTGCCATGAAAAAAACATTTATCGTCTTTGTT
CTG (SEQ ID NO: 115)

>CLUST.019911 | S.XXMH0-MGM_5 | 29288 | 29740
AAGCGCTGGGCAACTGATGATCTGCTCCGTATGGTCGGGGATCAGATCACTGTGATGAGGGGGTTGCTGGAAAAGGGAGAGGA
TTATCGGCCGGTGGTTTACAACAGCCGGTATTCCAGCGGGAAGAGCGGCCTGAAAAAAAAGACTTGAAAAGGTCTTGACATGG
GCCGGGAAAGGGGCTATGTTCTTCTGATTATAATATCAGATCAGAGGGAATATGGCCCTTATCCCGGGAATATCCTGTATTTC
AGGGGATCGGGCCTGTTTTCCGAATCGGATGTGGGATTGCTCCGGCCCTGCCTTATTTTCATATAAGACCGGCTTATCCGACT
ATCTCCCTAATATGACAGGGAAAATATCTTCCCGGACTTTTCACCGGGATGGTATAGAACAGGGAACCAGATCATCTGTTC
CCTGACCACTGGAAAGTTTTTCATATCAGTATGTTGAATCCTGTCACCCCTGGGGCACGGAGGGATTTCCAAATATCCGATCT
GATGTTCGTAATCACCGGCTTTTCCAGCCAATGGCTTGAGATGATTTAAGAAACTTGTGACTGGCTTTTTCTGGTAAATGGA
TTTTTGTATAATATCCTGTTG (SEQ ID NO: 116)

>CLUST.019911 | S.MJ1HS-PDG_1 | 18611 | 19304
CAGCTGGGTCTCGGCCTGGGCGCCAAAATCCGCCACGCTCTGACCATCCCAACCGCCGGCCGCTTTTTTGGCGGCTACCCGCT
GCCAGGCGGCGGACAGATTTTCCATGCGGTGATGGCGGCCAGTTGACGATAGGTGGTGGTAGACATCGGGACGGTGCCTCCT
GCAAGGTTCTATCCTGTTGGTCGTCGACGCAAGGCCTCAGGTGACCCCCTCTCCGTTATTCTGCCAATTTTTTCCTAGGGACC
GGCTCGGGCACCGTCTGCGGCGGGGGCTGCCGTTCAACCCCGGCCAGGGCCATGGACCAGATTTTCTTTGATTTATCATCAG
GTTGGCTCCTCTTTCGCAAATGCTCCGGCGCCGCGAGCGGCCAAACCATTTGCGAACTTGGCCGATAGGCGATTATTTTATGG
CAAATCAATAAGATAAGTGCTTTTGAGGCCCTTTGGCCCCTCGGCGGCGAGGGGCCAAAAGTTCGCAAATGCCCCTTTGGGG
GCCGGGCGCCCCACCATTTGCGAAAAAACCCGCCCGGCAGCGGCCGAGGCTTCTGCCGGCTGATTATATCTTATCGATATAAT
TGAATATTATTTTTCCCCAAGACCGGGTCGAAGGCCTATTTTCGCAAATGCCCGCCGCGGGCCGGGGGAGCCAACGTGTTGCG

TABLE 7-continued

Non-Coding Flank Sequences of Representative Type III-E (CLUST.019911) Systems

AAAATCCGGTTCTAAGCAAATCAAGGAGTTAGGCCAAAAAAAGTGATTTTTGGCAATCCGGCCAAGCGCCCTTTGGGGGCATT
TGCGAAAAAATCCGGCCGGCAAAAACTTCTTGACATTACCGGGCATTTTCCATTAGAGTATTGCGTAGCAGTACATATCTAGC
TGATTTCTCCGTT (SEQ ID NO: 117)

>CLUST.019911 | S.MJ1HS-PDG_1 | 19688 | 20000
TATGCGACGGCCTTGGGCCAGCAGGATGCTGGCCCTACGGGGTTGAGCAGAGGCGGCAGGCCTTGAGGACACGTTTTTGAGGG
CGTTTAACGGCAGGCGCAGGAGACGGGACGCGAAGTGGGGTTAGGGGAAATTACCGCCAGGCTGGAGAATAGCTGGCGGTTTTT
GTTTGGGGGGCCGGAAAAATTTTCTGCTCCTGTCACCTCGACGGTTCCAAGAGAGACTAATTTGTTAGACCAGGCTCCAGACT
GGAAGTATTTTTGGGCGCGGCCGCGGTGACGGCTGTCCAGCAAGCGGTTGGGACGGTTTAAACATGACTGCAGGACATTACCA
GACGATTTTGGAGGCCCAGATTGAGCTGGCCTTCTGCCTGCCGGAAGAGGCGCATAATGTGCTGTATGCGCGGGATGAGGCGT
GCCGTGAGCTGGTCCAAGCCTGCCGCAATCACCGGGGTAGCCTGCGT (SEQ ID NO: 118)

>CLUST.019911 | S.MJ1HS-PDG_1 | 22355 | 22370
GCAGAGAACGGAGGCGCCTGGTTCTATGAACTTTTATGGCAATGGCACAGGGATGAAATAGGACATCTTAGCAACATAAGGAA
TACGTTTGAAAGAATGAAAAGATTTGATAAATTTGCCCCCTGGAGGTCCGTGGGATTGGGTTGGTGAAAAAAAGAGGAGTGGA
TGTCTGCGCCTGAATATGAGATCGATCTGGATAACGATGACCACCCTACCATAATTTTAACAGACATGGATGAATGTTATCAT
ATATGCCTTAAAGCGGCAGGAAACGATCCTAGCTGTGCTCGATGCAAGATATTTATGGCAGATTTC (SEQ ID NO: 119)

>CLUST.019911 | S.TJLN2-PDG_0 | 19450 | 20000
TTTTAATTGACCCGCATTTTTTGTTATATCGAATAACCATGAAGAAAGGCGTCCTTCCCACTCCATCTCAAATCTATCAGGAT
TTGTTTCATAGATATGTTTGAGACGCTTTCGGCGCTTTGCTTTATCTCTTTTGGCGGCCTTTCCCATTAGTCCTCCTTCTTAG
TTCAATAATGGTTTTATCCATTGATTTTTCGACCTGATCAGAGGATCTAAACTCTGTTGGGCCGGTACCTAATTTGATTTAAT
CGAAAGAACGTTGTACTTTTTATCTCCTCTAATTCTTTTGTTTCGGATCGTCTGGATAGTCGTGATAAATCTCTTACATGTTA
CAGGGAATCGTAATTTTTCTATCTGAAATCTCACAAGCGCTATTTCGATAGTCGGGGCTAAGTAAAAAAATGTGACATGAATT
GCTGGGCCACCAGAAGAAATTTTTCACTAACCACTATAGTCTTCTGGAATGTGAAAAAGTGACAGAAAAAATATGAGGCTAAA
ATGTCACATTTTAAATAAAGCCCCGACTATAATTATACGGATATATCTATAGACAACCCCTTTTGATGAAACCTTACACCAAT
AATCGGATGTTAAAGTTATTGACATTACAAGATTTAATGTGTTATTTATTTAGGCTCAACTTTTCTCAAACCATCCAGACTAT
TTCAAAATATCTGTAAAGATAATAAGGGGGAATGTTATGTATTCCGACTTTCCTGCACTTAGGTTACCTGAATTATCTGTTGA
TCAAAAAAAATTATTTAAGATCTCCGGGACCAACCCACAGCTCATATACATCTTAATGAACGAATTTGATGGAGAGGGGATG
AGCCCTTCTTTACCGGACTT (SEQ ID NO: 120)

>CLUST.019911 | S.TJLN2-PDG_0 | 22274 | 22282
GTTTTAAATCTTTTATTCATGAAAGAAGGTCTTTTTGATCATTTTTTTGAGCAACAAAGAGAATGGTGGAAAGAAGAGTATGA
ACATACCGATTCGAACACAGCTCTCTATGATTGCTTGTGTTTTCGAATGTATCGGTGTTATTTTTAGGAAAATATATGCCCTC
ATACCCTTGCTTGAAATGGAATGGCGATTGTAGCAGATGTCCTGATTCGGCAACATGCAGAATCGCACAGAAAGGTTTGGGAA
AGGTATTTACGGTTTTTTTCAAGAAATATCTGGCGCGTTACTATTCTTCGAAATCCGAA (SEQ ID NO: 121)

>CLUST.019911 | S.TJLN2-PDG_0 | 26892 | 26965
ATGATGAGGCGGTTTTTCTTTGATACCAGTGCGCTTATCAAACTCTATCATGAAGAAACTGGTACAGAAAAACTGGATTCTCT
GATCGAGGCCGAAAATCCAGTTATCATTAATGATATGAAATTGCCTGGCGTTATGAGCTAATCCTTATATTAAATGCTTCAGG
CATCTGAACCTTGCAACATATCAGGATGGTATATAAACCACAGGAGGAATGATGAATATACCCTTACCCTAAATTTCATTGA
ACCGTTTCGCTTGATTGAATGGCACGATGCGCCAGATCGGGAAAACCTTCGATTGAGGGGGTTTTCTTTTGCCAGATGGCATA
AGGACAGGGAATTCGGACTGGGAAGGCCATATATT (SEQ ID NO: 122)

>CLUST.019911 | S.TJLN2-PDG_0 | 31645 | 31858
AATGGAATCCAGGTCCGTTATCCAAAATTGGAAAAAGAAAAAAAGATGACCCAGGTGAAAAGCCGGGCTATCTTGAGCTGGC
AGATGGCCCTTTCAGCACGGAAAATCGCAAGGAAAAATTAAAGGAGATTTGGGGTAATTGGGCCTGATTAACCAAATATCGAA
TAATCACCAAATACATAGCCTATTTTCAATGATATTCAATAGTTATAATACCTATTTAATAATTCAATATTTATAGAATCCAA
GGATTATGCATCGCCAAAAATACATCCATAAACGATTTAACAATATGAATTTACAAAATGAATTTATACCATTGGGTTTTAAG
AATCTTTTATAATAAGCAAACATAGGGGGGG (SEQ ID NO: 123)

>CLUST.019911 | S.J3DH2-PDG_7 | 19861 | 20000
GATGTTCCGCCAGGCACGGCAGCGATTCTCCTTGGGCTTTGTAGAGACGTGGACAGATTGAGGGCCGCCATTGATTCAATTGT
TTCGGGCAAGAAGACGCGGGATGATACGATATTCTGGATACTATACCACACCGTGCCGGAGAAATAGGGCCTGTCGCCAAATC
CACTCGGGCCTTCCACTACAAAAAGGCTTAACTCGATAGTATATGGGTTTCCTTTTTTGAGTCCGCCGGAGGCGGACGTTGT
ATAAAATCGCGAAGTGATTTTATGTACTGGAGAGGATATCATGGTCACGCCACAAGCTTCTAAGAACCCCGCAGTAGATGAAA
TCCTGAAACAGCTCACACCCTATGACATGGAGACTGAGAACGCAAAGGCTATCGAGACAAGGAAGTCTTGTATTGAGTGCCTG
AAAGGCATTTGCGAAAGGGCTCAA (SEQ ID NO: 124)

>CLUST.019911 | S.J3DH2-PDG_7 | 27996 | 28061
ATATTGCGCGATAACGGGGAAGATATATTTGTCCATCGGAGCGATATTAATGGTAGCCTTGGCACCCTGACAGAAGGGCAAAA
AGTAATCTTTGAGGTGAAGCAGGGTCCAAAGGGACTCCAGGCCACAAATGTGAAGGTAATTTCATAATCACTTGGCCGTATTG
CACCTTACCACAATATCTTTTTGAGAATTTCATAAGAGCTCATTTCAAAGTGAATATTCAATCCACGGCTGTTGAAAAAAAGC
GAAACGCCCTTGCTCTTTTTGTGCGCCTTCTCCTTTCATCGCCTCTCAAGGACTACGTCGCCAAGATAATCCTGTTTGGAAGT
GTGAGAAAAGGAAAAGCTAATTCAGAGAGTGAT (SEQ ID NO: 125)

>CLUST.019911 | S.J3DH2-PDG_7 | 30118 | 30312
TGCTTGAAATGGCGTGGGCATTTGCTTTTGGCCCCGGCTGATATCTACTCGGCAAAGCCACACCATACAATAATGGAGGCTGA
TTCAATGTGACATAAAATTTTGGGGTAGCGTCTACATGCAAAATCGGTGGTGATTCGTTTATACTTATAGAGTGGATCAT
TTTCTGAGCCGACACCCGAGATTGAGCTATGACTGCCACAATATTTGACAAATTTGCAAGCTTTGAAAACTTCTGGGCCGCCT
TCCAAAAAGTTGCTGCAAAGAATTCAGCGGGCGGCATAGACGGCACAACCGTTGAGACCTACCAAAAGCGAGCCAAGCAACGA
ATCAATGCCCTC (SEQ ID NO: 126)

Example 2: In Vivo Bacterial Validation of Engineered Type III-E (CLUST.019911) CRISPR-Cas Systems (FIGS. 7A-12)

Having identified the minimal components of Type III-E CRISPR-Cas systems, we selected one system for functional validation, from *Candidatus Scalindua brodae* (JRYO01000185, SEQ ID NO: 1, SEQ ID NO: 14).

Methods

Gene Synthesis and Oligo Library Cloning

The *E. coli* codon-optimized protein sequences for CRISPR effectors, accessory proteins were cloned into pET-28a(+) (EMD-Millipore) to create the Effector Plasmid. Noncoding sequences flanking Cas genes (including 150 nt of terminal CDS coding sequence) or the CRISPR array were synthesized (Genscript) into pACYC184 (New England Biolabs) to create the Non-coding Plasmid (FIG. 7A). Effector mutants (e.g., D513A or A513D) plasmids were cloned by site directed mutagenesis using the indicated primers in the sequence table: sequence changes were first introduced into PCR fragments, which were then re-assembled into a plasmid using NEBuilder HiFi DNA Assembly Master Mix or NEB Gibson Assembly Master Mix (New England Biolabs) following the manufacturer's instructions.

For the pooled spacer library, we first computationally designed an oligonucleotide library synthesis (OLS) pool (Agilent) to express a minimal CRISPR array of "repeat-spacer-repeat" sequences. The "repeat" elements were derived from the consensus direct repeat sequence found in the CRISPR array associated with the effector, and "spacer" represents ~8,900 sequences targeting the pACYC184 plasmid and *E. coli* essential genes, or negative control non-targeting sequences. The spacer length was determined by the mode of the spacer lengths found in the endogenous CRISPR array. Flanking the minimal CRISPR array were unique PCR priming sites that enabled amplification of a specific library from a larger pool of oligo synthesis.

We next cloned the minimal CRISPR array library into the Effector Plasmid to create an Effector Plasmid library. We appended flanking restriction sites, a unique molecular identifier, and a J23119 promoter for array expression onto the oligo library using PCR (NEBNext High-Fidelity 2×PCR Master Mix), and then used NEB Golden Gate Assembly Master Mix (New England Biolabs) to assemble the full plasmid library of effectors with their targeting arrays. This represented the "input library" for the screen.

In Vivo *E. coli* Screen

We performed the in vivo screen using electrocompetent *E. cloni* EXPRESS BL21(DE3) *E. coli* cells (Lucigen), unless otherwise indicated. Competent cells were co-transformed with the Effector Plasmid and/or Non-coding (FIG. 7B). The cells were electroporated with the "input library" according to the manufacturer's protocols using a Gene Pulser Xcell® (Bio-rad) with a 1.0 mm cuvette. The cells were plated onto bioassay plates containing both Chloramphenicol (Fisher) and Kanamycin (Alfa Aesar), and grown for 11 hours, after which we estimated the approximate colony count to ensure sufficient library representation and harvested the cells.

Plasmid DNA fractions were extracted from the harvested cells to create the 'output library' using a QIAprep® Spin Miniprep Kit (Qiagen), while total RNA=17 nt was harvested by lysing the harvested cells in Direct-Zol® (Zymo Research), followed by extraction using the Direct-zol RNA miniprep kit (Zymo Research).

The next generation sequencing library for the DNA depletion signal was prepared by performing a PCR on both the input and output libraries, using custom primers flanking the CRISPR array cassette of the Effector Plasmid library and containing barcodes and handles compatible with Illumina sequencing chemistry. This library was then normalized, pooled, and loaded onto a Nextseq 550 (Illumina) to evaluate the activity of the effectors.

Bacterial Screen Sequencing Analysis

Next generation sequencing data for screen input and output libraries were demultiplexed using Illumina bcl2fastq. Reads in resulting fastq files for each sample contained the CRISPR array elements for the screening plasmid library. The direct repeat sequence of the CRISPR array was used to determine the array orientation, and the spacer sequence was mapped to the source (pACYC184 or *E. coli* essential genes) or negative control sequence (GFP) to determine the corresponding target. For each sample, the total number of reads for each unique array element ($r_a$) in a given plasmid library was counted and normalized as follows: $(r_a+1)$/total reads for all library array elements. The depletion score was calculated by dividing normalized output reads for a given array element by normalized input reads.

To identify specific parameters resulting in enzymatic activity and bacterial cell death, we used next generation sequencing (NGS) to quantify and compare the representation of individual CRISPR arrays (i.e., repeat-spacer-repeat) in the PCR product of the input and output plasmid libraries. We defined the fold depletion for each CRISPR array as the normalized input read count divided by the normalized output read count (with 1 added to avoid division by zero). An array was considered to be "strongly depleted" if the fold depletion was greater than 3. When calculating the array fold depletion across biological replicates, we took the maximum fold depletion value for a given CRISPR array across all experiments (i.e. a strongly depleted array must be strongly depleted in all biological replicates).

FIG. 8 shows the degree of interference activity (depletion ratio) of the engineered Type III-E compositions by plotting for a given target the normalized ratio of sequencing reads in the screen output versus the screen input. The results are plotted for each crRNA transcriptional orientation. In the functional screen for each composition, an active effector, or effector and accessory complex, complexed with an active crRNA (expressed as a DR::spacer::DR) will interfere with *E. coli* essential gene function or the ability of the pACYC184 to confer *E. coli* resistance to chloramphenicol and tetracycline, resulting in cell death and depletion of the spacer element within the pool. Comparing the results of deep sequencing the initial DNA library (screen input) versus the surviving transformed *E. coli* (screen output) suggest specific target sequences and DR transcriptional orientation that enable an active, programmable CRISPR system. The screen also indicates that the effector complex is only active with one orientation of the DR.

FIG. 9 depicts the measured interference activity (depletion ratio) against the sequencing read coverage of the screen output. Notably, many of the points with depletion values above the hit threshold fall in the range where normalized output read counts are high (e.g. above 10), indicating the depletion ratio measurement is unlikely to be a technical artifact.

FIGS. 10 and 11 depict the location of strongly depleted targets for the Type III-E CRISPR-Cas system targeting pACYC184 and *E. coli E. Cloni* essential genes. Notably, the location of strongly depleted targets appears dispersed throughout the potential target space.

FIG. 12 depicts a weblogo of the sequences flanking depleted targets, indicating the absence of a prominent PAM.

Together, the interference activity displayed in the E. coli screen with the Type III-E CRISPR system suggests a programmable system capable of sequence-specific bacterial cell death or dormancy, which may yield new modalities of programmable CRISPR activities based on the Type III-E effectors.

Example 3—Identification of Transactivating RNA Elements

In addition to an effector protein, a crRNA, and an accessory protein, some CRISPR systems as described herein also include an additional small RNA that activates robust enzymatic activity referred to as a transactivating RNA (tracrRNA). Such tracrRNAs typically include a complementary region that hybridizes to the crRNA. The crRNA-tracrRNA hybrid forms a complex with an enzymatic module formed by an effector and an accessory protein resulting in the activation of programmable enzymatic activity.

TracrRNA sequences are identified as described herein by searching genomic sequences flanking CRISPR arrays for short sequence motifs that are homologous to the direct repeat portion of the crRNA. Search methods include exact or degenerate sequence matching for the complete direct repeat (DR) or DR subsequences. For example, a DR of length n nucleotides can be decomposed into a set of overlapping 6-10 nt kmers. These kmers are aligned to sequences flanking a CRISPR locus, and regions of homology with 1 or more kmer alignments are identified as DR homology regions for experimental validation as tracrRNAs. Alternatively, RNA cofold free energy can be calculated for the complete DR or DR subseqeunces and short kmer sequences from the genomic sequence flanking the elements of a CRISPR system.

Flanking sequence elements with low minimum free energy structures are identified as DR homology regions for experimental validation as tracrRNAs. Notably, tracrRNA elements frequently occur within close proximity to CRISPR associated genes or a CRISPR array. As an alternative to searching for DR homology regions to identify tracrRNA elements, non-coding sequences flanking CRISPR associated proteins or the CRISPR array can be isolated by cloning or gene synthesis for direct experimental validation of tracrRNAs.

Experimental validation of tracrRNA elements is performed using small RNA sequencing of the host organism for a CRISPR system or synthetic sequences expressed heterologously in non-native species. Alignment of small RNA sequences from the originating genomic locus is used to identify expressed RNA products containing DR homology regions and sterotyped processing typical of complete tracrRNA elements.

Complete tracrRNA candidates identified by RNA sequencing are validated in vitro or in vivo by expressing the crRNA and effector in combination with or without the tracrRNA candidate, and monitoring the activation of effector enzymatic activity. Constructs are engineered to have the expression of tracrRNAs can be driven bypromoters including, but not limited to, U6, U1, and H1 promoters for expression in mammalian cells or J23119 promoter for expression in bacteria. In some instances, a tracrRNA can be fused with a crRNA and expressed as a single guide RNA.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An engineered, non-naturally occurring Clustered Regularly Interspaced Short Palindromic Repeat (CRISPR)—Cas system comprising:
   an RNA guide comprising a direct repeat sequence and a spacer sequence capable of hybridizing to a target nucleic acid; and
   a CRISPR-associated protein, wherein the CRISPR-associated protein comprises an amino acid sequence that is at least 99% identical to the amino acid sequence of SEQ ID NO: 316, SEQ ID NO: 317, or SEQ ID NO: 318;
   wherein the CRISPR-associated protein is capable of binding to the RNA guide and of targeting the target nucleic acid sequence complementary to the spacer sequence.

2. The system of claim 1, wherein the CRISPR-associated protein comprises an amino acid sequence that is at least 99% identical to the amino acid sequence of SEQ ID NO: 316.

3. The system of claim 1, wherein the CRISPR-associated protein comprises the amino acid sequence of SEQ ID NO: 316.

4. The system of claim 1, wherein the CRISPR-associated protein comprises an amino acid sequence that is at least 99% identical to the amino acid sequence of SEQ ID NO: 317.

5. The system of claim 1, wherein the CRISPR-associated protein comprises the amino acid sequence of SEQ ID NO: 317.

6. The system of claim 1, wherein the CRISPR-associated protein comprises an amino acid sequence that is at least 99% identical to the amino acid sequence of SEQ ID NO: 318.

7. The system of claim 1, wherein the CRISPR-associated protein comprises the amino acid sequence of SEQ ID NO: 318.

8. The system of claim 1, wherein the CRISPR-associated protein comprises a RuvC domain.

9. The system of claim 1, wherein the CRISPR-associated protein comprises an OrfB_Zn_ribbon domain.

10. The system of claim 1, wherein the direct repeat sequence comprises a nucleic acid sequence of TGRGAC (SEQ NO: 319).

11. The system of claim 1, wherein the direct repeat sequence comprises a nucleic acid sequence of any of SEQ ID NOS: 321-328, or a sequence having at least 90% identity thereto.

12. The system of claim 1, wherein the direct repeat sequence forms a stem-loop.

13. The system of claim 1, wherein the spacer sequence has a length of 15-50 nucleotides.

14. The system of claim 1, wherein the CRISPR-associated protein is capable of recognizing a protospacer adjacent motif (PAM).

15. The system of claim 1, wherein the target nucleic acid is a DNA.

16. The system of claim 1, wherein the targeting of the target nucleic acid by the CRISPR-associated protein and RNA guide results in a modification in the target nucleic acid.

17. The system of claim 16, wherein the modification in the target nucleic acid is a double stranded cleavage event.

18. The system of claim 16, wherein the modification in the target nucleic acid is a single stranded cleavage event.

19. The system of claim 1, within a cell.

20. A method of targeting and editing a target nucleic acid, the method comprising contacting the target nucleic acid with a system of claim 1.

* * * * *

UNITED STATES PATENT AND TRADEMARK OFFICE
CERTIFICATE OF CORRECTION

PATENT NO. : 11,667,904 B2
APPLICATION NO. : 16/862261
DATED : June 6, 2023
INVENTOR(S) : Cheng et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 464 days.

Signed and Sealed this
Twelfth Day of November, 2024

Katherine Kelly Vidal
*Director of the United States Patent and Trademark Office*

SEQUENCE LISTING

```
<160> NUMBER OF SEQ ID NOS: 328

<210> SEQ ID NO 1
<211> LENGTH: 716
<212> TYPE: PRT
<213> ORGANISM: Candidatus Scalindua brodae

<400> SEQUENCE: 1

Met Asn Asn Thr Glu Glu Asn Ile Asp Arg Ile Gln Glu Pro Thr Arg
1               5                   10                  15

Glu Asp Ile Asp Arg Lys Glu Ala Glu Arg Leu Leu Asp Glu Ala Phe
            20                  25                  30

Asn Pro Arg Thr Lys Pro Val Asp Arg Lys Lys Ile Ile Asn Ser Ala
        35                  40                  45

Leu Lys Ile Leu Ile Gly Leu Tyr Lys Glu Lys Lys Asp Asp Leu Thr
    50                  55                  60

Ser Ala Ser Phe Ile Ser Ile Ala Arg Ala Tyr Tyr Leu Val Ser Ile
65                  70                  75                  80

Thr Ile Leu Pro Lys Gly Thr Thr Ile Pro Glu Lys Lys Lys Glu Ala
                85                  90                  95

Leu Arg Lys Gly Ile Glu Phe Ile Asp Arg Ala Ile Asn Lys Phe Asn
            100                 105                 110

Gly Ser Ile Leu Asp Ser Gln Arg Ala Phe Arg Ile Lys Ser Val Leu
        115                 120                 125
```

```
Ser Ile Glu Phe Asn Arg Ile Asp Arg Glu Lys Cys Asp Asn Ile Lys
    130                 135                 140

Leu Lys Asn Leu Leu Asn Glu Ala Val Asp Lys Gly Cys Thr Asp Phe
145                 150                 155                 160

Asp Thr Tyr Glu Trp Asp Ile Gln Ile Ala Ile Arg Leu Cys Glu Leu
                165                 170                 175

Gly Val Asp Met Glu Gly His Phe Asp Asn Leu Ile Lys Ser Asn Lys
                180                 185                 190

Ala Asn Asp Leu Gln Lys Ala Lys Ala Tyr Tyr Phe Ile Lys Lys Asp
            195                 200                 205

Asp His Lys Ala Lys Glu His Met Asp Lys Cys Thr Ala Ser Leu Lys
210                 215                 220

Tyr Thr Pro Cys Ser His Arg Leu Trp Asp Glu Thr Val Gly Phe Ile
225                 230                 235                 240

Glu Arg Leu Lys Gly Asp Ser Ser Thr Leu Trp Arg Asp Phe Ala Ile
                245                 250                 255

Lys Thr Tyr Arg Ser Cys Arg Val Gln Glu Lys Glu Thr Gly Thr Leu
                260                 265                 270

Arg Leu Arg Trp Tyr Trp Ser Arg His Arg Val Leu Tyr Asp Met Ala
            275                 280                 285

Phe Leu Ala Val Lys Glu Gln Ala Asp Asp Glu Glu Pro Asp Val Asn
290                 295                 300

Val Lys Gln Ala Lys Ile Lys Lys Leu Ala Glu Ile Ser Asp Ser Leu
305                 310                 315                 320

Lys Ser Arg Phe Ser Leu Arg Leu Ser Asp Met Glu Lys Met Pro Lys
                325                 330                 335

Ser Asp Asp Glu Ser Asn His Glu Phe Lys Lys Phe Leu Asp Lys Cys
                340                 345                 350

Val Thr Ala Tyr Gln Asp Gly Tyr Val Ile Asn Arg Ser Glu Asp Lys
            355                 360                 365

Glu Gly Gln Gly Glu Asn Lys Ser Thr Thr Ser Lys Gln Pro Glu Pro
370                 375                 380

Arg Pro Gln Ala Lys Leu Leu Glu Leu Thr Gln Val Pro Glu Gly Trp
385                 390                 395                 400

Val Val His Phe Tyr Leu Asn Lys Leu Glu Gly Met Gly Asn Ala
                405                 410                 415

Ile Val Phe Asp Lys Cys Ala Asn Ser Trp Gln Tyr Lys Glu Phe Gln
                420                 425                 430

Tyr Lys Glu Leu Phe Glu Val Phe Leu Thr Trp Gln Ala Asn Tyr Asn
            435                 440                 445

Leu Tyr Lys Glu Asn Ala Ala Glu His Leu Val Thr Leu Cys Lys Lys
450                 455                 460

Ile Gly Glu Thr Met Pro Phe Leu Phe Cys Asp Asn Phe Ile Pro Asn
465                 470                 475                 480

Gly Lys Asp Val Leu Phe Val Pro His Asp Phe Leu His Arg Leu Pro
                485                 490                 495

Leu His Gly Ser Ile Glu Asn Lys Thr Asn Gly Lys Leu Phe Leu Glu
                500                 505                 510

Asn His Ser Cys Cys Tyr Leu Pro Ala Trp Ser Phe Ala Ser Glu Lys
            515                 520                 525

Glu Ala Ser Thr Ser Asp Glu Tyr Val Leu Leu Lys Asn Phe Asp Gln
530                 535                 540
```

```
Gly His Phe Glu Thr Leu Gln Asn Asn Gln Ile Trp Gly Thr Gln Ser
545                 550                 555                 560

Val Lys Asp Gly Ala Ser Ser Asp Asp Leu Glu Asn Ile Arg Asn Asn
                565                 570                 575

Pro Arg Leu Leu Thr Ile Leu Cys His Gly Glu Ala Asn Met Ser Asn
                580                 585                 590

Pro Phe Arg Ser Met Leu Lys Leu Ala Asn Gly Gly Ile Thr Tyr Leu
            595                 600                 605

Glu Ile Leu Asn Ser Val Lys Gly Leu Lys Gly Ser Gln Val Ile Leu
        610                 615                 620

Gly Ala Cys Glu Thr Asp Leu Val Pro Pro Leu Ser Asp Val Met Asp
625                 630                 635                 640

Glu His Tyr Ser Val Ala Thr Ala Leu Leu Leu Ile Gly Ala Ala Gly
                645                 650                 655

Val Val Gly Thr Met Trp Lys Val Arg Ser Asn Lys Thr Lys Ser Leu
                660                 665                 670

Ile Glu Trp Lys Leu Glu Asn Ile Glu Tyr Lys Leu Asn Glu Trp Gln
            675                 680                 685

Lys Glu Thr Gly Gly Ala Ala Tyr Lys Asp His Pro Pro Thr Phe Tyr
        690                 695                 700

Arg Ser Ile Ala Phe Arg Ser Ile Gly Phe Pro Leu
705                 710                 715

<210> SEQ ID NO 2
<211> LENGTH: 849
<212> TYPE: PRT
<213> ORGANISM: Deltaproteobacteria bacterium

<400> SEQUENCE: 2

Met Asn Gln Asn Ile Asp Arg Ala Val Gly Ala Ile Leu Ala Ile Glu
1               5                   10                  15

Thr Ala Thr Pro Leu Thr Glu Ser Ser Thr Leu Ala Gln Arg Glu Arg
                20                  25                  30

His Gln Lys Leu Leu His Asp Glu Thr Lys Lys Ile Glu Gln Ala Phe
            35                  40                  45

Ile Ala Leu Ala Gln Pro Pro Gln Cys Arg Ala Val Glu Ile Ala Ala
        50                  55                  60

Leu Ser Arg Phe Leu Gln Met Thr Pro Leu Ala Val Gly Pro Leu Arg
65                  70                  75                  80

Lys Arg Val Ile Cys Arg Ala Glu Pro Leu Lys Asp Asp Ala His Glu
                85                  90                  95

Gln Glu Ile Ala Ser His Phe Asn Gly Leu Leu Leu Arg Leu Ala Lys
            100                 105                 110

Gly Leu Leu Ala Ser Ala Leu Asn Pro Ala Gly Ile Pro Trp Arg Arg
        115                 120                 125

Arg Val Leu Trp Leu Glu Lys Ala Ala His Ile Ala His Arg Phe Asp
    130                 135                 140

Lys Glu Pro Leu Ala Asp Asp Lys Glu Arg Thr Glu Ala Ala Gly Val
145                 150                 155                 160

Leu Ala Arg Cys Cys Leu His Leu Ala Leu Ala His Leu Pro Lys Gly
                165                 170                 175

Lys Asp Lys Ser Ala Met Ala Glu Arg Gln Glu Asp Leu Leu Gln Ser
            180                 185                 190

Leu Met Trp Ala Gln Lys Ala Ile Val Leu Ala Gly Gln Asp Lys Leu
        195                 200                 205
```

```
Ser Gly Glu Glu Tyr Lys Leu Leu Lys Ala Leu Val Leu Ile Glu Leu
    210                 215                 220

Asp Asn Leu Ser Pro Gly Arg Phe Gln Gln Gln Leu Asn Tyr Val Leu
225                 230                 235                 240

Tyr Asp Leu Ala Val Ile Trp Leu Glu Arg Asp Thr Ala Thr Lys Pro
                245                 250                 255

Phe His Pro Gln Glu Leu Phe Val Leu Trp Arg Tyr Leu Ala Thr Asp
            260                 265                 270

Phe Glu Pro Asp Leu Asn Met Leu Leu Phe Lys Gly Ser Asn Thr Ser
        275                 280                 285

Glu Arg Thr Ala Ala Val Gln Gln Ala Ser Pro Glu Ala Glu Arg Phe
290                 295                 300

Arg Pro Leu Leu Pro Leu Ile His Ala Trp Ser Ala Trp Lys Leu Asp
305                 310                 315                 320

Pro Pro Asn Asn Lys Ile Ala Glu Val Ile Leu Gln Ala Val Asn Asn
                325                 330                 335

Leu Asp Glu His Gln Val Tyr Glu Gln Val Trp Lys Trp Thr Val Asp
            340                 345                 350

Phe Leu Gln Glu Leu Arg Asn Thr Gly Ala Val Asp Trp Gln Leu Pro
        355                 360                 365

Ala Ile Ala Ala Trp Glu Leu Cys Asn Lys Lys Glu Lys Glu Leu Pro
370                 375                 380

Phe Gly Phe Gln Ile Arg Gln Tyr Trp Ser Arg Leu Asp Ser Leu Tyr
385                 390                 395                 400

Arg Leu Ala Phe Asp Gly Ala Leu Glu Leu Lys Asp Cys Met Thr Ala
                405                 410                 415

Ala Arg Ile Val Asp Ser Leu Lys Ser Arg Thr Pro Leu Thr Trp Arg
            420                 425                 430

Asp Met Asp Thr Leu Phe Ala Lys Leu Pro Lys Glu Lys Ala Asp Gln
        435                 440                 445

Leu Arg Glu Ala Phe Tyr Ser Met Glu Val Gln Ala Arg Met Gly Phe
450                 455                 460

Tyr Ala Glu Ala Lys Glu Asp Ala Asn Lys Leu Lys Lys Leu Leu Ala
465                 470                 475                 480

Ala Gln Val Arg Lys Ile Arg Asp Ile Glu Ser Val Pro Ala Gly Trp
                485                 490                 495

Thr Val Val His Phe His Leu Arg Glu Asp Gln Asp Leu Gly Tyr Ala
            500                 505                 510

Leu Ala Cys Arg Leu Thr Ala Asp Gly Met Ser Tyr Trp Thr Asn His
        515                 520                 525

Ile Phe Pro Val Ala Gly Ile Arg Arg Ala Tyr Asp Cys Trp Leu Glu
530                 535                 540

Ala Tyr His Gly Met Glu Pro Gly Ala Arg Glu Lys Ser Gly Tyr Gln
545                 550                 555                 560

Leu Val Glu Leu Ser Glu Ile Met Gly Lys Asp Leu Asp Phe Leu Phe
                565                 570                 575

Glu Leu Ala Gly Glu Asp Gly Ala Arg Gly Leu Leu Phe Val Pro His
            580                 585                 590

Gly Phe Ser His Leu Leu Pro Leu His Ala Ala Lys Lys Asp Gly Ser
        595                 600                 605

Tyr Leu Phe Glu Lys Ile Pro Ser Leu Thr Leu Pro Ala Trp Glu Phe
610                 615                 620
```

```
Ala Pro Asp Val Asp Gln Ile Pro Val Ser Asp Gly Gln Asp Phe Cys
625                 630                 635                 640

Phe Ile Ser Gln Arg Ala Asn Glu Gln Asp Leu Val Gly Asn Ile Glu
                645                 650                 655

Arg Ser His Thr Trp Asn Gly Val Cys Asn Lys Asn Ala Ala Trp Thr
            660                 665                 670

Asn Val Leu Asn Thr Asn Lys Glu Trp Ser Lys Ala Pro Pro Arg Trp
        675                 680                 685

Leu Val Phe Trp Cys His Gly Gln Ala Asp Pro His Val Ala Phe Arg
    690                 695                 700

Ser Lys Leu Leu Leu Gly Thr Leu Gly Val Ser Leu Phe Glu Ile Gln
705                 710                 715                 720

Glu Ala Ala Leu Ser Leu Thr Gly Thr Lys Val Val Leu Ala Val Cys
                725                 730                 735

Glu Ser Asp Leu Ala Pro Pro Glu Glu Tyr Glu Lys Thr Asp Asp His
            740                 745                 750

Leu Ser Leu Ala Ala Pro Phe Leu Leu Lys Gly Ala Arg Gln Val Leu
        755                 760                 765

Ala Ala Ile Trp Glu Gly Ala Gln Leu Asp Leu Leu Lys Ala Met Lys
    770                 775                 780

Glu Met Leu Ser Asn Gln Asp Lys His Ser Trp Glu Ile Leu Arg Glu
785                 790                 795                 800

Leu Gln Ser Cys Trp Met Arg Gln Pro Gly Ala Ile Phe Asn Asp Glu
                805                 810                 815

Tyr Ile Arg Leu Tyr Tyr Ala Ala Ser Phe Arg Ile Leu Gly Phe Pro
            820                 825                 830

Glu Val Ala Thr Thr Asn Met Ala Thr Ala Thr Ala Gln Glu Glu Ile
        835                 840                 845

Ala

<210> SEQ ID NO 3
<211> LENGTH: 751
<212> TYPE: PRT
<213> ORGANISM: Desulfonema ishimotonii

<400> SEQUENCE: 3

Met Ser Asn Pro Ile Arg Asp Ile Gln Asp Arg Leu Lys Thr Ala Lys
1               5                   10                  15

Phe Asp Asn Lys Asp Asp Met Met Asn Leu Ala Ser Ser Leu Tyr Lys
            20                  25                  30

Tyr Glu Lys Gln Leu Met Asp Ser Glu Ala Thr Leu Cys Gln Gln
        35                  40                  45

Gly Leu Ser Asn Arg Pro Asn Ser Phe Ser Gln Leu Ser Gln Phe Arg
    50                  55                  60

Asp Ser Asp Ile Gln Ser Lys Ala Gly Gly Thr Gly Lys Phe Trp
65                  70                  75                  80

Gln Asn Glu Tyr Glu Ala Cys Lys Asn Phe Gln Thr His Lys Glu Arg
                85                  90                  95

Arg Glu Thr Leu Glu Gln Ile Ile Arg Phe Leu Gln Asn Gly Ala Glu
            100                 105                 110

Glu Lys Asp Ala Asp Asp Leu Leu Lys Thr Leu Ala Arg Ala Tyr
        115                 120                 125

Phe His Arg Gly Leu Leu Tyr Arg Pro Lys Gly Phe Ser Val Pro Ala
    130                 135                 140
```

-continued

```
Arg Lys Val Glu Ala Met Lys Lys Ala Ile Ala Tyr Cys Glu Ile Ile
145                 150                 155                 160

Leu Asp Lys Asn Glu Glu Ser Glu Ala Leu Arg Ile Trp Leu Tyr
            165                 170                 175

Ala Ala Met Glu Leu Arg Arg Cys Gly Glu Glu Tyr Pro Glu Asn Phe
                180                 185                 190

Ala Glu Lys Leu Phe Tyr Leu Ala Asn Asp Gly Phe Ile Ser Glu Leu
            195                 200                 205

Tyr Asp Ile Arg Leu Phe Leu Glu Tyr Thr Glu Arg Glu Glu Asp Asn
    210                 215                 220

Asn Phe Leu Asp Met Ile Leu Gln Glu Asn Gln Asp Arg Glu Arg Leu
225                 230                 235                 240

Phe Glu Leu Cys Leu Tyr Lys Ala Arg Ala Cys Phe His Leu Asn Gln
                245                 250                 255

Leu Asn Asp Val Arg Ile Tyr Gly Glu Ser Ala Ile Asp Asn Ala Pro
            260                 265                 270

Gly Ala Phe Ala Asp Pro Phe Trp Asp Glu Leu Val Glu Phe Ile Arg
        275                 280                 285

Met Leu Arg Asn Lys Lys Ser Glu Leu Trp Lys Glu Ile Ala Ile Lys
    290                 295                 300

Ala Trp Asp Lys Cys Arg Glu Lys Glu Met Lys Val Gly Asn Asn Ile
305                 310                 315                 320

Tyr Leu Ser Trp Tyr Trp Ala Arg Gln Arg Glu Leu Tyr Asp Leu Ala
                325                 330                 335

Phe Met Ala Gln Asp Gly Ile Glu Lys Lys Thr Arg Ile Ala Asp Ser
            340                 345                 350

Leu Lys Ser Arg Thr Thr Leu Arg Ile Gln Glu Leu Asn Glu Leu Arg
        355                 360                 365

Lys Asp Ala His Arg Lys Gln Asn Arg Arg Leu Glu Asp Lys Leu Asp
    370                 375                 380

Arg Ile Ile Glu Gln Glu Asn Glu Ala Arg Asp Gly Ala Tyr Leu Arg
385                 390                 395                 400

Arg Asn Pro Pro Cys Phe Thr Gly Gly Lys Arg Glu Glu Ile Pro Phe
                405                 410                 415

Ala Arg Leu Pro Gln Asn Trp Ile Ala Val His Phe Tyr Leu Asn Glu
            420                 425                 430

Leu Glu Ser His Glu Gly Gly Lys Gly Gly His Ala Leu Ile Tyr Asp
        435                 440                 445

Pro Gln Lys Ala Glu Lys Asp Gln Trp Gln Asp Lys Ser Phe Asp Tyr
    450                 455                 460

Lys Glu Leu His Arg Lys Phe Leu Glu Trp Gln Glu Asn Tyr Ile Leu
465                 470                 475                 480

Asn Glu Glu Gly Ser Ala Asp Phe Leu Val Thr Leu Cys Arg Glu Ile
                485                 490                 495

Glu Lys Ala Met Pro Phe Leu Phe Lys Ser Glu Val Ile Pro Glu Asp
            500                 505                 510

Arg Pro Val Leu Trp Ile Pro His Gly Phe Leu His Arg Leu Pro Leu
        515                 520                 525

His Ala Ala Met Lys Ser Gly Asn Asn Ser Asn Ile Glu Ile Phe Trp
    530                 535                 540

Glu Arg His Ala Ser Arg Tyr Leu Pro Ala Trp His Leu Phe Asp Pro
545                 550                 555                 560

Ala Pro Tyr Ser Arg Glu Glu Ser Ser Thr Leu Leu Lys Asn Phe Glu
```

```
                    565                 570                 575
Glu Tyr Asp Phe Gln Asn Leu Glu Asn Gly Glu Ile Glu Val Tyr Ala
                580                 585                 590

Pro Ser Ser Pro Lys Lys Val Lys Glu Ala Ile Arg Glu Asn Pro Ala
            595                 600                 605

Ile Leu Leu Leu Cys His Gly Glu Ala Asp Met Thr Asn Pro Phe
        610                 615                 620

Arg Ser Cys Leu Lys Leu Lys Asn Lys Asp Met Thr Ile Phe Asp Leu
625                 630                 635                 640

Leu Thr Val Glu Asp Val Arg Leu Ser Gly Ser Arg Ile Leu Leu Gly
                645                 650                 655

Ala Cys Glu Ser Asp Met Val Pro Pro Leu Glu Phe Ser Val Asp Glu
            660                 665                 670

His Leu Ser Val Ser Gly Ala Phe Leu Ser His Lys Ala Gly Glu Ile
        675                 680                 685

Val Ala Gly Leu Trp Thr Val Asp Ser Glu Lys Val Asp Glu Cys Tyr
        690                 695                 700

Ser Tyr Leu Val Glu Glu Lys Asp Phe Leu Arg Asn Leu Gln Glu Trp
705                 710                 715                 720

Gln Met Ala Glu Thr Glu Asn Phe Arg Ser Glu Asn Asp Ser Ser Leu
                725                 730                 735

Phe Tyr Lys Ile Ala Pro Phe Arg Ile Ile Gly Phe Pro Ala Glu
            740                 745                 750

<210> SEQ ID NO 4
<211> LENGTH: 816
<212> TYPE: PRT
<213> ORGANISM: Unknown
<220> FEATURE:
<223> OTHER INFORMATION: Description of Unknown:
      Soil metagenome sequence

<400> SEQUENCE: 4

Met Glu His Lys Thr Met Thr Glu Pro Ala Gly Gln Asn Pro Ser Ala
1               5                   10                  15

Thr Asp Asn Asp Phe Glu Lys Phe Ile Ile Asp Thr Gly Cys Val Phe
                20                  25                  30

Phe Ala Thr Pro Gln Glu Asp Pro Lys Tyr Gln Asn Asn Lys Val Glu
            35                  40                  45

Trp His Gln Gly Leu Cys Arg Phe Ala Gln Asn Asp Ser Pro Thr
        50                  55                  60

Val Ile Gly Ser Ala Ile Phe Phe Leu Gln Lys Leu Gln Glu Pro Gly
65              70                  75                  80

Leu Phe Ser Gly Leu Pro Val Ser Pro Glu Leu Cys Ser Lys Ile Ser
                85                  90                  95

Lys Asp Lys Asn Glu Ile Val Ala Tyr His Gln Gln Cys Ile Leu Arg
            100                 105                 110

Leu Cys Glu Glu Leu Leu Val Lys Gly Arg Glu Ala Lys Glu His Arg
        115                 120                 125

Glu Arg Arg Gln Ala Phe Asp Gln Ala Ile Lys Phe Leu Leu Val Leu
    130                 135                 140

Lys Lys Gly Thr Ser Ser Asp Thr Pro Ser Pro Asn Gly His Ile His
145                 150                 155                 160

Phe Gln Asp Gln Val Ser Ile Leu Leu Ala Glu Ala Tyr Tyr Leu Arg
                165                 170                 175
```

```
Gly Lys Ile Ile Arg Pro Lys Gly Phe Ser Val Pro Ala Lys Lys Ile
            180                 185                 190

Glu Thr Leu Glu Val Ala Glu Lys Ile Leu Val Asp Leu Val Ala Arg
        195                 200                 205

Asp Thr Thr Gly Lys Ala Arg Arg Leu Arg Ala Met Val His Ile Asp
    210                 215                 220

Leu Ala Ala Leu Arg Asp Pro Ala Asp Asp Ser Gly Asn Leu Gln Asp
225                 230                 235                 240

Tyr Arg Gln Ala Leu Glu Gln Ala Val Ser Ser Ile Gly Asp Thr Lys
                245                 250                 255

Thr Cys Gly Arg Asp Glu Ile Val Ile Ile Leu Ala Arg Ala Glu Asp
            260                 265                 270

Asn Ala Gly Trp Thr Gly Ser Asp Gly Leu Ser Ala Arg Leu Glu Glu
        275                 280                 285

Leu Val Asn Asn Gly Ala Ala Gly Pro Leu Asp Gln Ala Arg Ala Tyr
    290                 295                 300

Leu Leu Leu Gly Gln Asn Asn Leu Ala Val Thr Gln Thr Glu Lys Ala
305                 310                 315                 320

Ile Thr Arg Met Ala Ala Thr Asp Asn Pro Thr Pro Phe Ser His Glu
                325                 330                 335

Asp Trp Arg Leu Leu Val Arg Leu Leu Arg Asp Leu Lys His Gln Asn
            340                 345                 350

Thr Ala Gly Ile Asp Lys Leu Ile Leu Asp Thr Trp Arg Lys Val His
        355                 360                 365

Gln Ile Glu Arg Gln Thr Lys Asn Gly Met His Val Arg Trp Tyr Trp
    370                 375                 380

Ser Arg Gln Arg Asp Leu Tyr Asp Leu Ala Phe His Ala Ala Gly Asn
385                 390                 395                 400

Asp Ala Arg Leu Lys Ala Gln Ile Ala Asp Ser Leu Lys Ala Arg Pro
                405                 410                 415

Ala Leu His Leu Gly Gln Ala Ala Asp Leu Gly Leu Ala Val Glu Gln
            420                 425                 430

Met Glu Ala Gly Leu Leu Asp Arg Tyr Met Pro Gly Lys Met Leu Glu
        435                 440                 445

Gln Thr Thr Asp Met Ala Ala Pro Ala Ala Pro Gly Ser Ala Gly Trp
    450                 455                 460

Pro Glu Leu Pro Arg Pro Trp Ile Ala Val His Phe Tyr Leu Ser Asn
465                 470                 475                 480

Gly Phe Gly His Pro Glu Gly Lys Gln Gln Gly His Ala Leu Ile Gln
                485                 490                 495

Asp Ser Ser Lys Gly Asp Gly Lys Asp Thr Trp Ser Glu Arg Thr Phe
            500                 505                 510

Asp Tyr Phe Pro Ile Trp Ala Ala Phe Met Thr Trp Gln Glu Asn Tyr
        515                 520                 525

Gln Arg Leu Lys Lys Glu Ala Ala Pro Asp Leu Glu Arg Leu Cys Gln
    530                 535                 540

Val Met Gly Arg Gln Met Pro Phe Leu Phe Ala Pro Glu Asp Leu Pro
545                 550                 555                 560

Leu Glu Arg Pro Val Phe Val Pro His Asp Phe Leu His Arg Leu
                565                 570                 575

Pro Leu His Ala Ala Leu Ile Asp Asn Gly Glu Glu Ser Gly Ile Pro
            580                 585                 590

Ala Gln Ser His Pro Ile Thr Tyr Leu Pro Gly Trp Trp Met Val Thr
```

-continued

```
                595                 600                 605
Ser Gln Ala Ala Asn Pro Asn Glu Thr Ala Ser Lys Asn Thr Pro Ser
    610                 615                 620

Pro Val Ala Pro Val Ala Leu Val His Trp Asp Asn Ser Glu Asp Ile
625                 630                 635                 640

His Asp Ile Ile Lys Gln Ala Asn Gly Thr Val Val Asn Ala Ser
                    645                 650                 655

Arg Ser Asp Trp Leu Lys Leu Lys His Asn Ala Val Gly Leu Lys Val
                660                 665                 670

Leu Tyr Cys His Gly Gln Ala Gly Tyr Thr Asn Pro Phe Ala Ser Ser
                    675                 680                 685

Leu Lys Leu Asp Gly Gly Leu Tyr Leu Lys Asp Val Val Lys Gly
    690                 695                 700

Pro Pro Leu Val Gly Arg Phe Ile Leu Ala Ala Cys Glu Ser Asp Leu
705                 710                 715                 720

Val Leu Pro Ala Ser Thr Thr Leu Asp Glu Tyr Phe Ser Phe Ser Thr
                    725                 730                 735

Gly Leu Leu Gln Lys Gly Ala Ala Glu Ile Leu Gly Thr Leu Trp Glu
                740                 745                 750

Val Asn Glu Thr Asp Ala Leu Ser Leu Ile Glu Thr Val Leu Arg Ala
                    755                 760                 765

Pro Ala Ser Gly Asn Leu Ser Phe Val Leu Arg Asp Trp Leu Arg Asp
770                 775                 780

Asn Leu Arg Ser Leu Thr Thr Glu Leu Phe Tyr Asp Ile Ala Ala Phe
785                 790                 795                 800

Arg Ala Leu Gly Gly Pro Tyr Pro Val Asp Thr Lys Glu His Arg
                    805                 810                 815

<210> SEQ ID NO 5
<211> LENGTH: 769
<212> TYPE: PRT
<213> ORGANISM: Unknown
<220> FEATURE:
<223> OTHER INFORMATION: Description of Unknown:
      Dolphin oral metagenome sequence

<400> SEQUENCE: 5

Met Asn Thr Val Glu Leu Leu Gln Glu Glu Arg Leu Thr Leu Asp
1               5                   10                  15

Leu Val Phe Leu Pro Pro Gly Ser Lys Asn Lys Glu Gln Lys Lys Asn
                20                  25                  30

Ala Leu Val Asp Leu Leu Lys Ile Val Glu His Gly Glu Leu Thr
                35                  40                  45

Arg Lys Tyr Ser Ala Leu Leu Thr Leu Ser Arg Gly Ala Leu Arg Gly
    50                  55                  60

Glu Val His Phe Gly Glu Lys Leu Leu Pro Ser Pro Glu Ala Cys Ala
65                  70                  75                  80

Asn Leu Ala Lys Pro Glu Glu Ile Lys Lys Met Ile Arg Gln His Phe
                85                  90                  95

Gln Tyr Arg Leu Asp Leu Leu Glu Ala Ile Val Lys Lys Ala Ala Asp
                    100                 105                 110

Asn Thr Tyr Ser His Ala Arg Arg Lys Ala Leu Arg Ile Ala Ile
                115                 120                 125

Lys Glu Leu Glu Gln Ile Cys Glu Glu Ala Leu Asp Glu Leu Cys Phe
            130                 135                 140
```

-continued

```
Lys Ala Arg Leu Leu Leu Ala Glu Ala Leu Phe Glu Arg Gly Arg Ile
145                 150                 155                 160

Val Arg Pro Lys Gly Phe Ser Glu Pro Gly Lys Lys Lys Glu Leu Phe
            165                 170                 175

Gln Lys Ala Ile Asn Cys Ile Glu Gly Asn Cys Ser Glu Glu Ala Leu
        180                 185                 190

Arg Leu Arg Ala Arg Ile Tyr Leu Gln Trp Tyr Arg Phe Phe His Asp
    195                 200                 205

Glu Pro Pro Cys Asp Leu Asp Asp Ile Phe Thr Lys Ala Leu Ala Val
210                 215                 220

Thr Asp Asp Lys Met Leu Lys Thr Glu Leu Leu Leu Cys Gly Glu
225                 230                 235                 240

Arg Lys Glu Pro Asp Pro Tyr Thr Asp Asp Leu Arg Ala Leu Leu Asn
            245                 250                 255

Asp Gln Asn Val Ser Pro Leu Ser Arg Ala Arg Ala Ala Val Leu Leu
        260                 265                 270

Glu Asp Trp Glu Arg Cys Asn Val Glu Ile Tyr Glu Ala Ile Glu Asp
    275                 280                 285

Leu Gly Lys Thr Asp Phe Phe Gln Gln Asp Trp Glu Leu Val Val Thr
290                 295                 300

Leu Leu Lys Lys Asn Tyr Asn Gln Phe His Gly Trp Ser Arg Ala Cys
305                 310                 315                 320

Thr Arg Leu Trp Glu Ile Thr Val Lys Glu Ser Lys Asp Ala Gly
            325                 330                 335

His Gly Cys Val Leu Arg Trp Tyr Trp Ser Arg Gln Arg Asp Val Tyr
        340                 345                 350

Asn Leu Ala Phe Ala Ala Phe Glu Glu Cys Glu Asp Lys Ala Arg Val
    355                 360                 365

Val Asp Ser Leu Lys Asn Arg Pro Ala His His Phe Ser Gln Leu Glu
370                 375                 380

Gln Leu Ala Gln Ser Ser Asp Ile Ile Lys Gln Trp Ile Glu Ser Glu
385                 390                 395                 400

Glu Ile Ile Asn Gln Asp Ser Phe Ala His Ser Leu Arg Arg His Glu
            405                 410                 415

Lys Gly Ala Lys Ser His Ser Gly Ser Leu Arg Ile Phe Pro Cys
        420                 425                 430

Leu Pro Lys Gly Trp Ile Ala Val His Phe Phe Leu Ala Ser Trp Pro
    435                 440                 445

Glu Pro Lys Gly Tyr Ala Leu Ile His Asn Ala Asp Thr Asn Thr Trp
450                 455                 460

Glu Gln Arg Asp Phe Lys Tyr Glu Gln Leu Trp Ala Thr Tyr Ile Ala
465                 470                 475                 480

Trp Gln Glu Val Ser Leu His Asn Lys Ile Arg Glu Ser Ala Leu Leu
            485                 490                 495

Leu Lys Ser Leu Cys Glu Thr Leu Gly Lys Glu Met Arg Trp Leu Phe
        500                 505                 510

Asp Glu Phe Leu Phe Pro Lys Glu Arg Arg Arg Val Leu Phe Val Pro
    515                 520                 525

His Asp Phe Leu His Arg Leu Pro Leu His Met Ala Ile Asp Ile Glu
530                 535                 540

Ser Gln Thr Val Phe Ala Ala Lys Gln Pro Val Cys Tyr Leu Pro Ala
545                 550                 555                 560

Tyr His Leu Gln Asn Asn Ile Thr Glu Asn Lys Lys Thr Ser Ile Tyr
```

```
                    565                 570                 575
Ala Leu Val Asn Leu Arg Glu Asn Lys Gln Gln Lys Lys Asp Glu Glu
                580                 585                 590

Ile Phe Ala Glu Lys Val Glu Lys Met Gly Ala Ile Val Arg Arg Pro
                595                 600                 605

Ala Leu Glu Ser Asp Leu Leu Asn Leu Asn Pro Val Pro Glu Lys Leu
            610                 615                 620

Val Leu Tyr Cys His Gly Ile Gly His Ser Ala Asn Pro Phe Ala Ser
625                 630                 635                 640

Lys Leu Cys Leu Gly Asp Thr Gly Val Ser Tyr Arg Asp Ile Leu Ala
                645                 650                 655

Leu Asn Arg Ser Leu Ala Gly Cys Arg Val Leu Leu Phe Ala Cys Glu
                660                 665                 670

Thr Asp Leu Val Pro Ala Gln Thr Ser Ser Ile Asp Glu His Leu Ser
                675                 680                 685

Ile Ser Asn Ala Leu Leu Gln Lys Gly Ala Phe Glu Val Leu Gly Ser
            690                 695                 700

Leu Trp Ala Leu Pro Gly Lys Thr Ile Tyr Gly Ile Thr Lys Thr Phe
705                 710                 715                 720

Ile Asp Asn Asp Asp Thr Ser Ala Val Leu His Ser Ser Leu Lys Arg
                725                 730                 735

Leu Phe Glu His Tyr Glu Lys Lys Asn Glu Lys Thr Arg Ala Gln Leu
                740                 745                 750

Leu Tyr Asn Trp Ala Ser Leu Arg Val Leu Ala Pro Ala Arg Glu Phe
            755                 760                 765

Ser

<210> SEQ ID NO 6
<211> LENGTH: 778
<212> TYPE: PRT
<213> ORGANISM: Unknown
<220> FEATURE:
<223> OTHER INFORMATION: Description of Unknown:
      Aquatic-marine-hydrothermal vent microbial mat sequence

<400> SEQUENCE: 6

Met Arg Tyr Ser Ser Arg Thr Asn Cys Glu Ala Ile Asp Asn Leu Ala
1               5                   10                  15

Glu Ala Leu Gln Asp Gln Glu Asn Met Pro Glu Ile Ala Arg Arg Val
                20                  25                  30

Leu Glu Phe Glu Ala Glu Asn Ala Lys Pro Glu Asn Ala Leu Cys Gln
            35                  40                  45

His Gly Leu Pro His Thr Lys Lys Ala Ala Ser Gln Ile Ala Gly Val
        50                  55                  60

Arg Asp Lys His Ser Glu Phe Tyr Asp Asn Ala Leu Leu Asp Leu Val
65                  70                  75                  80

Glu Glu Trp Leu Lys Thr Tyr Glu Glu Ala Lys Lys Leu Thr His Arg
                85                  90                  95

Glu Arg Arg Gln Glu Met Glu Asp Lys Ile Arg Val Leu Gln Pro Val
                100                 105                 110

Leu Gln Ala Lys Gly Lys Asp Ala Asp Pro Arg Phe Leu Ser Leu Leu
            115                 120                 125

Ala Arg Ile Tyr Leu Tyr Arg Gly Met Leu Phe Arg Pro Lys Gly Phe
        130                 135                 140

Thr Thr Pro Ala Arg Lys Ile Glu Ala Leu Lys Lys Ala Val Gln Leu
```

-continued

```
            145                 150                 155                 160
Ser Glu Lys Ala Val Glu Lys Glu Lys Asp Asn Pro Asn Phe Leu Arg
                        165                 170                 175
Thr Trp Ala Gln Ala Ala Leu Glu Leu Glu Ala Ile Pro Glu Thr Ser
                        180                 185                 190
Phe Lys Val Ser Ser Gly Leu Leu Lys Asp Ala Ala Val Cys Ile Asn
                        195                 200                 205
Arg Asp Gly Ile His Ser Leu Asn Asp Leu Gln Val Ile Leu Glu Tyr
            210                 215                 220
Ala Glu Ser Glu Gly Lys Thr Ser Phe Leu Gln His Val Leu Val Glu
225                 230                 235                 240
Lys Arg Tyr Trp Lys Arg Pro Phe Asp Leu Phe Leu Lys Ala Arg
                        245                 250                 255
Ala Ala Phe Ala Leu Asn Arg Met Asp Asp Val Arg Tyr Phe Leu Lys
                        260                 265                 270
Ser Ala Met Asp Lys Thr Pro Lys Ala Leu Ser Ser Pro Phe Trp Asp
                        275                 280                 285
His Leu Val Asp Phe Leu Lys Lys Leu Arg Thr Lys Glu Gly Ser Asp
            290                 295                 300
Leu Trp Lys Glu Met Ala Val Ala Ala His Arg Leu Cys Arg Glu Lys
305                 310                 315                 320
Glu Val Lys Ile Ala Asn Asn Ile Tyr Leu Tyr Arg His Trp Ala Arg
                        325                 330                 335
Gln Lys Ser Leu Tyr Asn Met Ala Phe Leu Ala Gln Asn Asp Leu Lys
                        340                 345                 350
Glu Lys Ala Lys Ile Ala Asp Ser Leu Lys Ser Arg Pro Val Leu Arg
                        355                 360                 365
Tyr Gln Ala Leu Arg Glu Met Lys Glu His Gln Asn Ile Ala Lys Leu
            370                 375                 380
Leu Glu Gln Asp Asp Gln Glu Arg Asp Gly Gly Tyr His Lys Gln Gln
385                 390                 395                 400
Val Glu Met Asp Glu Arg Thr Gly Lys Arg Leu Ser Glu Lys Met Glu
                        405                 410                 415
Lys Ala Gly Val Ser Tyr Glu Asn Leu Pro Val Pro Trp Ile Ser Val
                        420                 425                 430
His Phe Tyr Leu Asn Glu Ser Glu Asn Ser Glu Asp Glu Gly Ser Lys
            435                 440                 445
Gly Tyr Ala Leu Ile Phe Asp Ala Leu Thr Gln Ser Trp Lys Glu Arg
450                 455                 460
Arg Phe Asp Tyr Ala Lys Leu His Arg Lys Phe Met Thr Trp Gln Glu
465                 470                 475                 480
Ala Tyr Ile Ser Ala Lys Lys Ser Ser Phe Ala Lys Asp Ser Leu Val
                        485                 490                 495
Glu Leu Cys Arg Glu Ile Gly Asn Thr Met Pro Phe Leu Phe Asp Thr
                        500                 505                 510
Ala Cys Ile Arg Asp Gly Ala Pro Val Leu Trp Ile Pro His Gly Phe
                        515                 520                 525
Leu His Arg Leu Pro Leu His Ala Ala Ile Arg Asp Glu Ala Thr Asn
            530                 535                 540
Glu Ile Phe Leu Glu Asn His Ala Ser Arg Tyr Leu Pro Ala Trp Ser
545                 550                 555                 560
Ile Leu Asn Ser Ala Ser Ala Arg Arg Gly Lys Asp Ser Tyr Met Ile
                        565                 570                 575
```

```
Lys Arg Phe Arg Ala Glu Asp Tyr Glu Lys Glu Pro Phe Ser Glu Leu
                580                 585                 590

Glu Asp Met Glu Trp Asp Asn Glu His Glu Lys Leu Ala Thr Pro
            595                 600                 605

Asp Asp Leu Lys His Phe Met Ala Lys Asn Pro Gly Val Phe Ala Val
610                 615                 620

Leu Cys His Gly His Gly Asp Ile Leu Asn Pro Leu Lys Ser Trp Leu
625                 630                 635                 640

Glu Leu Glu Gly Gly Gly Val Ser Val Leu Asp Ile Leu Arg Tyr Glu
                645                 650                 655

Lys Ala Asn Leu Ser Gly Thr Arg Val Leu Leu Gly Ala Cys Glu Ala
            660                 665                 670

Asp Met Ala Pro Pro Val Glu Tyr Ala Ile Asp Glu His Val Ser Leu
        675                 680                 685

Ser Ala Ala Phe Leu Ser His Lys Ala Gln Glu Val Ile Ala Gly Leu
690                 695                 700

Trp Glu Ile Asn Ile Gly Glu Ala Asp Glu Cys Tyr Ala Glu Ile Leu
705                 710                 715                 720

Asp Cys Ser Asp Leu Ser Thr Glu Leu Lys Asp Trp Gln Cys Asp Trp
                725                 730                 735

Val Glu Lys Trp Arg Asp Asp Val Glu Ala Ser Gly Asp Asn Ser Thr
            740                 745                 750

Phe Tyr His Ile Thr Pro Phe Arg Ile Met Gly Phe Pro Leu Lys Leu
        755                 760                 765

Lys Glu Asn Asn Glu Ser Glu Ala Lys Gln
770                 775

<210> SEQ ID NO 7
<211> LENGTH: 860
<212> TYPE: PRT
<213> ORGANISM: Unknown
<220> FEATURE:
<223> OTHER INFORMATION: Description of Unknown:
      Aquatic-marine-deep subsurface sequence

<400> SEQUENCE: 7

Met Val Thr Pro Gln Ala Ser Lys Asn Pro Ala Val Asp Glu Ile Leu
1               5                   10                  15

Lys Gln Leu Thr Pro Tyr Asp Met Glu Thr Glu Asn Ala Lys Ala Ile
            20                  25                  30

Glu Thr Arg Lys Ser Cys Ile Glu Cys Leu Lys Gly Ile Cys Glu Arg
        35                  40                  45

Ala Gln Lys Gln Asn Asp Trp Val Ala Phe Gly Thr Ala Leu His Phe
    50                  55                  60

Leu His Glu Leu Ser Gly Thr Thr Ala Pro Val Phe Tyr Gly Ala Val
65                  70                  75                  80

Lys Gly Gln Ser Ala Cys Gly Gln Leu His Asn Met Gln Ala Ser Ile
                85                  90                  95

Lys Glu Ala Val Ala Arg Ile Thr Lys Ser Arg Ala Glu His Leu Arg
            100                 105                 110

Asp Lys Ala Leu Lys Pro Tyr Gly Ile Pro Tyr Leu Ser Arg His Arg
        115                 120                 125

Phe Leu Glu Lys Ala Ile Arg Met Val Trp Glu Leu Leu Gln Ser Asp
    130                 135                 140

Asn Gly Trp Pro Asp Ser Val Trp Leu His Arg Glu Ala Ser Gln Phe
```

```
145             150             155             160
Ile Ala Arg Cys Phe Leu Asp Arg Gly Arg Leu Val Leu Pro Lys Gly
                165             170             175
Ser Ser Ile Pro Gln Lys Lys Ile Glu Ala Leu Lys Lys Ala Trp His
                180             185             190
Trp Ala Leu Lys Gly Ala Leu Lys Ala Lys Glu Asp Asp Ala Asp Ser
                195             200             205
Met Lys Leu Trp Leu Glu Phe Arg Glu Tyr Ile Leu Gln Thr Ala Lys
    210             215             220
Glu Asn Asp Ala Asp Ile Asp Ser Met Lys Leu Leu Ile Glu Ile Gly
225             230             235             240
Leu Glu Leu Glu Leu Tyr Glu Lys Ser Phe Ser Pro Gln Val Asn Glu
                245             250             255
Leu Thr Arg Lys Ile Ala Ser Gly Lys Leu Leu Glu Asp Pro Lys Ser
                260             265             270
Ser Ala Asp Trp Pro Ile Ile Asp Arg Gly Arg Ser Ile Gly Cys Phe
                275             280             285
Asp Glu Lys Gln Asp Glu Ala Leu Phe Lys Leu Asp Leu Asn Lys Lys
                290             295             300
Glu Tyr Lys Glu Leu Pro Thr Leu Pro Leu Leu Arg Ala Lys Ala Gly
305             310             315             320
His Arg Leu Lys Arg Asp Leu Ala Ser Ala Phe Asp Glu Ala Ser Phe
                325             330             335
Phe Arg Val Val Cys Asp Ala Val Arg Lys Leu Ala Asp Val Pro Phe
                340             345             350
Ser Ser Pro Ile Trp Val Glu Thr Ile Glu Phe Leu Ala Gln Leu Asp
                355             360             365
Pro Gly Ser Glu Ile Arg Asn Ala Ala Ser Val Ala Ala Trp Gln Ile
                370             375             380
Cys Lys Leu Lys Glu Glu Asp Leu Asp Leu Gly Leu Gln Val Arg Met
385             390             395             400
Trp Trp Ser Arg His Lys Met Leu Tyr Asp Leu Ala Phe His Ala Ala
                405             410             415
Leu Ser Lys Asp Asp Trp Ala Leu Ala Ala Arg Ile Ala Asp Ser Pro
                420             425             430
Lys Ser Arg Pro Thr Ile Lys Ala Leu Ala Met Glu Ser Val Leu Asp
                435             440             445
Gly Asp Thr Leu Lys Gly Tyr Tyr Glu Leu Glu Ala Arg Gly Val Ala
    450             455             460
Arg Gly Tyr Asp Ser Thr Tyr His Arg Lys Lys Lys Ser Leu Glu Lys
465             470             475             480
Ala Glu Ala Lys Lys Lys Arg Ala Ser Lys Asp Thr Gln Gly Leu Arg
                485             490             495
Pro Leu Asp Phe Glu Glu Asp Ile Pro Ala Gly Trp Ala Ala Ile His
                500             505             510
Leu Tyr Leu Asp Gln Asp Lys Lys Gly His Ala Leu Met Arg Ser Ala
                515             520             525
Gly Ser Thr Lys Asp Gly Trp Leu Tyr Lys Asp Phe Glu Ile Ser Asp
                530             535             540
Ile Trp Gln Lys Phe Gln Ala Trp Gln Ala Ala Asp Arg Tyr Asn Pro
545             550             555             560
Lys Phe Gly Gly Ala Ala Thr Glu Leu His Ala Leu Cys Glu Ser Leu
                565             570             575
```

```
Gly Tyr Asp Asp Asp His Leu Gly Phe Leu Phe Asn Lys Asp Leu Pro
                580                 585                 590

Asp Asn Leu Ile Ile Ile Pro His Asp Ile Leu His Leu Val Pro Ile
            595                 600                 605

His Ser Val Met Lys Asn Gly Glu Ile Leu Leu Lys Gln Lys Lys Cys
610                 615                 620

Ile Tyr Leu Pro Ala Trp Gly Leu Pro Arg Glu Thr Asp Ser Ala Ser
625                 630                 635                 640

Thr Pro Glu Gly Glu Gly Leu Phe Asp Asn Phe Glu Asp His Asp Pro
                645                 650                 655

Leu Arg Gln Tyr Leu Gln Pro Val Leu Gln Ala Trp Lys His Ser Ser
                660                 665                 670

Val Ser Ala Arg Asn Ile Lys Val Pro Asp Ala Thr Ala Asn Asp Val
            675                 680                 685

Arg Asn Tyr Leu Lys Asn Thr Thr Asn Pro Glu Trp Met Val Phe Leu
            690                 695                 700

Cys His Gly Lys Ala Asp Pro Val Asn Pro Tyr Asn Ser Gly Leu Leu
705                 710                 715                 720

Leu Arg Gly Ser His Leu Thr His Ala Ala Leu Val Glu Leu Pro Lys
                725                 730                 735

Lys Met Ala Gly Thr Lys Val Phe Leu Gly Ala Cys Glu Thr Asp Met
                740                 745                 750

Ser Pro Pro Lys Gln Lys Ser Val Asp Glu His Leu Ser Val Ser Thr
            755                 760                 765

Ala Phe Phe Gln Lys Gly Ala Ser Glu Ile Ala Gly Gly Leu Trp Arg
            770                 775                 780

Val His Ser Ala Ile Ala Lys Lys Met Val Glu His Ile Ser Glu Asn
785                 790                 795                 800

Arg Lys Lys Pro Leu Val Asp Val Val Trp Glu Lys Gln Lys Asp Trp
                805                 810                 815

Trp Asp Asn Gly Ile Gln Tyr Val Val Asp Gly Ile Thr Val Lys Val
                820                 825                 830

Ser Asn Cys Phe Lys Lys Leu Tyr Tyr Leu Ser Ser Tyr Arg Val Val
            835                 840                 845

Gly Phe Pro Arg Ala Ile Gly Glu Asn Thr Asp Glu
        850                 855                 860

<210> SEQ ID NO 8
<211> LENGTH: 757
<212> TYPE: PRT
<213> ORGANISM: Unknown
<220> FEATURE:
<223> OTHER INFORMATION: Description of Unknown:
      Aquatic-freshwater-groundwater sequence

<400> SEQUENCE: 8

Met Tyr Ser Asp Phe Pro Ala Leu Arg Leu Pro Glu Leu Ser Val Asp
1               5                   10                  15

Gln Lys Lys Leu Phe Lys Ile Ser Gly Thr Asn Pro Gln Leu Ile Tyr
            20                  25                  30

Ile Leu Met Asn Glu Phe Asp Gly Glu Gly Asp Glu Pro Phe Phe Thr
        35                  40                  45

Gly Leu Val Pro Asp Glu Thr Asp Leu Ser Glu Asn Lys Gln Ala Pro
    50                  55                  60

Leu Leu Lys Glu Leu Ala Arg His Leu Leu Lys Glu Tyr Glu Asp Ile
```

-continued

```
                65                  70                  75                  80
        Gly Arg Asn Arg Trp Lys His Ala Asp Gln Arg Arg Val Leu Glu Lys
                            85                  90                  95

Ala Ile Arg Leu Leu Asp Lys Ser His Gln Ala Glu Glu Asn Val Ser
                           100                 105                 110

Leu Glu Leu Gly Lys Ala Tyr Leu Tyr Arg Ala Arg Ile Ile Arg Pro
                           115                 120                 125

Lys Gly Phe Thr Val Pro Ala Lys Lys Ile Glu Ala Leu Asn Asn Ala
                    130                 135                 140

Leu His Phe Cys Glu Asp Ala Thr Asn His Gly Lys Ala Trp Ala Asp
        145                 150                 155                 160

His Phe Ala Gly Leu Val Ala Leu Glu Leu Tyr Arg Cys Gly Lys Thr
                           165                 170                 175

His Asp Asn Leu Ser Glu Leu Leu Asn Lys Ala Thr Ala Asp Ala Glu
                           180                 185                 190

Leu Ser Glu Pro Asp Arg Arg Val Glu Phe Tyr Gln Met Arg Val Arg
                           195                 200                 205

Leu Glu Glu Leu Arg Gln Asp Glu Gly Asn Gly Ser Pro Tyr Phe Ile
                    210                 215                 220

Gln Asn Val Leu Thr Lys Ile Phe Glu Phe Gln Glu Pro Gly Met Glu
        225                 230                 235                 240

Leu Glu Lys Leu Lys Val Ser Leu Gln Ser Pro Ser Ser Ser Lys Asp
                           245                 250                 255

Lys Ile Ser Ser Ser Leu Glu Asp Leu Ile Leu Val Leu Lys Glu Tyr
                           260                 265                 270

Pro Phe Ser His Pro Leu Trp Glu Asp Thr Val Arg Phe Ala Arg Arg
                           275                 280                 285

Leu Tyr Phe Asn Arg Leu Glu Phe Trp Lys Glu Leu Ala Leu Arg Leu
                    290                 295                 300

Trp Glu Ala Ala Glu Asp Glu Ser Arg Lys Ile Ser Ser Val His Leu
        305                 310                 315                 320

Arg Trp Tyr Trp Ser Arg Gln Arg Asp Leu Tyr Asp Leu Ser Phe Leu
                           325                 330                 335

Ala Ala Leu Lys Gln Gly Asn Pro Asn Leu Ala Ala Gln Val Thr Asp
                           340                 345                 350

Ser Ala Lys Ser Arg Pro Ala Leu Ser Trp Gln Ala Ile Glu Arg Leu
                           355                 360                 365

Lys His Gly Asn Glu Glu Leu Lys Asp Glu Ile Glu Asn Tyr Ala Gln
                    370                 375                 380

Ala Leu Ser Gly Gly Tyr Ile Lys Gly Leu Leu Lys Pro Tyr Arg Lys
        385                 390                 395                 400

Pro Glu Val Pro Asn Glu Lys Pro Phe Phe Glu Gln His Leu Ile
                           405                 410                 415

Asp Asn Asn Leu Ile Ala Ile Gln Phe Tyr Leu Val His Leu Glu Glu
                           420                 425                 430

Phe Glu Lys Val Glu Arg Ser Arg Glu Arg Gly Tyr Ala Leu Ile Tyr
                           435                 440                 445

Asp Gln Glu Ser Glu Lys Lys Trp Ser Phe Lys Thr Phe Asp Phe Ala
                    450                 455                 460

Pro Ile Trp Glu Lys Tyr Val Ala Trp Gln Ser Val Tyr Phe Asp Leu
        465                 470                 475                 480

Pro Pro Gln Gln Arg Asp Ala Ser Gly Thr Gln Leu Arg Tyr Leu Cys
                           485                 490                 495
```

Glu Ala Leu Gly Lys Ala Leu Glu Phe Leu Phe Lys Ser Pro Glu Lys
                500                 505                 510

Gln Phe Ser Ser Asn Glu Lys Ser Lys Asp Ile Leu Phe Ile Pro His
            515                 520                 525

Asp Phe Leu His Arg Val Pro Leu His Gly Ala Met Leu Asp Asn Glu
        530                 535                 540

Asn Val Leu Leu Lys Thr Phe Asn Cys Phe Tyr Leu Pro Ala Ile Ser
545                 550                 555                 560

Tyr Ser Ala Lys Asn Gln Gly Pro Gln Gln Asn Lys Asn Ser Val Leu
            565                 570                 575

Leu Tyr Tyr Ser Gly Lys Ser Glu Glu Ser Asp Asp Pro Leu Phe Asn
        580                 585                 590

His Leu Lys Thr Lys Phe Asp Thr Pro Ile Asn Phe Ala Ser Ala Thr
    595                 600                 605

Asp Leu Leu Asp Ala Ala Gln Asn Pro Pro Ser Leu Leu Val Leu Tyr
        610                 615                 620

Cys His Gly Glu Ala Asp Ala Thr Asn Pro Tyr Leu Ser Arg Leu Lys
625                 630                 635                 640

Leu Lys Asp Asp Leu Met Leu Leu Asp Phe Ala Ser Ala Ala Gly Thr
            645                 650                 655

Phe Thr Gly Ser Lys Ile Phe Leu Gly Ala Cys Glu Thr Asp Leu Met
        660                 665                 670

Pro Pro Leu Asp Ala Pro Leu Asp Glu Gln Ile Ser Met Ala Thr Ile
    675                 680                 685

Phe Leu Ile Lys Arg Ser Glu Ser Val Ile Gly Ser Met Trp Glu Ala
        690                 695                 700

Lys Arg Met Lys Val Leu Asn Leu Leu Phe Met Lys Glu Gly Leu Phe
705                 710                 715                 720

Asp His Phe Phe Glu Gln Gln Arg Glu Trp Trp Lys Glu Glu Tyr Glu
            725                 730                 735

His Thr Asp Ser Asn Thr Ala Leu Tyr Asp Cys Leu Cys Phe Arg Met
        740                 745                 750

Tyr Arg Cys Tyr Phe
        755

<210> SEQ ID NO 9
<211> LENGTH: 822
<212> TYPE: PRT
<213> ORGANISM: Unknown
<220> FEATURE:
<223> OTHER INFORMATION: Description of Unknown:
      Bioremediation-terephthalate-wastewater bioreactor sequence

<400> SEQUENCE: 9

Met Phe Gly Gly Val Glu Lys Asn Cys Leu Ala Leu Ser Leu Gly Arg
1               5                   10                  15

His Glu Lys Arg Gln Ile Tyr Lys Ser Ile Leu Ala Ala Gly Gly Leu
            20                  25                  30

Leu Leu Ala Gln Pro Ala Asp Glu Thr Phe Leu Pro Met Ile Thr Lys
        35                  40                  45

Tyr Tyr Arg Glu Ile Leu Ala Glu Val Lys Leu Ala Phe Cys Leu
    50                  55                  60

Pro Asp Glu Ala His Asn Val Val Tyr Lys Arg Asp Glu Ala Cys Arg
65                  70                  75                  80

Glu Leu Val Gln Ala Cys Arg Asn Gln Ala Gly Gly Leu Thr Glu Gln

```
            85                  90                  95
Gly Tyr Gln Tyr Leu Gly Ser Ala Leu Leu Phe Leu Ser Gly Gly Leu
                100                 105                 110

Gly Glu Ala Pro Gly Leu Val Ala Leu Pro Val Leu Ser Gln Glu Leu
            115                 120                 125

Cys Glu Ala Leu Ala Ser Arg Glu Ala Asp Ile His Ala Phe His Ala
        130                 135                 140

Arg Gln Gly Leu Glu Val Ala Ala Ile Ile Glu Arg Ala Arg Glu
145                 150                 155                 160

Pro Gln Trp Gln His Ala Gln Arg Arg Gln Ala Leu Glu Ala Val Ile
                165                 170                 175

Lys Asp Leu Gln Gln Arg Ser Ala Ile Cys Pro Pro Asp Leu Gln Asp
            180                 185                 190

Arg Leu Arg Leu Leu Ala Gln Ala Tyr Leu Glu Arg Ser Arg Ile
        195                 200                 205

Ile Arg Pro Lys Gly Phe Thr Ile Ser Pro Lys Lys Lys Glu Ala Leu
    210                 215                 220

Asp Lys Ala Leu Glu Gln Leu Asp Gln Val Thr Asp Thr Gly Lys Thr
225                 230                 235                 240

Thr Leu Asp Tyr His Arg Phe Arg Gly Asp Ile Phe Leu Glu Leu Gly
                245                 250                 255

Arg Leu Glu Ala Arg Thr Gly Lys Glu Ile Glu Ala Cys Leu Ala Glu
            260                 265                 270

Ala Ile Leu Phe Leu Asp Pro Arg Thr Pro Ala Asn Leu Thr Pro Val
        275                 280                 285

Asp Cys Arg Leu Ile Val Ala Tyr Ala Arg Leu Ala Arg Asp Pro Ser
    290                 295                 300

Tyr Leu Pro Leu Val Leu Gly Ser Ser Lys Ala Thr Ala Leu Asp Arg
305                 310                 315                 320

Ala Trp Ala Ala Tyr Leu Ser Asn Asn Ala Ser Gly Ala Ala Lys Glu
                325                 330                 335

Ile Asn Thr Val Leu Gln Asp Leu Gln Arg Arg Trp Phe Ser His Pro
            340                 345                 350

Asp Trp Glu Gly Leu Val Asp Leu Leu Val Asp Trp Ala Arg Ser Ser
        355                 360                 365

Gln Lys Gly Trp Glu Asp Leu Ala Thr Ala Ala Trp Gln Val Cys Gln
    370                 375                 380

Lys Asn Glu Gln Glu Leu Arg Tyr Ser Gly Cys Gln Leu Arg Trp Tyr
385                 390                 395                 400

Trp Ser Arg His Gln Asp Leu Tyr Asp Leu Ala Phe Gln Ala Ala Pro
                405                 410                 415

Thr Leu Glu Glu Lys Ala Arg Val Ala Asp Ser Leu Lys Ser Arg Pro
            420                 425                 430

Leu Val Arg Leu Ala Leu Glu Gln Leu Ala Gln Ala Gln Ala Lys
        435                 440                 445

Lys Lys Arg Gly Ala Asp Val Asp Phe Ala Gln Leu Ile Glu Gln Asp
    450                 455                 460

Ala Arg Ala Tyr Ala Asn Gln Tyr Ile Ala Gly Gly Leu Ala Ala Gly
465                 470                 475                 480

Ser Ala Ser Ala Pro Val Ala Pro Leu Ser Phe Thr Glu Leu Pro Asp
                485                 490                 495

Glu Gln Trp Leu Ala Val His Phe Tyr Leu Ser Ser Gly Ala Ala Ala
            500                 505                 510
```

-continued

```
Gly Leu Lys Lys Asn Met Ala Tyr Ala Leu Val Tyr Asp Ala Lys Asp
            515                 520                 525

Gln Lys Trp Ser Cys Glu Gly Pro Tyr Glu Thr Thr Asp Leu Trp Gln
    530                 535                 540

Ala Tyr Arg Arg Trp Gln Asp Asn Tyr Ala Ala Val Ser Gln Ala Ser
545                 550                 555                 560

Ala Pro Glu Leu Glu Ser Leu Cys Arg Gln Ile Gly Thr Thr Phe Pro
                565                 570                 575

Phe Leu Trp Ala Leu Pro Ser Glu Arg Pro Val Val Phe Ile Pro His
            580                 585                 590

Gly Phe Leu His Arg Leu Pro Leu His Met Ala Leu Arg Glu Asp Gly
            595                 600                 605

Ala Thr Leu Glu Val Trp Ala Ala Thr His Pro Ser Thr Tyr Leu Pro
            610                 615                 620

Ala Trp Ser Leu Arg Pro Arg Ala Asp Ala Gly Gly Ser Gln Asn Val
625                 630                 635                 640

Ala Ala Val Tyr Leu Pro Asp Glu Leu His Asp Ala Glu Asp Phe Gln
                645                 650                 655

Asn Ile Leu Ala Gly Gln Ser Phe Ala Ala Ala Ser Trp Pro Val
            660                 665                 670

Phe Arg Lys Gln Ala Gly Gln Ala Arg Arg Leu Ala Leu Val Cys His
            675                 680                 685

Gly Leu Ala His Ala Val Asn Pro Phe Ala Ala Arg Leu Leu Leu Pro
            690                 695                 700

Glu Glu Pro Gln Leu Val Asp Phe Leu Thr Asp Leu Pro Ala Leu Pro
705                 710                 715                 720

Gly Ser Gln Val Phe Leu Ala Ala Cys Glu Ala Asp Met Ala Pro Ala
                725                 730                 735

Gln Glu Ala Pro Leu Asp Glu His Leu Ser Leu Ala Thr Ala Phe Leu
            740                 745                 750

Gln Lys Gly Ala Arg Glu Val Leu Gly Gly Val Phe Glu Val Asn Lys
            755                 760                 765

Tyr Leu Ala Asn Glu Leu Leu Ser Ser Phe Gly Ala Thr Ser Ala Ala
            770                 775                 780

Ala Cys Tyr Ser Leu Leu Trp Lys Trp Gln Gln Ala Arg Leu Asp Asn
785                 790                 795                 800

Phe Leu Asp Asn Pro Asp Pro Leu Asn Leu Tyr Trp Leu Ala Pro Trp
                805                 810                 815

Arg Val Leu Gly Leu Ser
            820

<210> SEQ ID NO 10
<211> LENGTH: 797
<212> TYPE: PRT
<213> ORGANISM: Unknown
<220> FEATURE:
<223> OTHER INFORMATION: Description of Unknown:
      Aquatic-freshwater-freshwater lake sediment sequence

<400> SEQUENCE: 10

Met Thr Glu Thr Asn His Leu Ser Ser Asp Tyr Gln Lys Ala Ile Thr
1               5                   10                  15

Leu Glu Thr Lys Leu Ala Phe Leu Arg Pro Thr Gln Glu Gln Asp Thr
            20                  25                  30

Ile Glu Ser Thr Arg Arg Glu Leu Ala Glu Thr Leu Ser Arg Leu Val
```

```
                35                  40                  45
Asn Gln Lys Ile Ser Pro Glu Thr Leu Ser Ala Ile Thr Thr Leu His
             50                  55                  60
Gly Met Asp Leu Gln Gly Leu Gly Val Leu Ser Gly Ser Leu Pro Asn
 65                  70                  75                  80
Lys Asp Arg Cys Ala Phe Ala Gly Asn Lys Lys Phe Ser Ala Ala
                 85                  90                  95
Trp Glu Phe His Trp Leu Gln Arg Ile Asp Leu Met Arg Lys Ile Ile
                100                 105                 110
Asp Lys Ala Ser Gly Gln Asp Lys Leu Ser His Ala Ser Arg Arg
            115                 120                 125
Gln Ala Leu Gly Val Ala Ile Asn Ser Leu Glu Lys Ala Ile Ala Glu
            130                 135                 140
Ile Gly Asp Thr Gly Ile Leu Val Ser Lys Ala Arg Leu Asp Leu Ala
145                 150                 155                 160
Arg Ala Leu Phe His Arg Gly Arg Ile Val Arg Pro Lys Gly Phe Ser
                165                 170                 175
Val Pro Gly Lys Lys Glu Leu Phe Leu Lys Ala Leu Asp Gln Ile
                180                 185                 190
Arg Ile Ala Thr Asn Asn Lys Asp Asp Gln Thr Leu Phe Leu Lys
            195                 200                 205
Ala Glu Ile Tyr Leu Glu Trp Leu Arg Phe Pro Met Glu Leu Pro
210                 215                 220
Glu Asp Leu Asp Val Val Phe Lys Ala Ala Gln Gln Lys Ala Asp Glu
225                 230                 235                 240
Pro Leu Lys Thr Asn Leu Ile Leu Met Ile Gly Glu Arg Gly Ser Ala
                245                 250                 255
Lys Pro Ile Glu Leu Glu Ala Leu Gln Asn Ile Glu Val Asp Glu Lys
            260                 265                 270
Gln Glu Pro Leu Thr Arg Ala Arg Ala Ala Ile Ser Gly Asn Trp
            275                 280                 285
Asp Ile Cys Ala Lys Tyr Leu Ser Glu Ala Ile Lys Lys Leu Glu Ile
    290                 295                 300
Lys Ser Phe Phe His Gln Asp Trp Glu Glu Ala Val Glu Leu Leu Lys
305                 310                 315                 320
Lys Gly Arg Thr Lys Ile Ser Asn Tyr Gln Trp Ala Thr Ile Cys Lys
                325                 330                 335
Ser Leu Trp Lys Leu Thr Val Gln Lys Glu Asn Arg Thr Ser Asn Gly
            340                 345                 350
Cys His Leu Arg Trp Tyr Trp Ser Arg Gln Arg Glu Val Tyr Asp Leu
            355                 360                 365
Ala Phe Glu Ala Ala Gly Asn Asp Tyr Ser Lys Lys Ala Lys Ile Thr
    370                 375                 380
Asp Ser Leu Lys Gly Arg Pro Ala Leu His Phe Ala Gln Met Glu Thr
385                 390                 395                 400
Ile Ala Glu Gly Glu Asp Glu Ile Lys Thr Trp Ile Glu His Gln Glu
                405                 410                 415
Ala Gly Phe Leu Asn Gln Tyr Ile Ser Ala Phe Glu Ser Ala Asp Gln
            420                 425                 430
Gly Lys Lys Pro Gly Asn Leu Ser Trp Pro Lys Leu Pro Lys Gly Trp
            435                 440                 445
Ile Ala Val His Phe Tyr Leu Gly Leu Gly Thr Cys Ser Gly Glu Lys
            450                 455                 460
```

Lys Gly Tyr Ala Leu Ile Gln Asn Gly Gln Asp Trp Tyr Gln Arg Thr
465                 470                 475                 480

Phe Asp Tyr Glu Val Leu Trp Val Ala Tyr Leu Ala Trp Gln Thr Met
            485                 490                 495

Tyr Gly Lys Cys Gly His Leu Asp Ile Leu Lys Gln Gln Glu Val
                500                 505                 510

Leu Ser Pro Val Val Glu Ser Leu Cys Glu Gln Ile Gly Lys Glu Met
        515                 520                 525

Pro Trp Leu Phe Asp Pro Gly Leu Phe Pro Glu Gly Gln Ala Val Val
        530                 535                 540

Phe Ile Pro His Asp Phe Leu His Arg Leu Pro Leu His Met Ala Leu
545                 550                 555                 560

Asp Pro Lys Pro Asp Pro Gly Lys Ala Gln Leu Phe Leu Ser Leu His
                565                 570                 575

Leu Val Leu Ser Leu Pro Ala Trp Trp Gln Ala Ser Glu Thr Asn Ser
            580                 585                 590

Pro Pro Ala Pro Asp Thr Val Lys Ala Asn Glu Lys Ile Phe Leu Ala
        595                 600                 605

Asn Phe Glu Asn Pro Ser Asp Ala Phe Gln Ser Leu Ile Asp Ala Ile
610                 615                 620

Pro Lys Ser Val Lys Val Glu Arg Val Ala Lys Lys Ser Asn Leu Leu
625                 630                 635                 640

Glu Ala Asn Ser Pro Ser Leu Leu Val Val Tyr Cys Asn Gly Glu Ala
                645                 650                 655

Gln Pro Gly Asn Pro Phe Ala Ser Arg Leu Leu Phe Ser Asp Ser Gly
            660                 665                 670

Leu Pro Val Ser Gly Ile Leu Gly Ser Thr Ile Asn Leu Arg Arg Ser
        675                 680                 685

Asn Ile Ile Leu Gly Ala Cys Glu Thr Asp Leu Met Leu Ala Leu Asn
690                 695                 700

Lys Thr Leu Asp Glu His Ile Thr Leu Ser Ser Ala Phe Ile Gln Lys
705                 710                 715                 720

Gly Ala Glu Leu Val Ser Gly Thr Leu Trp Lys Ile His Glu Asn Asp
                725                 730                 735

Glu Ile Asp Phe Ile Lys Leu Ala Leu Val Glu Asn Ser Ser Leu His
            740                 745                 750

Glu Gln Trp Leu Lys Trp Tyr Asp Thr Asn Ile Lys Ala Tyr Glu Asn
        755                 760                 765

Asp Pro Lys Asn Asn Pro Arg Val Phe Tyr Lys Ala Ala Ile Arg
        770                 775                 780

Ile Val Gly Lys Pro Trp Thr Ile Glu Asp Ile Gly Lys
785                 790                 795

<210> SEQ ID NO 11
<211> LENGTH: 789
<212> TYPE: PRT
<213> ORGANISM: Unknown
<220> FEATURE:
<223> OTHER INFORMATION: Description of Unknown:
      Bioremediation-terephthalate-wastewater bioreactor sequence

<400> SEQUENCE: 11

Met Ala Gln Pro Ala Asp Glu Thr Phe Leu Pro Met Ile Thr Lys Tyr
1               5                   10                  15

Tyr Arg Glu Ile Leu Ala Ala Glu Val Lys Leu Ala Phe Cys Leu Pro

-continued

```
                20                  25                  30
Asp Glu Ala His Asn Val Val Tyr Lys Arg Asp Glu Ala Cys Arg Glu
                35                  40                  45

Leu Val Gln Ala Cys Arg Asn Gln Ala Gly Gly Leu Thr Glu Gln Gly
                50                  55                  60

Tyr Gln Tyr Leu Gly Ser Ala Leu Leu Phe Leu Ser Gly Gly Leu Gly
 65                 70                  75                  80

Glu Ala Pro Gly Leu Val Ala Leu Pro Val Leu Ser Gln Glu Leu Cys
                85                  90                  95

Glu Ala Leu Ala Ser Arg Glu Ala Asp Ile His Ala Phe His Ala Arg
                100                 105                 110

Gln Gly Leu Glu Val Ala Ala Ile Ile Glu Arg Ala Arg Glu Pro
                115                 120                 125

Gln Trp Gln His Ala Gln Arg Gln Ala Leu Glu Ala Val Ile Lys
                130                 135                 140

Asp Leu Gln Gln Arg Ser Ala Ile Cys Pro Pro Asp Leu Gln Asp Arg
145                 150                 155                 160

Leu Arg Leu Leu Leu Ala Gln Ala Tyr Leu Glu Arg Ser Arg Ile Ile
                165                 170                 175

Arg Pro Lys Gly Phe Thr Ile Ser Pro Lys Lys Glu Ala Leu Asp
                180                 185                 190

Lys Ala Leu Glu Gln Leu Asp Gln Val Thr Asp Thr Gly Lys Thr Thr
                195                 200                 205

Leu Asp Tyr His Arg Phe Arg Gly Asp Ile Phe Leu Glu Leu Gly Arg
                210                 215                 220

Leu Glu Ala Arg Thr Gly Lys Glu Ile Glu Ala Cys Leu Ala Glu Ala
225                 230                 235                 240

Ile Leu Phe Leu Asp Pro Arg Thr Pro Ala Asn Leu Thr Pro Val Asp
                245                 250                 255

Cys Arg Leu Ile Val Ala Tyr Ala Arg Leu Ala Arg Asp Pro Ser Tyr
                260                 265                 270

Leu Pro Leu Val Leu Gly Ser Ser Lys Ala Thr Ala Leu Asp Arg Ala
                275                 280                 285

Trp Ala Ala Tyr Leu Ser Asn Asn Ala Ser Gly Ala Ala Lys Glu Ile
                290                 295                 300

Asn Thr Val Leu Gln Asp Leu Gln Arg Arg Trp Phe Ser His Pro Asp
305                 310                 315                 320

Trp Glu Gly Leu Val Asp Leu Leu Val Asp Trp Ala Arg Ser Ser Gln
                325                 330                 335

Lys Gly Trp Glu Asp Leu Ala Thr Ala Ala Trp Gln Val Cys Gln Lys
                340                 345                 350

Asn Glu Gln Glu Leu Arg Tyr Ser Gly Cys Gln Leu Arg Trp Tyr Trp
                355                 360                 365

Ser Arg His Gln Asp Leu Tyr Asp Leu Ala Phe Gln Ala Ala Pro Thr
                370                 375                 380

Leu Glu Glu Lys Ala Arg Val Ala Asp Ser Leu Lys Ser Arg Pro Leu
385                 390                 395                 400

Val Arg Leu Ala Leu Ala Glu Gln Leu Ala Gln Ala Gln Ala Lys Lys
                405                 410                 415

Lys Arg Gly Ala Asp Val Asp Phe Ala Gln Leu Ile Glu Gln Asp Ala
                420                 425                 430

Arg Ala Tyr Ala Asn Gln Tyr Ile Ala Gly Gly Leu Ala Ala Gly Ser
                435                 440                 445
```

Ala Ser Ala Pro Val Ala Pro Leu Ser Phe Thr Glu Leu Pro Asp Glu
    450                 455                 460

Gln Trp Leu Ala Val His Phe Tyr Leu Ser Ser Gly Ala Ala Ala Gly
465                 470                 475                 480

Leu Lys Lys Asn Met Ala Tyr Ala Leu Val Tyr Asp Ala Lys Asp Gln
                485                 490                 495

Lys Trp Ser Cys Glu Gly Pro Tyr Glu Thr Thr Asp Leu Trp Gln Ala
            500                 505                 510

Tyr Arg Arg Trp Gln Asp Asn Tyr Ala Ala Val Ser Gln Ala Ser Ala
        515                 520                 525

Pro Glu Leu Glu Ser Leu Cys Arg Gln Ile Gly Thr Thr Phe Pro Phe
    530                 535                 540

Leu Trp Ala Leu Pro Ser Glu Arg Pro Val Val Phe Ile Pro His Gly
545                 550                 555                 560

Phe Leu His Arg Leu Pro Leu His Met Ala Leu Arg Glu Asp Gly Ala
                565                 570                 575

Thr Leu Glu Val Trp Ala Ala Thr His Pro Ser Thr Tyr Leu Pro Ala
            580                 585                 590

Trp Ser Leu Arg Pro Arg Ala Asp Ala Gly Gly Ser Gln Asn Val Ala
        595                 600                 605

Ala Val Tyr Leu Pro Asp Glu Leu His Asp Ala Glu Asp Phe Gln Asn
    610                 615                 620

Ile Leu Ala Gly Gln Ser Phe Ala Ala Ala Ser Trp Pro Val Phe
625                 630                 635                 640

Arg Lys Gln Ala Gly Gln Ala Arg Arg Leu Ala Leu Val Cys His Gly
                645                 650                 655

Leu Ala His Ala Val Asn Pro Phe Ala Ala Arg Leu Leu Pro Glu
            660                 665                 670

Glu Pro Gln Leu Val Asp Phe Leu Thr Asp Leu Pro Ala Leu Pro Gly
        675                 680                 685

Ser Gln Val Phe Leu Ala Ala Cys Glu Ala Asp Met Ala Pro Ala Gln
    690                 695                 700

Glu Ala Pro Leu Asp Glu His Leu Ser Leu Ala Thr Ala Phe Leu Gln
705                 710                 715                 720

Lys Gly Ala Arg Glu Val Leu Gly Gly Val Phe Glu Val Asn Lys Tyr
                725                 730                 735

Leu Ala Asn Glu Leu Leu Ser Ser Phe Gly Ala Thr Ser Ala Ala Ala
            740                 745                 750

Cys Tyr Ser Leu Leu Trp Lys Trp Gln Ala Arg Leu Asp Asn Phe
    755                 760                 765

Leu Asp Asn Pro Asp Pro Leu Asn Leu Tyr Trp Leu Ala Pro Trp Arg
770                 775                 780

Val Leu Gly Leu Ser
785

<210> SEQ ID NO 12
<211> LENGTH: 809
<212> TYPE: PRT
<213> ORGANISM: Unknown
<220> FEATURE:
<223> OTHER INFORMATION: Description of Unknown:
      Aquatic-marine-marine sediment sequence

<400> SEQUENCE: 12

Met Val Ser Met Gln Gln Ser Ala Cys Asn Glu Ile Lys Asn Leu Glu

```
1               5                   10                  15
Asn Ser Ile Asp Lys Asp Val Ser Glu Leu Ala Glu Ala Leu Ser His
            20                  25                  30
Phe Val Gln Ala Asn Leu Gln Pro Gln Thr Ala Leu Cys Gln Arg Gly
            35                  40                  45
Ile Pro Asp Lys Asn Asn Ala Val Leu Lys Ile His Lys Ala His Asn
            50                  55                  60
Thr Asp Ile Val Phe Ser Thr Leu Phe Asn Ile Leu Glu Lys Arg Leu
65                  70                  75                  80
Val Val Tyr Glu Ser Glu Val Tyr Asp Glu Ser Lys Ser Ser Lys Lys
                85                  90                  95
Asn Met Asn His Arg Gln Arg Arg Gln Met Leu Glu Asp Ile Ile Gln
                100                 105                 110
Ala Leu Ile Pro Leu Lys Lys Lys Val Ser Asp Ser Glu Leu Lys Leu
                115                 120                 125
Glu Lys Leu Glu Arg Lys Glu Ser Asp Ser Val Thr Lys Leu Lys Ser
            130                 135                 140
Asp Ile Ala Gln Phe Asn Tyr Ile Tyr Ala Lys Val Tyr Phe Tyr Arg
145                 150                 155                 160
Ser Leu Leu Phe Arg Pro Lys Gly Arg Ser Ile Pro Ala Arg Lys Ile
                165                 170                 175
Glu Ala Ile Gln Glu Ala Tyr Ser Phe Ile Lys Lys Ser Leu Asn Leu
            180                 185                 190
Ser Glu Thr Leu Ser Ser Trp Arg Leu Leu Gly Lys Ile Thr Leu Glu
            195                 200                 205
Leu Leu Ser Leu Asn Glu Pro Tyr Leu Ser Asp Asp Ile Ile Ser Ser
        210                 215                 220
Gly Leu His Ile Asp Glu Asn Phe Cys Leu Glu Asn Asn Ser Phe Ile
225                 230                 235                 240
Leu Arg Asn Asp Ile Gln Thr Leu Leu Thr Phe Ser Glu Ile Thr Lys
            245                 250                 255
Asp Val Ser Phe Val Glu Lys Ile Pro Thr Phe Glu Asn Ile Asn Ile
            260                 265                 270
Lys Lys Lys Asp Lys Asp Tyr Leu Leu Leu Ile Phe Ala Arg Ile
        275                 280                 285
Ala Phe Leu Arg Asn Lys Ile Asn Glu Ser Asp Thr Leu Leu Thr Lys
        290                 295                 300
Ala Ile Ser Asn Ala Pro Glu Ala Phe Ala Asn Pro Phe Trp Asp Asp
305                 310                 315                 320
Leu Val Asp Phe Ile Thr Cys Leu Lys Arg Asn Asn Cys His Val Trp
                325                 330                 335
Lys Lys Ala Ala Ile Asp Ala His Lys Ala Cys Tyr Lys Asn Glu Thr
            340                 345                 350
Glu Ile Gly Asn Ile Tyr Leu Arg Trp Tyr Trp Ser Arg Gln Ser Asp
            355                 360                 365
Leu Tyr Asp Leu Ala Phe Ile Ser Glu Asn Lys Leu Glu Glu Lys Ala
        370                 375                 380
Arg Ile Ala Asp Ser Leu Lys Ser Arg Pro Ile Leu Gly Phe Gln Ala
385                 390                 395                 400
Leu Asn Asn Met Lys Lys Asn Ile Asp Ile Leu Glu Gln Ile Leu Glu
                405                 410                 415
Gln Glu Asn Glu Ala Arg Asp Asn Lys Tyr Leu Lys Lys Ile His Ser
            420                 425                 430
```

```
Lys Ser Arg Lys Ile Phe Lys Lys Glu Lys Phe Ile Asp Phe Lys Leu
        435                 440                 445

Leu Asp Asn His Trp Met Val Ile His Phe Tyr Leu Asn Glu Leu Glu
    450                 455                 460

Gln Cys Gly Tyr Ala Leu Ile Phe Asp Cys Glu Thr Lys Asn Thr Asn
465                 470                 475                 480

Ile Gln Thr Phe Arg Tyr Asn Glu Leu Phe Asn Thr Phe Leu Ser Trp
                485                 490                 495

Gln Glu Thr Glu Leu His Glu Gln Lys Gln Lys Glu Asn Asn Glu Glu
                500                 505                 510

Ile Phe Asn Lys Asp Leu Ile Gln Arg Gly Lys Ser Ile His Glu Leu
            515                 520                 525

Cys Cys Glu Ile Gly Lys Thr Met Pro Phe Ile Phe Glu Leu Pro Glu
    530                 535                 540

Asn Lys Ser Ile Leu Trp Val Pro His Gly Phe Ile His Arg Leu Pro
545                 550                 555                 560

Leu His Ala Ala Ile Ser Ile Gln Thr Asn Ala Phe Leu Phe Glu Lys
                565                 570                 575

His Glu Ser Arg Tyr Leu Ala Ala Trp His Gln Leu Asn Leu Lys Asn
                580                 585                 590

Phe Gly Asn Gly Glu Gly Lys His Phe Leu Arg Ser Gly Gly Ser Lys
            595                 600                 605

Phe Lys Thr Ile Thr Lys Lys Cys Lys Thr Asp Lys Trp Glu Met Val
    610                 615                 620

Lys Arg Lys Ala Asn Gln Lys His Phe Phe Glu Ser Leu Asn Lys Asn
625                 630                 635                 640

Leu Lys Thr Leu Val Ile Ile Cys His Gly Glu Cys Asp Ile Thr Asn
                645                 650                 655

Ser Phe Gln Ser Cys Leu Glu Ile Ser Ala Ser Ser Val Gly Glu Ser
                660                 665                 670

Asp Ser Asn Gly Leu Ile Asn Pro Leu Glu Lys Lys Ser Ile Thr Ile
        675                 680                 685

Leu Asp Leu Leu Lys Ser Glu Asn Asn Ile Lys Gly Cys Arg Ile Phe
    690                 695                 700

Leu Gly Ala Cys Glu Ser Asp Met Ala Ser Pro Ile Glu Phe Ile Val
705                 710                 715                 720

Asp Glu His Leu Ser Leu Ser Ala Val Leu Leu Ser Leu Gly Ala Lys
                725                 730                 735

Glu Val Ile Gly Gly Leu Trp Lys Leu Tyr Asp Ile Phe Val Glu Asp
            740                 745                 750

Cys Tyr His Gln Leu Leu Asp Ser Asn Asn Leu Ser Gln Ser Leu Asn
                755                 760                 765

Glu Trp Gln Leu Asn Met Ala Lys Glu Trp Lys Glu Asp Lys Thr Asp
    770                 775                 780

Met Arg Tyr Leu Lys Leu Tyr Ser Phe Ala Ser Phe Arg Val Thr Gly
785                 790                 795                 800

Phe Leu Pro Gln Lys Lys Gln Glu Pro
                805

<210> SEQ ID NO 13
<211> LENGTH: 760
<212> TYPE: PRT
<213> ORGANISM: Unknown
<220> FEATURE:
```

<223> OTHER INFORMATION: Description of Unknown:
      Anammox bioreactor sequence

<400> SEQUENCE: 13

```
Met Lys Asn Arg Val Gln Ile Glu Ala Ile Ile Arg Asn Leu Gln Gly
1               5                   10                  15

Ala Ala Arg Asp Ser Lys Thr Asn Lys Leu Ser Glu Asn Ile Ile Ala
            20                  25                  30

Tyr Asp Glu Tyr Arg Lys Ile His Lys Ser Ala Ser Leu Tyr Gln Phe
        35                  40                  45

Gly Ile Ile Pro Ala Lys Glu Ser Ser Val Leu Ala Glu Asn Glu
50                  55                  60

Thr Asn His Val Ala Tyr Glu Asn Ala Ile Phe Glu Met Ala Glu Lys
65                  70                  75                  80

Asn Ile Glu Asn Phe Ser Ser Glu Asp Ile His Lys Lys Arg Lys Glu
                85                  90                  95

Met Ile Glu Ser Ala Leu Arg Leu Leu Met Gly Leu Tyr Lys Asp Arg
            100                 105                 110

His Glu Lys Leu Gln Pro Arg Thr Phe Val Leu Ile Ala Lys Ala Tyr
        115                 120                 125

Leu Leu Arg Ser Leu Ile Thr Arg Pro Lys Gly Ile Thr Ile Pro Glu
130                 135                 140

Lys Lys Lys Glu Ala Leu Lys Lys Gly Ile Gly Phe Val Glu Ser Ala
145                 150                 155                 160

Ile Lys Lys Ile Gln Ser Ser Glu Asn Ile Leu Ser His Ser Ser Asp
                165                 170                 175

Ile Asp Leu Leu Glu Lys Ala Trp Arg Ile Lys Ser Gln Leu Tyr Leu
            180                 185                 190

Glu Tyr Tyr Arg Val Asn Lys Asp Glu Cys Asp Lys Asn Thr Leu Lys
        195                 200                 205

Glu Val Leu Glu Asn Ser Leu Ile Ser Gly Cys Asp Lys Phe Asp Lys
210                 215                 220

Asn Ile Glu Asp Val Gln Ile Ala Ile Arg Tyr Cys Glu Leu Glu Ser
225                 230                 235                 240

Ser Arg Glu Tyr Leu Glu Gln Ile Ile Ser Ser His Leu Glu Gly Ile
                245                 250                 255

Glu Phe Glu Lys Ala Arg Ala Tyr Lys Leu Leu Glu Leu Glu Asn Glu
            260                 265                 270

Asn Glu Asp Glu Ile Arg Lys Ser Met Lys Val Val Ile Glu Glu Tyr
        275                 280                 285

Leu Ser Gly Phe Ser Asp Pro Leu Trp Glu Asp Ala Val Glu Phe Ile
290                 295                 300

Asn Lys Leu Lys Ser Asp Asn Lys Asn Cys Trp Lys Glu Leu Ser Leu
305                 310                 315                 320

Asp Met Tyr Lys Val Cys Arg Glu Gln Glu Ala Glu Thr Ala Ser Leu
                325                 330                 335

His Leu Arg Trp Tyr Trp Ser Arg Gln Arg Arg Leu Tyr Asp Leu Ala
            340                 345                 350

Phe Ile Ala Ala Asp Lys Glu Glu Lys Ala Lys Ile Ala Asp Ser
        355                 360                 365

Leu Lys Ser Arg Leu Ser Leu Arg Trp Ser Ala Leu Glu Glu Thr Gly
370                 375                 380

Lys Lys Ser Lys Asn Lys Arg Glu Lys Glu Ile Ser Arg Ile Leu
385                 390                 395                 400
```

Glu Ala Glu Ala Val Ala Met Leu Gly Gly Tyr Ile Lys Gly Ala Arg
            405                 410                 415

Lys Ile Leu Lys Lys Arg Arg Arg Pro Leu Pro Asp Glu Gln Arg Ser
        420                 425                 430

Ile Pro Lys Asp Trp Ile Val Ile His Phe Tyr Val Asn Gln Leu Glu
    435                 440                 445

Asn Lys Cys Tyr Ala Leu Ile Tyr Asn Lys Asp Glu Asn Thr Trp Lys
450                 455                 460

Cys Glu Phe Val Lys Glu Tyr Gln Arg Leu Phe His Val Phe Leu Thr
465                 470                 475                 480

Trp Gln Thr Asn Tyr Asn Arg Cys Lys Glu Arg Ala Ala Asp Ser Leu
                485                 490                 495

Val Gln Leu Cys Lys Glu Ile Gly Asn Ala Met Pro Phe Leu Phe Asp
            500                 505                 510

Glu Cys Ile Ile Pro Gln Asp Lys Asn Val Leu Phe Ile Pro His Asp
        515                 520                 525

Phe Leu His Arg Leu Pro Leu His Gly Ala Ile His Glu Lys Asn Asn
    530                 535                 540

Gly Val Phe Leu Glu Asn His Pro Cys Cys Tyr Leu Pro Ala Trp Ser
545                 550                 555                 560

Phe Thr Ala Lys Glu Asn Asn Ala Val Val Gln Gly Ser Ile Leu Leu
                565                 570                 575

Lys Asn Phe Pro Glu Tyr Ser Tyr Glu Glu Leu Val Ser Asn Ser Thr
            580                 585                 590

Leu Trp Thr Ser Pro Val Lys Asp Pro Ala Ser Pro Asp Asp Leu Lys
        595                 600                 605

Thr Ile Ile Ala Ser Pro Glu Met Leu Val Ile Leu Cys His Gly Glu
    610                 615                 620

Ala Asp Ala Val Asn Pro Phe Asn Ala Arg Leu Lys Leu Thr Gly Asn
625                 630                 635                 640

Gly Ile Ser His Leu Glu Ile Leu Gln Ser Thr Lys Met Ile Leu Lys
                645                 650                 655

Gly Ser Lys Ile Ile Leu Gly Ala Cys Glu Thr Asp Leu Val Pro Pro
            660                 665                 670

Leu Ser Asp Ile Met Asp Glu His Leu Ser Ile Ala Thr Ala Phe Leu
        675                 680                 685

Thr Asn Gly Thr His Glu Ile Leu Gly Thr Met Trp Gln Ser Arg Pro
    690                 695                 700

Glu Asp Ile Glu Asp Ile Arg Leu Leu Cys Asp Lys Lys Thr Ser
705                 710                 715                 720

Asp Thr Lys Ala Arg Gly Asp Leu Trp Asn Trp Gln Lys Glu Arg Ile
                725                 730                 735

Arg Asp Tyr Trp Ala Gly Glu Asp Ala Met Phe Tyr Arg Ser Val Ala
            740                 745                 750

Phe Arg Ile Ile Gly Leu Thr Ile
        755                 760

<210> SEQ ID NO 14
<211> LENGTH: 1722
<212> TYPE: PRT
<213> ORGANISM: Candidatus Scalindua brodae

<400> SEQUENCE: 14

Met Lys Ser Asn Asp Met Asn Ile Thr Val Glu Leu Thr Phe Phe Glu

-continued

```
1               5                   10                  15
Pro Tyr Arg Leu Val Glu Trp Phe Asp Trp Asp Ala Arg Lys Lys Ser
                20                  25                  30
His Ser Ala Met Arg Gly Gln Ala Phe Ala Gln Trp Thr Trp Lys Gly
                35                  40                  45
Lys Gly Arg Thr Ala Gly Lys Ser Phe Ile Thr Gly Thr Leu Val Arg
                50                  55                  60
Ser Ala Val Ile Lys Ala Val Glu Glu Leu Leu Ser Leu Asn Asn Gly
65                  70                  75                  80
Lys Trp Glu Gly Val Pro Cys Cys Asn Gly Ser Phe Gln Thr Asp Glu
                85                  90                  95
Ser Lys Gly Lys Lys Pro Ser Phe Leu Arg Lys Arg His Thr Leu Gln
                100                 105                 110
Trp Gln Ala Asn Lys Asn Ile Cys Asp Lys Glu Ala Cys Pro
                115                 120                 125
Phe Cys Ile Leu Leu Gly Arg Phe Asp Asn Ala Gly Lys Val His Glu
                130                 135                 140
Arg Asn Lys Asp Tyr Asp Ile His Phe Ser Asn Phe Asp Leu Asp His
145                 150                 155                 160
Lys Gln Glu Lys Asn Asp Leu Arg Leu Val Asp Ile Ala Ser Gly Arg
                165                 170                 175
Ile Leu Asn Arg Val Asp Phe Asp Thr Gly Lys Ala Lys Asp Tyr Phe
                180                 185                 190
Arg Thr Trp Glu Ala Asp Tyr Glu Thr Tyr Gly Thr Tyr Thr Gly Arg
                195                 200                 205
Ile Thr Leu Arg Asn Glu His Ala Lys Lys Leu Leu Leu Ala Ser Leu
                210                 215                 220
Gly Phe Val Asp Lys Leu Cys Gly Ala Leu Cys Arg Ile Glu Val Ile
225                 230                 235                 240
Lys Lys Ser Glu Ser Pro Leu Pro Ser Asp Thr Lys Glu Gln Ser Tyr
                245                 250                 255
Thr Lys Asp Asp Thr Val Glu Val Leu Ser Glu Asp His Asn Asp Glu
                260                 265                 270
Leu Arg Lys Gln Ala Glu Val Ile Val Glu Ala Phe Lys Gln Asn Asp
                275                 280                 285
Lys Leu Glu Lys Ile Arg Ile Leu Ala Asp Ala Ile Arg Thr Leu Arg
                290                 295                 300
Leu His Gly Glu Gly Val Ile Glu Lys Asp Glu Leu Pro Asp Gly Lys
305                 310                 315                 320
Glu Glu Arg Asp Lys Gly His His Leu Trp Asp Ile Lys Val Gln Gly
                325                 330                 335
Thr Ala Leu Arg Thr Lys Leu Lys Glu Leu Trp Gln Ser Asn Lys Asp
                340                 345                 350
Ile Gly Trp Arg Lys Phe Thr Glu Met Leu Gly Ser Asn Leu Tyr Leu
                355                 360                 365
Ile Tyr Lys Lys Glu Thr Gly Gly Val Ser Thr Arg Phe Arg Ile Leu
                370                 375                 380
Gly Asp Thr Glu Tyr Tyr Ser Lys Ala His Asp Ser Glu Gly Ser Asp
385                 390                 395                 400
Leu Phe Ile Pro Val Thr Pro Pro Glu Gly Ile Glu Thr Lys Glu Trp
                405                 410                 415
Ile Ile Val Gly Arg Leu Lys Ala Ala Thr Pro Phe Tyr Phe Gly Val
                420                 425                 430
```

-continued

```
Gln Gln Pro Ser Asp Ser Ile Pro Gly Lys Glu Lys Lys Ser Glu Asp
        435                 440                 445
Ser Leu Val Ile Asn Glu His Thr Ser Phe Asn Ile Leu Leu Asp Lys
        450                 455                 460
Glu Asn Arg Tyr Arg Ile Pro Arg Ser Ala Leu Arg Gly Ala Leu Arg
465                 470                 475                 480
Arg Asp Leu Arg Thr Ala Phe Gly Ser Gly Cys Asn Val Ser Leu Gly
                485                 490                 495
Gly Gln Ile Leu Cys Asn Cys Lys Val Cys Ile Glu Met Arg Arg Ile
                500                 505                 510
Thr Leu Lys Asp Ser Val Ser Asp Phe Ser Glu Pro Glu Ile Arg
        515                 520                 525
Tyr Arg Ile Ala Lys Asn Pro Gly Thr Ala Thr Val Glu Asp Gly Ser
        530                 535                 540
Leu Phe Asp Ile Glu Val Gly Pro Glu Gly Leu Thr Phe Pro Phe Val
545                 550                 555                 560
Leu Arg Tyr Arg Gly His Lys Phe Pro Glu Gln Leu Ser Ser Val Ile
                565                 570                 575
Arg Tyr Trp Glu Glu Asn Asp Gly Lys Asn Gly Met Ala Trp Leu Gly
                580                 585                 590
Gly Leu Asp Ser Thr Gly Lys Gly Arg Phe Ala Leu Lys Asp Ile Lys
        595                 600                 605
Ile Phe Glu Trp Asp Leu Asn Gln Lys Ile Asn Glu Tyr Ile Lys Glu
        610                 615                 620
Arg Gly Met Arg Gly Lys Glu Lys Glu Leu Leu Glu Met Gly Glu Ser
625                 630                 635                 640
Ser Leu Pro Asp Gly Leu Ile Pro Tyr Lys Phe Phe Glu Glu Arg Glu
                645                 650                 655
Cys Leu Phe Pro Tyr Lys Glu Asn Leu Lys Pro Gln Trp Ser Glu Val
                660                 665                 670
Gln Tyr Thr Ile Glu Val Gly Ser Pro Leu Leu Thr Ala Asp Thr Ile
        675                 680                 685
Ser Ala Leu Thr Glu Pro Gly Asn Arg Asp Ala Ile Ala Tyr Lys Lys
        690                 695                 700
Arg Val Tyr Asn Asp Gly Asn Asn Ala Ile Glu Pro Glu Pro Arg Phe
705                 710                 715                 720
Ala Val Lys Ser Glu Thr His Arg Gly Ile Phe Arg Thr Ala Val Gly
                725                 730                 735
Arg Arg Thr Gly Asp Leu Gly Lys Glu Asp His Glu Asp Cys Thr Cys
                740                 745                 750
Asp Met Cys Ile Ile Phe Gly Asn Glu His Glu Ser Ser Lys Ile Arg
        755                 760                 765
Phe Glu Asp Leu Glu Leu Ile Asn Gly Asn Glu Phe Glu Lys Leu Glu
        770                 775                 780
Lys His Ile Asp His Val Ala Ile Asp Arg Phe Thr Gly Gly Ala Leu
785                 790                 795                 800
Asp Lys Ala Lys Phe Asp Thr Tyr Pro Leu Ala Gly Ser Pro Lys Lys
                805                 810                 815
Pro Leu Lys Leu Lys Gly Arg Phe Trp Ile Lys Lys Gly Phe Ser Gly
                820                 825                 830
Asp His Lys Leu Leu Ile Thr Thr Ala Leu Ser Asp Ile Arg Asp Gly
        835                 840                 845
```

-continued

Leu Tyr Pro Leu Gly Ser Lys Gly Gly Val Gly Tyr Gly Trp Val Ala
850             855                 860

Gly Ile Ser Ile Asp Asp Asn Val Pro Asp Asp Phe Lys Glu Met Ile
865             870              875                 880

Asn Lys Thr Glu Met Pro Leu Pro Glu Val Glu Glu Ser Asn Asn
            885                 890                 895

Gly Pro Ile Asn Asn Asp Tyr Val His Pro Gly His Gln Ser Pro Lys
            900                 905                 910

Gln Asp His Lys Asn Lys Asn Ile Tyr Tyr Pro His Tyr Phe Leu Asp
            915                 920                 925

Ser Gly Ser Lys Val Tyr Arg Glu Lys Asp Ile Ile Thr His Glu Glu
930                 935                 940

Phe Thr Glu Glu Leu Leu Ser Gly Lys Ile Asn Cys Lys Leu Glu Thr
945                 950                 955                 960

Leu Thr Pro Leu Ile Ile Pro Asp Thr Ser Asp Glu Asn Gly Leu Lys
                965                 970                 975

Leu Gln Gly Asn Lys Pro Gly His Lys Asn Tyr Lys Phe Phe Asn Ile
                980                 985                 990

Asn Gly Glu Leu Met Ile Pro Gly Ser Glu Leu Arg Gly Met Leu Arg
                995                 1000                1005

Thr His Phe Glu Ala Leu Thr Lys Ser Cys Phe Ala Ile Phe Gly
    1010                1015                1020

Glu Asp Ser Thr Leu Ser Trp Arg Met Asn Ala Asp Glu Lys Asp
    1025                1030                1035

Tyr Lys Ile Asp Ser Asn Ser Ile Arg Lys Met Glu Ser Gln Arg
    1040                1045                1050

Asn Pro Lys Tyr Arg Ile Pro Asp Glu Leu Gln Lys Glu Leu Arg
    1055                1060                1065

Asn Ser Gly Asn Gly Leu Phe Asn Arg Leu Tyr Thr Ser Glu Arg
    1070                1075                1080

Arg Phe Trp Ser Asp Val Ser Asn Lys Phe Glu Asn Ser Ile Asp
    1085                1090                1095

Tyr Lys Arg Glu Ile Leu Arg Cys Ala Gly Arg Pro Lys Asn Tyr
    1100                1105                1110

Lys Gly Gly Ile Ile Arg Gln Arg Lys Asp Ser Leu Met Ala Glu
    1115                1120                1125

Glu Leu Lys Val His Arg Leu Pro Leu Tyr Asp Asn Phe Asp Ile
    1130                1135                1140

Pro Asp Ser Ala Tyr Lys Ala Asn Asp His Cys Arg Lys Ser Ala
    1145                1150                1155

Thr Cys Ser Thr Ser Arg Gly Cys Arg Glu Arg Phe Thr Cys Gly
    1160                1165                1170

Ile Lys Val Arg Asp Lys Asn Arg Val Phe Leu Asn Ala Ala Asn
    1175                1180                1185

Asn Asn Arg Gln Tyr Leu Asn Asn Ile Lys Lys Ser Asn His Asp
    1190                1195                1200

Leu Tyr Leu Gln Tyr Leu Lys Gly Glu Lys Lys Ile Arg Phe Asn
    1205                1210                1215

Ser Lys Val Ile Thr Gly Ser Glu Arg Ser Pro Ile Asp Val Ile
    1220                1225                1230

Ala Glu Leu Asn Glu Arg Gly Arg Gln Thr Gly Phe Ile Lys Leu
    1235                1240                1245

Ser Gly Leu Asn Asn Ser Asn Lys Ser Gln Gly Asn Thr Gly Thr

```
            1250                1255                1260
Thr Phe Asn Ser Gly Trp Asp Arg Phe Glu Leu Asn Ile Leu Leu
    1265                1270                1275

Asp Asp Leu Glu Thr Arg Pro Ser Lys Ser Asp Tyr Pro Arg Pro
    1280                1285                1290

Arg Leu Leu Phe Thr Lys Asp Gln Tyr Glu Tyr Asn Ile Thr Lys
    1295                1300                1305

Arg Cys Glu Arg Val Phe Glu Ile Asp Lys Gly Asn Lys Thr Gly
    1310                1315                1320

Tyr Pro Val Asp Asp Gln Ile Lys Lys Asn Tyr Glu Asp Ile Leu
    1325                1330                1335

Asp Ser Tyr Asp Gly Ile Lys Asp Gln Glu Val Ala Glu Arg Phe
    1340                1345                1350

Asp Thr Phe Thr Arg Gly Ser Lys Leu Lys Val Gly Asp Leu Val
    1355                1360                1365

Tyr Phe His Ile Asp Gly Asp Asn Lys Ile Asp Ser Leu Ile Pro
    1370                1375                1380

Val Arg Ile Ser Arg Lys Cys Ala Ser Lys Thr Leu Gly Gly Lys
    1385                1390                1395

Leu Asp Lys Ala Leu His Pro Cys Thr Gly Leu Ser Asp Gly Leu
    1400                1405                1410

Cys Pro Gly Cys His Leu Phe Gly Thr Thr Asp Tyr Lys Gly Arg
    1415                1420                1425

Val Lys Phe Gly Phe Ala Lys Tyr Glu Asn Gly Pro Glu Trp Leu
    1430                1435                1440

Ile Thr Arg Gly Asn Asn Pro Glu Arg Ser Leu Thr Leu Gly Val
    1445                1450                1455

Leu Glu Ser Pro Arg Pro Ala Phe Ser Ile Pro Asp Asp Glu Ser
    1460                1465                1470

Glu Ile Pro Gly Arg Lys Phe Tyr Leu His His Asn Gly Trp Arg
    1475                1480                1485

Ile Ile Arg Gln Lys Gln Leu Glu Ile Arg Glu Thr Val Gln Pro
    1490                1495                1500

Glu Arg Asn Val Thr Thr Glu Val Met Asp Lys Gly Asn Val Phe
    1505                1510                1515

Ser Phe Asp Val Arg Phe Glu Asn Leu Arg Glu Trp Glu Leu Gly
    1520                1525                1530

Leu Leu Leu Gln Ser Leu Asp Pro Gly Lys Asn Ile Ala His Lys
    1535                1540                1545

Leu Gly Lys Gly Lys Pro Tyr Gly Phe Gly Ser Val Lys Ile Lys
    1550                1555                1560

Ile Asp Ser Leu His Thr Phe Lys Ile Asn Ser Asn Asn Asp Lys
    1565                1570                1575

Ile Lys Arg Val Pro Gln Ser Asp Ile Arg Glu Tyr Ile Asn Lys
    1580                1585                1590

Gly Tyr Gln Lys Leu Ile Glu Trp Ser Gly Asn Asn Ser Ile Gln
    1595                1600                1605

Lys Gly Asn Val Leu Pro Gln Trp His Val Ile Pro His Ile Asp
    1610                1615                1620

Lys Leu Tyr Lys Leu Leu Trp Val Pro Phe Leu Asn Asp Ser Lys
    1625                1630                1635

Leu Glu Pro Asp Val Arg Tyr Pro Val Leu Asn Glu Glu Ser Lys
    1640                1645                1650
```

-continued

```
Gly Tyr Ile Glu Gly Ser Asp Tyr Thr Tyr Lys Leu Gly Asp
    1655            1660                1665

Lys Asp Asn Leu Pro Tyr Lys Thr Arg Val Lys Gly Leu Thr Thr
    1670            1675                1680

Pro Trp Ser Pro Trp Asn Pro Phe Gln Val Ile Ala Glu His Glu
    1685            1690                1695

Glu Gln Glu Val Asn Val Thr Gly Ser Arg Pro Ser Val Thr Asp
    1700            1705                1710

Lys Ile Glu Arg Asp Gly Lys Met Val
    1715            1720

<210> SEQ ID NO 15
<211> LENGTH: 1403
<212> TYPE: PRT
<213> ORGANISM: Deltaproteobacteria bacterium
<220> FEATURE:
<221> NAME/KEY: MOD_RES
<222> LOCATION: (1394)..(1396)
<223> OTHER INFORMATION: Any amino acid

<400> SEQUENCE: 15

Met Thr Lys Lys Pro Gly Thr Glu Asp Lys Ala Thr Leu Trp Gly Lys
1               5                   10                  15

Glu Ser Ala Ser Lys Ser Val Lys Thr Ile Leu Glu Glu Ser Ile Gln
            20                  25                  30

Gly Phe Thr Val Glu Gln Lys Arg Ser Phe Ala Asn Leu Ala Asp
        35                  40                  45

Gln Leu Val Ser Arg Ala Gly Gln Gly Ala Lys Ser Val Arg Ser
    50                  55                  60

Gln Gly Leu Ile Ile Gly Arg Lys Glu Asn Tyr Ala Lys Pro Ser Ala
65                  70                  75                  80

Gln Glu Pro Thr Arg His His Leu Tyr Arg Gln Pro Ser Asn Ala Ser
                85                  90                  95

Ala Phe Leu Ala Thr Gly Trp Leu Ile Ala Glu Thr Pro Phe Phe Ile
            100                 105                 110

Gly Ser Gly Thr Glu Gly Gln Lys Gln Thr Asp Gln Ala Glu Ser
        115                 120                 125

Leu His Leu Arg Thr Leu Arg Asp Gly His Gly Arg Phe Arg Ile Pro
    130                 135                 140

Phe Thr Thr Ile Arg Gly Val Met Asp Lys Glu Leu Arg Asp Ile Leu
145                 150                 155                 160

Gln Ala Gly Cys Ala Lys Gly Arg Ser Leu Arg Ala Pro Cys Pro Cys
                165                 170                 175

Gln Val Cys Thr Leu Met Arg Arg Ile Gln Val Arg Asp Ala Ile Ala
            180                 185                 190

Ala Asp Ile Leu Pro Pro Asp Leu Arg Met Arg Thr Arg Ile Asp Pro
        195                 200                 205

Ser His Gly Thr Val Ala His Leu Phe Ser Leu Glu Met Ala Pro Gln
    210                 215                 220

Gly Leu Lys Leu Pro Phe Phe Leu Lys Leu Lys Gly Val Glu Thr Ile
225                 230                 235                 240

Asp Pro Asp Lys Glu Leu Leu Glu Ile Leu Asn Asp Trp Ser Ala Gly
                245                 250                 255

Gln Cys Phe Leu Gly Gly Leu Trp Gly Thr Gly Lys Gly Arg Phe Arg
            260                 265                 270
```

```
Leu Asp Asp Leu Gln Trp His Arg Leu Glu Leu Asp Asn Ala Asp Tyr
            275                 280                 285

Tyr Thr Pro Leu Leu Gln Asp Arg Phe Phe Ala Gly Glu Thr Ile Ser
        290                 295                 300

Asp Leu Arg Gln Gly Leu Gln Ser Ile Asn Ile Gln Pro Glu Arg Ile
305                 310                 315                 320

Pro Ala Gln Thr Pro Ser Arg Asn Met Pro Tyr Cys Arg Val Asp Cys
                325                 330                 335

Ile Leu Glu Phe Lys Ser Pro Val Leu Ser Gly Asp Pro Val Ala Ala
                340                 345                 350

Leu Phe Glu Ser Asp Ala Pro Asp Asn Val Ala Tyr Lys Lys Pro Val
            355                 360                 365

Val Gln Tyr Asp Glu Thr Gly Arg Leu Arg Thr Thr Asp Pro Gly Pro
        370                 375                 380

Val Glu Met Leu Thr Cys Leu Lys Gly Glu Gly Val Arg Gly Val Val
385                 390                 395                 400

Ala Tyr Leu Ala Gly Lys Ala Tyr Asp Gln His Asp Leu Ser His Asp
                405                 410                 415

Ser Cys Asn Cys Thr Phe Cys Gln Ala Phe Gly Asn Gly Gln Lys Ala
                420                 425                 430

Gly Ser Leu Arg Phe Asp Asp Phe Met Pro Val Gln Phe Glu Ser Asp
            435                 440                 445

Gln Ala Gly Asn Phe Ser Trp Ser Pro His Thr Pro His Ala Met Arg
            450                 455                 460

Ser Asp Arg Val Ala Leu Asp Val Phe Gly Gly Ala Met Pro Glu Ala
465                 470                 475                 480

Lys Phe Asp Asp Arg Pro Leu Ala Ala Ser Pro Gly Lys Pro Leu Asn
                485                 490                 495

Phe Lys Ser Thr Ile Trp Tyr Arg Glu Asp Met Gly Lys Glu Ala Gly
                500                 505                 510

Lys Ala Leu Lys Arg Ala Leu Ile Asp Leu Gln Asn Asn Met Ala Ala
            515                 520                 525

Ile Gly Ser Gly Gly Gly Ile Gly Arg Gly Trp Val Ser Arg Val Cys
            530                 535                 540

Phe Glu Gly Asp Ile Pro Asp Phe Leu Glu Asp Phe Pro Glu Pro Ile
545                 550                 555                 560

Thr Val Thr Glu Pro Glu Gln Asp Ser Gln Leu Leu Lys Asn Gln Ala
                565                 570                 575

Val Ala Asp Glu Thr Ala Val Ser Ala Cys Asp Thr Ala Asp Ala Pro
                580                 585                 590

His Pro Leu Ala Val Thr Leu Glu Pro Gly Ala Arg Tyr Phe Pro Arg
            595                 600                 605

Val Ile Ile Pro Arg Ala Pro Thr Val Lys Arg Asp Glu Cys Val Thr
        610                 615                 620

Gly Gln Arg Tyr His Thr Gly Arg Leu Ser Gly Lys Ile Phe Cys Glu
625                 630                 635                 640

Leu Asn Thr Leu Gly Pro Leu Phe Val Pro Asp Thr Asp Tyr Ser Ala
                645                 650                 655

Gly Val Pro Val Pro Ile Ser Asp Glu Gln Leu Ala Glu Cys Gln Leu
                660                 665                 670

Gln Ala Val Phe Glu Asn Thr Ser Lys Phe Asn Glu Phe Phe Ala Thr
            675                 680                 685

Tyr Pro Glu Glu Thr Val Thr Lys Leu Lys Asp Leu Leu Cys Ala Ala
```

-continued

```
            690             695             700

Asp Asp Lys Trp Ile Leu Ala Val Lys Asp Ile Thr Ala Asp Leu Arg
705             710             715             720

Gln Glu Ile Gly Glu Asp Thr Phe Gln Arg Ile Ile Arg Lys Ala Gly
                725             730             735

His Lys Thr Gln Arg Phe His Gln Ile Asn Asp Glu Ile Gly Leu Pro
            740             745             750

Gly Ala Ser Leu Arg Gly Met Val Leu Ser Asn Tyr Gln Ile Leu Thr
                755             760             765

Asn Ser Cys Tyr Arg Asn Leu Lys Ala Thr Glu Glu Ile Thr Arg Arg
770             775             780

Met Pro Ala Asp Glu Ala Lys Tyr Arg Lys Ala Gly Arg Val Thr Val
785             790             795             800

Ser Gly Asp Gly Ala Gln Lys Lys Tyr Ser Ile Gln Glu Met Glu Val
                805             810             815

Leu Arg Leu Pro Ile Tyr Asp Asn Met Asn Thr Pro Asp Asn Met Pro
                820             825             830

Asp Val Ala Lys Gln Ala Thr Thr Ala Lys Arg Cys Asn Asn Leu Met
                835             840             845

Asn Glu Ala Ala Lys Thr Ser Arg Val Glu Leu Lys Ala Arg Trp Arg
850             855             860

Glu Gly Gln Ser Lys Ile Lys Tyr Gln Ile Ile Asp Ala Leu Asn Lys
865             870             875             880

Val Asp Pro Ile Ile Gln Val Ile Ser Ser Lys Gln Ile Asn Pro
                885             890             895

Asn Asn Gly Lys Thr Gly Trp Gly Tyr Val Lys Tyr Thr Gly Ala Asn
                900             905             910

Val Phe Ala Lys Ser Leu Val Ala Pro Ile Asp Cys Leu Arg Lys Lys
                915             920             925

Asp Ala Gly His Val Cys Cys Gln Val Asn Leu Asn Pro Ala Trp Glu
                930             935             940

Ala Ser Asn Phe Asp Ile Leu Ile Asn Glu Lys Cys Pro Val Glu Arg
945             950             955             960

Gln Ser Gly Pro Arg Pro Thr Leu Arg Cys Lys Gly Gln Asp Ser Ala
                965             970             975

Trp Tyr Thr Leu Thr Lys Arg Ser Glu Arg Ile Phe Thr Asp Lys Lys
                980             985             990

Pro Val Pro Asp Pro Ile Asn Ile Pro Pro Arg Glu Val  Lys Arg Tyr
                995            1000            1005

Asn Glu  Leu Arg Asp Ser Tyr  Lys Lys Asn Thr Ala  His Val Pro
     1010             1015            1020

Lys Pro  Leu Gln Thr Phe Phe  Asn Gln Glu Ser Leu  Ala Asn Gly
     1025             1030             1035

Asp Leu  Val Tyr Phe Glu Val  Asn Gln Phe Gly Glu  Ala Ser Gln
     1040             1045             1050

Leu Thr  Pro Val Ser Ile Ser  Arg Thr Thr Asp Leu  Phe Pro Ile
     1055             1060             1065

Gly Gly  Arg Leu Pro Gln Gly  His Lys Asp Leu Phe  Pro Cys Thr
     1070             1075             1080

Ala Met  Cys Leu Ser Glu Cys  Lys Asn Cys Val Pro  Ala Ser Phe
     1085             1090             1095

Cys Glu  Phe His Ser Arg Ser  His Glu Lys Leu Cys  Pro Ala Cys
     1100             1105             1110
```

```
Ser Leu Ala Gly Thr Thr Gly Asn Arg Gly Arg Ile Lys Phe Ser
    1115                1120                1125

Glu Ala Trp Leu Ser Gly Leu Pro Lys Trp His Ser Val Ser Gln
    1130                1135                1140

Asp Asn Val Gly Arg Gly Leu Gly Val Thr Met Pro Arg Leu Glu
    1145                1150                1155

Arg Ser Arg Arg Thr Trp His Leu Pro Thr Lys Asp Ala Tyr Leu
    1160                1165                1170

Leu Gly Gln Ser Ile Tyr Leu Asn His Pro Val Pro Ala Ile Leu
    1175                1180                1185

Pro Ser Asp Gln Val Pro Ser Glu Asn Asn Gln Thr Val Glu Pro
    1190                1195                1200

Leu Gly Pro Lys Asn Ile Phe Ser Phe Gln Leu Ala Phe Asp Asn
    1205                1210                1215

Leu Ser Ile Glu Glu Leu Gly Leu Leu Leu Tyr Ser Leu Glu Leu
    1220                1225                1230

Glu Ser Gly Met Ala His Arg Leu Gly Arg Gly Arg Ala Leu Gly
    1235                1240                1245

Met Gly Ser Val Gln Ile Ser Val Lys Asp Ile Gln Ile Arg Asp
    1250                1255                1260

Asn Lys Ser Phe Leu Phe Ser Ser Asn Ile Ser Lys Lys Ser Glu
    1265                1270                1275

Trp Ile Gln Cys Gly Lys Asp Glu Phe Ala Gln Glu Ala Trp Phe
    1280                1285                1290

Gly Glu Ser Trp Asp Asn Ile Asp His Ile Gln Arg Leu Arg Gln
    1295                1300                1305

Ala Leu Thr Ile Pro Val Lys Gly Asp Val Gly Cys Ile Arg Tyr
    1310                1315                1320

Pro Lys Leu Glu Ala Glu Gly Gly Met Pro Asp Tyr Ile Lys Leu
    1325                1330                1335

Arg Lys Arg Leu Thr Pro Leu Cys Asp Arg Glu Glu Pro Val Arg
    1340                1345                1350

Tyr Arg Ile Asn Pro Val Gln Leu Ala Arg Met Ile Leu Pro Phe
    1355                1360                1365

Val Pro Trp His Gly Ala Cys Pro Ala Leu Leu Asn Glu Gln Val
    1370                1375                1380

Met Ile Glu Ala Lys Arg Leu Thr Glu Leu Xaa Xaa Xaa Asp Arg
    1385                1390                1395

Ala Asn Trp Pro Cys
    1400

<210> SEQ ID NO 16
<211> LENGTH: 1601
<212> TYPE: PRT
<213> ORGANISM: Desulfonema ishimotonii

<400> SEQUENCE: 16

Met Thr Thr Thr Met Lys Ile Ser Ile Glu Phe Leu Glu Pro Phe Arg
1               5                   10                  15

Met Thr Lys Trp Gln Glu Ser Thr Arg Arg Asn Lys Asn Asn Lys Glu
                20                  25                  30

Phe Val Arg Gly Gln Ala Phe Ala Arg Trp His Arg Asn Lys Lys Asp
            35                  40                  45

Asn Thr Lys Gly Arg Pro Tyr Ile Thr Gly Thr Leu Leu Arg Ser Ala
```

```
                50                  55                  60
Val Ile Arg Ser Ala Glu Asn Leu Leu Thr Leu Ser Asp Gly Lys Ile
 65                  70                  75                  80

Ser Glu Lys Thr Cys Cys Pro Gly Lys Phe Asp Thr Glu Asp Lys Asp
                 85                  90                  95

Arg Leu Leu Gln Leu Arg Gln Arg Ser Thr Leu Arg Trp Thr Asp Lys
                100                 105                 110

Asn Pro Cys Pro Asp Asn Ala Glu Thr Tyr Cys Pro Phe Cys Glu Leu
                115                 120                 125

Leu Gly Arg Ser Gly Asn Asp Gly Lys Ala Glu Lys Lys Asp Trp
130                 135                 140

Arg Phe Arg Ile His Phe Gly Asn Leu Ser Leu Pro Gly Lys Pro Asp
145                 150                 155                 160

Phe Asp Gly Pro Lys Ala Ile Gly Ser Gln Arg Val Leu Asn Arg Val
                165                 170                 175

Asp Phe Lys Ser Gly Lys Ala His Asp Phe Phe Lys Ala Tyr Glu Val
                180                 185                 190

Asp His Thr Arg Phe Pro Arg Phe Glu Gly Glu Ile Thr Ile Asp Asn
                195                 200                 205

Lys Val Ser Ala Glu Ala Arg Lys Leu Leu Cys Asp Ser Leu Lys Phe
                210                 215                 220

Thr Asp Arg Leu Cys Gly Ala Leu Cys Val Ile Arg Phe Asp Glu Tyr
225                 230                 235                 240

Thr Pro Ala Ala Asp Ser Gly Lys Gln Thr Glu Asn Val Gln Ala Glu
                245                 250                 255

Pro Asn Ala Asn Leu Ala Glu Lys Thr Ala Glu Gln Ile Ile Ser Ile
                260                 265                 270

Leu Asp Asp Asn Lys Lys Thr Glu Tyr Thr Arg Leu Leu Ala Asp Ala
                275                 280                 285

Ile Arg Ser Leu Arg Arg Ser Ser Lys Leu Val Ala Gly Leu Pro Lys
                290                 295                 300

Asp His Asp Gly Lys Asp His Tyr Leu Trp Asp Ile Gly Lys Lys
305                 310                 315                 320

Lys Lys Asp Glu Asn Ser Val Thr Ile Arg Gln Ile Leu Thr Thr Ser
                325                 330                 335

Ala Asp Thr Lys Glu Leu Lys Asn Ala Gly Lys Trp Arg Glu Phe Cys
                340                 345                 350

Glu Lys Leu Gly Glu Ala Leu Tyr Leu Lys Ser Lys Asp Met Ser Gly
                355                 360                 365

Gly Leu Lys Ile Thr Arg Arg Ile Leu Gly Asp Ala Glu Phe His Gly
                370                 375                 380

Lys Pro Asp Arg Leu Glu Lys Ser Arg Ser Val Ser Ile Gly Ser Val
385                 390                 395                 400

Leu Lys Glu Thr Val Val Cys Gly Glu Leu Val Ala Lys Thr Pro Phe
                405                 410                 415

Phe Phe Gly Ala Ile Asp Glu Asp Ala Lys Gln Thr Asp Leu Gln Val
                420                 425                 430

Leu Leu Thr Pro Asp Asn Lys Tyr Arg Leu Pro Arg Ser Ala Val Arg
                435                 440                 445

Gly Ile Leu Arg Arg Asp Leu Gln Thr Tyr Phe Asp Ser Pro Cys Asn
                450                 455                 460

Ala Glu Leu Gly Gly Arg Pro Cys Met Cys Lys Thr Cys Arg Ile Met
465                 470                 475                 480
```

```
Arg Gly Ile Thr Val Met Asp Ala Arg Ser Glu Tyr Asn Ala Pro Pro
                485                 490                 495

Glu Ile Arg His Arg Thr Arg Ile Asn Pro Phe Thr Gly Thr Val Ala
            500                 505                 510

Glu Gly Ala Leu Phe Asn Met Glu Val Ala Pro Glu Gly Ile Val Phe
        515                 520                 525

Pro Phe Gln Leu Arg Tyr Arg Gly Ser Glu Asp Gly Leu Pro Asp Ala
    530                 535                 540

Leu Lys Thr Val Leu Lys Trp Trp Ala Glu Gly Gln Ala Phe Met Ser
545                 550                 555                 560

Gly Ala Ala Ser Thr Gly Lys Gly Arg Phe Arg Met Glu Asn Ala Lys
                565                 570                 575

Tyr Glu Thr Leu Asp Leu Ser Asp Glu Asn Gln Arg Asn Asp Tyr Leu
            580                 585                 590

Lys Asn Trp Gly Trp Arg Asp Glu Lys Gly Leu Glu Glu Leu Lys Lys
        595                 600                 605

Arg Leu Asn Ser Gly Leu Pro Glu Pro Gly Asn Tyr Arg Asp Pro Lys
    610                 615                 620

Trp His Glu Ile Asn Val Ser Ile Glu Met Ala Ser Pro Phe Ile Asn
625                 630                 635                 640

Gly Asp Pro Ile Arg Ala Ala Val Asp Lys Arg Gly Thr Asp Val Val
                645                 650                 655

Thr Phe Val Lys Tyr Lys Ala Glu Gly Glu Ala Lys Pro Val Cys
            660                 665                 670

Ala Tyr Lys Ala Glu Ser Phe Arg Gly Val Ile Arg Ser Ala Val Ala
        675                 680                 685

Arg Ile His Met Glu Asp Gly Val Pro Leu Thr Glu Leu Thr His Ser
    690                 695                 700

Asp Cys Glu Cys Leu Leu Cys Gln Ile Phe Gly Ser Glu Tyr Glu Ala
705                 710                 715                 720

Gly Lys Ile Arg Phe Glu Asp Leu Val Phe Glu Ser Asp Pro Glu Pro
                725                 730                 735

Val Thr Phe Asp His Val Ala Ile Asp Arg Phe Thr Gly Gly Ala Ala
            740                 745                 750

Asp Lys Lys Lys Phe Asp Asp Ser Pro Leu Pro Gly Ser Pro Ala Arg
        755                 760                 765

Pro Leu Met Leu Lys Gly Ser Phe Trp Ile Arg Arg Asp Val Leu Glu
    770                 775                 780

Asp Glu Glu Tyr Cys Lys Ala Leu Gly Lys Ala Leu Ala Asp Val Asn
785                 790                 795                 800

Asn Gly Leu Tyr Pro Leu Gly Gly Lys Ser Ala Ile Gly Tyr Gly Gln
                805                 810                 815

Val Lys Ser Leu Gly Ile Lys Gly Asp Asp Lys Arg Ile Ser Arg Leu
            820                 825                 830

Met Asn Pro Ala Phe Asp Glu Thr Asp Val Ala Val Pro Glu Lys Pro
        835                 840                 845

Lys Thr Asp Ala Glu Val Arg Ile Glu Ala Glu Lys Val Tyr Tyr Pro
    850                 855                 860

His Tyr Phe Val Glu Pro His Lys Lys Val Glu Arg Glu Glu Lys Pro
865                 870                 875                 880

Cys Gly His Gln Lys Phe His Glu Gly Arg Leu Thr Gly Lys Ile Arg
                885                 890                 895
```

-continued

Cys Lys Leu Ile Thr Lys Thr Pro Leu Ile Val Pro Asp Thr Ser Asn
            900                 905                 910

Asp Asp Phe Phe Arg Pro Ala Asp Lys Glu Ala Arg Lys Glu Lys Asp
            915                 920                 925

Glu Tyr His Lys Ser Tyr Ala Phe Phe Arg Leu His Lys Gln Ile Met
            930                 935                 940

Ile Pro Gly Ser Glu Leu Arg Gly Met Val Ser Ser Val Tyr Glu Thr
945                 950                 955                 960

Val Thr Asn Ser Cys Phe Arg Ile Phe Asp Glu Thr Lys Arg Leu Ser
            965                 970                 975

Trp Arg Met Asp Ala Asp His Gln Asn Val Leu Gln Asp Phe Leu Pro
            980                 985                 990

Gly Arg Val Thr Ala Asp Gly Lys His Ile Gln Lys Phe Ser Glu Thr
            995                 1000                1005

Ala Arg Val Pro Phe Tyr Asp Lys Thr Gln Lys His Phe Asp Ile
            1010                1015                1020

Leu Asp Glu Gln Glu Ile Ala Gly Glu Lys Pro Val Arg Met Trp
            1025                1030                1035

Val Lys Arg Phe Ile Lys Arg Leu Ser Leu Val Asp Pro Ala Lys
            1040                1045                1050

His Pro Gln Lys Lys Gln Asp Asn Lys Trp Lys Arg Arg Lys Glu
            1055                1060                1065

Gly Ile Ala Thr Phe Ile Glu Gln Lys Asn Gly Ser Tyr Tyr Phe
            1070                1075                1080

Asn Val Val Thr Asn Asn Gly Cys Thr Ser Phe His Leu Trp His
            1085                1090                1095

Lys Pro Asp Asn Phe Asp Gln Glu Lys Leu Glu Gly Ile Gln Asn
            1100                1105                1110

Gly Glu Lys Leu Asp Cys Trp Val Arg Asp Ser Arg Tyr Gln Lys
            1115                1120                1125

Ala Phe Gln Glu Ile Pro Glu Asn Asp Pro Asp Gly Trp Glu Cys
            1130                1135                1140

Lys Glu Gly Tyr Leu His Val Val Gly Pro Ser Lys Val Glu Phe
            1145                1150                1155

Ser Asp Lys Lys Gly Asp Val Ile Asn Asn Phe Gln Gly Thr Leu
            1160                1165                1170

Pro Ser Val Pro Asn Asp Trp Lys Thr Ile Arg Thr Asn Asp Phe
            1175                1180                1185

Lys Asn Arg Lys Arg Lys Asn Glu Pro Val Phe Cys Cys Glu Asp
            1190                1195                1200

Asp Lys Gly Asn Tyr Tyr Thr Met Ala Lys Tyr Cys Glu Thr Phe
            1205                1210                1215

Phe Phe Asp Leu Lys Glu Asn Glu Glu Tyr Glu Ile Pro Glu Lys
            1220                1225                1230

Ala Arg Ile Lys Tyr Lys Glu Leu Leu Arg Val Tyr Asn Asn Asn
            1235                1240                1245

Pro Gln Ala Val Pro Glu Ser Val Phe Gln Ser Arg Val Ala Arg
            1250                1255                1260

Glu Asn Val Glu Lys Leu Lys Ser Gly Asp Leu Val Tyr Phe Lys
            1265                1270                1275

His Asn Glu Lys Tyr Val Glu Asp Ile Val Pro Val Arg Ile Ser
            1280                1285                1290

Arg Thr Val Asp Asp Arg Met Ile Gly Lys Arg Met Ser Ala Asp

```
              1295                1300                1305

Leu  Arg  Pro  Cys  His  Gly  Asp  Trp  Val  Glu  Asp  Gly  Asp  Leu  Ser
         1310                1315                1320

Ala  Leu  Asn  Ala  Tyr  Pro  Glu  Lys  Arg  Leu  Leu  Leu  Arg  His  Pro
    1325                1330                1335

Lys  Gly  Leu  Cys  Pro  Ala  Cys  Arg  Leu  Phe  Gly  Thr  Gly  Ser  Tyr
1340                1345                1350

Lys  Gly  Arg  Val  Arg  Phe  Gly  Phe  Ala  Ser  Leu  Glu  Asn  Asp  Pro
         1355                1360                1365

Glu  Trp  Leu  Ile  Pro  Gly  Lys  Asn  Pro  Gly  Asp  Pro  Phe  His  Gly
    1370                1375                1380

Gly  Pro  Val  Met  Leu  Ser  Leu  Leu  Glu  Arg  Pro  Arg  Pro  Thr  Trp
1385                1390                1395

Ser  Ile  Pro  Gly  Ser  Asp  Asn  Lys  Phe  Lys  Val  Pro  Gly  Arg  Lys
         1400                1405                1410

Phe  Tyr  Val  His  His  His  Ala  Trp  Lys  Thr  Ile  Lys  Asp  Gly  Asn
    1415                1420                1425

His  Pro  Thr  Thr  Gly  Lys  Ala  Ile  Glu  Gln  Ser  Pro  Asn  Asn  Arg
1430                1435                1440

Thr  Val  Glu  Ala  Leu  Ala  Gly  Gly  Asn  Ser  Phe  Ser  Phe  Glu  Ile
         1445                1450                1455

Ala  Phe  Glu  Asn  Leu  Lys  Glu  Trp  Glu  Leu  Gly  Leu  Leu  Ile  His
    1460                1465                1470

Ser  Leu  Gln  Leu  Glu  Lys  Gly  Leu  Ala  His  Lys  Leu  Gly  Met  Ala
1475                1480                1485

Lys  Ser  Met  Gly  Phe  Gly  Ser  Val  Glu  Ile  Asp  Val  Glu  Ser  Val
         1490                1495                1500

Arg  Leu  Arg  Lys  Asp  Trp  Lys  Gln  Trp  Arg  Asn  Gly  Asn  Ser  Glu
    1505                1510                1515

Ile  Pro  Asn  Trp  Leu  Gly  Lys  Gly  Phe  Ala  Lys  Leu  Lys  Glu  Trp
1520                1525                1530

Phe  Arg  Asp  Glu  Leu  Asp  Phe  Ile  Glu  Asn  Leu  Lys  Lys  Leu  Leu
         1535                1540                1545

Trp  Phe  Pro  Glu  Gly  Asp  Gln  Ala  Pro  Arg  Val  Cys  Tyr  Pro  Met
    1550                1555                1560

Leu  Arg  Lys  Lys  Asp  Asp  Pro  Asn  Gly  Asn  Ser  Gly  Tyr  Glu  Glu
1565                1570                1575

Leu  Lys  Asp  Gly  Glu  Phe  Lys  Lys  Glu  Asp  Arg  Gln  Lys  Lys  Leu
         1580                1585                1590

Thr  Thr  Pro  Trp  Thr  Pro  Trp  Ala
    1595                1600

<210> SEQ ID NO 17
<211> LENGTH: 1575
<212> TYPE: PRT
<213> ORGANISM: Unknown
<220> FEATURE:
<223> OTHER INFORMATION: Description of Unknown:
      Soil metagenome sequence

<400> SEQUENCE: 17

Met  Arg  Leu  Lys  Ile  Asn  Ile  His  Phe  Leu  Glu  Pro  Phe  Arg  Leu  Ile
1                 5                  10                  15

Glu  Trp  His  Glu  Gln  Asp  Arg  Arg  Asn  Lys  Gly  Asn  Ser  Arg  Trp  Gln
              20                  25                  30
```

-continued

```
Arg Gly Gln Ser Phe Ala Arg Trp His Arg Arg Lys Asp Asn Asp Gln
            35                  40                  45

Gly Arg Pro Tyr Ile Thr Gly Thr Leu Leu Arg Ser Val Val Ile Arg
 50                  55                  60

Ala Val Glu Glu Glu Leu Ala Arg Pro Asp Thr Ala Trp Gln Ser Cys
 65                  70                  75                  80

Gly Gly Leu Phe Ile Thr Pro Asp Gly Gln Thr Lys Pro Gln His Leu
                 85                  90                  95

Arg His Arg Ala Thr Val Arg Ala Gln Thr Ala Lys Asp Lys Cys
                100                 105                 110

Ala Asp Arg Gln Ser Ala Cys Pro Phe Cys Leu Leu Leu Gly Arg Phe
            115                 120                 125

Asp Gln Val Gly Lys Asp Gly Asp Lys Lys Gly Glu Gly Leu Arg Phe
        130                 135                 140

Asp Val Arg Phe Ser Asn Leu Asp Leu Pro Lys Asp Phe Ser Pro Arg
145                 150                 155                 160

Asp Phe Asp Gly Pro Gln Glu Ile Gly Ser Arg Arg Thr Ile Asn Arg
                165                 170                 175

Val Asp Asp Glu Thr Gly Lys Ala His Asp Phe Phe Ser Ile Trp Glu
            180                 185                 190

Val Asp Ala Val Arg Glu Phe Gln Gly Glu Ile Val Leu Ala Ala Asp
        195                 200                 205

Leu Pro Ser Arg Asp Gln Val Glu Ser Leu Leu His His Ala Leu Gly
    210                 215                 220

Phe Val Asp Arg Leu Cys Gly Ala Arg Cys Val Ile Ser Ile Ala Asp
225                 230                 235                 240

Gln Lys Pro Ala Glu Arg Glu Arg Thr Val Ala Ala Gly Asp Glu
                245                 250                 255

Lys Ala Thr Ile Ala Asp Tyr Asp Gln Val Lys Gly Leu Pro Tyr Thr
            260                 265                 270

Arg Leu Arg Pro Leu Ala Asp Ala Val Arg Asn Leu Arg Gln Leu Asp
        275                 280                 285

Leu Ala Glu Leu Asn Lys Pro Asp Gly Lys Phe Leu Pro Pro Gly Arg
    290                 295                 300

Val Asn Lys Asp Gly Arg Arg Val Pro His Tyr Val Trp Asp Ile Pro
305                 310                 315                 320

Leu Gly Lys Gly Asp Thr Leu Arg Lys Arg Leu Glu Phe Leu Ala Ala
                325                 330                 335

Ser Cys Glu Gly Asp Gln Ala Lys Trp Arg Asn Ile Cys Glu Ser Glu
            340                 345                 350

Gly Gln Ala Leu Tyr Glu Lys Ser Lys Lys Leu Lys Asp Ser Pro Ala
        355                 360                 365

Ala Pro Gly Arg His Leu Gly Ala Ala Glu Gln Val Arg Pro Pro Gln
    370                 375                 380

Pro Pro Val Ser Tyr Ser Glu Glu Ser Ile Asn Ser Asp Leu Pro Leu
385                 390                 395                 400

Ala Glu Trp Ile Ile Thr Gly Thr Leu Arg Ala Glu Thr Pro Phe Ala
                405                 410                 415

Ile Gly Met Asp Ala Pro Ile Asp Asp Gln Thr Ser Ser Arg Thr
            420                 425                 430

Leu Val Asp Arg Asp Gly Arg Tyr Arg Leu Pro Arg Ser Thr Leu Arg
        435                 440                 445

Gly Ile Leu Arg Arg Asp Leu Ser Leu Ala Ser Gly Asp Gln Gly Cys
```

```
            450                 455                 460
Gln Val Arg Leu Gly Pro Glu Arg Pro Cys Thr Cys Pro Val Cys Leu
465                 470                 475                 480

Ile Leu Arg Gln Val Val Ile Ala Asp Thr Val Ser Glu Thr Thr Val
                485                 490                 495

Pro Ala Asp Ile Arg Gln Arg Ile Arg Arg Asn Pro Ile Thr Gly Thr
                500                 505                 510

Ala Ala Asp Gly Gly Leu Phe Asp Thr Glu Arg Gly Pro Lys Gly Ala
                515                 520                 525

Gly Phe Pro Phe Ser Leu Arg Tyr Arg Gly His Ala Pro Met Pro Lys
                530                 535                 540

Ala Leu Arg Thr Val Leu Gln Trp Trp Ser Ala Gly Lys Cys Phe Ala
545                 550                 555                 560

Gly Ser Asp Gly Gly Val Gly Cys Gly Arg Phe Ala Leu Asp Asn Leu
                565                 570                 575

Glu Val Tyr Arg Trp Asp Leu Gly Thr Phe Ala Phe Arg Gln Ala Tyr
                580                 585                 590

Ser Glu Asn Asn Gly Leu Arg Ser Pro Glu Glu Phe Asp Leu Ala
                595                 600                 605

Val Ile His Glu Leu Ala Glu Gly Leu Ala Lys Glu Asp Gly Gln Lys
                610                 615                 620

Ile Leu Lys Gly Thr Glu Pro Phe Thr Cys Trp Gln Glu Arg Ser Trp
625                 630                 635                 640

Gln Phe Ser Phe Thr Gly Pro Leu Leu Gln Gly Asp Pro Leu Ala Ala
                645                 650                 655

Leu Asn Ser Asp Thr Ala Asp Ile Ile Ser Phe Arg Arg Thr Val Val
                660                 665                 670

Asp Asn Gly Glu Val Leu Arg Glu Pro Val Leu Arg Gly Glu Gly Leu
                675                 680                 685

Arg Gly Leu Leu Arg Thr Ala Val Gly Arg Val Ala Gly Asp Asp Leu
                690                 695                 700

Leu Thr Arg Ser His Gln Asp Cys Lys Cys Glu Ile Cys Gln Leu Phe
705                 710                 715                 720

Gly Ser Glu His Arg Ala Gly Ile Leu Arg Phe Glu Asp Leu Pro Pro
                725                 730                 735

Val Ser Pro Thr Thr Val Ala Asp Lys Arg Leu Asp His Val Ala Ile
                740                 745                 750

Asp Arg Phe Asp Gln Ser Val Val Glu Lys Tyr Asp Asp Arg Pro Leu
                755                 760                 765

Val Gly Ser Pro Lys Gln Pro Leu Val Phe Lys Gly Cys Phe Trp Val
                770                 775                 780

Gln Thr Ser Gly Met Thr His Gln Leu Thr Glu Leu Leu Ala Gln Ala
785                 790                 795                 800

Trp Arg Asp Ile Ala Ala Gly His Tyr Pro Val Gly Lys Gly Lys Gly
                805                 810                 815

Ile Gly Tyr Gly Trp Ile Asn Ser Leu Val Val Asp Gly Glu Lys Ile
                820                 825                 830

Thr Cys Arg Pro Asp Gly Asp Ser Ile Ser Leu Thr Thr Val Thr Gly
                835                 840                 845

Asp Ile Pro Pro Arg Pro Ala Leu Thr Pro Ala Gly Ala Ile Tyr
                850                 855                 860

Tyr Pro His Tyr Phe Leu Pro Pro Asn Pro Glu His Lys Pro Lys Arg
865                 870                 875                 880
```

-continued

```
Ser Asp Lys Ile Ile Gly His His Thr Phe Ala Thr Asp Pro Asp Ser
            885                 890                 895

Phe Thr Gly Arg Ile Thr Cys Lys Leu Glu Val Val Thr Pro Leu Ile
            900                 905                 910

Val Pro Asp Thr Glu Gly Glu Gln Pro Lys Asp Gln His Lys Asn Phe
            915                 920                 925

Pro Phe Phe Lys Ile Asn Asp Glu Ile Met Leu Pro Gly Ala Pro Leu
            930                 935                 940

Trp Ala Ala Val Ser Gln Val Tyr Glu Ala Leu Thr Asn Ser Cys Phe
945                 950                 955                 960

Arg Val Met Lys Gln Lys Arg Phe Leu Ser Trp Arg Met Glu Ala Glu
            965                 970                 975

Asp Tyr Lys Asp Phe Tyr Pro Gly Arg Val Leu Asp Gly Gly Lys Gln
            980                 985                 990

Ile Lys Lys Met Gly Asp Lys Ala  Ile Arg Met Pro Leu Tyr Asp Asp
            995                 1000                1005

Ser Thr Ala Thr Gly Ser Ile  Lys Asp Asp Gln Leu  Ile Ser Asp
     1010                1015                1020

Cys Cys Pro Lys Ser Asp Glu  Lys Leu Gln Lys Ala  Leu Ala Thr
     1025                1030                1035

Asn Gln Lys Ile Ala Leu Ala  Ala Lys His Asn Gln  Glu Tyr Leu
     1040                1045                1050

Ala Gln Leu Ser Pro Asp Glu  Arg Glu Ala Leu Gln  Gly Leu
     1055                1060                1065

Lys Lys Val Ser Phe Trp Thr  Glu Ser Leu Ala Asn  Asn Glu Ala
     1070                1075                1080

Pro Pro Phe Leu Ile Ala Lys  Leu Gly Glu Glu Arg  Gly Lys Pro
     1085                1090                1095

Lys Arg Ala Gly Tyr Leu Lys  Ile Thr Gly Pro Asn  Asn Ala Asn
     1100                1105                1110

Ile Ala Asn Thr Asn Asn Pro  Asp Asp Gly Gly Tyr  Ile Pro Ser
     1115                1120                1125

Trp Lys Asp Gln Phe Asp Tyr  Ser Phe Arg Leu Leu  Gly Pro Pro
     1130                1135                1140

Arg Cys Leu Pro Asn Thr Lys  Gly Asn Arg Glu Tyr  Pro Arg Pro
     1145                1150                1155

Gly Phe Thr Cys Val Ile Asp  Gly Lys Glu Tyr Ser  Leu Thr Lys
     1160                1165                1170

Arg Cys Glu Arg Ile Phe Glu  Asp Ile Ser Gly Gly  Glu Asn Gln
     1175                1180                1185

Val Val Arg Ala Val Thr Glu  Arg Val Arg Glu Gln  Tyr Arg Glu
     1190                1195                1200

Ile Leu Ala Ser Tyr Arg Ala  Asn Ala Ala Gly Ile  Ala Glu Gly
     1205                1210                1215

Phe Arg Thr Arg Met Tyr Asp  Thr Glu Glu Leu Arg  Glu Asn Asp
     1220                1225                1230

Leu Val Tyr Phe Lys Thr Ala  Lys Gln Ala Asp Gly  Lys Glu Arg
     1235                1240                1245

Val Val Ala Ile Ser Pro Val  Cys Ile Ser Arg Glu  Ala Asp Asp
     1250                1255                1260

Arg Pro Leu Gly Lys Arg Leu  Pro Ala Gly Phe Gln  Pro Cys Ser
     1265                1270                1275
```

```
His Val Cys Leu Glu Asp Cys Asn Thr Cys Ser Ala Lys Asn Cys
    1280                1285                1290

Pro Val Pro Leu Tyr Arg Glu Gly Trp Pro Val Asn Gly Leu Cys
    1295                1300                1305

Pro Ala Cys Arg Leu Phe Gly Ala Gln Met Tyr Lys Gly Arg Val
    1310                1315                1320

Asn Phe Gly Phe Ala Arg Leu Pro Asp Asp Lys Gln Pro Glu Thr
    1325                1330                1335

Lys Thr Leu Thr Leu Pro Leu Leu Glu Arg Pro Arg Pro Thr Trp
    1340                1345                1350

Val Leu Pro Lys Ser Val Lys Gly Ser Asn Thr Glu Asp Ala Thr
    1355                1360                1365

Ile Pro Gly Arg Lys Phe Tyr Leu Arg His Asp Gly Trp Arg Ile
    1370                1375                1380

Val Met Ala Gly Thr Asn Pro Ile Thr Gly Glu Ser Ile Glu Lys
    1385                1390                1395

Thr Ala Asn Asn Ala Thr Val Glu Ala Ile Met Pro Gly Ala Thr
    1400                1405                1410

Phe Thr Phe Asp Ile Val Cys Glu Asn Leu Asp Gln Gln Glu Leu
    1415                1420                1425

Gly Leu Leu Leu Tyr Ser Leu Glu Leu Glu Gly Met Ser His
    1430                1435                1440

Thr Leu Gly Arg Gly Lys Pro Leu Gly Phe Gly Asn Val Arg Ile
    1445                1450                1455

Lys Val Glu Lys Ile Glu Lys Arg Leu Ser Asp Gly Ser Arg Arg
    1460                1465                1470

Glu Met Ile Pro Pro Lys Gly Ala Gly Leu Phe Met Thr Asp Lys
    1475                1480                1485

Val Gln Asp Ala Leu Arg Gly Leu Thr Glu Gly Gly Asp Trp His
    1490                1495                1500

Gln Arg Pro His Ile Ser Gly Leu Arg Arg Leu Leu Thr Arg Tyr
    1505                1510                1515

Pro Glu Ile Lys Ala Arg Tyr Pro Lys Leu Ser Gln Gly Glu Asp
    1520                1525                1530

Lys Glu Pro Gly Tyr Ile Glu Leu Lys Ser Gln Lys Asp Glu Asn
    1535                1540                1545

Gly Val Pro Ile Tyr Asn Pro Asn Arg Glu Leu Arg Val Ser Glu
    1550                1555                1560

Asn Gly Pro Leu Pro Trp Phe Leu Leu Ala Lys Lys
    1565                1570                1575

<210> SEQ ID NO 18
<211> LENGTH: 1801
<212> TYPE: PRT
<213> ORGANISM: Unknown
<220> FEATURE:
<223> OTHER INFORMATION: Description of Unknown:
      Dolphin oral metagenome sequence

<400> SEQUENCE: 18

Met Ile Pro Asp Leu Arg Ser Leu Val Val His Ile Ser Phe Leu Thr
1               5                   10                  15

Pro Tyr Arg Gln Ala Pro Trp Phe Pro Pro Glu Lys Arg Arg Asn Asn
            20                  25                  30

Asn Arg Asp Trp Leu Arg Met Gln Ser Tyr Ala Arg Trp His Lys Val
        35                  40                  45
```

```
Ala Pro Glu Glu Gly His Pro Phe Ile Thr Gly Thr Leu Leu Arg Ser
    50                  55                  60

Arg Val Ile Arg Ala Val Glu Glu Leu Cys Leu Ala Asn Gly Ile
65                  70                  75                  80

Trp Arg Gly Val Ala Cys Cys Pro Gly Glu Phe Asn Ser Gln Ala Lys
                    85                  90                  95

Lys Lys Pro Lys His Leu Arg Arg Thr Thr Leu Gln Trp Tyr Pro
            100                 105                 110

Glu Gly Ala Lys Ser Cys Ser Lys Gln Asp Gly Arg Glu Asn Ala Cys
            115                 120                 125

Pro Phe Cys Leu Leu Leu Asp Arg Phe Gly Gly Lys Ser Glu Glu
    130                 135                 140

Gly Arg Lys Lys Asn Asn Asp Tyr Asp Val His Phe Ser Asn Leu Asn
145                 150                 155                 160

Pro Phe Tyr Pro Gly Ser Ser Pro Lys Val Trp Ser Gly Pro Glu Glu
                    165                 170                 175

Ile Gly Arg Leu Arg Thr Leu Asn Arg Ile Asp Arg Leu Thr Thr Lys
            180                 185                 190

Ala Gln Asp Phe Phe Arg Ile Tyr Glu Val Asp Gln Val Arg Asp Phe
            195                 200                 205

Phe Gly Thr Ile Thr Leu Ala Gly Asp Leu Pro Arg Lys Val Asp Val
    210                 215                 220

Glu Phe Leu Leu Arg Arg Gly Leu Gly Phe Val Ser Thr Leu Cys Gly
225                 230                 235                 240

Ala Gln Cys Glu Ile Lys Val Val Asp Leu Lys Lys Lys Gln Asn Asn
                    245                 250                 255

Lys Glu Asp Ser Ile Leu Pro Val Ser Glu Val Pro Phe Phe Leu Glu
            260                 265                 270

Pro Glu Val Leu Ala Lys Met Cys Gln Asp Val Phe Pro Ser Gly Lys
            275                 280                 285

Leu Arg Met Leu Ala Asp Val Ile Leu Arg Leu Arg Glu Glu Gly Pro
    290                 295                 300

Asp Asn Leu Thr Leu Pro Met Gly Ser Gln Gly Leu Gly Gly Arg Leu
305                 310                 315                 320

Pro His His Leu Trp Asp Val Pro Leu Val Ser Lys Asp Arg Glu Thr
                    325                 330                 335

Gln Thr Leu Arg Ser Cys Leu Glu Lys Ile Ala Ala Gln Cys Lys Ser
            340                 345                 350

Glu Gln Thr Gln Phe Arg Leu Phe Cys Gln Lys Leu Gly Ser Ser Leu
            355                 360                 365

Phe Arg Ile Asn Lys Gly Val Tyr Leu Ala Pro Asn Ser Lys Ile Ser
    370                 375                 380

Pro Glu Pro Cys Leu Asp Pro Ser Lys Thr Ile Arg Thr Lys Gly Pro
385                 390                 395                 400

Val Pro Gly Lys Gln Lys His Arg Phe Ser Leu Leu Pro Pro Phe Glu
                    405                 410                 415

Trp Ile Ile Thr Gly Thr Leu Lys Ala Gln Thr Pro Phe Phe Ile Pro
            420                 425                 430

Asp Glu Gln Gly Ser His Asp His Thr Ser Arg Lys Ile Leu Leu Thr
            435                 440                 445

Arg Asp Phe Tyr Tyr Arg Leu Pro Arg Ser Leu Leu Arg Gly Ile Ile
    450                 455                 460
```

```
Arg Arg Asp Leu His Glu Ala Thr Asp Lys Gly Cys Arg Val Glu
465                 470                 475                 480

Leu Ala Pro Asp Val Pro Cys Thr Cys Gln Val Cys Arg Leu Leu Gly
                485                 490                 495

Arg Met Leu Leu Ala Asp Thr Thr Ser Thr Thr Lys Val Ala Pro Asp
            500                 505                 510

Met Arg His Arg Val Gly Val Asp Arg Ser Cys Gly Ile Val Arg Asp
            515                 520                 525

Gly Ala Leu Phe Asp Thr Glu Tyr Gly Ile Glu Gly Val Cys Phe Pro
    530                 535                 540

Leu Glu Ile Arg Tyr Arg Gly Asn Lys Asp Leu Glu Gly Pro Ile Arg
545                 550                 555                 560

Gln Leu Leu Ser Trp Trp Gln Gln Gly Leu Leu Phe Leu Gly Gly Asp
                565                 570                 575

Phe Gly Ile Gly Lys Gly Arg Phe Arg Leu Glu Asn Met Lys Ile His
            580                 585                 590

Arg Trp Asp Leu Arg Asp Glu Ser Ala Arg Ala Asp Tyr Val Gln Lys
    595                 600                 605

Cys Gly Leu Arg Arg Gly Val Gly Asp Asp Thr Ala Ile Asn Leu Glu
    610                 615                 620

Lys Asp Leu Ser Leu Asn Leu Pro Glu Ser Gly Tyr Pro Trp Lys Lys
625                 630                 635                 640

His Ala Trp Lys Leu Ser Phe Gln Val Pro Leu Leu Thr Ala Asp Pro
                645                 650                 655

Ile Met Ala Gln Thr Arg His Glu Glu Asp Ser Val Tyr Phe Gln Lys
            660                 665                 670

Arg Ile Phe Thr Ser Asp Gly Arg Val Val Leu Val Pro Ala Leu Arg
            675                 680                 685

Gly Glu Gly Leu Arg Gly Leu Leu Arg Thr Ala Val Ser Arg Ala Tyr
    690                 695                 700

Gly Ile Ser Leu Ile Asn Asp Glu His Glu Asp Cys Asp Cys Pro Leu
705                 710                 715                 720

Cys Lys Ile Phe Gly Asn Glu His His Ala Gly Met Leu Arg Phe Asp
            725                 730                 735

Asp Met Val Pro Val Gly Thr Trp Asn Asp Lys Lys Ile Asp His Val
            740                 745                 750

Ser Cys Ser Arg Phe Asp Ala Ser Val Val Asn Lys Phe Asp Asp Arg
    755                 760                 765

Ser Leu Val Gly Ser Pro Asp Ser Pro Leu His Phe Glu Gly Thr Phe
    770                 775                 780

Trp Leu His Arg Asp Phe Gln Asn Asp Val Glu Ile Lys Thr Ala Leu
785                 790                 795                 800

Gln Asp Phe Ala Asp Gly Leu Tyr Ser Ile Gly Lys Gly Ile
                805                 810                 815

Gly Tyr Gly Trp Leu Phe Asp Met Glu Ile Pro Arg Ser Leu Arg Lys
            820                 825                 830

Leu Asn Ser Gly Phe Arg Glu Ala Ser Ile Gln Asp Ala Leu Leu
    835                 840                 845

Asp Ser Ala Lys Glu Ile Pro Leu Ser Ala Pro Leu Thr Phe Thr Pro
    850                 855                 860

Val Lys Gly Ala Val Tyr Asn Pro Tyr Tyr Leu Pro Phe Pro Ala
865                 870                 875                 880

Glu Lys Pro Glu Arg Cys Leu Val Pro Pro Ser His Ala Arg Leu Gln
```

-continued

```
                885                 890                 895
Ser Asp Arg Tyr Thr Gly Cys Leu Thr Cys Glu Leu Glu Thr Val Ser
                    900                 905                 910
Pro Leu Leu Leu Pro Asp Thr Cys Arg Glu Lys Asp Gly Asn Tyr Lys
            915                 920                 925
Glu Tyr Pro Ser Phe Arg Leu Asn Asn Thr Pro Met Ile Pro Gly Ala
        930                 935                 940
Gly Leu Arg Ala Ala Val Ser Gln Val Tyr Glu Val Leu Thr Asn Ser
945                 950                 955                 960
Cys Ile Arg Ile Met Asp Gln Gly Gln Thr Leu Ser Trp Arg Met Ser
                965                 970                 975
Thr Ser Glu His Lys Asp Tyr Gln Pro Gly Lys Ile Thr Asp Asn Gly
            980                 985                 990
Arg Lys Ile Gln Pro Met Gly Lys Gln Ala Ile Arg Leu Pro Leu Tyr
        995                 1000                1005
Asp Glu Val Ile His His Val Ser Thr Pro Gly Asp  Thr Asp Asp
    1010                1015                1020
Leu Glu Lys Leu Lys Ala Ile Val Leu Glu Leu Thr  Arg Pro Trp
    1025                1030                1035
Lys Glu Leu Pro Glu Glu Gln Lys Lys Lys Arg Phe  Glu Lys Cys
    1040                1045                1050
Lys Asn Ile Leu Asp Gly Arg Met Leu Gln Gln Lys  Glu Leu Arg
    1055                1060                1065
Ala Leu Glu Asn Ser Gly Phe Ala Tyr Trp Arg Asp  Lys Thr Ser
    1070                1075                1080
Leu Thr Phe Asp Ser Phe Leu Lys Asp Ala Ile Glu  Gln Glu Tyr
    1085                1090                1095
Pro Arg Tyr Ser Gly Asp Tyr Gln Arg Ile Lys Ala  Leu Val Val
    1100                1105                1110
Asn Ile Thr Leu Pro Trp Lys Leu Leu Lys Lys Glu  Glu Arg His
    1115                1120                1125
Lys Arg Phe Asp Lys Cys Arg Arg Ile Leu Lys Gly  Gln Gln Pro
    1130                1135                1140
Leu Thr Lys Asp Glu Arg Lys Ala Leu Glu Glu Ser  Gly Phe Ala
    1145                1150                1155
Asn Trp His Gly Arg Glu Leu Leu Phe Asp Arg Phe  Leu Lys Asp
    1160                1165                1170
Glu Asn Ser Cys Leu Ile Lys Ala Glu Thr Thr Asp  Arg Val Ile
    1175                1180                1185
Ala Ser Val Ala Lys Asn Asn Arg Asp Tyr Leu Phe  Glu Ile Lys
    1190                1195                1200
Gln Gln Asp Phe Ala Arg Tyr Lys Arg Ile Ile Gln  Gly Leu Glu
    1205                1210                1215
Arg Val Pro Phe Ser Leu Arg Ser Leu Ala Lys Ser  Lys Glu Thr
    1220                1225                1230
Ser Phe Gln Ile Ala Cys Leu Gly Leu Arg Arg Gly  Arg Phe Leu
    1235                1240                1245
Arg Lys Gly Tyr Leu Lys Ile Ser Gly Pro Asn Asn  Ala Asn Val
    1250                1255                1260
Glu Ile Ser Gly Gly Ser His Ser Asn Ser Gly Tyr  Ser Asp Ile
    1265                1270                1275
Trp Asp Asp Pro Leu Asp Phe Ser Phe Arg Leu Ser  Gly Lys Ser
    1280                1285                1290
```

-continued

```
Glu Leu Arg Pro Asn Thr Gln Lys Thr Arg Glu Tyr Pro Arg Pro
    1295                1300                1305

Ser Phe Thr Cys Thr Val Asp Gly Lys Gln Tyr Thr Val Asn Lys
    1310                1315                1320

Arg Cys Glu Arg Val Phe Glu Asp Ser Ala Ala Pro Ala Ile Glu
    1325                1330                1335

Leu Pro Arg Met Val Arg Glu Gly Tyr Lys Gly Ile Leu Thr Asp
    1340                1345                1350

Tyr Glu Gln Asn Ala Lys His Ile Pro Gln Gly Phe Gln Thr Arg
    1355                1360                1365

Phe Ser Ser Tyr Arg Glu Leu Asn Asp Gly Asp Leu Val Tyr Tyr
    1370                1375                1380

Lys Thr Asp Ser Gln Gly Arg Val Thr Asp Leu Ala Pro Val Cys
    1385                1390                1395

Leu Ser Arg Leu Ala Asp Asp Arg Pro Leu Gly Lys Arg Leu Pro
    1400                1405                1410

Glu Glu Tyr Arg Pro Cys Ala His Val Cys Leu Glu Glu Cys Asp
    1415                1420                1425

Pro Cys Thr Gly Lys Asp Cys Pro Val Pro Ile Tyr Arg Glu Gly
    1430                1435                1440

Tyr Pro Ala Arg Gly Phe Cys Pro Ala Cys Gln Leu Phe Gly Thr
    1445                1450                1455

Gln Met Tyr Lys Gly Arg Val Arg Phe Ser Phe Gly Val Pro Val
    1460                1465                1470

Asn Ser Thr Arg Ser Pro Gln Leu Lys Tyr Val Thr Leu Pro Ser
    1475                1480                1485

Gln Glu Arg Pro Arg Pro Thr Trp Val Leu Pro Glu Ser Cys Lys
    1490                1495                1500

Gly Lys Glu Lys Asp Val Pro Gly Arg Lys Phe Tyr Leu Arg His
    1505                1510                1515

Asp Gly Trp Arg Glu Met Trp Gly Asp Asp Lys Pro Asp Ser
    1520                1525                1530

Arg Pro Ser Ser Glu Glu Cys Gln Asp Ile Ile Glu Gly Ile Gly
    1535                1540                1545

Pro Gly Glu Lys Phe His Phe Arg Val Ala Phe Glu Asn Leu Asp
    1550                1555                1560

Lys Asn Glu Leu Gly Arg Leu Leu Tyr Ser Leu Glu Leu Asp Ala
    1565                1570                1575

Gly Met Asn His His Leu Gly Arg Gly Lys Ala Phe Gly Phe Gly
    1580                1585                1590

Gln Val Lys Ile Arg Val Thr Lys Leu Glu Arg Arg Leu Glu Pro
    1595                1600                1605

Gly Gln Trp Arg Ser Glu Lys Ile Cys Thr Asp Leu Pro Val Thr
    1610                1615                1620

Ser Ser Glu Leu Val Ile Ser Ser Leu Lys Lys Val Glu Glu Arg
    1625                1630                1635

Arg Lys Leu Leu Arg Leu Val Met Thr Pro Tyr Lys Gly Leu Thr
    1640                1645                1650

Ala Cys Tyr Pro Gly Leu Glu Arg Glu Asn Gly Arg Pro Gly Tyr
    1655                1660                1665

Thr Asp Leu Lys Met Leu Ala Thr Tyr Asp Pro Tyr Arg Glu Leu
    1670                1675                1680
```

```
Val Val Gln Ile Gly Ser Asn Gln Pro Leu Arg Pro Trp Tyr Glu
    1685                1690                1695

Pro Gly Lys Ser Phe Lys Pro Ser Pro Gly Asn Asp Cys Thr Gly
    1700                1705                1710

Arg Gly Gly Ser Val Ser Lys Ser Leu Ile Ser Glu Pro Lys Val
    1715                1720                1725

Val Pro Ala Ile Ala Pro Phe Cys Glu Gly Val Lys Trp Phe
    1730                1735                1740

Asn Ser Val Lys Gly Phe Gly Phe Ile Glu Thr Lys Glu Gln Arg
    1745                1750                1755

Asp Ile Phe Val His Phe Ser Ala Ile Arg Gly Glu Gly Tyr Lys
    1760                1765                1770

Ile Leu Glu Pro Gly Glu Lys Val Arg Phe Glu Ile Gly Glu Gly
    1775                1780                1785

Arg Lys Gly Pro Gln Ala Ile Asn Val Ile Arg Ile Arg
    1790                1795                1800

<210> SEQ ID NO 19
<211> LENGTH: 1652
<212> TYPE: PRT
<213> ORGANISM: Unknown
<220> FEATURE:
<223> OTHER INFORMATION: Description of Unknown:
      Aquatic-marine-hydrothermal vent microbial mat sequence

<400> SEQUENCE: 19

Met Ile Ile Asn Ile Thr Val Lys Phe Leu Gly Pro Phe Arg Met Leu
1               5                   10                  15

Glu Trp Thr Asp Pro Asp Asn Arg Asn Arg Lys Asn Arg Glu Phe Met
                20                  25                  30

Arg Gly Gln Ala Phe Ala Arg Trp His Asn Ser Asn Pro Gln Lys Gly
            35                  40                  45

Ser Gln Pro Tyr Ile Thr Gly Thr Leu Val Arg Ser Ala Val Ile Arg
        50                  55                  60

Ser Ala Glu Asn Leu Leu Met Leu Ser Glu Gly Lys Val Gly Lys Glu
65                  70                  75                  80

Lys Cys Cys Pro Gly Glu Phe Arg Thr Glu Asn Arg Lys Lys Arg Asp
                85                  90                  95

Ala Met Leu His Leu Arg Gln Arg Ser Thr Leu Gln Trp Lys Thr Asp
            100                 105                 110

Lys Pro Leu Cys Asn Gly Lys Ser Leu Cys Pro Ile Cys Glu Leu Leu
        115                 120                 125

Gly Arg Arg Ile Gly Lys Thr Asp Glu Val Lys Lys Lys Gly Asp Phe
    130                 135                 140

Arg Ile His Phe Gly Asn Leu Thr Pro Leu Asn Arg Tyr Asp Asp Pro
145                 150                 155                 160

Ser Asp Ile Gly Thr Gln Arg Thr Leu Asn Arg Val Asp Tyr Ala Thr
                165                 170                 175

Gly Lys Ala His Asp Phe Phe Lys Val Trp Glu Ile Asp His Ser Leu
            180                 185                 190

Leu Ser Val Phe Gln Gly Lys Ile Ser Ile Ala Asp Asn Ile Gly Asp
        195                 200                 205

Gly Ala Thr Lys Leu Leu Glu Asp Ser Leu Arg Phe Thr Asp Arg Leu
    210                 215                 220

Cys Gly Ala Ile Cys Val Ile Ser Tyr Asp Cys Ile Glu Asn Ser Asp
225                 230                 235                 240
```

```
Gly Lys Glu Asn Gly Lys Thr Gly Glu Ala Ala His Ile Met Gly Glu
                245                 250                 255

Ser Asp Ala Gly Lys Thr Asp Ala Glu Asn Ile Ala Asn Ala Ile Ala
            260                 265                 270

Asp Met Met Gly Thr Ala Gly Glu Pro Glu Lys Leu Arg Ile Leu Ala
        275                 280                 285

Asp Ala Val Arg Ala Leu Arg Ile Gly Lys Asn Thr Val Ser Gln Leu
    290                 295                 300

Pro Leu Asp His Glu Gly Lys Glu Asn His His Leu Trp Asp Ile Gly
305                 310                 315                 320

Glu Gly Lys Ser Ile Arg Glu Leu Leu Leu Lys Ala Glu Ser Leu
                325                 330                 335

Pro Ser Asp Gln Trp Arg Lys Phe Cys Glu Asp Val Gly Glu Ile Leu
                340                 345                 350

Tyr Leu Lys Ser Lys Asp Pro Thr Gly Gly Leu Thr Val Ser Gln Arg
            355                 360                 365

Ile Leu Gly Asp Glu Ala Phe Trp Ser Lys Ala Asp Arg Gln Leu Asn
        370                 375                 380

Pro Ser Ala Val Ser Ile Pro Val Thr Thr Glu Thr Leu Ile Cys Gly
385                 390                 395                 400

Lys Leu Ile Ser Glu Thr Pro Phe Phe Phe Gly Thr Glu Ile Glu Asp
                405                 410                 415

Ala Lys His Thr Asn Leu Lys Val Leu Leu Asp Arg Gln Asn Arg Tyr
            420                 425                 430

Arg Leu Pro Arg Ser Ala Ile Arg Gly Val Leu Arg Arg Asp Leu Arg
        435                 440                 445

Thr Ala Phe Gly Gly Lys Gly Cys Asn Val Glu Leu Gly Gly Arg Pro
    450                 455                 460

Cys Leu Cys Asp Val Cys Arg Ile Met Arg Gly Ile Thr Ile Met Asp
465                 470                 475                 480

Ala Arg Ser Glu Tyr Ala Glu Pro Pro Glu Ile Arg His Arg Ile Arg
                485                 490                 495

Leu Asn Pro Tyr Thr Gly Thr Val Ala Glu Gly Ala Leu Phe Asp Met
            500                 505                 510

Glu Leu Gly Pro Gln Gly Leu Ser Phe Asp Phe Ile Leu Arg Tyr Arg
        515                 520                 525

Gly Lys Gly Lys Ser Ile Pro Lys Ala Leu Arg Asn Val Leu Lys Trp
    530                 535                 540

Trp Thr Lys Gly Gln Ala Phe Leu Ser Gly Ala Ala Ser Thr Gly Lys
545                 550                 555                 560

Gly Ile Phe Arg Leu Asp Asp Leu Lys Tyr Ile Ser Phe Asp Leu Ser
                565                 570                 575

Asp Lys Asp Lys Arg Lys Asp Tyr Leu Asp Asn Tyr Gly Trp Arg Asn
            580                 585                 590

Arg Ile Glu Ala Leu Ser Leu Glu Lys Met Pro Leu Asp Arg Met Asn
        595                 600                 605

Asp Tyr Ala Glu Pro Leu Trp Gln Lys Val Ser Val Glu Ile Glu Ile
    610                 615                 620

Gly Ser Pro Phe Leu Asn Gly Asp Pro Ile Arg Ala Leu Ile Glu Lys
625                 630                 635                 640

Asp Gly Ser Asp Ile Val Ser Phe Arg Lys Tyr Ala Asp Asp Ser Gly
                645                 650                 655
```

```
Lys Glu Val Tyr Ala Tyr Lys Ala Glu Ser Phe Arg Gly Val Val Arg
            660                 665                 670

Ala Ala Leu Ala Arg Gln His Phe Asp Lys Glu Gly Lys Pro Leu Asp
            675                 680                 685

Lys Glu Gly Lys Pro Leu Leu Thr Leu Ile His Gln Asp Cys Glu Cys
            690                 695                 700

Leu Ile Cys Arg Leu Phe Gly Ser Glu His Glu Thr Gly Arg Leu Arg
705                 710                 715                 720

Phe Glu Asp Leu Leu Phe Asp Pro Gln Pro Glu Pro Met Ile Phe Asp
                    725                 730                 735

His Val Ala Ile Asp Arg Phe Thr Gly Gly Ala Val Asp Lys Lys Lys
                740                 745                 750

Phe Asp Asp Cys Ser Leu Pro Gly Thr Pro Gly His Pro Leu Thr Leu
            755                 760                 765

Lys Gly Cys Phe Trp Ile Arg Lys Glu Leu Glu Lys Pro Asp Glu Asp
            770                 775                 780

Lys Ser Glu Arg Glu Ala Leu Ser Lys Ala Leu Ala Asp Ile His Asn
785                 790                 795                 800

Gly Leu Tyr Pro Leu Gly Gly Lys Gly Ala Ile Gly Tyr Gly Gln Val
                    805                 810                 815

Met Asn Leu Lys Ile Lys Gly Ala Gly Asp Val Ile Lys Ala Ala Leu
            820                 825                 830

Gln Ser Glu Ser Ser Arg Met Ser Ala Ser Glu Pro Glu His Lys Lys
            835                 840                 845

Pro Asp Ser Gly Leu Lys Leu Ser Phe Asp Asp Lys Lys Ala Val Tyr
850                 855                 860

Tyr Pro His Tyr Phe Leu Lys Pro Ala Ala Glu Glu Val Asn Arg Lys
865                 870                 875                 880

Pro Ile Pro Thr Gly His Glu Thr Leu Asn Ser Gly Leu Leu Thr Gly
                    885                 890                 895

Lys Ile Arg Cys Arg Leu Thr Thr Arg Thr Pro Leu Ile Val Pro Asp
            900                 905                 910

Thr Ser Asn Asp Asp Phe Phe Gln Thr Gly Val Glu Gly His Glu Ser
            915                 920                 925

Tyr Ala Phe Phe Ser Val Asn Gly Asp Ile Met Leu Pro Gly Ser Glu
            930                 935                 940

Ile Arg Gly Met Leu Ser Ser Val Tyr Glu Ala Leu Thr Asn Ser Cys
945                 950                 955                 960

Phe Arg Val Phe Asp Glu Gly Tyr Arg Leu Ser Trp Arg Met Glu Ala
                    965                 970                 975

Asp Arg Asn Val Leu Met Gln Phe Lys Pro Gly Arg Val Thr Asp Asn
                980                 985                 990

Gly Leu Arg Ile Glu Glu Met Lys  Glu Tyr Arg Tyr Pro  Phe Tyr Asp
            995                 1000                 1005

Arg Asp  Cys Ser Asp Lys Lys  Ser Gln Glu Ala Tyr  Phe Asp Glu
        1010                 1015                 1020

Trp Glu  Arg Ser Ile Thr Leu  Thr Asp Asp Ser Leu  Glu Lys Met
        1025                 1030                 1035

Ala Glu  Arg Lys Gly Asp Ile  Ser Pro Lys Asp Leu  Lys Val Leu
        1040                 1045                 1050

Lys Ser  Leu Lys Gly Lys Asn  Tyr Lys Ser Thr Glu  Gly Leu Leu
        1055                 1060                 1065

Ala Ala  Phe Lys Asp Lys Gly  Gly Asp Thr Gly Gly  Asn Ile Leu
```

-continued

```
            1070                1075                1080
Gly Leu Ile Phe Lys Tyr Ala Glu Arg Ile Gly Asp Val Pro Arg
            1085                1090                1095
Tyr Glu His Pro Thr Asp Thr Asp Arg Met Met Leu Ser Leu Ser
            1100                1105                1110
Glu Tyr Asn Arg Asn Gln Lys Ser Asp Gly Lys Arg Ala Tyr Lys
            1115                1120                1125
Ile Ile Lys Pro Ala Ser Lys Leu Gly Lys Gly Ala Tyr Phe Met
            1130                1135                1140
Phe Ala Gly Thr Ser Val Glu Asn Lys Arg Ile Cys Asn Pro Ala
            1145                1150                1155
Cys Thr Asp Lys Ala Asn Lys Ser Val Lys Gly Tyr Leu Lys Ile
            1160                1165                1170
Ser Gly Pro Asn Lys Leu Glu Lys Tyr Asn Ile Ser Glu Pro Glu
            1175                1180                1185
Leu Asp Gly Val Pro Glu Asp Arg Asn Cys Gln Ile Ile His Asn
            1190                1195                1200
Arg Ile Tyr Leu Arg Lys Ile Phe Val Ala Asn Ala Lys Lys Arg
            1205                1210                1215
Lys Glu Arg Asp Arg Leu Val Gly Glu Phe Ala Cys Tyr Asp Pro
            1220                1225                1230
Glu Lys Lys Val Thr Tyr Ser Met Thr Lys Arg Cys Glu Arg Ile
            1235                1240                1245
Phe Ile Lys Asp Arg Gly Arg Thr Leu Pro Ile Thr His Glu Ala
            1250                1255                1260
Ser Glu Leu Phe Glu Ile Leu Val Gln Glu Tyr Arg Glu Asn Ala
            1265                1270                1275
Lys Arg Gln Asp Thr Pro Glu Val Phe Gln Thr Leu Leu Pro Asp
            1280                1285                1290
Asn Gly Arg Leu Asn Pro Gly Asp Leu Val Tyr Phe Arg Glu Glu
            1295                1300                1305
Lys Gly Lys Thr Val Glu Ile Ile Pro Val Arg Ile Ser Arg Lys
            1310                1315                1320
Ile Asp Asp Ser Pro Ile Gly Lys Arg Leu Arg Glu Asp Leu Arg
            1325                1330                1335
Pro Cys His Gly Glu Trp Ile Glu Gly Asp Asp Leu Ser Gln Leu
            1340                1345                1350
Ser Glu Tyr Pro Glu Lys Lys Leu Phe Thr Arg Asn Thr Glu Gly
            1355                1360                1365
Leu Cys Pro Ala Cys Arg Leu Phe Gly Thr Gly Ala Tyr Lys Gly
            1370                1375                1380
Arg Leu Arg Phe Gly Phe Ala Lys Leu Glu Asn Asp Pro Lys Trp
            1385                1390                1395
Leu Met Lys Asn Ser Asp Gly Pro Ser His Gly Gly Pro Leu Thr
            1400                1405                1410
Leu Pro Leu Leu Glu Arg Pro Arg Pro Thr Trp Ser Met Pro Asp
            1415                1420                1425
Asp Thr Leu Asn Arg Leu Lys Lys Asp Gly Lys Gln Glu Pro Lys
            1430                1435                1440
Lys Gln Lys Gly Lys Lys Gly Pro Gln Val Pro Gly Arg Lys Phe
            1445                1450                1455
Tyr Val His His Asp Gly Trp Lys Glu Ile Asn Cys Gly Cys His
            1460                1465                1470
```

```
Pro Thr Thr Lys Glu Asn Ile Val Gln Asn Gln Asn Asn Arg Thr
    1475                1480                1485

Val Glu Pro Leu Asp Lys Gly Asn Thr Phe Ser Phe Glu Ile Cys
    1490                1495                1500

Phe Glu Asn Leu Glu Pro Tyr Glu Leu Gly Leu Leu Leu Tyr Thr
    1505                1510                1515

Leu Glu Leu Glu Lys Gly Leu Ala His Lys Leu Gly Met Ala Lys
    1520                1525                1530

Pro Met Gly Phe Gly Ser Ile Asp Ile Glu Val Glu Asn Val Ser
    1535                1540                1545

Leu Arg Thr Asp Ser Gly Gln Trp Lys Asp Ala Asn Glu Gln Ile
    1550                1555                1560

Ser Glu Trp Thr Asp Lys Gly Lys Lys Asp Ala Gly Lys Trp Phe
    1565                1570                1575

Lys Thr Asp Trp Glu Ala Ala Glu His Ile Lys Asn Leu Lys Lys
    1580                1585                1590

Leu Leu Phe Leu Pro Gly Glu Glu Gln Asn Pro Arg Val Ile Tyr
    1595                1600                1605

Pro Ala Leu Lys Gln Lys Asp Ile Pro Asn Ser Arg Leu Pro Gly
    1610                1615                1620

Tyr Glu Glu Leu Lys Lys Asn Leu Asn Met Glu Lys Arg Lys Glu
    1625                1630                1635

Met Leu Thr Thr Pro Trp Ala Pro Trp His Pro Ile Lys Lys
    1640                1645                1650

<210> SEQ ID NO 20
<211> LENGTH: 1806
<212> TYPE: PRT
<213> ORGANISM: Unknown
<220> FEATURE:
<223> OTHER INFORMATION: Description of Unknown:
      Aquatic-marine-deep subsurface sequence

<400> SEQUENCE: 20

Met Ser Asp Asn Arg Ile Asp Tyr Asp Ile Lys Leu Thr Phe Phe Glu
1               5                   10                  15

Pro Phe Arg Met Ser Pro Trp Val Lys Ser His Ala Arg Ala Lys Ser
                20                  25                  30

Lys Thr Phe Phe Arg Thr Leu Ser Phe Val Arg Trp Leu Glu Thr Ser
                35                  40                  45

Pro Glu Thr Lys Glu Gly Lys Glu Gly Asp Ser Ile Gly Val Pro Phe
            50                  55                  60

Ile Pro Gly Thr Leu Leu Arg Ser Ala Leu Leu Lys Glu Val Glu Phe
65                  70                  75                  80

Leu Ile Thr Leu Lys Asn Lys Tyr Asp Cys Cys Cys Gly Glu Phe Glu
                85                  90                  95

Thr Pro Arg Gln Lys Arg Asp Glu Lys Lys Gln Gly Arg Arg Phe
                100                 105                 110

Phe Gly Arg Lys Arg Pro Thr Tyr Glu Phe Gly Asn Ser Gln Pro Cys
            115                 120                 125

Thr Asp Phe Glu Asn Ala Cys Pro Phe Cys Ser Ile Leu Ser Arg Ser
        130                 135                 140

Phe Asn Asn Asp Asp Trp Phe Asp Asp Arg Gly Asn Pro Ile Val Gly
145                 150                 155                 160

Lys Val Pro Val His Phe Ser Asn Leu Asp Val Thr Asp Ser Lys Leu
```

```
                165                 170                 175
Lys Arg Ile Arg Leu Ser Ala Ile Ala Asn Gln Arg Ile Val Asn Arg
            180                 185                 190

Val Asp Phe Arg Ser Gly Lys Ala Gln Asp Tyr Phe Lys Ile Trp Glu
        195                 200                 205

Val Asp Asn Arg Leu Cys Pro Ser Phe Cys Gly Lys Ile Thr Ile Arg
    210                 215                 220

Gln Asp Ile Asn Gln Val Asp Asp Leu Thr Cys Leu Leu Ala Ala Gly
225                 230                 235                 240

Leu Ala Lys Ile Lys Thr Leu Ala Gly Ala Leu Cys Arg Val Asp Ile
            245                 250                 255

Ile Arg Asp Lys Thr Ile Asp Phe His Gln Arg Leu Ile Gln Lys Tyr
        260                 265                 270

Val Gly Pro Pro Gly Pro Pro His Asn Pro Thr Ala His Pro Thr Leu
    275                 280                 285

Pro Ser Gln Pro Thr Leu Ser Val Asp Val His Gly Leu Ala Arg Thr
290                 295                 300

Ile Ala Gly Thr Leu Thr Gly Ser Asp Lys Glu Ala Tyr Leu Arg Arg
305                 310                 315                 320

Ile Ala Asp Ala Val Arg Glu Met Arg Asn Arg Lys Cys Ser Ile Leu
            325                 330                 335

His Glu Pro Pro Phe Thr Lys Thr Gly Asp Lys Glu Pro Val Trp Thr
        340                 345                 350

Ile Pro Ala Val Gln Lys Ala Leu Lys Glu Thr Thr Ala Cys Val Ala
    355                 360                 365

Arg Glu Ser Trp Arg Leu Phe Cys Glu Glu Leu Gly Glu Ala Leu Tyr
    370                 375                 380

Lys Lys Ala Lys Glu Leu Lys Lys Asp Glu Ala Ile Pro Arg Leu
385                 390                 395                 400

Leu Gly Asp Thr Glu Tyr Tyr Gly Gln Gln Ala Glu Ala Pro Val Gly
            405                 410                 415

Thr Asp Tyr Arg Leu Thr Ala Ser Ala Leu Pro Lys Tyr Glu Trp Ile
        420                 425                 430

Ile Asn Gly Trp Leu Glu Ala Arg Thr Pro Phe Phe Gly Val Glu
    435                 440                 445

Ser Ala Ser Glu Gln Thr Ser Leu Ala Ile Leu Leu Thr Arg Asp His
    450                 455                 460

Arg Tyr Arg Leu Pro Arg Ser Val Leu Arg Gly Ala Leu Arg Arg Asp
465                 470                 475                 480

Leu Arg Thr Val Ile Gly Ser Gly Cys Asn Val Glu Leu Gly Val Asp
            485                 490                 495

Thr Pro Cys Asp Cys Asp Val Cys Arg Ile Met Ser Arg Val Ile Val
        500                 505                 510

Met Asp Ser Leu Ser Asp Tyr Gln Glu Pro Pro Asp Ile Arg His Arg
    515                 520                 525

Ile Arg Ile Asn Gln His Ser Gly Thr Val Asp Glu Gly Ala Leu Phe
530                 535                 540

Asp Met Glu Leu Gly Pro Glu Gly Leu Arg Phe Pro Phe Arg Met Tyr
545                 550                 555                 560

Phe Ser Ala Thr Cys Pro Thr Ala Asp Val Pro Leu Ala Lys Val Leu
            565                 570                 575

Lys Met Trp Gln Asp Arg Pro Ala Phe Leu Gly Gly Asp Ala Gly Thr
        580                 585                 590
```

-continued

```
Gly Asn Gly Arg Phe Arg Leu Ile Lys Ala Lys Thr Arg Ser Glu Pro
            595                 600                 605

Phe Asp Trp Asp Gly Pro Lys Ser Ser Leu Asn Leu Leu Met Ala Arg
    610                 615                 620

Ser Tyr Ile Asp Leu Glu Asp His Asp Thr Leu Leu Asp Ser Lys Leu
625                 630                 635                 640

Glu Cys Ala Lys Ala Trp Lys Val Lys Asp Glu Leu Thr Ser Val Trp
                645                 650                 655

Thr Asp Tyr Gln Tyr Glu Ile Asp Leu His Ser Pro Ile Leu Ser Asn
            660                 665                 670

Asp Pro Ile Ala Ala Leu Leu Asp Pro Asp Trp Arg Asp Ala Val Pro
        675                 680                 685

Val Lys Lys Arg Val Leu Gln Asp Gly Gly Leu Val Pro Thr Glu Lys
    690                 695                 700

Tyr Tyr Ile Lys Gly Ser Gly Ile Arg Gly Ile Leu Arg Thr Ala Val
705                 710                 715                 720

Gly Arg Asn Cys Val Asn Glu Asp Gly Ile His Leu His Asn Leu Pro
                725                 730                 735

His Asp Asp Cys Pro Cys Val Leu Cys Gln Leu Phe Gly Ser Glu His
            740                 745                 750

His Gln Gly Met Leu Arg Phe Glu Asp Ala His Phe Glu Asn Asp Pro
        755                 760                 765

Met Pro Glu Thr Leu Asp His Val Ala Ile Asp Arg Phe Thr Gly Arg
    770                 775                 780

Ala Arg Asp Lys Phe Lys Phe Glu Asp Ala Pro Leu Ile Ala Thr Pro
785                 790                 795                 800

Asp Gln Pro Ile Lys Leu Lys Gly Thr Phe Trp Leu Lys Arg Glu Leu
                805                 810                 815

His Glu Ala Ser Gln Glu Val Phe Gly Lys Ile Asp Asp Phe Glu Cys
            820                 825                 830

Lys Pro Lys Glu Asp Ser Asp Ser Leu Leu Gly Ala Ala Arg Ala Leu
        835                 840                 845

Trp Cys Ala Phe Leu Asp Leu Lys His Gly Leu Phe Pro Ile Gly Ser
    850                 855                 860

Asn Gly Gly Ile Gly Tyr Gly Trp Val Ser Gly Leu Ser Val Ser Glu
865                 870                 875                 880

Pro Asp Lys Asn Lys Lys Ile Pro Leu Gly Gln Leu Cys Arg Asn Glu
                885                 890                 895

Gly Ala Gln Glu Thr Ala Ser Thr Ser Gly Glu Lys Gly Glu Tyr Asn
            900                 905                 910

Pro Ser Asp Ala Pro Asn Ser Leu Arg Gln Glu Gly His Val Phe Asn
        915                 920                 925

Pro His Tyr Phe Leu Arg Ser Tyr Arg Tyr Glu Asp Lys Asn Gly Lys
    930                 935                 940

Ile Ala Thr His Val Glu Arg Ile Asp Leu Pro Val Thr His Glu Ala
945                 950                 955                 960

Tyr Gln Asp Lys Leu Thr Gly Lys Ile Thr Cys Lys Leu Asn Thr Arg
                965                 970                 975

Gly Pro Val Phe Val Ala Asp Pro Ser Asp Leu Val Val Tyr Phe Thr
            980                 985                 990

Ala Lys Glu Tyr Glu Asp Phe Val  Lys Arg Trp Pro Lys  Ser Ala Glu
        995                 1000                1005
```

-continued

```
Leu Leu Gln Ser Leu Val His Glu Lys Asp Gly Met Lys Leu Ile
    1010                1015                1020

Pro Val Lys Gln Ile Pro Lys Asp Ser Pro Glu Asp Gly Ala Leu
    1025                1030                1035

Lys Glu Ile Ser Glu His Gln Gly His Lys Gly Tyr Lys Phe Phe
    1040                1045                1050

Arg Leu Asn Gly Ser Val Met Ile Pro Gly Ser Glu Ile Arg Gly
    1055                1060                1065

Met Val Ser Ser Val Tyr Glu Ala Leu Thr Asn Ser Cys Phe Arg
    1070                1075                1080

Val Phe Asp Gln Arg Arg Ile Leu Ser Lys Arg Met Glu Ala Asp
    1085                1090                1095

Phe Arg Thr Val Leu Thr His Phe Lys Ala Ala Arg Val Val Pro
    1100                1105                1110

Asp Asn Asn Ser Gly Ser Gly Leu Ser Val Lys Glu Phe Thr Asn
    1115                1120                1125

Met Val Arg Val Pro Val Tyr Asn Cys Pro Gln Thr Phe Phe Asp
    1130                1135                1140

Gly Leu Thr Gln Gly Gln Ile Ser Gly Lys Glu Glu Thr Lys Leu
    1145                1150                1155

Trp Val Lys Asn Tyr Glu Trp Arg Ile Ser Leu Cys Asn Pro Trp
    1160                1165                1170

Thr His His Ser Arg Lys Ser Lys Lys Glu Trp Glu Lys Asn Ile
    1175                1180                1185

Pro Gly Arg Ile Leu Asn Asn Gln Gly Asp Lys Ile Val Leu Asn
    1190                1195                1200

Ile Ser Tyr Lys Gln Glu Glu Arg Lys Ile Thr Leu Ile Leu Asp
    1205                1210                1215

Asp Lys Asp Arg Val Val Leu Asp Gly Ile Thr Pro Lys Gln Leu
    1220                1225                1230

Gly Gly Lys Glu Glu Ile Arg Leu Trp Leu Arg Ile Ser Gln Tyr
    1235                1240                1245

Gln Lys Ala Phe Arg Lys Lys Pro Asp Asn Asn Gly Gly Trp Lys
    1250                1255                1260

Met Gln Thr Gly Tyr Leu His Ile Met Gly Pro Asn Lys Val Glu
    1265                1270                1275

Ile Asp Ser Ser Gly Thr Ser Arg Glu Gly Leu Gln Asp Leu Pro
    1280                1285                1290

Glu Thr Trp Lys Asp Ala Gln Cys Asn Ser Pro Asp Gly Lys Ile
    1295                1300                1305

Phe Ser Gly Lys Asp Gly Asn Ala Val Tyr Thr Met Asn Lys Tyr
    1310                1315                1320

Cys Glu Met Phe Phe Tyr Asn Glu Gln Lys Lys Ser Tyr Arg Val
    1325                1330                1335

Pro Gln Ala Val Leu Asn Gln Tyr Arg Gln Met Ile Glu Glu Ser
    1340                1345                1350

Met Ser Asn Pro Gln Ala Pro Pro Ala Ile Phe Arg Ser Lys Pro
    1355                1360                1365

Ile Arg Glu Lys Asp Thr Ala Leu Lys Ala Gly Asp Leu Val Tyr
    1370                1375                1380

Phe Arg Lys Asn Glu Asn Arg Glu Gly Glu Val Asp Ala Val Ile
    1385                1390                1395

Pro Val Arg Ile Tyr Arg Glu Ser His Arg Lys Pro Leu Gly Lys
```

-continued

```
            1400                1405                1410

Arg Phe Pro Asp Gly Leu His Asp Leu Arg Pro Cys Thr Phe Glu
    1415                1420                1425

Cys Leu Asp Asp Cys Asp Lys Cys Pro Asp Arg Cys Asn Glu Leu
    1430                1435                1440

Lys Glu Phe Phe Asn Pro His Pro Lys Gly Leu Cys Pro Ala Cys
    1445                1450                1455

Arg Leu Phe Gly Thr Thr Ser Tyr Lys Ser Arg Val Ser Phe Gly
    1460                1465                1470

Phe Ala Arg Leu Cys Ser Glu Asp Lys Lys Ala Lys Trp Tyr Gly
    1475                1480                1485

Val Glu Glu Asp Ala Glu Gln Gly Lys Pro Leu Thr Leu Pro Leu
    1490                1495                1500

Leu Glu Arg Pro Arg Pro Thr Trp Ser Met Pro Asp Lys Asp Ala
    1505                1510                1515

Lys Ile Pro Gly Arg Lys Phe Tyr Val His His Pro His Ser Val
    1520                1525                1530

Asp Ser Ser Ile Arg Asp Met Gln Phe Asp Pro Glu Leu Ser Asp
    1535                1540                1545

Lys Glu Asn Gln Gly Lys Ile Arg Pro Asn Lys Asn Asn Arg Thr
    1550                1555                1560

Val Glu Pro Leu Asp Lys Gly Asn Glu Phe Thr Phe Asp Ile Arg
    1565                1570                1575

Phe Met Asn Leu Lys Glu Trp Glu Leu Gly Leu Leu Leu Tyr Ser
    1580                1585                1590

Leu Gln Leu Glu Thr Gly Leu Ala His Lys Leu Gly Met Gly Lys
    1595                1600                1605

Ala Gln Gly Phe Gly Ser Val Glu Ile Asp Val Glu Lys Val Glu
    1610                1615                1620

Ile Arg Asn Gly Pro Gly Asp Trp Lys Ser Lys Thr Ser His Lys
    1625                1630                1635

Ile Thr Glu Trp Ile Thr Lys Gly Lys Asp Lys Leu Glu Lys Trp
    1640                1645                1650

Phe Lys Thr Asp Asp Trp Asn Asn Val Asp His Ile Ala Asp Leu
    1655                1660                1665

Lys Lys Phe Leu Tyr Phe Leu Asp Pro Gln Glu Ile Lys Pro Lys
    1670                1675                1680

Val Arg Tyr Pro Ser Leu Ser Arg Asp Asp Lys Lys Asp His
    1685                1690                1695

Phe Pro Gly Tyr Val Asp Leu Lys Arg Lys Pro Ser Lys Glu Lys
    1700                1705                1710

Pro Asn Pro Tyr Tyr Val Pro Glu Asp Lys Arg Arg Ala Leu Leu
    1715                1720                1725

Thr Arg Pro Trp Glu Pro Trp Tyr Val Met Pro Lys Ser Ser Met
    1730                1735                1740

Gly Thr Val Lys Trp Phe Asn Glu Glu Lys Asn Tyr Gly Phe Ile
    1745                1750                1755

Leu Arg Asp Asn Gly Glu Asp Ile Phe Val His Arg Ser Asp Ile
    1760                1765                1770

Asn Gly Ser Leu Gly Thr Leu Thr Glu Gly Gln Lys Val Ile Phe
    1775                1780                1785

Glu Val Lys Gln Gly Pro Lys Gly Leu Gln Ala Thr Asn Val Lys
    1790                1795                1800
```

```
Val Ile  Ser
    1805

<210> SEQ ID NO 21
<211> LENGTH: 1559
<212> TYPE: PRT
<213> ORGANISM: Unknown
<220> FEATURE:
<223> OTHER INFORMATION: Description of Unknown:
      Aquatic-freshwater-groundwater sequence

<400> SEQUENCE: 21

Met Glu Tyr Thr Leu Thr Leu Asn Phe Ile Glu Pro Phe Arg Leu Ile
1               5                   10                  15

Glu Trp His Asp Ala Pro Asp Arg Glu Asn Leu Arg Leu Arg Gly Phe
            20                  25                  30

Ser Phe Ala Arg Trp His Lys Asp Arg Glu Phe Gly Leu Gly Arg Pro
        35                  40                  45

Tyr Ile Thr Gly Thr Leu Ile Arg Ser Ala Val Ile Arg Ala Val Glu
    50                  55                  60

Glu Phe Leu Trp Leu Asn Asn Gly Lys Thr Gly Asp Val His Cys Cys
65                  70                  75                  80

Gln Gly Glu Phe Thr Lys Ala Arg Phe Tyr Arg Glu Leu Thr Glu Lys
                85                  90                  95

Arg Leu Arg Arg Arg Gln Thr Leu Val Trp Asp Asn Gly Val Cys
            100                 105                 110

Asn Gln Asp Gln Pro Cys Pro Phe Cys Leu Leu Leu Gly Arg Tyr Trp
        115                 120                 125

Gln Pro Gly Pro Gly Tyr Ser Glu Asn Asn Asp Val Asn Phe Gly Asn
    130                 135                 140

Phe Ser Ile Pro Gln Lys Lys Lys Val Leu Leu Asn Leu Glu Asp Ile
145                 150                 155                 160

Ala Glu Pro Arg Ile Ile Asn Arg Val Asp Gln Gln Ser Gly Lys Ala
                165                 170                 175

Glu Asp Phe Phe Glu Ile Arg Glu Ile Asp His Arg Ser Cys Ala Leu
            180                 185                 190

Phe Glu Gly Lys Ile Ser Leu Ser Glu Arg Ala Ala Glu Asn Lys Ala
        195                 200                 205

Leu Ile Ser Leu Leu Asn Ala Ala Leu Pro Leu Val Asn Arg Ile Ser
    210                 215                 220

Gly Ala Leu Cys Tyr Leu Thr Met Glu Glu Val Lys Val Met Asp Lys
225                 230                 235                 240

Ser Val Asn Gly Gly Ser Asp Asn Leu Ser Gly Glu Ala Met Glu Leu
                245                 250                 255

Lys Lys Ser Asp Arg Pro Gly Glu Gly Ser His Phe Ala Arg His Pro
            260                 265                 270

Ile Gly Ala Glu His Ala Ser Tyr Glu Lys Ile Lys Thr Ser Ala Gly
        275                 280                 285

Glu Val Val Asn Ala Phe Glu Glu Ser Asn Lys Leu Val His Leu Arg
    290                 295                 300

Val Phe Ser Asp Val Ile Arg Glu Leu Arg Arg His Asp Pro Arg Lys
305                 310                 315                 320

Leu Asn Leu Pro Gly Gly His Glu Asp Arg Ser Gly Lys Ile Thr Asp
                325                 330                 335

His Phe Leu Trp Asp Met Lys Val Glu Ser Lys Pro Leu Arg Asn Trp
```

-continued

```
            340                 345                 350
Leu Pro Asp Lys Phe Asn Glu Phe Asn Glu Lys His Lys Leu Pro Trp
            355                 360                 365
Arg Ile Phe Cys Glu Ser Leu Gly Gln Ala Leu Phe Leu Glu Ala Lys
            370                 375                 380
Asp Lys Ala Pro Glu Gln Phe Thr Ser Ala Arg Pro Leu Gly Ala Met
385                 390                 395                 400
Val Ser Thr Leu Glu Ser Lys Glu Pro Glu Phe Leu Pro Gly Arg Ser
            405                 410                 415
Arg Gln Gly Pro Arg Tyr Glu Trp Leu Met Arg Gly Gln Leu Val Ala
            420                 425                 430
Glu Val Pro Phe Phe Gly Trp Ser Val Asp Lys Asn Asp Thr Asp
            435                 440                 445
His Ile Ser Met Arg Leu Leu Ser Ala Arg Asp Gly Arg Leu Arg Leu
            450                 455                 460
Pro Arg Ser Ala Leu Arg Gly Ile Leu Arg Arg Asp Leu Asn Leu Ala
465                 470                 475                 480
Phe Gly Thr Asn Gly Cys Arg Ala Lys Leu Gly Leu Arg Arg Pro Cys
            485                 490                 495
Pro Cys Pro Val Cys Asn Leu Leu Lys Asn Ile Thr Ile Arg Asp Ser
            500                 505                 510
Leu Ser Asp Tyr Lys Arg Pro Pro Gln Ile Arg His Arg Ile Arg Leu
            515                 520                 525
Asp His Arg Ser Gly Thr Val Ala Lys Gly Ala Leu Phe Asp Met Glu
            530                 535                 540
Val Gly Pro Thr Gly Ala Ile Phe Pro Phe Glu Leu Arg Leu Arg Ser
545                 550                 555                 560
Thr Ser Asp Lys Phe Ser Lys Glu Leu Glu Gln Val Leu Leu Trp Trp
            565                 570                 575
Lys Gln Gly Leu Ala Phe Leu Ser Gly Ala Gly Gly Thr Gly Lys Gly
            580                 585                 590
Arg Phe Arg Leu Lys Glu Leu Lys Cys Ile Phe Trp Asp Leu Gln Asn
            595                 600                 605
Asp Ala Gly Phe Ala His Tyr Lys Glu Thr Tyr Gly Gly Arg Lys Lys
            610                 615                 620
Arg Ile Ser Asp Asp Glu Leu Ile Pro Trp Gln Val Thr Ser Gly Asp
625                 630                 635                 640
Pro Val Ser Glu Pro Pro Trp Thr Ala Trp Glu Ile Asn Phe Leu Val
            645                 650                 655
Cys Ser Pro Phe Leu Thr Lys Asp Pro Val Glu Ser Leu Leu Asp Pro
            660                 665                 670
Gly Gly Thr Asp Ala Val Cys Tyr Arg Ala Val Tyr Leu Gly Glu Asn
            675                 680                 685
Gly Gly Ile Lys Lys Arg Tyr Leu Leu Lys Gly Glu Ser Phe Arg Gly
            690                 695                 700
Ile Leu Arg Thr Ala Val Gly Arg Arg Glu Asn Ser Leu Leu Lys Glu
705                 710                 715                 720
His Glu Glu Cys Asp Cys Val Leu Cys Arg Leu Phe Gly Asn Glu His
            725                 730                 735
Glu Ala Gly Lys Ile Arg Val Glu Asp Leu Leu Ile Gln Asp Glu Pro
            740                 745                 750
Lys Glu Lys Asn Leu Asp Arg Val Ala Ile Asp Arg Phe Thr Gly Gly
            755                 760                 765
```

```
Ala Arg Asp Lys His Lys Phe Asp Gln Lys Pro Leu Thr Gly Thr Pro
    770             775             780

Ala Phe Pro Leu Val Leu Met Gly Lys Ile Trp Ile Lys Asn Asp Leu
785             790             795             800

Thr Asp Asp Asp Lys Ala Ile Leu Lys Gln Ala Leu Glu Asp Ile Arg
            805             810             815

Cys Gly Leu Tyr Pro Phe Gly Gly Leu Gly Asn Val Gly Phe Gly Trp
            820             825             830

Val Asn Tyr Leu Thr Cys Asn Ser Asp Phe Glu Gln Asn Phe Asp Ser
            835             840             845

Met Asn Leu Cys Phe Ser Asp Lys Val Lys Val Glu Asn Glu Pro Asp
850             855             860

Lys Ile Tyr Trp Pro His Tyr Phe Ile Pro Phe Gly Pro Lys Val Val
865             870             875             880

Arg Glu Asn Lys Pro Pro Gly His Ala Tyr Pro Lys Thr Glu Phe His
                885             890             895

Ser Gly Arg Leu Ile Cys Ser Leu Lys Thr Leu Thr Pro Leu Ile Ile
            900             905             910

Pro Asp Gly Gln Pro Ala Ser Gln Glu Ala Asn Gly His Lys Ser Tyr
            915             920             925

Asn Phe Phe Glu Leu Ser Gly Glu Leu Cys Ile Pro Gly Ser Glu Ile
930             935             940

Lys Gly Met Ile Ser Ser Val Tyr Glu Ala Leu Thr Asn Ser Cys Met
945             950             955             960

Arg Ile Phe Glu Glu Lys Lys Arg Leu Ser Trp Arg Met Lys Ala Glu
                965             970             975

Asn Leu Asp Gln Trp Ser Pro Gly Arg Ile Thr Glu Glu Ala Asp Glu
            980             985             990

Leu Phe Val Glu Glu Met Glu Glu Ile Arg Leu Pro Leu Tyr Asp Asn
            995             1000            1005

Pro Asp Leu Leu Pro Asn Ile Lys Lys Glu Gly Glu Lys Gly Phe
    1010            1015            1020

Tyr Arg Thr Lys Lys Ile Arg Asp Ser Asn Gly Arg Glu Arg Leu
    1025            1030            1035

Lys Lys Gly Gln Pro Thr Gly Thr Asp Ser Leu Ile Asn Ile His
    1040            1045            1050

Ser Ala Glu Ile Arg Glu Phe Leu Lys Glu Asn Lys His Leu Ser
    1055            1060            1065

Ser Gly Gln Ile Pro Thr Lys Trp Phe Arg Cys Phe Pro His Pro
    1070            1075            1080

Gly Lys Arg Gly Phe Asp Gly Leu Ala Leu Leu Lys Ile Pro Lys
    1085            1090            1095

Glu Trp His Asn Lys Asn Thr Ser Gly Trp Ile Ala Glu Gly Tyr
    1100            1105            1110

Val Asn Leu Thr Gly Thr Asn Lys Val Glu Thr Arg Arg Ser Gly
    1115            1120            1125

Lys Gly Ile Ser Ile Arg Glu Thr Ser Lys Asp Glu Gln Ile Asn
    1130            1135            1140

Ile Ile His Asn Glu Val Thr Leu Glu Glu Lys Pro Val Asn Ser
    1145            1150            1155

Ser Lys Leu Gly Gln Val Leu Arg Lys Arg Ala Ile Pro Lys Tyr
    1160            1165            1170
```

-continued

```
Val Thr Tyr Lys Asn Gly Tyr Glu Tyr Thr Met Thr Lys Arg Cys
1175                1180                1185

Glu Arg Ile Phe Ile Pro Leu Gln Lys Pro Thr Lys His Ile Val
1190                1195                1200

Ser Arg Asn Val Glu Asn Lys Phe Leu Gln Leu Cys Glu Glu Tyr
1205                1210                1215

Lys Gln Asn Ala Glu Lys Ile Pro Lys Val Phe Arg Thr Arg Met
1220                1225                1230

Pro Lys Asn Tyr Lys Leu Asn Asp Gly Asp Leu Ile Tyr Phe Arg
1235                1240                1245

Gln Glu Leu Gly Glu Val Val Glu Ile Ile Pro Val Arg Ile Ser
1250                1255                1260

Arg Ala Val Asp Asp Glu Val Leu Gly Glu Lys Phe Val Asn Asp
1265                1270                1275

Asp Phe Arg Pro Cys Val Arg Glu Ile Leu Asn Arg Glu Thr Glu
1280                1285                1290

Lys Lys Ile Thr Ser Ala Gly Phe Lys Glu Val Phe His His His
1295                1300                1305

Pro Lys Gly Leu Cys Pro Ala Cys Ala Ile Phe Gly Thr Thr Phe
1310                1315                1320

Tyr Lys Gly Arg Val Ser Phe Gly Phe Ala Tyr Leu Lys Asn Asn
1325                1330                1335

Glu Thr Lys Leu Val Glu Asn Gly Ala Tyr Ile Thr Leu Pro Leu
1340                1345                1350

Leu Glu Arg Pro Arg Pro Thr Trp Ala Met Pro Thr Lys Asp Ser
1355                1360                1365

Lys Val Pro Gly Arg Lys Phe Tyr Val His His Gln Gly Trp Lys
1370                1375                1380

Asn Ile Val Glu Asp Ser Lys Asn Glu Ser Thr Glu Lys Asn Glu
1385                1390                1395

Asn Asn Arg Ser Val Gln Ala Ile Asp Arg Asn Gln Val Phe Leu
1400                1405                1410

Phe Glu Val Arg Phe Glu Asn Leu Arg Pro Trp Glu Leu Gly Leu
1415                1420                1425

Leu Ile Tyr Ser Leu Gln Leu Glu Pro Lys Leu Ala His Lys Leu
1430                1435                1440

Gly Met Gly Lys Pro Leu Gly Phe Gly Ser Val Lys Ile Lys Val
1445                1450                1455

Glu Asn Val Thr Ser Ser Arg Gln Lys Asp Val Asn Asp Asn Thr
1460                1465                1470

Leu Pro Glu Ala Val Glu Lys Glu Leu Lys Glu Ile Trp Gly Lys
1475                1480                1485

Glu Thr Glu Pro Asp Phe Thr Arg Ser Leu Glu Gly Leu Tyr Lys
1490                1495                1500

Ala Leu His Tyr Glu Ser Lys Asn Gly Ile Gln Val Arg Tyr Pro
1505                1510                1515

Lys Leu Glu Lys Glu Lys Lys Asp Asp Pro Gly Glu Lys Pro Gly
1520                1525                1530

Tyr Leu Glu Leu Ala Asp Gly Pro Phe Ser Thr Glu Asn Arg Lys
1535                1540                1545

Glu Lys Leu Lys Glu Ile Trp Gly Asn Trp Ala
1550                1555
```

```
<210> SEQ ID NO 22
<211> LENGTH: 1549
<212> TYPE: PRT
<213> ORGANISM: Unknown
<220> FEATURE:
<223> OTHER INFORMATION: Description of Unknown:
      Bioremediation-terephthalate-wastewater bioreactor sequence

<400> SEQUENCE: 22

Met Asn Arg Tyr Lys Val Ser Leu Glu Phe Leu Glu Pro Trp Arg Ile
1               5                   10                  15

Asn His Leu Gly Asp Asp Arg Gly Ala Ala Trp Ala Arg Trp Val Gln
            20                  25                  30

Thr Arg Glu Gly Tyr Gln Arg Pro Glu Ile Thr Gly Thr Leu Val Arg
        35                  40                  45

Ser Ala Val Ile Arg Ala Ala Glu Glu Leu Leu Ala Leu Thr Gly Gly
    50                  55                  60

Val Trp Ala Gly Gln Lys Cys Cys Pro Gly Glu Phe Cys Thr Pro Gly
65                  70                  75                  80

Gly Ser Lys Pro Thr Phe Arg Arg Gln Arg Ala Thr Arg Trp Trp Gly
                85                  90                  95

Glu Asp Ser Leu Cys Thr Pro Asp Ser Pro Cys Pro Phe Cys Gln Leu
            100                 105                 110

Leu Gly Arg His Asp Leu Ala Gly Lys Gln Ala Arg Arg Gly Gly Gly
        115                 120                 125

Phe His Val His Phe Gly Asn Leu Tyr Pro Val Ala Arg Glu Gly Tyr
130                 135                 140

Gly Ser Leu Ala Glu Ile Thr Arg Gln Arg Thr Ser Asn Arg Leu Asp
145                 150                 155                 160

Trp Leu Thr Gly Lys Ala Gln Asp Ile Leu Thr Ile Cys Glu Val Glu
                165                 170                 175

Glu Leu Arg Arg Phe Ser Gly Leu Ile Thr Val Ala Pro Glu Leu Ala
            180                 185                 190

Asn Gly Glu Ala Val Ser Ser Leu Leu Thr Ala Ala Ala Leu Val
        195                 200                 205

Asp Arg Leu Ser Gly Ala Ala Cys Arg Leu Lys Leu Gln Pro Val Glu
210                 215                 220

Glu Leu Trp Ser Gly Thr Ala Val Ser Leu Thr Arg Ala Ala Val Pro
225                 230                 235                 240

Glu Thr Ala Tyr Arg Gln Gln Leu Glu Glu Asp Ile Asp Asn Tyr Phe
                245                 250                 255

Gln Glu Leu Ile Gly Asp Gly Ser Gln Leu Gly Pro Glu Arg Leu Arg
            260                 265                 270

Leu Leu Ala Asp Ala Ile Arg Glu Leu Arg Tyr Leu Pro Pro Glu Gln
        275                 280                 285

Thr Leu Pro Asp Trp Leu Gln Ser Leu Pro Gln Gly Lys Asp Gly Lys
    290                 295                 300

Ala His Arg Leu Trp Asp Ala Leu Thr Ala Gln Arg Arg Pro Leu Arg
305                 310                 315                 320

Asn Met Leu Gln Glu Val Ala Ala Ala Tyr Ala Ala Pro Ala Thr Trp
                325                 330                 335

Arg Asp Val Val Gln Gly Leu Gly Gln Ala Leu Tyr Ala His Tyr Lys
            340                 345                 350

Lys Leu Trp Pro Gln Ala Met Pro Val Arg Pro Val Gly Glu Ala Glu
        355                 360                 365
```

-continued

```
Tyr Trp Gln Thr Lys Phe Arg Asp Arg Gln Pro Ser Arg Gln Arg Gly
    370                 375                 380

Thr Trp Ser His Glu Trp Ile Ile Thr Gly Ala Leu Gln Thr Leu Thr
385                 390                 395                 400

Pro Leu Tyr Leu Gly Thr Gln Val Glu Ala Ala Arg Gln Thr Ser Leu
                405                 410                 415

Thr Val Leu Leu Thr Ala Glu Gly Arg Tyr Arg Leu Pro Arg Thr Ala
                420                 425                 430

Leu Arg Gly Ala Leu Arg Gln Asp Leu Gln Leu Ala Ser Arg Gly Gln
                435                 440                 445

Gly Cys Leu Met Glu Leu Asn Pro Glu Arg Pro Cys Ser Cys Pro Ile
450                 455                 460

Cys Gln Ile Met Arg Arg Leu Thr Val Arg Asp Val Thr Ser Ser Ile
465                 470                 475                 480

Ala Leu Pro Pro Leu Val Arg Gln Arg Val Arg Arg Asn Pro Trp
                485                 490                 495

Thr Gly Ile Val Asp Glu Gly Ala Leu Phe Asp Gln Glu Val Ala Pro
                500                 505                 510

Glu Gly Leu Arg Phe Pro Phe Ile Leu Arg Tyr Arg Gly Phe Gly Gly
                515                 520                 525

Leu Asp Ala Trp Leu Gln Thr Val Leu Ser Trp Trp Gln Glu Gly Arg
530                 535                 540

Leu Phe Leu Gly Gly Ala Gly Gly Thr Gly Lys Gly Arg Leu Arg Leu
545                 550                 555                 560

Thr Asp Leu Arg Ile Trp Arg Trp Ala Leu Asp Glu Thr Gly Leu Pro
                565                 570                 575

Thr Tyr Val Ala His Leu Gly Tyr Arg Gly Arg Glu Glu Leu Ala
                580                 585                 590

Asn Ser Ala Ser Leu Pro Ala Gly Val Glu Ala Val Thr Cys Ser Asp
                595                 600                 605

Pro Ala Thr Val Pro Ser Pro Trp Gln Glu Val Asp Trp Glu Phe Arg
                610                 615                 620

Phe His Gly Pro Val Leu Ala Asn His Pro Leu Thr Ala Leu Leu Arg
625                 630                 635                 640

Gly Glu Ala Asp Ala Val Phe Thr Trp Lys Val Gln Leu Glu Ala Asp
                645                 650                 655

Gln Gln His Tyr Arg Glu Val Cys Thr Leu Lys Gly Glu Thr Val Arg
                660                 665                 670

Gly Leu Val Arg Gly Leu Phe Gly Lys Ser Gln Gly Leu Leu Thr Lys
                675                 680                 685

Ala His Ala Asp Cys Thr Cys Leu Leu Cys Arg Val Phe Gly Asn Glu
                690                 695                 700

His Gln Arg Gly Lys Val Arg Phe Glu Asp Leu Thr Leu Ala Gly Glu
705                 710                 715                 720

Thr Val Pro Lys Lys Arg Leu Asp His Val Ala Ile Asp Arg Ile Ser
                725                 730                 735

Gly Gly Ala Ala Glu Gln Leu Lys Phe Asp Thr Gln Pro Leu Tyr Gly
                740                 745                 750

Thr Pro Glu Asn Pro Leu Val Phe Ala Gly Lys Phe Trp Val His Thr
                755                 760                 765

Glu Leu Asp Glu Glu Glu Gln Lys Ala Leu Arg Ala Ala Leu Thr Ala
770                 775                 780

Leu Arg Asp Gly Leu Ala Thr Val Gly Ala Lys Gly Ser Val Gly Tyr
```

-continued

```
           785                 790                 795                 800
       Gly Trp Leu Asn Gly Leu Arg Leu His Ser Gly Pro Ala Trp Leu Thr
                       805                 810                 815
       Asp Asn Trp Gln Glu Thr Ala Ala Pro Ser Asp Thr Asn Thr Pro
                       820                 825                 830
       Pro Glu Phe Ser Trp Pro Gln Leu Pro Asp Leu Thr Leu Asp Ser Arg
                       835                 840                 845
       Lys Ile Tyr Tyr Pro His Tyr Phe Leu Pro Pro Asp Leu Gln Val Pro
                       850                 855                 860
       Arg Leu Ser Gln Pro His Thr His Ser Leu Phe Asp Pro Gln Lys Tyr
           865                 870                 875                 880
       Thr Gly Trp Leu Thr Cys Arg Leu Thr Thr Leu Thr Pro Leu Ile Ile
                       885                 890                 895
       Pro Asp Thr Ser Ser Asp Gln Thr Leu Thr Thr Gly Gly Pro Phe Pro
                       900                 905                 910
       Ala Gly His Gln Ala Phe Gln Phe Phe Arg Leu Gly Asp Gln Pro Leu
                       915                 920                 925
       Ile Pro Gly Ala Glu Leu Arg Gly Met Ile Ser Ser Val Phe Glu Ala
                       930                 935                 940
       Ile Thr Asn Ser Cys Phe Arg Val Ile Arg Pro Arg Glu Arg Leu Ser
       945                 950                 955                 960
       Trp Arg Met Pro Ala Ala Leu Ala Pro Gln Phe Arg Ser Gly Arg Val
                       965                 970                 975
       Glu Ile Val Asn Asn Gln Tyr Tyr Ile Arg Gln Met Asp Met Gly Arg
                       980                 985                 990
       Leu Pro Leu Tyr Asp Asp Pro Ala Thr Arg Arg Leu Phe Thr Pro Leu
                       995                 1000                1005
       Ser Leu Thr Ser Gly His Thr Leu Asp Phe Val Asp Asp Asn Arg
                       1010                1015                1020
       Thr Leu Leu Gln Ser Asn Pro Gly Ile Arg Glu Gly Ala Ile Arg
                       1025                1030                1035
       Thr Asp Leu Cys Phe Leu Asn Arg Phe Trp Leu Leu Arg Pro Pro
                       1040                1045                1050
       Ser Ala Ala Arg Cys Pro Arg Gly Asn Phe Ser Leu Thr Ser Gly
                       1055                1060                1065
       Tyr Val Lys Phe Thr Gly Pro Asn Lys Val Glu Val Ser Arg Ala
                       1070                1075                1080
       Gly Ala Gly Ala Gly Gly Leu Pro Ala Pro Pro Ala Asp Trp Thr
                       1085                1090                1095
       Gly Val Arg Leu Asn Gln Val Ala Gly Asn Val Pro Phe Tyr Gln
                       1100                1105                1110
       Ala Glu Gln Ser Gly Val Ile Phe Thr Val Asn Lys Arg Arg Glu
                       1115                1120                1125
       Arg Phe Phe Ile Ser Arg Gly Asn Ala Arg Ser Tyr Pro Val Pro
                       1130                1135                1140
       Leu Ala Thr Leu Lys Arg Tyr Glu Gln Val Leu Lys Glu Tyr Arg
                       1145                1150                1155
       His Phe Ala Gln Arg Gly Glu Val Pro Ala Val Phe Arg Thr Val
                       1160                1165                1170
       Leu Pro Asp Val Arg His Gly Ala Ser Gly Tyr Asn Arg Leu Asn
                       1175                1180                1185
       Asn Gly Asp Leu Val Tyr Phe Arg Val Lys Asp Asp Arg Trp Asn
                       1190                1195                1200
```

Asp Gln Asn Ala Pro Val Glu His Ile Ile Pro Val Ser Ile Ser
    1205                1210                1215

Arg Leu Val Asp Gln Lys Phe Leu Gly Glu Arg Val Pro Glu Pro
    1220                1225                1230

Leu Arg Pro Cys Ala His Val Cys Leu Glu Glu Cys Glu Ala Cys
    1235                1240                1245

Leu Lys Gln Glu Ser Cys Pro Ser Ser Phe Tyr Arg Glu Gly Thr
    1250                1255                1260

Pro Ser Arg Gly Leu Cys Pro Ala Cys His Leu Phe Gly Thr Thr
    1265                1270                1275

Gly Tyr Gln Gly Arg Val Arg Phe Gly Phe Ala Arg Leu Glu Arg
    1280                1285                1290

Glu Pro Ala Trp Arg Gln Asn Asp Ala Gly Ser Thr Ala Ile Thr
    1295                1300                1305

Leu Pro Leu Leu Glu Gln Pro Arg Leu Thr Trp Ser Met Leu Trp
    1310                1315                1320

Glu Arg Arg Asn Ala Glu Gly Thr Val Glu Glu Arg Gln Pro Val
    1325                1330                1335

Asn Trp Val Pro Gly Arg Lys Phe Tyr Val His His Gln Gly Trp
    1340                1345                1350

Arg Thr Ile Val Ala Gln Gly Ile Asn Pro Ile Asp Gly Gln Arg
    1355                1360                1365

Leu Glu Arg Asn Glu Asn Asn Arg Thr Val Glu Val Leu Asp Thr
    1370                1375                1380

Gly Arg Thr Phe Thr Phe Gln Val Phe Glu Asn Leu Asp Ala
    1385                1390                1395

Trp Glu Leu Gly Leu Leu Leu Tyr Ser Leu Glu Leu Glu Pro Gly
    1400                1405                1410

Leu Ala His Lys Leu Gly Met Ala Lys Ala Trp Gly Phe Gly Ser
    1415                1420                1425

Val Gln Ile Asp Val Ala Ser Leu Arg Arg Tyr Gln Ala Pro Gly
    1430                1435                1440

Ser Met Thr Asp Ile Thr Cys Glu Lys Asp Thr Leu Leu Gln Ala
    1445                1450                1455

Gly Phe Ala Trp Leu Lys Glu Gln Ala Asn Ser Ser Ser Trp Asp
    1460                1465                1470

Glu Ile Pro Arg Leu Arg Gln Leu Arg Gln Leu Leu Arg Tyr Gln
    1475                1480                1485

Glu Asp Gly Thr Leu Thr Val Arg Tyr Pro Ile Leu Lys Gln Glu
    1490                1495                1500

Asn Ala Ala Ser Gly Gln Val Pro Gly Tyr Val Glu Leu Arg Asp
    1505                1510                1515

Gln Gly Tyr Arg Pro Glu Glu Gln Leu Arg Ile Pro Trp Ser Pro
    1520                1525                1530

Trp Tyr Ser Pro Pro Leu Glu Pro Pro Ala Ala Thr Ala Ala
    1535                1540                1545

Ala

<210> SEQ ID NO 23
<211> LENGTH: 1668
<212> TYPE: PRT
<213> ORGANISM: Unknown
<220> FEATURE:
<223> OTHER INFORMATION: Description of Unknown:

Aquatic-freshwater-freshwater lake sediment sequence

<400> SEQUENCE: 23

```
Met Thr Thr Leu Thr Ile His Leu His Phe Leu Glu Pro Phe Arg Met
1               5                   10                  15
Ala Pro Trp Phe Ser Val Glu Lys Arg Lys Asn Asn Pro Asp Trp
            20                  25                  30
Gln Arg Val Gln Thr Tyr Ala Arg Trp His Lys Asn Thr Ala Gly Asp
                35                  40                  45
Gly Arg Gly Arg Pro Phe Ile Thr Gly Tyr Leu Leu Arg Ser Ala Leu
        50                  55                  60
Ile Gln Ala Val Glu Glu Leu Val Phe Ser Arg Gly Val Trp Ser
65                  70                  75                  80
Gly Ile Ser Cys Cys Pro Gly Leu Phe Phe Thr Glu Pro Asp Lys Asp
                85                  90                  95
Lys Glu Lys Pro Leu Asn Glu Arg Arg Arg Ala Thr Leu Gly Trp Thr
                100                 105                 110
Glu Asn Lys Ala Ile Cys Gln Glu Glu Gly Arg Glu Lys Ala Cys
            115                 120                 125
Pro Leu Cys Leu Leu Ile Asn Arg Phe Lys Glu Asn Gly Glu Asp Asn
        130                 135                 140
Val His Phe Gly Asn Leu Ser Leu Pro Gly Ser Glu Asn Glu Arg Pro
145                 150                 155                 160
Val Trp Asp Gln Pro Glu Gln Ile Ala Lys Leu Arg Thr Leu Asn Arg
                165                 170                 175
Val Asp Arg Ala Thr Thr Lys Ala His Asp His Phe Lys Val Tyr Glu
            180                 185                 190
Val Glu Asp Leu Thr Asp Phe Tyr Gly Thr Ile Thr Phe Ala Asp Asp
        195                 200                 205
Leu Pro Gln Arg Glu Val Ile Glu Ser Leu Ile Arg Arg Gly Leu Gly
        210                 215                 220
Phe Ile Ser Asp Leu Cys Gly Ala Leu Cys Glu Ile Arg Val Glu Lys
225                 230                 235                 240
Gln Lys Pro Leu Pro Thr Glu Pro Lys Gly Ile Thr Gln Ser Lys Ala
                245                 250                 255
Ser Tyr Val Ser Gly Leu Ala Glu Met Cys Trp Glu Lys Met Ala Glu
            260                 265                 270
Thr Glu Leu Arg Ser Leu Ala Gly Ala Val Leu Gln Leu Arg Cys Ser
        275                 280                 285
Asp Pro Lys Lys Phe Thr Leu Pro Lys Gly Arg Ile Asp Arg Asn Gly
        290                 295                 300
Asn Arg Leu Pro His His Ile Trp Asp Ile Glu Leu Glu Gly Asn Gly
305                 310                 315                 320
Asp Lys Lys Thr Leu Arg Lys His Leu Lys Glu Thr Ala Glu Lys Met
                325                 330                 335
Ala Glu Gly Gly Thr Ala Phe Arg Leu Phe Cys Glu Asp Val Gly Asn
            340                 345                 350
Arg Leu Phe Arg Leu Ser Lys Gly Ile Pro Gln Glu Thr Pro Asn Arg
        355                 360                 365
Gln Asp Ala Phe Ser Asp Pro Ser Gln Val Phe Asn Leu Gly Arg Pro
        370                 375                 380
Val Tyr Gly Gln Glu Asn His Arg Asp Pro Met Ile Pro Ser Cys Glu
385                 390                 395                 400
```

```
Trp Ile Ile Thr Gly Thr Leu Thr Ala Ala Ser Pro Phe Phe Ile Ala
                405                 410                 415

Asp Glu Leu Ile Asp Asp His Ile Ser Arg Lys Leu Leu Thr Thr
            420                 425                 430

Gln Asp Phe His Tyr Arg Leu Pro Arg Ser Leu Leu Arg Gly Ile Leu
        435                 440                 445

Arg Arg Asp Leu His Glu Ala Ser Gly Gly Lys Gly Cys Arg Ala Glu
450                 455                 460

Leu Gly Pro Glu Ser Ser Cys Ile Cys Pro Val Cys Arg Ile Leu Asn
465                 470                 475                 480

Gln Val Lys Ile Arg Asp Ala Arg Ser Asp Ser Phe Val Pro Pro Asp
            485                 490                 495

Ile Arg Gln Arg Val Lys Gln Ser His His His Arg Ile Val Gln Asp
        500                 505                 510

Gly Ala Leu Phe Asp Thr Glu Tyr Gly Leu Glu Gly Val Val Phe Pro
            515                 520                 525

Phe Glu Leu Arg Phe Lys Gly Glu Lys Thr Ile Asp Lys Glu Leu Arg
        530                 535                 540

Thr Val Met Gly Trp Trp Glu Glu Gly Leu Leu Phe Leu Gly Gly Asp
545                 550                 555                 560

Phe Gly Thr Gly Lys Gly Ala Phe Lys Leu Gly Ile Lys Gln Ile His
            565                 570                 575

Arg Trp Asp Leu Ser Thr Pro Gly Ala Arg Glu Glu Tyr Glu Gln Thr
            580                 585                 590

Cys Gly Phe Arg Ala Gly Val Pro Leu Asp Ala Asn Cys Gln Gly Leu
        595                 600                 605

Ser Pro Val Ser Asn Ile Asp Phe Pro Lys Val Asp Tyr Pro Trp Gln
    610                 615                 620

Lys Val Pro Trp Glu Leu Ala Phe Glu Ser Pro Leu Leu Thr Ala Asp
625                 630                 635                 640

Pro Ile Ala Ala Ile Thr Gln Asp Glu Ala Asp Thr Ile Tyr Phe Gln
            645                 650                 655

Lys Arg Arg Leu Lys Ser Asp Gly Ser Val Glu Tyr Ile Pro Ala Leu
        660                 665                 670

Arg Gly Glu Gly Leu Arg Gly Leu Ile Arg Thr Ala Thr Ala Arg Ala
    675                 680                 685

Ser Gly Ser Asp His Leu Thr Val Glu His Glu Asp Cys Thr Cys Val
    690                 695                 700

Leu Cys Lys Thr Phe Gly Asn Glu His Arg Ser Gly Leu Leu Arg Phe
705                 710                 715                 720

Asp Asp Leu Glu Pro Lys Asn Trp Lys Asp Lys Arg Ile Asp His Val
            725                 730                 735

Ser Ile Asp Arg Phe Asp Ala Ser Val Val Glu Lys Phe Asp Asp Arg
        740                 745                 750

Pro Leu Ile Gly Ser Pro Asp Lys Pro Leu Val Phe Ala Gly Ala Phe
        755                 760                 765

Trp Ile His Arg Asp Phe Thr Glu Asn Lys Ala Leu Ser Asn Gly Phe
    770                 775                 780

Gln Asp Leu Lys Ser Gly Leu Tyr Pro Leu Gly Gly Lys Val Gly Ile
785                 790                 795                 800

Gly Tyr Gly Arg Leu Ser Lys Leu Glu Leu Pro Ser Asp Trp Leu Pro
            805                 810                 815

Asn Ser Ala Glu Asn Glu Ser Ile Ser Val Ser Gly Leu Leu Glu Gly
```

-continued

```
                820                 825                 830
Ser Pro Glu Thr Ser Gly Ile Pro Glu Lys Pro Thr Trp Lys Pro Glu
            835                 840                 845
Pro Asp Ala Ile Tyr Asn Pro Tyr Tyr Leu Ser Arg Pro Gly Asp
        850                 855                 860
Gly Pro Lys Arg Thr Leu Thr Pro Val Ser His Ala Thr Leu Ser Lys
865                 870                 875                 880
Glu Arg Tyr Thr Gly Arg Ile Ala Cys Phe Leu Lys Val Lys Ser Pro
                885                 890                 895
Leu Leu Leu Pro Asp Ser Glu His Asp Pro Val Ala Pro Asp Lys Asn
            900                 905                 910
Gly Thr Met Lys Ala Phe Arg Leu Asn Gly Thr Leu Met Ile Pro Gly
        915                 920                 925
Ser Ala Leu Arg Ser Ala Val Ser Gln Val Tyr Glu Ala Leu Thr Asp
        930                 935                 940
Ser Cys Phe Arg Val Met Asp Gln Lys Arg Val Leu Ser Trp Arg Met
945                 950                 955                 960
Glu Thr Gly Asp His Gly Asn Tyr Lys Pro Gly Arg Ile Ser Glu Ser
                965                 970                 975
Gly Asp Gln Ile Phe Pro Met Gly Glu Lys Ala Leu Arg Leu Pro Leu
            980                 985                 990
Tyr Asp Met Ala Pro Gly Thr His  Ser Ala Lys Tyr Ile  Lys Glu Leu
        995                 1000                 1005
Glu Glu  Leu His Lys Lys Ala  Leu Glu Gly Asn Ile  His Arg Leu
    1010                 1015                 1020
Thr Ile  Ala Pro Trp Glu Glu  Met Pro Glu Lys Thr  Arg Glu Lys
    1025                 1030                 1035
Lys Phe  Glu Lys Cys Asn Lys  Ile Leu Gly Arg Asn  Leu Thr Glu
    1040                 1045                 1050
Glu Glu  Lys Lys Asn Leu Thr  Asp Gln Gly Met Ala  Lys Leu Lys
    1055                 1060                 1065
Ile Ser  Glu Met Glu Leu Lys  Thr Leu Ile Gly Arg  Phe Lys Lys
    1070                 1075                 1080
Asp Glu  Glu Ser Cys Ile Glu  Lys Ala Gln Lys Thr  Asp Ser Asn
    1085                 1090                 1095
Ile Ala  Glu Ile Ala Lys His  Asn Arg Asp Ile Leu  Asn Val Leu
    1100                 1105                 1110
Glu Lys  Glu Thr Arg Gln Arg  Val Leu Ala Gly Lys  Glu Lys Val
    1115                 1120                 1125
Pro Phe  Leu Thr Glu Arg Leu  Ala Pro Asn Asn Asp  Ile Asn Phe
    1130                 1135                 1140
Gln Ile  Val Lys Leu Leu Lys  Asn Ser Glu Lys Asn  Lys Lys Asn
    1145                 1150                 1155
Lys Glu  Ile Arg Trp Gly Tyr  Leu Lys Ile Thr Gly  Pro Asn Asn
    1160                 1165                 1170
Ala Asn  Asp Ala Val Val Glu  Thr Lys Glu Glu Asp  Asp Lys Tyr
    1175                 1180                 1185
Lys Leu  Glu Trp Glu Asp Pro  Leu Asp Phe Ser Phe  Cys Leu Thr
    1190                 1195                 1200
Gly Pro  Pro Lys Asn Gln Pro  Asn Thr Gln Lys Ser  Arg Asp Phe
    1205                 1210                 1215
Pro Arg  Pro Gly Phe Glu Cys  Ile Lys Asp Asp Lys  Arg Tyr Thr
    1220                 1225                 1230
```

-continued

```
Ile Ser Lys Arg Cys Glu Arg Leu Phe Glu Ala Asp Glu Lys Ser
1235                1240                1245

Lys Pro Ile Pro Ile Pro Lys Arg Val Arg Glu Gly Tyr Lys Gly
    1250                1255                1260

Ile Leu Glu Asp Tyr Gln Lys Asn Ala Lys Lys Ile Pro Lys Ala
1265                1270                1275

Phe Gln Thr Arg Leu Asn Ser Asp Leu Val Tyr Lys Ser Asp
    1280                1285                1290

Tyr Val Glu Asn Gln Ile Asn Val Thr Ala Leu Ala Pro Val Cys
1295                1300                1305

Ile Ser Arg Leu Ala Asp Asp Arg Pro Leu Gly Lys Arg Leu Pro
1310                1315                1320

Val Gly Tyr Gln Pro Cys Ser His Ile Cys Leu Glu Asp Cys Glu
1325                1330                1335

Arg Cys Thr Gly Lys Ala Cys Pro Ile Pro Leu Tyr Arg Glu Gly
1340                1345                1350

Tyr Pro Val Asn Gly Leu Cys Pro Ala Cys Gln Leu Phe Gly Ala
1355                1360                1365

Gln Met Tyr Lys Gly Arg Val Asn Phe Ser Phe Ala Thr Leu Thr
1370                1375                1380

Pro Gly Lys Asn Leu Glu Leu Arg Asn Val Thr Leu Pro Ala Gln
1385                1390                1395

Glu Arg Pro Arg Pro Thr Trp Ile Leu Pro Lys Asn Val Gln Gly
1400                1405                1410

Lys Asp Thr Glu Ile Pro Gly Ala Lys Phe Tyr Leu Arg His Gly
1415                1420                1425

Met Trp Lys Lys Ile Trp Thr Asp Arg Lys Asp Pro Arg Thr Asp
1430                1435                1440

Lys Pro Ile Glu Glu Lys Asn Pro Asn Asn Val Thr Ile Glu Gly
1445                1450                1455

Ile Asn Thr Gly Ala Glu Phe Arg Phe Asp Val Ser Phe Glu Asn
1460                1465                1470

Leu Asp Glu Asn Glu Leu Gly Trp Leu Leu Tyr Cys Leu Glu Leu
1475                1480                1485

Glu Glu Asp Met Ser His Met Leu Gly Arg Gly Lys Pro Phe Gly
1490                1495                1500

Phe Gly Gln Val Glu Ile Lys Ile Asn Glu Leu Ala Arg Arg Leu
1505                1510                1515

Ala Pro Asn Ala Trp Tyr Thr Glu Ser Pro Lys Glu Gly Ser Leu
1520                1525                1530

Ile His Ser Lys Leu Ile Val Lys Ala Leu Ala Gly Leu Lys Ser
1535                1540                1545

Leu Asp Ser Leu Arg Leu Leu Thr Gln Tyr Asn Asn Leu Thr
1550                1555                1560

Ala Tyr Tyr Pro Glu Leu Glu Gly Lys Gly Gly Lys Pro Gly Tyr
1565                1570                1575

Asp Thr Leu Lys Asn Ser Ser Gly Tyr Asn Pro His Cys Phe Leu
1580                1585                1590

Thr Leu Gln Thr Lys Gly Asn Thr Pro Phe Val Tyr Pro Trp Phe
1595                1600                1605

Pro Ile Pro Ile Ser Lys Pro Gln Ala Thr Lys Ser Asp Ile Lys
1610                1615                1620
```

-continued

```
Pro Lys Val Glu Asn His Gly Ile Thr Gly Asn Gly Phe Lys Lys
    1625                1630                1635

Leu Val Glu Gly Asp Lys Val Thr Phe Glu Ile Glu Glu Arg Pro
    1640                1645                1650

Lys Gly Pro Cys Ala Val Asn Val Arg Lys Val Lys Asp Ile Pro
    1655                1660                1665

<210> SEQ ID NO 24
<211> LENGTH: 1821
<212> TYPE: PRT
<213> ORGANISM: Unknown
<220> FEATURE:
<223> OTHER INFORMATION: Description of Unknown:
      Terrestrial-soil sequence

<400> SEQUENCE: 24

Met Thr Thr Gly Asn Thr Ser Ala Ser His Pro Gln Phe Val Thr Leu
1               5                   10                  15

Thr Val Cys Leu Arg Phe Cys Ser Pro Phe Gln Ile Arg Pro Trp Ile
            20                  25                  30

Lys Glu Thr Val Arg Asn Lys Val Lys Met Pro Ser Thr Val Asn Ala
        35                  40                  45

His Ala Glu Thr Ala His Leu Pro Asp Asp Gln Asp Thr Asp Asp Thr
    50                  55                  60

Gln Asp Leu Leu Glu Glu Arg Phe Glu Arg Tyr Ala Thr Ala Ala
65                  70                  75                  80

Asp Trp His Lys Gly Ser Ile Asn Gly Asn Ala Lys Tyr Ser Pro Tyr
                85                  90                  95

Val Arg Gly Asp Leu Val Arg Ser Val Val Asp Arg Glu Leu Gln Glu
            100                 105                 110

His Phe His Cys Tyr Asn Glu Lys Leu Ala Asn Glu Asn Lys Gly Cys
        115                 120                 125

Pro Gly Lys Arg Asp Arg His Ile Asn Ala Gly Gly Lys Ala Ser Gly
    130                 135                 140

Phe Met Ala His Leu Pro Ala Ile Lys Asp Pro Ala Gly Lys Glu Ile
145                 150                 155                 160

Cys Lys Gly Ser Asp Asn Ile Cys Pro Val Cys His Phe Leu Gly Ala
                165                 170                 175

Phe Ala Glu Gly Ile Lys Pro Val Lys Phe Arg Asn Phe Phe Ser Gly
            180                 185                 190

Tyr Tyr Val Ala Lys Thr Glu Asp Leu Ala Lys Gln Arg Gly Arg Asn
        195                 200                 205

Cys Tyr Ser Gly Gln Ser Arg Lys Ser Leu Asp Asn Phe Thr Val Trp
    210                 215                 220

Glu Ala Asp His Thr Ala Cys Pro Val Phe Gly Arg Ile Glu Val
225                 230                 235                 240

Asn Lys Thr Leu Leu Pro Lys Glu Gln Ile Leu Ala Leu Leu Ala Gly
                245                 250                 255

Gly Leu Ala Arg Leu Asp Asn Leu Ala Gly Ser Ala Cys Arg Phe Asp
            260                 265                 270

Ile Ile Asp Lys Tyr Glu Gly Val Phe Glu Asp His Glu Trp Thr Ala
        275                 280                 285

Asn Ile Leu Pro Asn Leu Leu Ile Ala Ala Arg Glu Ala Leu Gly Leu
    290                 295                 300

Pro Asp Asp Glu His Gln Ala Leu Leu Asn Asp Phe Ser Arg Phe Phe
305                 310                 315                 320
```

```
Ile Asn Pro Glu Lys Ser Pro Ala Val Tyr Thr Ser Ser Pro Val Ile
                325                 330                 335

Val Pro Val Gln Gly Ala Val Asp Lys Val Val Leu Leu Glu Lys Ala
                340                 345                 350

Gln Asp Ile Ala Gly Arg Ile Ala Ala Cys Val Ser Asp Asn Pro Arg
                355                 360                 365

His Leu His Arg Leu Ala Ala Ala Ile Arg Thr Leu Gly Trp Pro Gly
            370                 375                 380

Arg Ser Leu Ala Ser Val Met Thr Lys Lys Pro Gly Thr Glu Asp Lys
385                 390                 395                 400

Ala Thr Leu Trp Gly Lys Glu Ser Ala Ser Lys Ser Val Lys Thr Ile
                405                 410                 415

Leu Glu Glu Ser Ile Gln Gly Phe Thr Val Glu Gln Lys Arg Ser Phe
                420                 425                 430

Phe Ala Asn Leu Ala Asp Gln Leu Val Ser Arg Ala Gly Glu Gln Gly
            435                 440                 445

Ala Lys Ser Val Arg Ser Gln Gly Leu Ile Ile Gly Arg Lys Glu Asn
            450                 455                 460

Tyr Ala Lys Pro Ser Ala Gln Glu Pro Thr Arg His His Leu Tyr Arg
465                 470                 475                 480

Gln Pro Ser Asn Ala Ser Ala Phe Leu Ala Thr Gly Trp Leu Ile Ala
                485                 490                 495

Glu Thr Pro Phe Phe Ile Gly Ser Gly Thr Glu Gly Gln Lys Gln Thr
                500                 505                 510

Asp Asp Gln Ala Glu Ser Leu His Leu Arg Thr Leu Arg Asp Gly His
            515                 520                 525

Gly Arg Phe Arg Ile Pro Phe Thr Thr Ile Arg Gly Val Met Asp Lys
            530                 535                 540

Glu Leu Arg Asp Ile Leu Gln Ala Gly Cys Ala Lys Gly Arg Ser Leu
545                 550                 555                 560

Arg Ala Pro Cys Pro Cys Gln Val Cys Thr Leu Met Arg Arg Ile Gln
                565                 570                 575

Val Arg Asp Ala Ile Ala Ala Asp Ile Leu Pro Pro Asp Leu Arg Met
            580                 585                 590

Arg Thr Arg Ile Asp Pro Ser His Gly Thr Val Ala His Leu Phe Ser
            595                 600                 605

Leu Glu Met Ala Pro Gln Gly Leu Lys Leu Pro Phe Phe Leu Lys Leu
            610                 615                 620

Lys Gly Val Glu Thr Ile Asp Pro Asp Lys Glu Leu Leu Glu Ile Leu
625                 630                 635                 640

Asn Asp Trp Ser Ala Gly Gln Cys Phe Leu Gly Gly Leu Trp Gly Thr
                645                 650                 655

Gly Lys Gly Arg Phe Arg Leu Asp Asp Leu Gln Trp His Arg Leu Glu
                660                 665                 670

Leu Asp Asn Ala Asp Tyr Tyr Thr Pro Leu Leu Gln Asp Arg Phe Phe
            675                 680                 685

Ala Gly Glu Thr Ile Ser Asp Leu Arg Gln Gly Leu Gln Ser Ile Asn
            690                 695                 700

Ile Gln Pro Glu Arg Ile Pro Ala Gln Thr Pro Ser Arg Asn Met Pro
705                 710                 715                 720

Tyr Cys Arg Val Asp Cys Ile Leu Glu Phe Lys Ser Pro Val Leu Ser
                725                 730                 735
```

```
Gly Asp Pro Val Ala Ala Leu Phe Glu Ser Asp Ala Pro Asp Asn Val
            740                 745                 750

Ala Tyr Lys Lys Pro Val Val Gln Tyr Asp Glu Thr Gly Arg Leu Arg
        755                 760                 765

Thr Thr Asp Pro Gly Pro Val Glu Met Leu Thr Cys Leu Lys Gly Glu
    770                 775                 780

Gly Val Arg Gly Val Val Ala Tyr Leu Ala Gly Lys Ala Tyr Asp Gln
785                 790                 795                 800

His Asp Leu Ser His Asp Ser Cys Asn Cys Thr Phe Cys Gln Ala Phe
                805                 810                 815

Gly Asn Gly Gln Lys Ala Gly Ser Leu Arg Phe Asp Asp Phe Met Pro
            820                 825                 830

Val Gln Phe Glu Ser Asp Gln Ala Gly Asn Phe Ser Trp Ser Pro His
        835                 840                 845

Thr Pro His Ala Met Arg Ser Asp Arg Val Ala Leu Asp Val Phe Gly
    850                 855                 860

Gly Ala Met Pro Glu Ala Lys Phe Asp Asp Arg Pro Leu Ala Ala Ser
865                 870                 875                 880

Pro Gly Lys Pro Leu Asn Phe Lys Ser Thr Ile Trp Tyr Arg Glu Asp
                885                 890                 895

Met Gly Lys Glu Ala Gly Lys Ala Leu Lys Arg Ala Leu Ile Asp Leu
            900                 905                 910

Gln Asn Asn Met Ala Ala Ile Gly Ser Gly Gly Ile Gly Arg Gly
        915                 920                 925

Trp Val Ser Arg Val Cys Phe Glu Gly Asp Ile Pro Asp Phe Leu Glu
    930                 935                 940

Asp Phe Pro Glu Pro Ile Thr Val Thr Glu Pro Glu Gln Asp Ser Gln
945                 950                 955                 960

Leu Leu Lys Asn Gln Ala Val Ala Asp Glu Thr Ala Val Ser Ala Cys
                965                 970                 975

Asp Thr Ala Asp Ala Pro His Pro Leu Ala Val Thr Leu Glu Pro Gly
            980                 985                 990

Ala Arg Tyr Phe Pro Arg Val Ile Ile Pro Arg Ala Pro Thr Val Lys
        995                 1000                1005

Arg Asp Glu Cys Val Thr Gly Gln Arg Tyr His Thr Gly Arg Leu
    1010                1015                1020

Ser Gly Lys Ile Phe Cys Glu Leu Asn Thr Leu Gly Pro Leu Phe
    1025                1030                1035

Val Pro Asp Thr Asp Tyr Ser Ala Gly Val Pro Val Pro Ile Ser
    1040                1045                1050

Asp Glu Gln Leu Ala Glu Cys Gln Leu Gln Ala Val Phe Glu Asn
    1055                1060                1065

Thr Ser Lys Phe Asn Glu Phe Phe Ala Thr Tyr Pro Glu Glu Thr
    1070                1075                1080

Val Thr Lys Leu Lys Asp Leu Leu Cys Ala Ala Asp Asp Lys Trp
    1085                1090                1095

Ile Leu Ala Val Lys Asp Ile Thr Ala Asp Leu Arg Gln Glu Ile
    1100                1105                1110

Gly Glu Asp Thr Phe Gln Arg Ile Ile Arg Lys Ala Gly His Lys
    1115                1120                1125

Thr Gln Arg Phe His Gln Ile Asn Asp Glu Ile Gly Leu Pro Gly
    1130                1135                1140

Ala Ser Leu Arg Gly Met Val Leu Ser Asn Tyr Gln Ile Leu Thr
```

-continued

|  | 1145 |  |  |  | 1150 |  |  |  | 1155 |  |  |
|---|---|---|---|---|---|---|---|---|---|---|---|

Asn Ser Cys Tyr Arg Asn Leu Lys Ala Thr Glu Glu Ile Thr Arg
    1160                 1165                 1170

Arg Met Pro Ala Asp Glu Ala Lys Tyr Arg Lys Ala Gly Arg Val
    1175                 1180                 1185

Thr Val Ser Gly Asp Gly Ala Gln Lys Lys Tyr Ser Ile Gln Glu
    1190                 1195                 1200

Met Glu Val Leu Arg Leu Pro Ile Tyr Asp Asn Met Asn Thr Pro
    1205                 1210                 1215

Asp Asn Met Pro Asp Val Ala Lys Gln Ala Thr Thr Ala Lys Arg
    1220                 1225                 1230

Cys Asn Asn Leu Met Asn Glu Ala Ala Lys Thr Ser Arg Val Glu
    1235                 1240                 1245

Leu Lys Ala Arg Trp Arg Glu Gly Gln Ser Lys Ile Lys Tyr Gln
    1250                 1255                 1260

Ile Ile Asp Ala Leu Asn Lys Val Asp Pro Ile Ile Gln Val Ile
    1265                 1270                 1275

Ser Ser Ser Lys Gln Ile Asn Pro Asn Asn Gly Lys Thr Gly Trp
    1280                 1285                 1290

Gly Tyr Val Lys Tyr Thr Gly Ala Asn Val Phe Ala Lys Ser Leu
    1295                 1300                 1305

Val Ala Pro Ile Asp Cys Leu Arg Lys Lys Asp Ala Gly His Val
    1310                 1315                 1320

Cys Cys Gln Val Asn Leu Asn Pro Ala Trp Glu Ala Ser Asn Phe
    1325                 1330                 1335

Asp Ile Leu Ile Asn Glu Lys Cys Pro Val Glu Arg Gln Ser Gly
    1340                 1345                 1350

Pro Arg Pro Thr Leu Arg Cys Lys Gly Gln Asp Ser Ala Trp Tyr
    1355                 1360                 1365

Thr Leu Thr Lys Arg Ser Glu Arg Ile Phe Thr Asp Lys Lys Pro
    1370                 1375                 1380

Val Pro Asp Pro Ile Asn Ile Pro Pro Arg Glu Val Lys Arg Tyr
    1385                 1390                 1395

Asn Glu Leu Arg Asp Ser Tyr Lys Lys Asn Thr Ala His Val Pro
    1400                 1405                 1410

Lys Pro Leu Gln Thr Phe Phe Asn Gln Glu Ser Leu Ala Asn Gly
    1415                 1420                 1425

Asp Leu Val Tyr Phe Glu Val Asn Gln Phe Gly Glu Ala Ser Gln
    1430                 1435                 1440

Leu Thr Pro Val Ser Ile Ser Arg Thr Thr Asp Leu Phe Pro Ile
    1445                 1450                 1455

Gly Gly Arg Leu Pro Gln Gly His Lys Asp Leu Phe Pro Cys Thr
    1460                 1465                 1470

Ala Met Cys Leu Ser Glu Cys Lys Asn Cys Val Pro Ala Ser Phe
    1475                 1480                 1485

Cys Glu Phe His Ser Arg Ser His Glu Lys Leu Cys Pro Ala Cys
    1490                 1495                 1500

Ser Leu Ala Gly Thr Thr Gly Asn Arg Gly Arg Ile Lys Phe Ser
    1505                 1510                 1515

Glu Ala Trp Leu Ser Gly Leu Pro Lys Trp His Ser Val Ser Gln
    1520                 1525                 1530

Asp Asn Val Gly Arg Gly Leu Gly Val Thr Met Pro Arg Leu Glu
    1535                 1540                 1545

Arg Ser Arg Arg Thr Trp His Leu Pro Thr Lys Asp Ala Tyr Leu
    1550            1555                1560

Leu Gly Gln Ser Ile Tyr Leu Asn His Pro Val Pro Ala Ile Leu
    1565            1570                1575

Pro Ser Asp Gln Val Pro Ser Glu Asn Asn Gln Thr Val Glu Pro
    1580            1585                1590

Leu Gly Pro Lys Asn Ile Phe Ser Phe Gln Leu Ala Phe Asp Asn
    1595            1600                1605

Leu Ser Ile Glu Glu Leu Gly Leu Leu Leu Tyr Ser Leu Glu Leu
    1610            1615                1620

Glu Ser Gly Met Ala His Arg Leu Gly Arg Gly Arg Ala Leu Gly
    1625            1630                1635

Met Gly Ser Val Gln Ile Ser Val Lys Asp Ile Gln Ile Arg Asp
    1640            1645                1650

Asn Lys Ser Phe Leu Phe Ser Ser Asn Ile Ser Lys Lys Ser Glu
    1655            1660                1665

Trp Ile Gln Cys Gly Lys Asp Glu Phe Ala Gln Glu Ala Trp Phe
    1670            1675                1680

Gly Glu Ser Trp Asp Asn Ile Asp His Ile Gln Arg Leu Arg Gln
    1685            1690                1695

Ala Leu Thr Ile Pro Val Lys Gly Asp Val Gly Cys Ile Arg Tyr
    1700            1705                1710

Pro Lys Leu Glu Ala Glu Gly Gly Met Pro Asp Tyr Ile Lys Leu
    1715            1720                1725

Arg Lys Arg Leu Thr Pro Leu Cys Asp Arg Glu Glu Pro Val Arg
    1730            1735                1740

Tyr Arg Ile Asn Pro Val Gln Leu Ala Arg Met Ile Leu Pro Phe
    1745            1750                1755

Val Pro Trp His Gly Ala Cys Pro Ala Leu Leu Asn Glu Gln Val
    1760            1765                1770

Met Ile Glu Ala Lys Arg Leu Thr Glu Leu Leu Ala Gln Glu Asn
    1775            1780                1785

Leu Asp Met Ile Cys Arg Thr Lys Asn Cys Ala Asn Cys Lys Gln
    1790            1795                1800

Glu Thr Lys Lys Asp Cys Leu Ala Phe Arg Tyr Asp Arg Ala Asn
    1805            1810                1815

Trp Pro Cys
    1820

<210> SEQ ID NO 25
<211> LENGTH: 1940
<212> TYPE: PRT
<213> ORGANISM: Unknown
<220> FEATURE:
<223> OTHER INFORMATION: Description of Unknown:
      Aquatic-marine-marine sediment sequence

<400> SEQUENCE: 25

Met Lys Val Arg Ile Lys Phe Phe Glu Pro Ile Arg Val Met Pro Trp
1               5                   10                  15

Val Asn Pro Ser Asp Arg Lys Ile Ser Asn Glu Gln Phe Met Arg Gly
            20                  25                  30

Gln Ser Phe Ala Arg Trp His Arg Tyr Asn Lys Asn Ser Asn Ser Gly
        35                  40                  45

Lys Pro Phe Ile Thr Gly Thr Leu Val Arg Ser Ala Val Ile Arg Ala

```
                50              55              60
Ala Glu Val Leu Leu Ser Leu Ser Asn Gly Ile Ile Glu Asn Lys Ala
65                      70                      75                  80

Cys Cys Pro Gly Met Phe Glu Thr Glu Gly Ala Ala Arg Lys Lys Lys
                        85                      90                      95

Met His Phe Arg Gln Arg Ser Thr Pro Lys Trp Thr Glu Asn Ser Thr
                        100                     105                     110

Cys Asn Lys Asp Asn Gln Cys Pro Phe Cys Glu Leu Leu Gly Arg Phe
                115                     120                     125

Gly Asn Asp Glu Ile Gly Ala Val Ile Glu Lys Glu Asn Asn Thr Lys
                130                     135                     140

Arg Leu Lys Tyr Asn Phe His Phe Ser Asn Phe Gln Pro Ser Gly Asn
145                     150                     155                     160

Asn Ser Tyr Pro Asp His Ile Ile Ile Lys Arg Thr Val Asn Arg Val
                        165                     170                     175

Asp Tyr Thr Thr Gly Lys Ala His Asp Phe Phe Thr Ile Ser Glu Ile
                        180                     185                     190

Asp Asn Ser Phe Phe Pro Ala Phe Glu Gly His Ile Ser Ile Ser Asp
                195                     200                     205

Arg Val Ser His Glu Ala Lys Lys Leu Leu Ser Asp Ser Leu Lys Phe
                210                     215                     220

Ile Asp Lys Leu Cys Gly Ser Ile Cys Val Phe Glu Phe Asp Asp Ser
225                     230                     235                     240

Thr Trp Asp Asp His Leu His Ile Glu Lys Ser Met Glu Lys Asn Asp
                        245                     250                     255

Gly Lys Glu Lys Ser Glu Glu Ile Thr Lys Gln Ile Ile Lys Ile Leu
                260                     265                     270

Glu Ser Asn Ser Lys Leu Asp Tyr Leu Arg Ile Leu Ser Asp Ala Ile
                275                     280                     285

Arg Glu Leu Ala Arg Asp Lys Glu Met Val His Lys Leu Pro Leu Asp
                290                     295                     300

Tyr Lys Gly Lys Lys Lys His Tyr Ile Trp Asp Leu Ala Tyr Asn Lys
305                     310                     315                     320

Ile Ser Ile Arg Glu Ile Leu Cys Asn Gln Ala Asn Lys Asn Ala Lys
                        325                     330                     335

Asn Asp Tyr Val Glu Leu Cys Lys Thr Ile Gly Lys Glu Leu Tyr His
                        340                     345                     350

Glu Ser Gln Lys Lys Thr Glu Leu Leu Thr Lys Pro His Arg Ile Leu
                355                     360                     365

Gly Ser Lys Ser Phe Tyr Gly Lys Pro Gln Arg Asp Ile Gln Pro Thr
                370                     375                     380

Asp Ala Lys Ile Val Pro Thr Glu Glu Thr Ile Phe Thr Gly Lys Leu
385                     390                     395                     400

Val Ser Glu Thr Pro Phe Phe Phe Gly Leu Glu Asn Glu Asp Lys Gln
                        405                     410                     415

Gln Thr Asp Phe Thr Val Leu Leu Asp Ser Gln Asn Arg Phe Arg Ile
                        420                     425                     430

Pro Arg Ser Ala Leu Arg Gly Val Leu Arg Arg Asp Ile Arg Met Met
                435                     440                     445

Ser Gly Gly Asn Gly Cys Asp Val Lys Leu Gly Gly Arg Gln Cys Leu
                450                     455                     460

Cys Pro Val Cys Arg Met Met Arg Asn Ile Thr Ile Met Asp Val Arg
465                     470                     475                     480
```

-continued

Ser Asn Lys Asp Ile Ile Pro Asp Ile Arg Gln Arg Ile Arg Ile Asn
                485                 490                 495

Pro Tyr Thr Gly Ser Val Ala Glu Gly Ala Leu Phe Ser Met Glu Leu
                500                 505                 510

Gly Pro Gln Gly Met Glu Phe Asp Phe Val Leu Arg Phe Arg Gly Asn
                515                 520                 525

Asp Ser Ile Pro Lys Ser Leu Lys Lys Val Leu Leu Cys Trp Ala Lys
                530                 535                 540

Gly Gln Ala Phe Leu Ser Gly Ala Ser Ser Thr Gly Lys Gly Arg Phe
545                 550                 555                 560

Lys Leu Lys Asn Leu Lys Phe Lys Ser Phe Asp Leu Ser Thr Lys Glu
                565                 570                 575

Ile Arg Asn Asp Tyr Leu Asn Gln Arg Gly Trp Arg Asn Arg Glu Asn
                580                 585                 590

Glu Leu Pro Leu Glu Pro Leu Phe Leu Thr Asp Lys Tyr Lys Glu Ile
                595                 600                 605

Asn Thr Thr Leu Trp Asn Lys Val Ser Val Glu Ile Lys Leu Ser Ser
                610                 615                 620

Pro Phe Leu Asn Gly Asp Pro Val Arg Ser Leu Val Gln Gly Gln Gly
625                 630                 635                 640

Ala Asp Ile Val Ser Phe Lys Lys Thr Ser Leu Ile Asp Asp Glu Asp
                645                 650                 655

Ile Tyr Ala Tyr Lys Ala Glu Ser Leu Lys Gly Ile Phe Arg Thr Ala
                660                 665                 670

Leu Ala Arg Arg Phe His Tyr Lys Asp Lys Ile Ser Gln Lys Val Leu
                675                 680                 685

Pro Leu Thr Ala Ile Ser His Lys Asp Cys Asp Cys Pro Leu Cys Arg
                690                 695                 700

Leu Phe Gly Ser Glu Phe Glu Thr Gly Lys Ile Arg Phe Glu Asp Leu
705                 710                 715                 720

Glu Phe Ser Thr Asn Pro Ile Pro Lys Lys Phe Asp His Val Ala Ile
                725                 730                 735

Asp Arg Phe Thr Gly Gly Ala Val Asp Lys Lys Lys Phe Asp Asp Cys
                740                 745                 750

Ala Leu Ser Ala Thr Lys Gln Lys Pro Leu Leu Leu Lys Gly Asn Phe
                755                 760                 765

Trp Leu Arg Pro Asp Met Thr Lys Asp Phe Lys Tyr Phe Glu Lys
770                 775                 780

Ala Phe Leu Asp Ile Lys Ser Gly Phe Tyr Pro Leu Gly Ala Lys Ser
785                 790                 795                 800

Gly Ile Gly Tyr Gly Gln Ile Glu Asp Ile Ser Ile Ser Ile Ser Asp
                805                 810                 815

Ser Asp Asp Tyr Pro Arg Ala Ile Lys Glu Asn Ile Lys Thr Ile Asn
                820                 825                 830

Asn Lys Ser Tyr Thr Gln Glu Ala Lys Asn Asn Ile Asn Asp Lys Asp
                835                 840                 845

Thr Asp Glu Ser Lys Gln Ser Asp Phe Gln Ile Asp Leu Lys Asp Asp
850                 855                 860

Ala Ile Tyr Tyr Pro His Tyr Phe Leu Lys Pro Asn Lys Lys Val Asp
865                 870                 875                 880

Arg Lys Thr Ile Pro Ile Asn His Leu Thr Leu His Asp Glu Cys His
                885                 890                 895

```
Thr Gly Lys Ile Val Cys Thr Leu Thr Thr Lys Thr Pro Leu Ile Ile
            900                 905                 910

Pro Asp Thr Glu Asn Asp Asp Ala Phe Gly Leu Lys Lys Ala Lys Leu
        915                 920                 925

Ala Glu Asp Gly Glu Lys Tyr His Lys Ser Tyr Ser Phe Phe Ser Val
        930                 935                 940

Asn Asp Glu Ile Met Ile Ser Gly Ser Glu Ile Arg Gly Met Ile Ser
945                 950                 955                 960

Ser Ile Tyr Glu Ala Ile Thr Asn Ser Cys Phe Arg Ile Phe Glu Glu
                965                 970                 975

Lys His Arg Leu Ser Trp Arg Met Glu Ala Val Pro Glu Val Leu Glu
            980                 985                 990

Lys Phe Ile Pro Gly Arg Ile Ile Lys Ile Asn Gly Glu Leu Lys Met
        995                 1000                1005

Val Glu Met Glu Glu Val Arg Tyr Pro Phe Tyr Asp Lys Asn Cys
    1010                1015                1020

Pro Asp Thr Lys Thr Gln Lys Asp His Phe Ser Ser Lys Gly Lys
    1025                1030                1035

Gly Lys Leu Tyr Tyr Glu Gln Pro Thr Phe Ser Asp Lys Met Ile
    1040                1045                1050

Leu Ser Leu Ser Glu Tyr Asn Arg Lys His Gln Asn Pro Gly Lys
    1055                1060                1065

Lys Glu Lys Tyr Lys Ile Ile Lys Pro Asp Ser Lys Ser Asn Ala
    1070                1075                1080

Asn Phe Met Phe Thr Ala Thr Pro Ala Asn Asn Thr Glu Gly Tyr
    1085                1090                1095

Asp Met Asp Cys Val His Lys His Ser Val Lys Gly Tyr Leu Lys
    1100                1105                1110

Val Ser Gly Pro Asn Lys Ile Glu Lys Glu Arg Thr Asp Gln Pro
    1115                1120                1125

Ala Ser Asn Lys Ile Pro Met Glu Asn Glu Ile Val Ile His Gln
    1130                1135                1140

Lys Thr Asn Arg Arg Glu Ile Thr Val Gln Asn Ala Lys Lys Asn
    1145                1150                1155

Lys Lys Arg Tyr Arg Leu Ile Pro Glu Tyr Ile Cys Ser Glu Lys
    1160                1165                1170

Asp Thr Asn Tyr Ile Met Asn Lys Arg Cys Glu Arg Val Phe Ile
    1175                1180                1185

Glu Pro Glu Lys Cys Asn His Asp Gly Ile Pro Ile Ser Lys Asn
    1190                1195                1200

Ala Ile Glu Leu Phe Lys His Leu Val Asp Glu Tyr Lys Lys Asn
    1205                1210                1215

Ala Asp Gln Gln Glu Thr Pro Lys Val Phe Arg Thr Lys Leu Pro
    1220                1225                1230

Glu Lys Gly Glu Leu Lys Glu Gly Ser Leu Val Tyr Phe Arg Lys
    1235                1240                1245

Asp Ser Asn Glu Val Val Glu Ile Ile Pro Val Lys Ile Ser Arg
    1250                1255                1260

Lys Ile Asp Asp Arg Phe Ile Gly Lys Arg Leu Thr Lys Asn Leu
    1265                1270                1275

Arg Pro Cys His Gly Glu Trp Ile Glu Lys Asp Asp Leu Ser Ile
    1280                1285                1290

Leu Asp Gln Tyr Pro Glu Lys Lys Leu Phe Thr Arg His Pro Lys
```

```
                1295                1300                1305
Gly Leu Cys Pro Ala Cys Gln Leu Phe Gly Thr Gly Ala Tyr Lys
    1310                1315                1320
Gly Arg Leu Arg Phe Gly Phe Ala Thr Leu Thr Asn Lys Pro Glu
    1325                1330                1335
Trp Leu Asn Lys Glu Asp Lys Asp His Lys Leu Thr Leu Pro Leu
    1340                1345                1350
Leu Glu Arg Pro Arg Pro Thr Trp Ala Ile Pro Asp Ala Thr Gln
    1355                1360                1365
Ala Ser Lys Val Pro Gly Arg Lys Phe Phe Ile His His His Ala
    1370                1375                1380
Trp Thr Asp Ile Glu Lys Gly Ile Asp Pro Val Thr Gly Lys Ala
    1385                1390                1395
Ile Gln Ile Asp Val Asn Asn Arg Thr Val Gln Pro Leu Asp Ser
    1400                1405                1410
Asn Asn Thr Phe Thr Phe Glu Ile Asn Phe Glu Asn Leu Glu Pro
    1415                1420                1425
His Glu Leu Gly Leu Leu Leu Tyr Ser Leu Gln Leu Glu Asn Ser
    1430                1435                1440
Leu Ser His Lys Leu Gly Met Gly Lys Ala Phe Gly Phe Gly Ser
    1445                1450                1455
Ile Asp Ile Lys Val Glu Asn Leu Leu Leu Phe Asp Ser Thr Ile
    1460                1465                1470
Asp Lys Tyr Lys Asn Lys Thr Asp Gln Val Lys Arg Phe Val Asp
    1475                1480                1485
Glu Gly Lys Asn Asn Leu Leu Glu Ile Phe Glu Asn Glu Phe Asp
    1490                1495                1500
Asp Ile Glu His Ile Lys Asp Leu Lys Ser Leu Leu Tyr Phe Pro
    1505                1510                1515
Asn Asp Lys Asn Ile Arg Val Gln Tyr Pro Leu Leu Arg Lys Glu
    1520                1525                1530
Asp Tyr Pro Asp Lys Asp Leu Pro Gly Tyr Lys Glu Leu Lys Asp
    1535                1540                1545
Asn Phe Ser Asn Gly Ile Gln Ile Arg His Asn Leu Leu Thr Ile
    1550                1555                1560
Pro Trp Ser Pro Trp Ala Tyr Gln Ser Lys Lys Lys Leu Glu Asn
    1565                1570                1575
Glu Lys Thr Ile Tyr Pro Pro Leu Lys Lys Ile Glu Ile Asn Asn
    1580                1585                1590
Tyr Tyr Asp Ile Lys Lys Val Asn Ile Lys Ile Pro Asp Asn Ala
    1595                1600                1605
Gln Trp Val Phe Leu Thr Gly Asn Asn Ser Ile Gly Lys Ser Leu
    1610                1615                1620
Phe Leu Lys Ala Ile Ala Thr Gly Leu Tyr Gly Lys Ile Thr Glu
    1625                1630                1635
Asp Asp Glu Asn Asp Ile Asp Thr Asn Cys Gly Ile Arg Val Phe
    1640                1645                1650
Ile Thr Asn Glu Trp Val Asp Val Lys Lys Asp Tyr Phe Asn
    1655                1660                1665
Gln Lys Leu Ser Tyr Lys Asn Tyr Ala Thr Tyr Gly Pro Ser Arg
    1670                1675                1680
Leu Asn Lys Leu Ala Glu Gly Lys Lys Thr Lys Phe Pro Tyr Phe
    1685                1690                1695
```

Ser Leu Phe Asn Thr Glu Gly Val Phe Tyr His Asp Ile Glu Lys
    1700                1705                1710

Glu Phe Ile Lys Trp Cys Asp Arg Asp Ser Ser Lys Phe Asn Leu
    1715                1720                1725

Leu Lys Asn Ile Phe Ile Lys Leu Leu Pro Thr Ile Asp Asp Ile
    1730                1735                1740

Lys Gly Ile Gln Thr Lys Thr Asp Phe Tyr Ile Gly Tyr Lys Glu
    1745                1750                1755

Met Glu Thr Gly Lys Tyr Glu Lys Gln Ser Lys Leu Ala Thr Gly
    1760                1765                1770

Asn Ile Ser Ile Leu Arg Met Phe Gly Asp Met Phe Ile Arg Phe
    1775                1780                1785

Ser Lys Glu Gln Pro Asp Thr Leu Pro Glu Asp Phe Ser Gly Ile
    1790                1795                1800

Val Ile Ile Asp Glu Leu Asp Leu His Leu His Pro Ile Trp Leu
    1805                1810                1815

Lys Lys Ile Pro Gly Leu Val Ser Lys Leu Phe Pro Lys Ile Arg
    1820                1825                1830

Phe Ile Ala Ser Thr His Ser Ala Ile Pro Phe Leu Gly Ala Pro
    1835                1840                1845

Lys Asn Ser Val Tyr Leu Asn Val Ile Arg Asp Glu Asp Asn Asn
    1850                1855                1860

Ile His Val Gln Glu Ile Asp Ile Asp Leu Thr Asn Leu Leu Pro
    1865                1870                1875

Asn Thr Ile Leu Thr Ser Pro Leu Phe Asn Met Glu Asp Ile Thr
    1880                1885                1890

Gln Ile Asn Leu Pro Asp Ile Thr Asp Val Arg Thr Glu Asp Thr
    1895                1900                1905

Tyr Lys Glu Ile Ile Glu Ile Asp Lys Ile Lys Ala Arg Leu Lys
    1910                1915                1920

Lys Phe Ala Lys Lys Asp Thr Leu Phe Pro Asp Lys Leu Phe Lys
    1925                1930                1935

Glu Leu
    1940

<210> SEQ ID NO 26
<211> LENGTH: 1812
<212> TYPE: PRT
<213> ORGANISM: Unknown
<220> FEATURE:
<223> OTHER INFORMATION: Description of Unknown:
      Anammox bioreactor sequence

<400> SEQUENCE: 26

Met Ser Lys Lys His Phe Ile His Leu Thr Phe Leu Glu Pro Tyr Arg
1               5                   10                  15

Leu Ala Glu Trp His Ala Lys Ala Asp Arg Lys Lys Asn Lys Arg Tyr
                20                  25                  30

Leu Arg Gly Met Ser Phe Ala Gln Trp His Lys Asp Lys Asp Gly Ile
            35                  40                  45

Gly Lys Pro Tyr Ile Thr Gly Thr Leu Leu Arg Ser Ala Val Leu Asn
        50                  55                  60

Ala Ala Glu Glu Leu Ile Ser Leu Asn Gln Gly Met Trp Ala Lys Glu
65                  70                  75                  80

Pro Cys Cys Asn Gly Lys Phe Glu Thr Glu Lys Asp Lys Pro Ala Val

```
                        85                  90                  95
Leu Arg Lys Arg Pro Thr Ile Gln Trp Lys Thr Gly Arg Pro Ala Ile
                100                 105                 110

Cys Asp Pro Glu Lys Gln Glu Lys Lys Asp Ala Cys Pro Leu Cys Met
            115                 120                 125

Leu Leu Gly Arg Phe Asp Lys Ala Gly Lys Arg His Arg Asp Asn Lys
        130                 135                 140

Tyr Asp Lys His Asp Tyr Asp Ile His Phe Asp Asn Leu Asn Leu Ile
145                 150                 155                 160

Thr Asp Lys Lys Phe Ser His Pro Asp Asp Ile Ala Ser Glu Arg Ile
                165                 170                 175

Leu Asn Arg Val Asp Tyr Thr Gly Lys Ala His Asp Tyr Phe Lys
            180                 185                 190

Val Trp Glu Val Asp Asp Gln Trp Trp Gln Phe Thr Gly Thr Ile
        195                 200                 205

Thr Met His Asp Asp Cys Ser Lys Ala Lys Gly Leu Leu Ala Ser
    210                 215                 220

Leu Cys Phe Val Asp Lys Leu Cys Gly Ala Leu Cys Arg Ile Glu Val
225                 230                 235                 240

Thr Gly Asn Asn Ser Gln Asp Glu Asn Lys Glu Tyr Ala His Pro Asp
                245                 250                 255

Thr Gly Ile Ile Thr Ser Leu Asn Leu Lys Tyr Gln Asn Asn Ser Thr
            260                 265                 270

Ile His Gln Asp Ala Val Pro Leu Ser Gly Ser Ala His Asp Asn Asp
        275                 280                 285

Glu Pro Pro Val His Asp Asn Asp Ser Ser Leu Asp Asn Asp Thr Ile
    290                 295                 300

Thr Leu Leu Ser Met Lys Ala Lys Glu Ile Val Gly Ala Phe His Glu
305                 310                 315                 320

Ser Gly Lys Ile Glu Lys Ala Arg Thr Leu Ala Asp Val Ile Arg Ala
                325                 330                 335

Met Arg Leu Gln Lys Pro Asp Ile Trp Glu Lys Leu Pro Lys Gly Ile
            340                 345                 350

Asn Asp Lys His His Leu Trp Asp Arg Glu Val Asn Gly Lys Lys Leu
        355                 360                 365

Arg Asn Ile Leu Glu Glu Leu Trp Arg Leu Met Ser Lys Arg Asn Ala
    370                 375                 380

Trp Arg Thr Phe Cys Glu Val Leu Gly Asn Glu Leu Tyr Arg Cys Tyr
385                 390                 395                 400

Lys Glu Lys Thr Gly Gly Ile Val Leu Arg Phe Arg Thr Leu Gly Glu
                405                 410                 415

Thr Glu Tyr Tyr Pro Glu Pro Glu Lys Thr Glu Pro Cys Leu Ile Ser
            420                 425                 430

Asp Asn Ser Ile Pro Ile Thr Pro Leu Gly Gly Val Lys Glu Trp Ile
        435                 440                 445

Ile Ile Gly Arg Leu Lys Ala Glu Thr Pro Phe Tyr Phe Gly Ala Gln
    450                 455                 460

Ser Ser Phe Asp Ser Thr Gln Asp Asp Leu Asp Leu Val Pro Asp Ile
465                 470                 475                 480

Val Asn Thr Asp Glu Lys Leu Glu Ala Asn Glu Gln Thr Ser Phe Arg
                485                 490                 495

Ile Leu Met Asp Lys Lys Gly Arg Tyr Arg Ile Pro Arg Ser Leu Ile
            500                 505                 510
```

-continued

```
Arg Gly Val Leu Arg Arg Asp Leu Arg Thr Ala Phe Gly Gly Ser Gly
            515                 520                 525
Cys Ile Val Glu Leu Gly Arg Met Ile Pro Cys Asp Cys Lys Val Cys
        530                 535                 540
Ala Ile Met Arg Lys Ile Thr Val Met Asp Ser Arg Ser Glu Asn Ile
545                 550                 555                 560
Glu Leu Pro Asp Ile Arg Tyr Arg Ile Arg Leu Asn Pro Tyr Thr Ala
                565                 570                 575
Thr Val Asp Glu Gly Ala Leu Phe Asp Met Glu Ile Gly Pro Glu Gly
            580                 585                 590
Ile Thr Phe Pro Phe Val Phe Arg Tyr Arg Gly Glu Asp Ala Leu Pro
        595                 600                 605
Arg Glu Leu Trp Ser Val Ile Arg Tyr Trp Met Asp Gly Met Ala Trp
    610                 615                 620
Leu Gly Gly Ser Gly Ser Thr Gly Lys Gly Arg Phe Ala Leu Ile Asp
625                 630                 635                 640
Ile Lys Val Phe Glu Trp Asp Leu Cys Asn Glu Gly Leu Lys Ala
                645                 650                 655
Tyr Ile Cys Ser Arg Gly Leu Arg Gly Ile Glu Lys Glu Val Leu Leu
            660                 665                 670
Glu Asn Lys Thr Ile Thr Glu Ile Thr Asn Leu Phe Lys Thr Glu Glu
        675                 680                 685
Val Lys Phe Phe Glu Ser Tyr Ser Lys His Ile Lys Gln Leu Cys His
    690                 695                 700
Glu Gly Ile Ile Asn Gln Met Ser Phe Ser Gly Gly Leu Arg Ser Tyr
705                 710                 715                 720
His Glu Tyr Leu Ser Pro Leu Trp Thr Glu Val Lys Tyr Glu Ile Lys
                725                 730                 735
Ile Ala Ser Pro Leu Leu Ser Ser Asp Thr Ile Ser Ala Leu Leu Asn
            740                 745                 750
Lys Asp Asn Ile Asp Cys Ile Ala Tyr Glu Lys Arg Lys Trp Glu Asn
        755                 760                 765
Gly Gly Ile Lys Phe Val Pro Thr Ile Lys Gly Glu Thr Ile Arg Gly
    770                 775                 780
Ile Val Arg Met Ala Val Gly Lys Arg Ser Gly Asp Leu Gly Met Asp
785                 790                 795                 800
Asp His Glu Asp Cys Ser Cys Thr Leu Cys Thr Ile Phe Gly Asn Glu
                805                 810                 815
His Glu Ala Gly Lys Leu Arg Phe Glu Asp Leu Glu Val Val Glu Glu
            820                 825                 830
Lys Leu Pro Ser Glu Gln Asn Ser Asp Ser Asn Lys Ile Pro Phe Gly
        835                 840                 845
Pro Val Gln Asp Gly Asp Gly Asn Arg Glu Lys Glu Cys Val Ala Glu
    850                 855                 860
Val Lys Ile Tyr Lys Lys Leu Ile Asp His Val Ala Ile Asp Arg
865                 870                 875                 880
Phe His Gly Gly Ala Glu Asp Lys Met Lys Phe Asn Thr Leu Pro Leu
                885                 890                 895
Val Gly Ser Pro Glu Arg Pro Ile Ile Leu Lys Gly Arg Phe Trp Ile
            900                 905                 910
Lys Lys Asp Met Val Lys Asp Tyr Arg Lys Lys Ile Glu Asp Ala Met
        915                 920                 925
```

```
Val Asp Ile Arg Asp Gly Leu Tyr Pro Ile Gly Gly Lys Thr Gly Ile
930                 935                 940

Gly Tyr Gly Trp Val Thr Asp Leu Thr Ile Leu Asn Pro Gln Ser Gly
945                 950                 955                 960

Phe Gln Ile Pro Val Lys Lys Asp Ile Ser Pro Glu Pro Gly Thr Tyr
            965                 970                 975

Leu Thr Tyr Pro Ser Tyr Ser Ala Pro Ser Leu Asn Arg Gly His Ile
            980                 985                 990

Tyr Tyr Pro His Tyr Phe Leu Ala Pro Ala Asn Thr Val His Arg Glu
        995                 1000                1005

Gln Glu Met Ile Gly His Glu Gln Phe His Lys Glu Gln Lys Gly
    1010            1015            1020

Glu Leu Leu Val Ser Gly Lys Ile Val Cys Thr Leu Lys Thr Val
    1025            1030            1035

Thr Pro Leu Ile Ile Pro Asp Thr Glu Asn Glu Asp Ala Phe Gly
    1040            1045            1050

Leu Gln Asn Thr Tyr Ser Gly His Lys Asn Tyr Gln Phe Phe His
    1055            1060            1065

Ile Asn Asp Glu Ile Met Val Pro Gly Ser Glu Ile Arg Gly Met
    1070            1075            1080

Ile Ser Ser Val Tyr Glu Ala Ile Thr Asn Ser Cys Phe Arg Val
    1085            1090            1095

Tyr Asp Glu Thr Lys Tyr Ile Thr Arg Arg Leu Ser Ser Glu Lys
    1100            1105            1110

Lys Asp Glu Ser Asn Asp Lys Asn Lys Ser Gln Asp Asp Ala Ser
    1115            1120            1125

Gln Lys Ile Arg Lys Gly Leu Val Lys Lys Thr Asp Glu Gly Phe
    1130            1135            1140

Ser Ile Ile Glu Val Glu Arg Tyr Ser Met Lys Thr Lys Gly Arg
    1145            1150            1155

Thr Lys Leu Val Asp Lys Val Tyr Arg Leu Pro Leu Tyr Asp Ser
    1160            1165            1170

Glu Ala Val Ile Ala Ser Ile Lys Phe Glu Gln Tyr Gly Glu Lys
    1175            1180            1185

Asn Glu Lys Arg Asn Ala Lys Ile Leu Ala Ala Ile Lys Arg Asn
    1190            1195            1200

Asn Val Ile Ala Glu Val Ala Arg Lys Asn Leu Ile Phe Leu Arg
    1205            1210            1215

Ser Leu Thr Pro Glu Glu Leu Lys Lys Val Leu Gln Gly Glu Ile
    1220            1225            1230

Leu Val Lys Phe Ser Leu Lys Ser Gly Glu Asn Pro Asn Asp Tyr
    1235            1240            1245

Leu Ala Glu Leu His Glu Asn Gly Thr Glu Arg Gly Leu Ile Lys
    1250            1255            1260

Phe Thr Gly Leu Asn Met Val Asn Ile Lys Asn Val Asn Glu Glu
    1265            1270            1275

Asp Lys Asp Phe Asn Asp Thr Trp Asp Trp Glu Lys Leu Asn Ile
    1280            1285            1290

Phe His Asn Ala His Glu Lys Arg Asn Ser Leu Lys Gln Gly Tyr
    1295            1300            1305

Pro Arg Pro Val Leu Lys Phe Ile Lys Asp Arg Val Glu Tyr Thr
    1310            1315            1320

Ile Pro Lys Arg Cys Glu Arg Ile Phe Cys Ile Pro Val Lys Asn
```

```
            1325                1330                1335

Thr Ile Glu Tyr Lys Val Ser Ser Lys Val Cys Lys Gln Tyr Lys
    1340                1345                1350

Asp Val Leu Ser Asp Tyr Glu Lys Asn Phe Gly His Ile Asn Lys
    1355                1360                1365

Ile Phe Thr Thr Lys Ile Gln Lys Arg Glu Leu Thr Asp Gly Asp
    1370                1375                1380

Leu Val Tyr Phe Ile Pro Asn Glu Gly Ala Asp Lys Thr Val Gln
    1385                1390                1395

Ala Ile Met Pro Val Pro Leu Ser Arg Ile Thr Asp Ser Arg Thr
    1400                1405                1410

Leu Gly Glu Arg Leu Pro His Lys Asn Leu Leu Pro Cys Val His
    1415                1420                1425

Glu Val Asn Glu Gly Leu Leu Ser Gly Ile Leu Asp Ser Leu Asp
    1430                1435                1440

Lys Lys Leu Leu Ser Ile His Pro Glu Gly Leu Cys Pro Thr Cys
    1445                1450                1455

Arg Leu Phe Gly Thr Thr Tyr Tyr Lys Gly Arg Val Arg Phe Gly
    1460                1465                1470

Phe Ala Asn Leu Ile Asn Lys Pro Lys Trp Leu Thr Glu Arg Glu
    1475                1480                1485

Asn Gly Cys Gly Gly Tyr Val Thr Leu Pro Leu Leu Glu Arg Pro
    1490                1495                1500

Arg Leu Thr Trp Ser Val Pro Ser Asp Lys Cys Asp Val Pro Gly
    1505                1510                1515

Arg Lys Phe Tyr Val His His Asn Gly Trp Gln Glu Val Leu Arg
    1520                1525                1530

Asn Asn Asp Ile Thr Pro Lys Thr Glu Asn Asn Arg Thr Val Glu
    1535                1540                1545

Pro Leu Ala Ala Asp Asn Arg Phe Thr Phe Asp Val Tyr Phe Glu
    1550                1555                1560

Asn Leu Arg Glu Trp Glu Leu Gly Leu Leu Cys Tyr Cys Leu Glu
    1565                1570                1575

Leu Glu Pro Gly Met Gly His Lys Leu Gly Met Gly Lys Pro Leu
    1580                1585                1590

Gly Phe Gly Ser Val Lys Ile Ala Ile Glu Arg Leu Gln Thr Phe
    1595                1600                1605

Thr Val His Gln Asp Asp Ile Asn Trp Lys Pro Ser Glu Asn Glu
    1610                1615                1620

Ile Gly Val Tyr Val Gln Arg Gly Arg Glu Lys Leu Val Glu Trp
    1625                1630                1635

Phe Thr Pro Ser Asp Ser His Lys Asn Met Glu Trp Asn Glu Val
    1640                1645                1650

Lys His Ile Lys Asp Leu Arg Ser Leu Leu Ser Ile Pro Asp Asp
    1655                1660                1665

Lys Pro Thr Val Lys Tyr Pro Ala Leu Asn Lys Gly Ala Glu Gly
    1670                1675                1680

Ala Ile Ser Asp Tyr Thr Tyr Glu Arg Leu Ser Asp Thr Lys Leu
    1685                1690                1695

Leu Pro His Asp Lys Arg Val Glu Tyr Leu Arg Thr Pro Trp Gly
    1700                1705                1710

Pro Trp Asn Ala Phe Val Lys Glu Ala Glu Tyr Ser Thr Ser Glu
    1715                1720                1725
```

Asn Ser Asp Glu Lys Gly Arg Glu Thr Ile Arg Thr Lys Pro Lys
    1730                1735                1740

Ser Leu Pro Ser Val Lys Ser Ile Gly Lys Val Lys Trp Phe Asp
    1745                1750                1755

Glu Gly Lys Gly Phe Gly Ile Leu Ile Met Asp Asp Gly Lys Glu
    1760                1765                1770

Val Ser Ile Ser Lys Asn Ser Ile Arg Gly Asn Asn Leu Leu Lys
    1775                1780                1785

Lys Asp Gln Lys Val Thr Phe His Ile Val Gln Gly Leu Ile Pro
    1790                1795                1800

Lys Ala Glu Asp Ile Glu Ile Ala Lys
    1805                1810

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gttatgaaac aagagaagga cttaatgtca cggtac                        36

<210> SEQ ID NO 28
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gttggtgcat cagcccggaa ttatgatgtt ttggtac                       37

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ggttggaaag ccggttttct ttgatgtcac ggaac                         35

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
attgccccag ccgataaacc cttaatgtca cggaac                        36

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
atagatatag acagaagctt ttaatgtgat gggac                                   35

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gttggaaaag ccggtttat ttgatgtcac ggaac                                    35

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
attgggggga ttagattctg ataatgtcac ggtac                                   35

<210> SEQ ID NO 34
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggttggattc agccccagat gttttatgtg acggaac                                 37

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gttaaggaga gacggcattc attgatgtca cggcac                                  36

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gttagcatca ggacaatacc ttcgatgtta cgggac                                  36

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 37
gttccgtgac atcaaaagcc gtccatttct caaac                              35

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cttgaagact aaaggaagga attgatgtca cggtac                             36

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000
```

<210> SEQ ID NO 48

<400> SEQUENCE: 48

000

<210> SEQ ID NO 49

<400> SEQUENCE: 49

000

<210> SEQ ID NO 50
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ala Tyr Leu Val Gly Leu Tyr Thr Leu Thr Pro Thr His Pro Gly Ser
1               5                   10                  15

Gly Thr Glu Leu Gly Val Val Asp Gln Pro Ile Gln Arg Glu Arg His
            20                  25                  30

Thr Gly Phe Pro Val Ile Trp Gly Gln Ser Leu Lys Gly Val Leu Arg
        35                  40                  45

Ser Tyr Leu Lys Leu Val Glu Lys Val Asp Glu Glu Lys Ile Asn Lys
    50                  55                  60

Ile Phe Gly Pro Pro Thr Glu Lys Ala His Glu Gln Ala Gly Leu Ile
65                  70                  75                  80

Ser Val Gly Asp Ala Lys Ile Leu Phe Phe Pro Val Arg Ser Leu Lys
                85                  90                  95

Gly Val Tyr Ala Tyr Val Thr Ser Pro Leu Val Leu Asn Arg Phe Lys
            100                 105                 110

Arg Asp Leu Glu Leu Ala Gly Val
        115                 120

<210> SEQ ID NO 51
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

His His His His Asp Met Leu Asn Ser Leu His Ala Ile Thr Gly Lys
1               5                   10                  15

Phe Lys Thr Gln Ser Arg Leu Val Val Gly Leu Gly Asp Glu Ser Val
            20                  25                  30

Tyr Glu Thr Ser Ile Arg Leu Leu Arg Asn Tyr Gly Val Pro Tyr Ile
        35                  40                  45

Pro Gly Ser Ala Ile Lys Gly Val Thr Arg His Leu Thr Tyr Tyr Val
    50                  55                  60

Leu Ala Glu Phe
65

<210> SEQ ID NO 52

```
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
000

<210> SEQ ID NO 58
<400> SEQUENCE: 58
000

<210> SEQ ID NO 59
<400> SEQUENCE: 59
000

<210> SEQ ID NO 60
<400> SEQUENCE: 60
000

<210> SEQ ID NO 61
<400> SEQUENCE: 61
000

<210> SEQ ID NO 62
<400> SEQUENCE: 62
000

<210> SEQ ID NO 63
<400> SEQUENCE: 63
```

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

```
<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97
```

000

<210> SEQ ID NO 98

<400> SEQUENCE: 98

000

<210> SEQ ID NO 99
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t or g
<220> FEATURE:
<221> NAME/KEY: modified_base
<222> LOCATION: (9)..(9)
<223> OTHER INFORMATION: a, c, t or g

<400> SEQUENCE: 99
tgtnwyggna c                                                          11

<210> SEQ ID NO 100
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: a, c, t or g
<220> FEATURE:
<221> NAME/KEY: modified_base
<222> LOCATION: (7)..(7)
<223> OTHER INFORMATION: a, c, t or g
<220> FEATURE:
<221> NAME/KEY: modified_base
<222> LOCATION: (9)..(9)
<223> OTHER INFORMATION: a, c, t or g
<220> FEATURE:
<221> NAME/KEY: modified_base
<222> LOCATION: (16)..(16)
<223> OTHER INFORMATION: a, c, t or g

<400> SEQUENCE: 100
gttrnrnanm rmcrsnwdyy wttratgtba cggdac                               36

<210> SEQ ID NO 101
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
accggctttt cca                                                        13

<210> SEQ ID NO 102
<211> LENGTH: 338
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 102

```
ttttccgaat cggatgtggg attgctccgg ccctgcctta ttttcatata agaccggctt      60
atccgactat ctccctaata tgacagggaa aatatcttcc cggacttttc accgggatgg     120
tataagaaca gggaaccaga atcatctgtt ccctgaccac tggaaagttt ttcatatcag     180
tatgttgaat cctgtcaccc ctggggcacg gagggatttc caaatatccg atctgatgtt     240
cgtaatcacc ggcttttcca gccaatggct tgagatgatt taagaaactt gtgactggct     300
ttttctggta aaatggattt ttgtataata tcctgttg                             338
```

<210> SEQ ID NO 103
<211> LENGTH: 791
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
agagtcagga caacactctg taccatagtt gtgggataca gaaagccttt gattaccatc      60
ggaaatccca caaacatccc aatgtgtata taatgatttg atctcagcta tgcgttcctg     120
gtataagttt cttttcggtt ttgcctgcat tgtattaacc tctttcttc ataataata      180 aaattataaa atactaaacg ttgaaatatt atgcatctcc ttctcgaaaa atcagatcat     240
ataaaatcaa tttcacccct caccataata agacgtacac tgtgggtgaa aagtgacact     300 cttttttaaat attttttaaat tcaaataact gtttatattg agcaaatgga aatgcatcct     360
ttcctcgtgt tatcatcagt gctgtcattt gaattaatcg tatttaatgg agaaaaggtg     420 acaattttt ataaaaagac ttgtacaaaa aaattaaatt gtactgaact ttttttttgtc     480 actttggttt ggtgattaac gactgaatat attagagtat tttttttctct ttttattctt     540 gaaaaaattg ttcttgaata acagtgttta cttaactaaa gtacctctaa taaatatttg     600
ttcacaccaa aaacagtaag gttataaaga agaaatctgt catgaacaat acagaagaaa     660
acattgaccg tatccaggaa ccgaccagag aagacattga tagaaaagaa gcagaacggc     720
ttcttgatga ggcttttaat ccaaggacca aacccgtcga taggaagaag ataattaatt     780
ctgccctgaa g                                                          791
```

<210> SEQ ID NO 104
<211> LENGTH: 304
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

```
aagttgaaga gtgtatccat tactgaaaag ggtcaacgca catatcctgt agatgcatcc      60
ggtagcagga tagcggaaga ggtcagggat tatacgcaga aaccactaaa cgttgttgtg     120
ctgattatta aatatacata tgaagagtaa cgatatgaac atcactgtag aactcacctt     180
ctttgaaccc taccgtctgg ttgagtggtt tgactgggac gcaagaaaaa agagtcatag     240
cgcaatgaga ggtcaggctt tcgcgcagtg gacgtggaaa ggaaaaggtc gcacagcagg     300
caag                                                                  304
```

<210> SEQ ID NO 105
<211> LENGTH: 680
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105

```
agcaccgtta agaagtttgg attcatcagt aaaggtgatg gagaagatat ttttgaaaga      60
atcaaggaaa aatatattaa agcattggaa acaatatac aattatttga gatctatttg      120
tcggatgaaa aggatactcg gaataaataa cagacaaacg gtttgcgaag aaatacgcga     180
cagggtgatt ggaccgtaac ctcatgatta tatgattgat acacgattta accctgactt     240
gccggttttt gaaaaagttc gcaaaccctg ttttgcttca tgaagtgagt tgggtttgcg     300
aaaaaaggtt attacagcct gatatctaag tagaagagta ccggtattga agaccaaagt     360
tgctgcgtat ggcggtccgg ttgtccttgc tttcgcaagg attccaatac tggaatcctc     420
ccgaaaggga ggtcgcaaaa ggccgttttt cgaaaccat agtttcatac aaaccggcga     480
tgaggtttgc gaacttttg attgtagtaa gtattattaa aataatggct taatattttt     540
ggtatataca attctcaact ttttcacctt gccggaaatg aggtttgcga aattttagag     600
agccgcatat ctatattatt tacaatcagt tacaaaatgg cccttctcg ccatatacgt      660 aacctcagag ttgttggagg                                                 680
```

<210> SEQ ID NO 106
<211> LENGTH: 386
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 106

```
ggtttgattg aatattgatg gttgaaaatc gtctgcccta tggggaggc aatgtcattg       60 aattaagggc aaaatatgga gtgcatcatc cctgcccgag aatgacacta cagtgtcaac     120
atccctttag gtaggcgtcc acgtcagcct ggcgggaatc cagcaacctc tgctttgaga     180
gtcaattcca ttttagttgt cacctttctg atagaatcct cgactaaatc agtaagatga     240
caactgatac tctacttgaa caattttaa gcaagtccaa tttcatttct gcctatgagc      300
gtattgcctc aaagaaggct gcaggcggat tggataatgt cacggttgaa tcattcggca     360
accgactgga ccagcatatc agcaaa                                          386
```

<210> SEQ ID NO 107
<211> LENGTH: 392
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 107

```
gttatccttg gccatttaga ggcttcggtc aaaaaggcgc tcgatgcggt cgaaaacatt      60
gcgtctggcc agccaagtaa tgaggactcg ccagtattac ccacgagccc ggcggaggtg    120
gcggttattc actggagcat aaaccagtga ccacaaattt ccggaaatga tgtccacttc    180
gatagtgtag atggtgcgga cgtatcaccc cttccccaag gcagctcaag gagagcaatg    240
```

| | |
|---|---|
| atatgaatca aaatatcgat cgtgcggttg gtgcaattct agcgattgaa acagcgacac | 300 |
| cccttaccga atcttcaaca ctcgcgcaac gtgaaaggca tcagaagctg ctgcatgatg | 360 |
| aaaccaaaaa gattgagcaa gccttcatag cc | 392 |

<210> SEQ ID NO 108
<211> LENGTH: 1348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108

| | |
|---|---|
| ctgcaaagct gttggatgcg ccaacccggt gccatttta atgatgagta catccgcctt | 60 |
| tattatgccg cctcttccg gatactgggt ttcccggaag ttgcgactac aaatatggcg | 120 |
| actgcaaccg cccaggagga aatagcatga ctaccggcaa cacttccgct tctcacccgc | 180 |
| aatttgtcac gttgacagtc tgtttgcgct tttgcagccc cttccagatc cgaccctgga | 240 |
| tcaaggaaac ggtgcgcaac aaggttaaaa tgccatccac tgtcaacgct catgctgaaa | 300 |
| ctgctcacct gccggatgac caggataccg acgacacaca agatctattg gaagaagaac | 360 |
| gttttgagcg gtatgccact gccgctgatt ggcacaaggg aagtatcaac ggaaacgcga | 420 |
| agtattcacc ctatgtgagg ggcgatctgg tccgcagcgt ggtggacagg gaattgcagg | 480 |
| agcatttcca ctgttataat gaaaagcttg ccaatgagaa taagggtgc cctggaaaac | 540 |
| gggaccgcca tattaacgcc ggcggcaagg cgtccggttt tatggcacac ctgcccgcga | 600 |
| tcaaggaccc ggccggcaag gagatctgca agggcagcga taacatctgc ccggtctgcc | 660 |
| atttcctcgg ggcgtttgcg gaaggaataa agccggttaa gttcaggaat cggaagatct | 720 |
| ggccaagcag cgcggccgga actgttacag cgggcaaagc cggaaatccc ttgataattt | 780 |
| tactgtctgg gaagcggatc ataccgcctg ccctgttttc ttcggcagaa tcgaggtgaa | 840 |
| caaaactctt ttgccgaaag aacaaatcct cgccctgctg gctggcggcc ttgctcggct | 900 |
| tgacaatttg gcgggtgcgg cgagggaggc acttgggcta ccagacgacg agcaccaggc | 960 |
| actcctcaac gattttcaa gattttcat taatcccgag aaatcgcctg ctgtttatac | 1020 |
| ttcctccccg gttattgtcc ctgtccaggg agctgttgat aaggttgtgc tcttggaaaa | 1080 |
| agcccaagat atcgccggca gaattgccgc gtgtgtctcc gacaatcccc gccacctcca | 1140 |
| tcggctggct gcggctatcc ggaccctggg ctggccgggc cggtctcttg cttcggttat | 1200 |
| gactaaaaaa ccgggtaccg aagacaaggc caccctctgg ggaaaagaat cagcgagtaa | 1260 |
| atcggtcaag acgattctgg aagaatcaat ccaaggcttc actgtagaac aaaagcgaag | 1320 |
| ctttttttgcc aaccttgccg accagctc | 1348 |

<210> SEQ ID NO 109
<211> LENGTH: 340
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 109

| | |
|---|---|
| cgtatcaatc cggtacaact cgcccgaatg attttaccat ttgtaccttg gcatggtgca | 60 |
| tgtcctgctt tgctgaacga acaggtaatg atagaggcca aacgattgac tgagttagac | 120 |
| cgcgccaatt ggccatgttg aatgccagca caaccagcta atatatcgaa atcgctggca | 180 | aagttagctt ttattgtaaa attagatgat taggaacgat ccggcaggtt atttaaatga    240 agtaaagtct ggggtcgtag cataatcgca aaaaaaatta tttaacagaa acaaacaaat    300 agacagcata aagttgaatt gagtattata gaaagcaggg    340

<210> SEQ ID NO 110
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
tttttctgta actattcagc acaccatatt ttagcataac aactgagtag tcattggggc    60
atcataaatt gaggccattt cccttcaaat aataagcgca    100

<210> SEQ ID NO 111
<211> LENGTH: 841
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
gagacaaaag agcaacggga tattttgtt cattttagcg ctattcgggg tgagggttat    60
aaaatcctgg aaccgggcga aaagtacgt tttgaaatag gtgagggag aaaaggtccc    120 caggccatca atgttattcg tataagatga caaaattact ccagtctcta ttcttttgt    180 aattacttgt tcgctgtttt gtgaagatta ttaagcta tggagctttc aggtaaaaaa    240
gcgtaaagta cgcgaatatt ctgcgtaaaa ctattccggc tatgaaagat gatgttcata    300
gccggaatag ttttttatcg agtttggtgg ggtattcatt tgggagatg gttgatgaaa    360 gtttcaaggc agggtttcat ttattggcga tggtttaaat atctctttat tctttcttca    420
acaatctgat attattgttt ttttatctaa agatactctg ttttattta tcgtaaaata    480 ttcgacatac atatgaaacc tttgaaaagg caggagtttg gcgaagatgt agtgattgtg    540
gctaaaatta cggaaaaatt tttttgtaa aattaaggtg atatgaatat agttttctg    600 gtgcggtcgc caatttcctt ttttgaaatt aggaaactgg tttggcgaat ttttgacag    660 tatctttta taataaatac gaatagttgt gattagacag gtgttaattt agtagtattt    720
cccctttaac tgaagaatga ttggcgtaat atttaataac atgagagaac tccttggtat    780
aatagagatt attaagtata gtgtcagaat gcagcttttg tttgttcttt gattctaaag    840
g    841

<210> SEQ ID NO 112
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
tctcaaaata atgttaaaga aattttcatt ttattttgat ggtttaggcc acactgactt    60
tgtggttctc tttataccga tagaaaaatt ttatttttc gaaaaaaaac actcttccat    120
tcgtaaggtt aaataaaggc aattacttaa ccatctagca atggaggatt gatcatgaaa    180

```
agcacacatt ctcttttta ccgttttgct catgttgata cctttcgctc cgcatatgaa    240
agaatttctc taaaaaattc cagcccggga cttgatagag tttccgtaga agagttcggc   300
aagaaacttg aaaaaaatat ccaa                                          324
```

<210> SEQ ID NO 113
<211> LENGTH: 303
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

```
attcaggcaa tcctcaatag attggggcag gaggtaaaag gtcgaggtaa ggctttaaca    60
ttgcaggaaa tgatccatcg gcaggcgcag ttgttgaaaa gctatttgat ggataaatct   120
gtttacaaac catatctggc aaggtggtaa cctatgaata cagtcgaatt acttcaggag   180
gaagaacgct tgaccctgga tttggtcttt ttgccaccag gtagtaagaa taaagagcaa   240
aaaaagaatg ctttggtaga cctttttgttg aaaatagtgg agcatgggga attaacccgt   300
aaa                                                                 303
```

<210> SEQ ID NO 114
<211> LENGTH: 403
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114

```
atcgacaatg atgataccct cgctgtgctc catagttcat taaaaagatt atttgagcat    60
tacgagaaga aaaatgaaaa aactcgtgca cagcttctct ataattgggc gtctttacgt   120
gttctcgctc ctgccaggga atttagttga aaaaaaatca taaaatttcc gaaaaaatag   180
atgatgtcga acgtaatagg ttttagagca acgaataacc gttgctctaa aacctatact   240
ctgggagaac atcatgaaaa aagagcacgg taaagaaaac tattctatcg aaacagttgt   300
tttcgtcgtt ttgcaggaca tcatgagtat tgttctaata ccgtttgcgg taatcgcctc   360
aatttatctt tcttattttt ttgagttatc tgtatacaaa tct                     403
```

<210> SEQ ID NO 115
<211> LENGTH: 584
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
ccccgcgtta tttatccggc cctgaagcag aaggatattc ctaacagcag gcttcccggg    60
tatgaggagt tgaagaagaa cctcaatatg gagaaacgga agagatgct gacgacccct    120 tgggcccct ggcatcccat caaaaaataa gatgcctgcg aattcccgga atatgacag    180 cggatttaaa ggattgaacg gatatcattt tcccaaaaaa tgacagcgga tttaaaggat   240
tgagcggata tccgtttcat cctttgatcc gttgtcatat ttcctacaaa tatgtcgccc   300
ctacggggct ttaatccttt cctcttcttt gtgtcctttg tggctttgtg tgagaaaaac   360
aaaaaatttt tgtcacattt tcagcacaga acacgactaa gtatgcagag aagggaaacg   420
```

```
ccctccttttt ctttgtgtcc tttgtggctt tgtgtgagaa aaacaaaaaa ttttttgtcac    480 attttcagca cgacatacga ctaagtttgc agaaagggaa aaaacatatc tttttactca     540
taaaggaggt tgccatgaaa aaaacatttta tcgtctttgt tctg                      584
```

<210> SEQ ID NO 116
<211> LENGTH: 602
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116

```
aagcgctggg caactgatga tctgctccgt atggtcgggg atcagatcac tgtgatgagg     60
gggttgctgg aaaagggaga ggattatcgg ccggtggttt acaacagccg gtattccagc    120
gggaagagcg gcctgaaaaa aaagacttga aaaggtcttg acatgggccg ggaaaggggc    180
tatgttcttc tgattataat atcagatcag agggaatatg gcccttatcc cgggaatatc    240
ctgtatttca ggggatcggg cctgttttcc gaatcggatg tgggattgct ccggccctgc    300
cttattttca tataagaccg gcttatccga ctatctccct aatatgacag ggaaaatatc    360
ttcccggact tttcaccggg atggtataag aacagggaac cagaatcatc tgttccctga    420
ccactggaaa gttttttcata tcagtatgtt gaatcctgtc accctgggg cacggaggga    480 tttccaaata tccgatctga tgttcgtaat caccggcttt tccagccaat ggcttgagat    540
gatttaagaa acttgtgact ggcttttttct ggtaaaatgg atttttgtat aatatcctgt    600
tg                                                                    602
```

<210> SEQ ID NO 117
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

```
cagctgggtc tcggcctggg cgccaaaatc cgccacgctc tgaccatccc aaccgccggc     60
cgcttttttg gcggctaccc gctgccaggc ggcggacaga ttttccatgg cggtgatggc    120
ggccagttga cgataggtgg tggtagacat cgggacggtg cctcctgcaa ggttctatcc    180
tgttggtcgt cgacgcaagg cctcaggtga ccccctctcc gttattctgc caattttttc    240
ctagggaccg gcctgggcac cgtctgcggc gggggctgc cgttcaaccc cggccagggc    300 catgaccag atttctttg atttatcatc aggttggctc ctctttcgca aatgctccgg     360
cgccgcgagc ggccaaacca tttgcgaact tggccgatag gcgattattt tatggcaaat    420
caataagata agtgcttttg aggccctttg gcccctcggc ggcgagggc caaaaagttc    480 gcaaatgccc ctttgggggc cgggcgcccc accatttgcg aaaaaacccg cccggcagcg    540
gccgaggctt ctgccggctg attatatctt atcgatataa ttgaatatta ttttccccca    600
agaccgggtc gaaggcctat tttcgcaaat gcccgccgcg ggccgggga ccaacgtgt     660 tgcgaaaatc cggttctaag caaatcaagg agttaggcca aaaaagtga tttttggcaa    720 tccggccaag cgcccttttgg gggcattttgc gaaaaaatcc ggccggcaaa aacttcttga    780
cattaccggg cattttccat tagagtattg cgtagcagta catatctagc tgatttctcc    840
```

```
                                gtt                                      843

<210> SEQ ID NO 118
<211> LENGTH: 462
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
tatgcgacgg ccttgggcca gcaggatgct ggccctacgg ggttgagcag aggcggcagg       60
ccttgaggac acgtttttga gggcgtttaa cggcaggcgc aggagacggg acgcgaagtg      120
gggttaggga aattaccgcc aggctggaga atagctggcg gttttgttt ggggggccgg       180 aaaaattttc tgctcctgtc acctcgacgg ttccaagaga gactaatttg ttagaccagg      240
ctccagactg gaagtatttt tgggcgcggc cgcggtgacg gctgtccagc aagcggttgg      300
gacggtttaa acatgactgc aggacattac cagacgattt tggaggccca gattgagctg      360
gccttctgcc tgccggaaga ggcgcataat gtgctgtatg cgcgggatga ggcgtgccgt      420
gagctggtcc aagcctgccg caatcaccgg ggtagcctgc gt                         462

<210> SEQ ID NO 119
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
gcagagaacg gaggcgcctg gttctatgaa cttttatggc aatggcacag ggatgaaata       60
ggacatctta gcaacataag gaatacgttt gaaagaatga aagatttga taaatttgcc      120 ccctggaggt ccgtgggatt gggttggtga aaaaagagg agtggatgtc tgcgcctgaa      180
tatgagatcg atctggataa cgatgaccac cctaccataa ttttaacaga catggatgaa      240
tgttatcata tatgccttaa agcggcagga aacgatccta gctgtgctcg atgcaagata      300
tttatggcag atttc                                                       315

<210> SEQ ID NO 120
<211> LENGTH: 850
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
ttttaattga cccgcatttt tgttatatc gaataaccat gaagaaaggc gtccttccca        60
ctccatctca aatctatcag gatttgtttc atagatatgt ttgagacgct ttcggcgctt      120
tgctttatct cttttggcgg cctttcccat tagtcctcct tcttagttca ataatggttt      180
tatccattga tttttcgacc tgatcagagg atctaaactc tgttgggccg gtacctaatt      240
tgatttaatc gaaagaacgt tgtactttt atctcctcta attctttgt ttcggatcgt        300 ctggatagtc gtgataaatc tcttacatgt tacagggaat cgtaattttt ctatctgaaa      360
tctcacaagc gctatttcga tagtcggggc taagtaaaaa aatgtgacat gaattgctgg      420
gccaccagaa gaaatttttc actaaccact atagtcttct ggaatgtgaa aaagtgacag      480
```

```
aaaaaatatg aggctaaaat gtcacatttt aaataaagcc ccgactataa ttatacggat    540
atatctatag acaacccctt ttgatgaaac cttacaccaa taatcggatg ttaaagttat    600
tgacattaca agatttaatg tgttatttat ttaggctcaa cttttctcaa accatccaga    660
ctatttcaaa atatctgtaa agataataag ggggaatgtt atgtattccg actttcctgc    720
acttaggtta cctgaattat ctgttgatca aaaaaaatta tttaagatct ccgggaccaa    780
cccacagctc atatacatct taatgaacga atttgatgga gaggggatg agcccttctt    840 taccggactt                                                           850
```

```
<210> SEQ ID NO 121
<211> LENGTH: 308
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
gttttaaatc ttttattcat gaaagaaggt cttttttgatc atttttttga gcaacaaaga     60
gaatggtgga aagaagagta tgaacatacc gattcgaaca cagctctcta tgattgcttg    120
tgttttcgaa tgtatcggtg ttatttttag gaaaatatat gccctcatac ccttgcttga    180
aatggaatgg cgattgtagc agatgtcctg attcggcaac atgcagaatc gcacagaaag    240
gtttgggaaa ggtatttacg gttttttttca agaaatatct ggcgcgttac tattcttcga    300
aatccgaa                                                              308
```

```
<210> SEQ ID NO 122
<211> LENGTH: 367
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
atgatgaggc ggttttttctt tgataccagt gcgcttatca aactctatca tgaagaaact     60
ggtacagaaa aactggattc tctgatcgag gccgaaaatc cagttatcat taatgatatg    120
aaattgcctg gcgttatgag ctaatcctta tattaaatgc ttcaggcatc tgaaccttgc    180
aacatatcag gatggtatat aaaccacagg aggaatgatg gaatataccc ttaccctaaa    240
tttcattgaa ccgtttcgct tgattgaatg gcacgatgcg ccagatcggg aaaaccttcg    300 attgagggg ttttcttttg ccagatggca taaggacagg gaattcggac tgggaaggcc    360
atatatt                                                              367
```

```
<210> SEQ ID NO 123
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
aatggaatcc aggtccgtta tccaaaattg gaaaagaaa aaaagatga cccaggtgaa     60 aagccgggct atcttgagct ggcagatggc cctttcagca cggaaaatcg caaggaaaaa    120
ttaaaggaga tttgggtaa ttgggcctga ttaaccaaat atcgaataat caccaaatac    180
```

```
atagcctatt ttcaatgata ttcaatagtt ataataccta tttaataatt caatatttat    240
agaatccaag gattatgcat cgccaaaaat acatccataa acgatttaac aatatgaatt    300
tacaaaatga atttatacca ttgggtttta agaatctttt ataataagca aacatagggg    360
ggg                                                                 363

<210> SEQ ID NO 124
<211> LENGTH: 439
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
gatgttccgc caggcacggc agcgattctc cttgggcttt gtagagacgt ggacagattg    60
agggccgcca ttgattcaat tgtttcgggc aagaagacgc gggatgatac gatattctgg   120
atactatacc acaccgtgcc ggagaaatag ggcctgtcgc caaatccact cgggccttcc   180
actacaaaaa ggcttaactc gatagtatat gggtttcctt tttttgagtc cgccggaggc   240
ggacgttgta taaatcgcg  aagtgatttt atgtactgga gaggatatca tggtcacgcc   300
acaagcttct aagaaccccg cagtagatga atcctgaaa  cagctcacac cctatgacat   360
ggagactgag aacgcaaagg ctatcgagac aaggaagtct tgtattgagt gcctgaaagg   420
catttgcgaa agggctcaa                                                439

<210> SEQ ID NO 125
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
atattgcgcg ataacgggga agatatattt gtccatcgga gcgatattaa tggtagcctt    60
ggcaccctga cagaagggca aaagtaatc  tttgaggtga agcagggtcc aaagggactc   120
caggccacaa atgtgaaggt aatttcataa tcacttggcc gtattgcacc ttaccacaat   180
atctttttga gaatttcata agagctcatt tcaaagtgaa tattcaatcc acggctgttg   240
aaaaaaagcg aaacgccctt gctctttttg tgcgccttct cctttcatcg cctctcaagg   300
actacgtcgc caagataatc ctgtttggaa gtgtgagaaa aggaaaagct aattcagaga   360
gtgat                                                               365

<210> SEQ ID NO 126
<211> LENGTH: 344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
tgcttgaaat ggcgtgggca tttgcttttg gccccggctg atatctactc ggcaaagcca    60
caccatacaa taatggaggc tgattcaatg tgacataaaa ttttggggta gcgtctacat   120
gcaaaaatct cggtggtgat tcgtttatac ttatagagtg gatcatttc  tgagccgaca   180 cccgagattg agctatgact gccacaatat ttgacaaatt tgcaagcttt gaaaacttct   240
```

-continued

```
gggccgcctt ccaaaaagtt gctgcaaaga attcagcggg cggcatagac ggcacaaccg    300
ttgagaccta ccaaaagcga gccaagcaac gaatcaatgc cctc                    344
```

<210> SEQ ID NO 127
<400> SEQUENCE: 127
000

<210> SEQ ID NO 128
<400> SEQUENCE: 128
000

<210> SEQ ID NO 129
<400> SEQUENCE: 129
000

<210> SEQ ID NO 130
<400> SEQUENCE: 130
000

<210> SEQ ID NO 131
<400> SEQUENCE: 131
000

<210> SEQ ID NO 132
<400> SEQUENCE: 132
000

<210> SEQ ID NO 133
<400> SEQUENCE: 133
000

<210> SEQ ID NO 134
<400> SEQUENCE: 134
000

<210> SEQ ID NO 135
<400> SEQUENCE: 135
000

<210> SEQ ID NO 136
<400> SEQUENCE: 136
000

<210> SEQ ID NO 137
<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

```
<210> SEQ ID NO 149
<400> SEQUENCE: 149
000

<210> SEQ ID NO 150
<400> SEQUENCE: 150
000

<210> SEQ ID NO 151
<400> SEQUENCE: 151
000

<210> SEQ ID NO 152
<400> SEQUENCE: 152
000

<210> SEQ ID NO 153
<400> SEQUENCE: 153
000

<210> SEQ ID NO 154
<400> SEQUENCE: 154
000

<210> SEQ ID NO 155
<400> SEQUENCE: 155
000

<210> SEQ ID NO 156
<400> SEQUENCE: 156
000

<210> SEQ ID NO 157
<400> SEQUENCE: 157
000

<210> SEQ ID NO 158
<400> SEQUENCE: 158
000

<210> SEQ ID NO 159
<400> SEQUENCE: 159
000

<210> SEQ ID NO 160
```

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

```
<400> SEQUENCE: 205
000

<210> SEQ ID NO 206
<400> SEQUENCE: 206
000

<210> SEQ ID NO 207
<400> SEQUENCE: 207
000

<210> SEQ ID NO 208
<400> SEQUENCE: 208
000

<210> SEQ ID NO 209
<400> SEQUENCE: 209
000

<210> SEQ ID NO 210
<400> SEQUENCE: 210
000

<210> SEQ ID NO 211
<400> SEQUENCE: 211
000

<210> SEQ ID NO 212
<400> SEQUENCE: 212
000

<210> SEQ ID NO 213
<400> SEQUENCE: 213
000

<210> SEQ ID NO 214
<400> SEQUENCE: 214
000

<210> SEQ ID NO 215
<400> SEQUENCE: 215
000

<210> SEQ ID NO 216
<400> SEQUENCE: 216
```

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

```
<400> SEQUENCE: 239
000

<210> SEQ ID NO 240
<400> SEQUENCE: 240
000

<210> SEQ ID NO 241
<400> SEQUENCE: 241
000

<210> SEQ ID NO 242
<400> SEQUENCE: 242
000

<210> SEQ ID NO 243
<400> SEQUENCE: 243
000

<210> SEQ ID NO 244
<400> SEQUENCE: 244
000

<210> SEQ ID NO 245
<400> SEQUENCE: 245
000

<210> SEQ ID NO 246
<400> SEQUENCE: 246
000

<210> SEQ ID NO 247
<400> SEQUENCE: 247
000

<210> SEQ ID NO 248
<400> SEQUENCE: 248
000

<210> SEQ ID NO 249
<400> SEQUENCE: 249
000

<210> SEQ ID NO 250
<400> SEQUENCE: 250
```

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

```
000

<210> SEQ ID NO 296
<400> SEQUENCE: 296

000

<210> SEQ ID NO 297
<400> SEQUENCE: 297

000

<210> SEQ ID NO 298
<400> SEQUENCE: 298

000

<210> SEQ ID NO 299
<400> SEQUENCE: 299

000

<210> SEQ ID NO 300
<211> LENGTH: 7
<212> TYPE: PRT
<213> ORGANISM: Simian virus 40

<400> SEQUENCE: 300

Pro Lys Lys Lys Arg Lys Val
1               5

<210> SEQ ID NO 301
<211> LENGTH: 16
<212> TYPE: PRT
<213> ORGANISM: Unknown
<220> FEATURE:
<223> OTHER INFORMATION: Description of Unknown:
      Nucleoplasmin bipartite NLS sequence

<400> SEQUENCE: 301

Lys Arg Pro Ala Ala Thr Lys Lys Ala Gly Gln Ala Lys Lys Lys Lys
1               5                   10                  15

<210> SEQ ID NO 302
<211> LENGTH: 9
<212> TYPE: PRT
<213> ORGANISM: Unknown
<220> FEATURE:
<223> OTHER INFORMATION: Description of Unknown:
      C-myc NLS sequence

<400> SEQUENCE: 302

Pro Ala Ala Lys Arg Val Lys Leu Asp
1               5

<210> SEQ ID NO 303
<211> LENGTH: 11
<212> TYPE: PRT
<213> ORGANISM: Unknown
<220> FEATURE:
<223> OTHER INFORMATION: Description of Unknown:
      C-myc NLS sequence

<400> SEQUENCE: 303
```

Arg Gln Arg Arg Asn Glu Leu Lys Arg Ser Pro
1               5                   10

<210> SEQ ID NO 304
<211> LENGTH: 38
<212> TYPE: PRT
<213> ORGANISM: Homo sapiens

<400> SEQUENCE: 304

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
            35

<210> SEQ ID NO 305
<211> LENGTH: 42
<212> TYPE: PRT
<213> ORGANISM: Unknown
<220> FEATURE:
<223> OTHER INFORMATION: Description of Unknown:
      IBB domain from importin-alpha sequence

<400> SEQUENCE: 305

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
            35                  40

<210> SEQ ID NO 306
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 306

Val Ser Arg Lys Arg Pro Arg Pro
1               5

<210> SEQ ID NO 307
<211> LENGTH: 8
<212> TYPE: PRT
<213> ORGANISM: Unknown
<220> FEATURE:
<223> OTHER INFORMATION: Description of Unknown:
      Myoma T protein sequence

<400> SEQUENCE: 307

Pro Pro Lys Lys Ala Arg Glu Asp
1               5

<210> SEQ ID NO 308
<211> LENGTH: 8
<212> TYPE: PRT
<213> ORGANISM: Homo sapiens

<400> SEQUENCE: 308

Pro Gln Pro Lys Lys Lys Pro Leu
1               5

```
<210> SEQ ID NO 309
<211> LENGTH: 12
<212> TYPE: PRT
<213> ORGANISM: Mus musculus

<400> SEQUENCE: 309

Ser Ala Leu Ile Lys Lys Lys Lys Met Ala Pro
1               5                   10

<210> SEQ ID NO 310
<211> LENGTH: 5
<212> TYPE: PRT
<213> ORGANISM: Influenza virus

<400> SEQUENCE: 310

Asp Arg Leu Arg Arg
1               5

<210> SEQ ID NO 311
<211> LENGTH: 7
<212> TYPE: PRT
<213> ORGANISM: Influenza virus

<400> SEQUENCE: 311

Pro Lys Gln Lys Lys Arg Lys
1               5

<210> SEQ ID NO 312
<211> LENGTH: 10
<212> TYPE: PRT
<213> ORGANISM: Hepatitis delta virus

<400> SEQUENCE: 312

Arg Lys Leu Lys Lys Lys Ile Lys Lys Leu
1               5                   10

<210> SEQ ID NO 313
<211> LENGTH: 10
<212> TYPE: PRT
<213> ORGANISM: Mus musculus

<400> SEQUENCE: 313

Arg Glu Lys Lys Lys Phe Leu Lys Arg Arg
1               5                   10

<210> SEQ ID NO 314
<211> LENGTH: 20
<212> TYPE: PRT
<213> ORGANISM: Homo sapiens

<400> SEQUENCE: 314

Lys Arg Lys Gly Asp Glu Val Asp Gly Val Asp Glu Val Ala Lys Lys
1               5                   10                  15

Lys Ser Lys Lys
            20

<210> SEQ ID NO 315
<211> LENGTH: 17
<212> TYPE: PRT
<213> ORGANISM: Homo sapiens

<400> SEQUENCE: 315

Arg Lys Cys Leu Gln Ala Gly Met Asn Leu Glu Ala Arg Lys Thr Lys
```

-continued

```
1               5                   10                  15

Lys

<210> SEQ ID NO 316
<211> LENGTH: 793
<212> TYPE: PRT
<213> ORGANISM: Unknown
<220> FEATURE:
<223> OTHER INFORMATION: Description of Unknown: Aquatic-freshwater-
      freshwater sediment sequence

<400> SEQUENCE: 316

Met Ser Ser Leu Pro Thr Pro Leu Glu Leu Lys Gln Lys His Ala
1               5                   10                  15

Asp Leu Phe Lys Gly Leu Gln Phe Ser Ser Lys Asp Asn Lys Met Ala
            20                  25                  30

Gly Lys Val Leu Lys Lys Asp Gly Glu Ala Ala Leu Ala Phe Leu
        35                  40                  45

Ser Glu Arg Gly Val Ser Arg Gly Glu Leu Pro Asn Phe Arg Pro Pro
    50                  55                  60

Ala Lys Thr Leu Val Val Ala Gln Ser Arg Pro Phe Glu Glu Phe Pro
65                  70                  75                  80

Ile Tyr Arg Val Ser Glu Ala Ile Gln Leu Tyr Val Tyr Ser Leu Ser
                85                  90                  95

Val Lys Glu Leu Glu Thr Val Pro Ser Gly Ser Ser Thr Lys Lys Glu
            100                 105                 110

His Gln Arg Phe Phe Gln Asp Ser Ser Val Pro Asp Phe Gly Tyr Thr
        115                 120                 125

Ser Val Gln Gly Leu Asn Lys Ile Phe Gly Leu Ala Arg Gly Ile Tyr
    130                 135                 140

Leu Gly Val Ile Thr Arg Gly Glu Asn Gln Leu Gln Lys Ala Lys Ser
145                 150                 155                 160

Lys His Glu Ala Leu Asn Lys Lys Arg Arg Ala Ser Gly Glu Ala Glu
                165                 170                 175

Thr Glu Phe Asp Pro Thr Pro Tyr Glu Tyr Met Thr Pro Glu Arg Lys
            180                 185                 190

Leu Ala Lys Pro Pro Gly Val Asn His Ser Ile Met Cys Tyr Val Asp
        195                 200                 205

Ile Ser Val Asp Glu Phe Asp Phe Arg Asn Pro Asp Gly Ile Val Leu
    210                 215                 220

Pro Ser Glu Tyr Ala Gly Tyr Cys Arg Glu Ile Asn Thr Ala Ile Glu
225                 230                 235                 240

Lys Gly Thr Val Asp Arg Leu Gly His Leu Lys Gly Gly Pro Gly Tyr
                245                 250                 255

Ile Pro Gly His Gln Arg Lys Glu Ser Thr Thr Glu Gly Pro Lys Ile
            260                 265                 270

Asn Phe Arg Lys Gly Arg Ile Arg Arg Ser Tyr Thr Ala Leu Tyr Ala
        275                 280                 285

Lys Arg Asp Ser Arg Arg Val Arg Gln Gly Lys Leu Ala Leu Pro Ser
    290                 295                 300

Tyr Arg His His Met Met Arg Leu Asn Ser Asn Ala Glu Ser Ala Ile
305                 310                 315                 320

Leu Ala Val Ile Phe Phe Gly Lys Asp Trp Val Val Phe Asp Leu Arg
                325                 330                 335

Gly Leu Leu Arg Asn Val Arg Trp Arg Asn Leu Phe Val Asp Gly Ser
```

```
              340              345              350
Thr Pro Ser Thr Leu Leu Gly Met Phe Gly Asp Pro Val Ile Asp Pro
            355              360              365
Lys Arg Gly Val Val Ala Phe Cys Tyr Lys Glu Gln Ile Val Pro Val
        370              375              380
Val Ser Lys Ser Ile Thr Lys Met Val Lys Ala Pro Glu Leu Leu Asn
385              390              395              400
Lys Leu Tyr Leu Lys Ser Glu Asp Pro Leu Val Leu Val Ala Ile Asp
                405              410              415
Leu Gly Gln Thr Asn Pro Val Gly Val Gly Val Tyr Arg Val Met Asn
            420              425              430
Ala Ser Leu Asp Tyr Glu Val Val Thr Arg Phe Ala Leu Glu Ser Glu
        435              440              445
Leu Leu Arg Glu Ile Glu Ser Tyr Arg Gln Arg Thr Asn Ala Phe Glu
    450              455              460
Ala Gln Ile Arg Ala Glu Thr Phe Asp Ala Met Thr Ser Glu Glu Gln
465              470              475              480
Glu Glu Ile Thr Arg Val Arg Ala Phe Ser Ala Ser Lys Ala Lys Glu
                485              490              495
Asn Val Cys His Arg Phe Gly Met Pro Val Asp Ala Val Asp Trp Ala
            500              505              510
Thr Met Gly Ser Asn Thr Ile His Ile Ala Lys Trp Val Met Arg His
        515              520              525
Gly Asp Pro Ser Leu Val Glu Val Leu Glu Tyr Arg Lys Asp Asn Glu
    530              535              540
Ile Lys Leu Asp Lys Asn Gly Val Pro Lys Lys Val Lys Leu Thr Asp
545              550              555              560
Lys Arg Ile Ala Asn Leu Thr Ser Ile Arg Leu Arg Phe Ser Gln Glu
                565              570              575
Thr Ser Lys His Tyr Asn Asp Thr Met Trp Glu Leu Arg Arg Lys His
            580              585              590
Pro Val Tyr Gln Lys Leu Ser Lys Ser Lys Ala Asp Phe Ser Arg Arg
        595              600              605
Val Val Asn Ser Ile Ile Arg Arg Val Asn His Leu Val Pro Arg Ala
    610              615              620
Arg Ile Val Phe Ile Ile Glu Asp Leu Lys Asn Leu Gly Lys Val Phe
625              630              635              640
His Gly Ser Gly Lys Arg Glu Leu Gly Trp Asp Ser Tyr Phe Glu Pro
                645              650              655
Lys Ser Glu Asn Arg Trp Phe Ile Gln Val Leu His Lys Ala Phe Ser
            660              665              670
Glu Thr Gly Lys His Lys Gly Tyr Tyr Ile Ile Glu Cys Trp Pro Asn
        675              680              685
Trp Thr Ser Cys Thr Cys Pro Lys Cys Ser Cys Asp Ser Glu Asn
    690              695              700
Arg His Gly Glu Val Phe Arg Cys Leu Ala Cys Gly Tyr Thr Cys Asn
705              710              715              720
Thr Asp Phe Gly Thr Ala Pro Asp Asn Leu Val Lys Ile Ala Thr Thr
                725              730              735
Gly Lys Gly Leu Pro Gly Pro Lys Arg Cys Lys Gly Ser Ser Lys
            740              745              750
Gly Lys Asn Pro Lys Ile Ala Arg Ser Ser Glu Thr Gly Val Ser Val
        755              760              765
```

Thr Glu Ser Gly Ala Pro Lys Val Lys Lys Ser Ser Pro Thr Gln Thr
    770             775                 780

Ser Gln Ser Ser Ser Gln Ser Ala Pro
785                 790

<210> SEQ ID NO 317
<211> LENGTH: 761
<212> TYPE: PRT
<213> ORGANISM: Unknown
<220> FEATURE:
<223> OTHER INFORMATION: Description of Unknown: Terrestrial-soil-arctic
      peat soil sequence

<400> SEQUENCE: 317

Met Ser Asn Lys Thr Thr Pro Pro Ser Pro Leu Ser Leu Leu Leu Arg
1               5                   10                  15

Ala His Phe Pro Gly Leu Lys Phe Glu Ser Gln Asp Tyr Lys Ile Ala
            20                  25                  30

Gly Lys Lys Leu Arg Asp Gly Gly Pro Glu Ala Val Ile Ser Tyr Leu
        35                  40                  45

Thr Gly Lys Gly Gln Ala Lys Leu Lys Asp Val Lys Pro Pro Ala Lys
50                  55                  60

Ala Phe Val Ile Ala Gln Ser Arg Pro Phe Ile Glu Trp Asp Leu Val
65                  70                  75                  80

Arg Val Ser Arg Gln Ile Gln Glu Lys Ile Phe Gly Ile Pro Ala Thr
                85                  90                  95

Lys Gly Arg Pro Lys Gln Asp Gly Leu Ser Glu Thr Ala Phe Asn Glu
            100                 105                 110

Ala Val Ala Ser Leu Glu Val Asp Gly Lys Ser Lys Leu Asn Glu Glu
        115                 120                 125

Thr Arg Ala Ala Phe Tyr Glu Val Leu Gly Leu Asp Ala Pro Ser Leu
130                 135                 140

His Ala Gln Ala Gln Asn Ala Leu Ile Lys Ser Ala Ile Ser Ile Arg
145                 150                 155                 160

Glu Gly Val Leu Lys Lys Val Glu Asn Arg Asn Glu Lys Asn Leu Ser
                165                 170                 175

Lys Thr Lys Arg Arg Lys Glu Ala Gly Glu Ala Thr Phe Val Glu
            180                 185                 190

Glu Lys Ala His Asp Glu Arg Gly Tyr Leu Ile His Pro Pro Gly Val
        195                 200                 205

Asn Gln Thr Ile Pro Gly Tyr Gln Ala Val Val Ile Lys Ser Cys Pro
210                 215                 220

Ser Asp Phe Ile Gly Leu Pro Ser Gly Cys Leu Ala Lys Glu Ser Ala
225                 230                 235                 240

Glu Ala Leu Thr Asp Tyr Leu Pro His Asp Arg Met Thr Ile Pro Lys
                245                 250                 255

Gly Gln Pro Gly Tyr Val Pro Glu Trp Gln His Pro Leu Leu Asn Arg
            260                 265                 270

Arg Lys Asn Arg Arg Arg Asp Trp Tyr Ser Ala Ser Leu Asn Lys
        275                 280                 285

Pro Lys Ala Thr Cys Ser Lys Arg Ser Gly Thr Pro Asn Arg Lys Asn
290                 295                 300

Ser Arg Thr Asp Gln Ile Gln Ser Gly Arg Phe Lys Gly Ala Ile Pro
305                 310                 315                 320

Val Leu Met Arg Phe Gln Asp Glu Trp Val Ile Ile Asp Ile Arg Gly

```
                 325                 330                 335
Leu Leu Arg Asn Ala Arg Tyr Arg Lys Leu Leu Lys Glu Lys Ser Thr
                340                 345                 350
Ile Pro Asp Leu Leu Ser Leu Phe Thr Gly Asp Pro Ser Ile Asp Met
                355                 360                 365
Arg Gln Gly Val Cys Thr Phe Ile Tyr Lys Ala Gly Gln Ala Cys Ser
                370                 375                 380
Ala Lys Met Val Lys Thr Lys Asn Ala Pro Glu Ile Leu Ser Glu Leu
385                 390                 395                 400
Thr Lys Ser Gly Pro Val Val Leu Val Ser Ile Asp Leu Gly Gln Thr
                405                 410                 415
Asn Pro Ile Ala Ala Lys Val Ser Arg Val Thr Gln Leu Ser Asp Gly
                420                 425                 430
Gln Leu Ser His Glu Thr Leu Leu Arg Glu Leu Leu Ser Asn Asp Ser
                435                 440                 445
Ser Asp Gly Lys Glu Ile Ala Arg Tyr Arg Val Ala Ser Asp Arg Leu
                450                 455                 460
Arg Asp Lys Leu Ala Asn Leu Ala Val Glu Arg Leu Ser Pro Glu His
465                 470                 475                 480
Lys Ser Glu Ile Leu Arg Ala Lys Asn Asp Thr Pro Ala Leu Cys Lys
                485                 490                 495
Ala Arg Val Cys Ala Ala Leu Gly Leu Asn Pro Glu Met Ile Ala Trp
                500                 505                 510
Asp Lys Met Thr Pro Tyr Thr Glu Phe Leu Ala Thr Ala Tyr Leu Glu
                515                 520                 525
Lys Gly Gly Asp Arg Lys Val Ala Thr Leu Lys Pro Lys Asn Arg Pro
                530                 535                 540
Glu Met Leu Arg Arg Asp Ile Lys Phe Lys Gly Thr Glu Gly Val Arg
545                 550                 555                 560
Ile Glu Val Ser Pro Glu Ala Ala Glu Ala Tyr Arg Glu Ala Gln Trp
                565                 570                 575
Asp Leu Gln Arg Thr Ser Pro Glu Tyr Leu Arg Leu Ser Thr Trp Lys
                580                 585                 590
Gln Glu Leu Thr Lys Arg Ile Leu Asn Gln Leu Arg His Lys Ala Ala
                595                 600                 605
Lys Ser Ser Gln Cys Glu Val Val Met Ala Phe Glu Asp Leu Asn
                610                 615                 620
Ile Lys Met Met His Gly Asn Gly Lys Trp Ala Asp Gly Gly Trp Asp
625                 630                 635                 640
Ala Phe Phe Ile Lys Lys Arg Glu Asn Arg Trp Phe Met Gln Ala Phe
                645                 650                 655
His Lys Ser Leu Thr Glu Leu Gly Ala His Lys Gly Val Pro Thr Ile
                660                 665                 670
Glu Val Thr Pro His Arg Thr Ser Ile Thr Cys Thr Lys Cys Gly His
                675                 680                 685
Cys Asp Lys Ala Asn Arg Asp Gly Glu Arg Phe Ala Cys Gln Lys Cys
690                 695                 700
Gly Phe Val Ala His Ala Asp Leu Glu Ile Ala Thr Asp Asn Ile Glu
705                 710                 715                 720
Arg Val Ala Leu Thr Gly Lys Pro Met Pro Lys Pro Glu Ser Glu Arg
                725                 730                 735
Ser Gly Asp Ala Lys Lys Ser Val Gly Ala Arg Lys Ala Ala Phe Lys
                740                 745                 750
```

Pro Glu Glu Asp Ala Glu Ala Glu
        755                 760

<210> SEQ ID NO 318
<211> LENGTH: 721
<212> TYPE: PRT
<213> ORGANISM: Unknown
<220> FEATURE:
<223> OTHER INFORMATION: Description of Unknown: Terrestrial-soil-forest
      soil sequence

<400> SEQUENCE: 318

Met Ile Ser Lys Met Ile Lys Pro Thr Val Ser Gln Phe Leu Thr Pro
1               5                   10                  15

Gly Phe Lys Leu Ile Arg Asn His Ser Arg Thr Ala Gly Leu Lys Leu
            20                  25                  30

Lys Asn Glu Gly Glu Glu Ala Cys Lys Lys Phe Val Arg Glu Asn Glu
        35                  40                  45

Ile Pro Lys Asp Glu Cys Pro Asn Phe Gln Gly Gly Pro Ala Ile Ala
    50                  55                  60

Asn Ile Ile Ala Lys Ser Arg Glu Phe Thr Glu Trp Glu Ile Tyr Gln
65                  70                  75                  80

Ser Ser Leu Ala Ile Gln Glu Val Ile Phe Thr Leu Pro Lys Asp Lys
                85                  90                  95

Leu Pro Glu Pro Ile Leu Lys Glu Glu Trp Arg Ala Gln Trp Leu Ser
            100                 105                 110

Glu His Gly Leu Asp Thr Val Pro Tyr Lys Glu Ala Ala Gly Leu Asn
        115                 120                 125

Leu Ile Ile Lys Asn Ala Val Asn Thr Tyr Lys Gly Val Gln Val Lys
    130                 135                 140

Val Asp Asn Lys Asn Lys Asn Asn Leu Ala Lys Ile Asn Arg Lys Asn
145                 150                 155                 160

Glu Ile Ala Lys Leu Asn Gly Glu Gln Glu Ile Ser Phe Glu Glu Ile
                165                 170                 175

Lys Ala Phe Asp Asp Lys Gly Tyr Leu Leu Gln Lys Pro Ser Pro Asn
            180                 185                 190

Lys Ser Ile Tyr Cys Tyr Gln Ser Val Ser Pro Lys Pro Phe Ile Thr
        195                 200                 205

Ser Lys Tyr His Asn Val Asn Leu Pro Glu Glu Tyr Ile Gly Tyr Tyr
    210                 215                 220

Arg Lys Ser Asn Glu Pro Ile Val Ser Pro Tyr Gln Phe Asp Arg Leu
225                 230                 235                 240

Arg Ile Pro Ile Gly Glu Pro Gly Tyr Val Pro Lys Trp Gln Tyr Thr
                245                 250                 255

Phe Leu Ser Lys Lys Glu Asn Lys Arg Arg Lys Leu Ser Lys Arg Ile
            260                 265                 270

Lys Asn Val Ser Pro Ile Leu Gly Ile Ile Cys Ile Lys Lys Asp Trp
        275                 280                 285

Cys Val Phe Asp Met Arg Gly Leu Leu Arg Thr Asn His Trp Lys Lys
    290                 295                 300

Tyr His Lys Pro Thr Asp Ser Ile Asn Asp Leu Phe Asp Tyr Phe Thr
305                 310                 315                 320

Gly Asp Pro Val Ile Asp Thr Lys Ala Asn Val Val Arg Phe Arg Tyr
                325                 330                 335

Lys Met Glu Asn Gly Ile Val Asn Tyr Lys Pro Val Arg Glu Lys Lys

```
            340                 345                 350
Gly Lys Glu Leu Leu Glu Asn Ile Cys Asp Gln Asn Gly Ser Cys Lys
            355                 360                 365

Leu Ala Thr Val Asp Val Gly Gln Asn Asn Pro Val Ala Ile Gly Leu
        370                 375                 380

Phe Glu Leu Lys Lys Val Asn Gly Glu Leu Thr Lys Thr Leu Ile Ser
385                 390                 395                 400

Arg His Pro Thr Pro Ile Asp Phe Cys Asn Lys Ile Thr Ala Tyr Arg
                405                 410                 415

Glu Arg Tyr Asp Lys Leu Glu Ser Ser Ile Lys Leu Asp Ala Ile Lys
            420                 425                 430

Gln Leu Thr Ser Glu Gln Lys Ile Glu Val Asp Asn Tyr Asn Asn Asn
        435                 440                 445

Phe Thr Pro Gln Asn Thr Lys Gln Ile Val Cys Ser Lys Leu Asn Ile
450                 455                 460

Asn Pro Asn Asp Leu Pro Trp Asp Lys Met Ile Ser Gly Thr His Phe
465                 470                 475                 480

Ile Ser Glu Lys Ala Gln Val Ser Asn Lys Ser Glu Ile Tyr Phe Thr
                485                 490                 495

Ser Thr Asp Lys Gly Lys Thr Lys Asp Val Met Lys Ser Asp Tyr Lys
            500                 505                 510

Trp Phe Gln Asp Tyr Lys Pro Lys Leu Ser Lys Glu Val Arg Asp Ala
        515                 520                 525

Leu Ser Asp Ile Glu Trp Arg Leu Arg Arg Glu Ser Leu Glu Phe Asn
    530                 535                 540

Lys Leu Ser Lys Ser Arg Glu Gln Asp Ala Arg Gln Leu Ala Asn Trp
545                 550                 555                 560

Ile Ser Ser Met Cys Asp Val Ile Gly Ile Glu Asn Leu Val Lys Lys
                565                 570                 575

Asn Asn Phe Phe Gly Ser Gly Lys Arg Glu Pro Gly Trp Asp Asn
            580                 585                 590

Phe Tyr Lys Pro Lys Lys Glu Asn Arg Trp Trp Ile Asn Ala Ile His
        595                 600                 605

Lys Ala Leu Thr Glu Leu Ser Gln Asn Lys Gly Lys Arg Val Ile Leu
    610                 615                 620

Leu Pro Ala Met Arg Thr Ser Ile Thr Cys Pro Lys Cys Lys Tyr Cys
625                 630                 635                 640

Asp Ser Lys Asn Arg Asn Gly Glu Lys Phe Asn Cys Leu Lys Cys Gly
                645                 650                 655

Ile Glu Leu Asn Ala Asp Ile Asp Val Ala Thr Glu Asn Leu Ala Thr
            660                 665                 670

Val Ala Ile Thr Ala Gln Ser Met Pro Lys Pro Thr Cys Glu Arg Ser
        675                 680                 685

Gly Asp Ala Lys Lys Pro Val Arg Ala Arg Lys Ala Lys Ala Pro Glu
    690                 695                 700

Phe His Asp Lys Leu Ala Pro Ser Tyr Thr Val Val Leu Arg Glu Ala
705                 710                 715                 720

Val

<210> SEQ ID NO 319
<211> LENGTH: 6
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 319 tgrgac                                                                        6

<210> SEQ ID NO 320
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (28)..(28)
<223> OTHER INFORMATION: a, c, t, g, unknown or other

<400> SEQUENCE: 320
acgshwncra nvcyhdywsa kkgsyymnwd yrhkgrgacs ag                                42

<210> SEQ ID NO 321
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
cctgcgaagc cttttgattg ctcagtacgc tgagac                                      36

<210> SEQ ID NO 322
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
cctgcgaaac cttttgattg ctcagtacgc tgagac                                      36

<210> SEQ ID NO 323
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
cctgcgaaac cttttgattg ctcagttcgc tgagac                                      36

<210> SEQ ID NO 324
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 324
cccttttgat tgcccaattc gttgggacca g                                    31

<210> SEQ ID NO 325
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
ggatccaatc cttttgatt gcccaattcg ttgggac                               37

<210> SEQ ID NO 326
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
acggatccaa tcctttttga ttgcccaatt cgttgggacg a                         41

<210> SEQ ID NO 327
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
ctttcaagac taatagattg ctccttacga ggagac                               36

<210> SEQ ID NO 328
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
ccaacaacac ccgctcaggg gttccagtac tgagac                               36
```